(12) United States Patent
Raj et al.

(10) Patent No.: US 12,369,597 B2
(45) Date of Patent: Jul. 29, 2025

(54) LACTASE ENZYMES WITH IMPROVED ACTIVITY AT LOW TEMPERATURES

(71) Applicant: Kerry Group Services International Ltd, Tralee (IE)

(72) Inventors: Hans Raj, Hoersholm (DK); Pernille Smith, Broenshoej (DK); Thomas Eckhardt, Birkeroed (DK); Vojislav Vojinovic, Graested (DK); Charlotte Elisabeth Grüner Schöller, Virum (DK); Johannes Maarten Van Den Brink, Herlev (DK)

(73) Assignee: Kerry Group Services International Ltd, Tralee (IE)

( * ) Notice: Subject to any disclaimer, the term of this patent is extended or adjusted under 35 U.S.C. 154(b) by 1270 days.

(21) Appl. No.: 16/604,134

(22) PCT Filed: Apr. 11, 2018

(86) PCT No.: PCT/EP2018/059289
§ 371 (c)(1),
(2) Date: Oct. 9, 2019

(87) PCT Pub. No.: WO2018/189242
PCT Pub. Date: Oct. 18, 2018

(65) Prior Publication Data
US 2023/0210121 A1    Jul. 6, 2023

(30) Foreign Application Priority Data

Apr. 11, 2017  (EP) ..................................... 17166021
Aug. 31, 2017  (EP) ..................................... 17188732

(51) Int. Cl.
*A23C 9/12*       (2006.01)
*C12N 9/38*       (2006.01)

(52) U.S. Cl.
CPC .......... *A23C 9/1206* (2013.01); *C12N 9/2471* (2013.01)

(58) Field of Classification Search
CPC ................ A23C 9/1206; C12N 9/2471; C12Y 302/01023; C07K 14/195
USPC ........................................................ 426/42
See application file for complete search history.

(56) References Cited

U.S. PATENT DOCUMENTS

| | | | |
|---|---|---|---|
| 8,030,049 B2 | 10/2011 | Tzortzis et al. | |
| 10,058,107 B2 | 8/2018 | Hendriksen et al. | |
| 10,306,902 B2 | 6/2019 | Hendriksen et al. | |
| 10,555,541 B2 | 2/2020 | Hendriksen et al. | |
| 11,525,129 B2 | 12/2022 | Raj et al. | |
| 2009/0110770 A1* | 4/2009 | Tzortzis | C12P 19/18 435/207 |
| 2009/0117080 A1 | 5/2009 | Tzortzis et al. | |
| 2009/0297660 A1 | 12/2009 | Silver et al. | |
| 2010/0113383 A1 | 5/2010 | Mills et al. | |
| 2010/0285175 A1* | 11/2010 | Hendriksen | A23C 9/123 426/42 |
| 2012/0058223 A1 | 3/2012 | Stougaard et al. | |
| 2016/0333331 A1* | 11/2016 | De Jong | C12Y 302/01107 |
| 2017/0215449 A1 | 8/2017 | Nagahata et al. | |
| 2019/0343138 A1 | 11/2019 | Ba et al. | |
| 2020/0120946 A1 | 4/2020 | Hendriksen et al. | |
| 2020/0123519 A1 | 4/2020 | Bongiorni et al. | |
| 2021/0032615 A1 | 2/2021 | Raj et al. | |
| 2021/0037844 A1 | 2/2021 | Hendriksen et al. | |
| 2021/0348147 A1 | 11/2021 | Raj et al. | |
| 2021/0355471 A1 | 11/2021 | Raj et al. | |
| 2023/0076578 A1 | 3/2023 | Raj et al. | |

FOREIGN PATENT DOCUMENTS

| | | |
|---|---|---|
| CN | 103431042 B | 1/2015 |
| EP | 1 227 152 A1 | 7/2002 |
| EP | 2 530 148 A1 | 12/2012 |
| EP | 2 957 180 B1 | 12/2015 |
| RU | 2278160 C2 | 9/2005 |
| RU | 2009120742 | 12/2010 |
| WO | WO-2005/084411 A2 | 9/2005 |
| WO | WO-2005/086794 A2 | 9/2005 |
| WO | WO-2007/088324 A1 | 8/2007 |
| WO | WO-2007/110619 A1 | 10/2007 |
| WO | WO-2008/033520 A2 | 3/2008 |
| WO | WO-2009/009142 A2 | 1/2009 |
| WO | WO-2009/071539 A1 | 6/2009 |
| WO | WO-2010/092057 A1 | 8/2010 |
| WO | WO-2013/160413 A1 | 10/2013 |
| WO | WO-2015/107050 A1 | 7/2015 |
| WO | WO-2017/216000 A1 | 12/2017 |
| WO | WO-2018/041869 A1 | 3/2018 |

(Continued)

OTHER PUBLICATIONS

Seq Alignment Result (16604134 SEQ #7vs Tzortis SEQ #2 using SLIC and ABSS SEQ-to SEQ (aa), PI note : copied sequence from SLIC had MET instead of M which were aligned(MET 3 letters) instead of one 'M' even if ABSS SEQ-to SEQ, , therefore, 1052 amino acid shows 3×1052= 3156. Retrieved on Jun. 27, 2023. (Year: 2023).*

(Continued)

*Primary Examiner* — Erik Kashnikow
*Assistant Examiner* — Bhaskar Mukhopadhyay
(74) *Attorney, Agent, or Firm* — Foley & Lardner LLP

(57) ABSTRACT

The present invention relates to new improved peptide or dimeric peptides exhibiting beta-galactosidase enzyme activity as well as improved methods for reducing the lactose content in compositions in particular at low temperatures.

21 Claims, 30 Drawing Sheets

Figure 1:
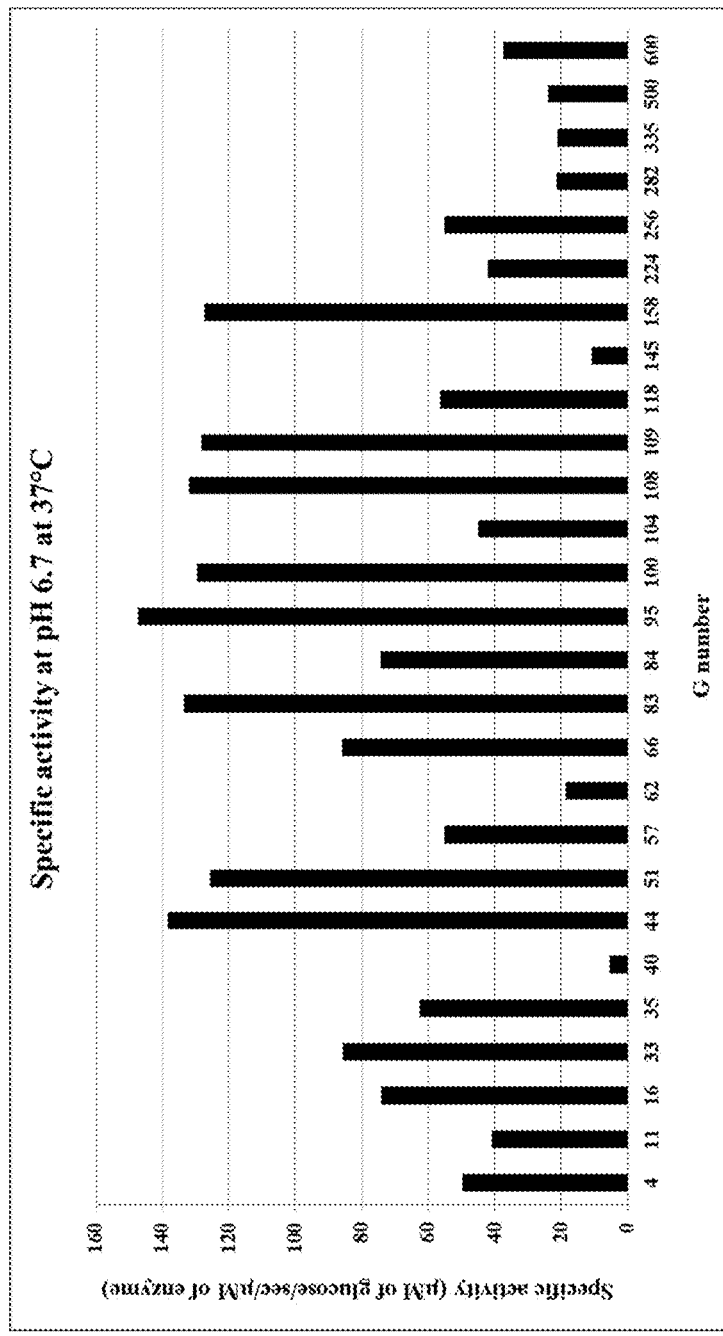

Specification includes a Sequence Listing.

(56) References Cited

FOREIGN PATENT DOCUMENTS

| WO | WO-2018/130630 A1 | 7/2018 |
|---|---|---|
| WO | WO-2018/187524 A1 | 10/2018 |
| WO | WO-2018/189224 A1 | 10/2018 |
| WO | WO-2018/189238 A1 | 10/2018 |

OTHER PUBLICATIONS

Cecchini et al. (This ref was considered from Result 2 of Uniport (426 kb) as posted on and collected from "Search Results" [as posted on Feb. 1, 2022 ] from U.S. Appl. No. 16/604,129-A (matches SEQ ID #22 99.4% match and SEQ ID #22 of 16604134 A-22 has 100% match with U.S. Appl. No. 16/604,129 A-22) (Year: 2013).*

Wierzbicka-Woś et al. Microbial Cell Factories 2011, 10:108 (Year: 2011).*

Google search Result for Wierzbicka-Wos et al. [Retrieved on Apr. 14, 2024]. (Year: 2024).*

Broune et al. "Catalytic Plasticity of Fatty Acid Modification Enzymes Underlying Chemical Diversity of Plant Lipids," Science, vol. 282, pp. 1315-1317 (1998).

Devos et al., "Practical Limits of Function Prediction," Proteins: Structure, Function, and Genetics, vol. 41, pp. 98-107 (Aug. 2000).

Seffernick et al., "Melamine Deaminase and Atrazine Chlorohydrolase: 98 Percent Identical but Functionally Different," Journal of Bacteriology, vol. 183, No. 8, pp. 2405-2410 (Apr. 2001).

Whisstock et al., "Prediction of protein function from protein sequence and structure," Quarterly Reviews of Biophysics, vol. 36, No. 3 (pp. 307-340) (2003).

Witkowski et al. "Conversion of β-Ketoacyl Synthase to a Malonyl Decarboxylase by Replacement of the Active-Site Cysteine with Glutamine," Biochemistry, vol. 38, pp. 11643-11650 (1999).

"Chapter 3 Lactose content of milk and milk products," The American Journal of Clinical Nutrition, vol. 48, No. 4 pp. 1099-1044 (Oct. 1988) Available online, URL: https://academic.oup.com/ajcn/article-abstract/48/4/1099/4791817?redirectedFrom=fulltext.

Kreft et al., "Lactose hydrolysing ability of sonicated cultures of Lactobacillus delbrueckii ssp. bulgaricus 11842," le Lait, INRA Editions 81(3) pp. 355-364 (2001).

Office Action issued on Jun. 9, 2021, in Application No. U.S. Appl. No. 16/998,706 (US 2021-0032615).

Rhimi et al., "Exploring the acidotolerance of B-galactosidase from Lactobacillus delbrueckii subsp. bulgaricus: an attractive enzyme for lactose bioconversion," Research in Microbiology, vol. 160 pp. 775-784 (2009) (Available online Sep. 2009).

UNIPROT:G6F860 (Oct. 2020).

Van De Guchte, et al., Beta-galactosidase [Lactobacillus delbrueckii subsp. bulgaaricus ATCC 11842 = JCM 1002] GenBank: CAI98003 [Feb. 2015].

U.S. Appl. No. 17/986,618, filed Nov. 14, 2022, Raj et al.

Skripnyuk A.A., et al.; "Modern methods for producing beta-galactosidase"; Science Innovations Technologies, 3; 2014; pp. 198-204.

Office Action issued on Jan. 22, 2021, in U.S. Appl. No. 16/998,706 (US 2021-0032615).

U.S. Appl. No. 16/604,129, filed Oct. 9, 2019, Raj et al.

U.S. Appl. No. 16/604,133, filed Oct. 9, 2019, Raj et al.

"UNIPROT: A0A0B5J47" (Apr. 1, 2015), Retrieved from the Internet, URL:http://ibis/exam/dbfetch.jsp?id=UNIPROT:A0A0B5J47 (Retrieved on May 11, 2017).

"UNIPROT: A0AS2MCC8—beta galactosidase," (Feb. 17, 2016) Retrieved from the Internet, URL: https://ibis/exam/dbfetch.jsp?id=UNIPROT:A0AOS2MCC8 [retrieved on Mar. 9, 2018).

Horner et al., "β-Galactosidase activity of commercial lactase samples in raw and pasteurized milk at refrigerated temperatures," J. Dairy Sci. 94: 3242-3249 (2011).

Nakagawa et al., "Overexpression and functional analysis of cold-active β-galactosidase from Arthrobacter psychrolocatohilus strain F2," Protein Expression and Purification 54 (2007) 295-299 (Available on line Mar. 2007).

Palak-Szukalska et al., "A novel cold-active β-D-galactosidase with transglycosylation activity from the Arthrobacter sp. 32cB—Gene cloning, purification and characterization," Process Biochemistry 49 (214) 2122-2133 (Available online Sep. 28, 2014).

Schmidt et al., "Identification, cloning and expression of a cold-active β-galactosidase from a novel Arctic bacterium, Alkalilactibacillus ikkense," (2010) Environmental Technology, 31:10, 1107-1114 (Published online Jun. 2010).

Wang et al., "A novel cold-adapted β-galactosidase isolated from Halomonas sp. S62: gene cloning, purification and enzymatic characterization," World J. Microbiol Biotechnol (2013) 29:1473-1480 (Published on line Mar. 2013).

Wierzbicka-Wos et al., "A novel cold-active β-D-galactosidase from the Paracoccus sp. 32d—gene cloning, purification and characterization," Microbial Cell Factories 2011, 10:108 pp. 1-12.

GenBank Accession No. CAI98003.1.

Kreft et al., "Lactose hydrolysing ability of sonicated cultures of Lactobacillus delbrueckii ssp. bulgaricus 11842," Le Lait, vol. 81, No. 3, pp. 355-364 (Jan. 2001).

Office Action issued on Apr. 12, 2022 in U.S. Appl. No. 16/998,706 (US 2021-0032615).

Office Action issued on Apr. 29, 2022 in U.S. Appl. No. 16/604,129 (US 2021-0355471).

Rhimi et al., "Exploring the acidotolerance of B-galactosidase from Lactobacillus delbrueckii subsp. bulgaricus: an attractive enzyme for lactose bioconversion," Research in Microbiology, vol. 160, pp. 775-784 (Sep. 2009).

UniProt Accession No. F0K2P6, May 3, 2011.

UniProt Accession No. G6F860, Jan. 25, 2012.

Database GenBank: ACE06986.1, (Jun. 8, 2012).

Database GenBank: CDR82630.1, (Jun. 11, 2014).

UniProtKB—A0A076JKA5 (A0A076JKA5_BIFAD); Oct. 29, 2014; 7 pages.

UniProtKB—A0A0A1GLP4 (A0A0A1GLP4_BIFLN); Feb. 4, 2015; 8 pages.

UniProtKB—A0A0A715K5 (A0A0A715K5_9BIFI); Mar. 4, 2015; 8 pages.

UniProtKB—A0A0H2P357 (A0A0H2P357_BIFBI); Sep. 16, 2015; 7 pages.

UniProtKB—A0AOU5FVZ6 (A0A0U5FVZ6_LACDE); Mar. 16, 2016; 9 pages.

UniProtKB—A0A126SWK6 (A0A126SWK6_9BIFI); Jul. 6, 2016; 8 pages.

UniProtKB—A0A174BAQ4 (A0A174BAQ4_9BIFI); Sep. 7, 2016; 8 pages.

UniProtKB—A0A174BB61 (A0A174BB61_BIFAD); Sep. 7, 2016; 8 pages.

UniProtKB—A0A174BH17 (A0A174BH17_9FIRM); Sep. 7, 2016; 5 pages.

UniProtKB—A0A1D7UM07 (A0A1D7UM07_BIFLN); Jan. 18, 2017; 8 pages.

UniProtKB—A0A1D7ZXL7 (A0A1D7ZXL7_LIMFE); Jan. 18, 2017; 7 pages.

UniProtKB—A0A1S2W2V3 (A0A1S2W2V3_BIFLN); Apr. 12, 2017; 8 pages.

UniProtKB—A0A1X2Z956 (A0A1X2Z956_BIFAD); Jul. 5, 2017; 8 pages.

UniProtKB—A0A1X2ZA47 (A0A1X2ZA47_BIFAD); Jul. 5, 2017; 7 pages.

UniProtKB—A0A1X2ZAP4 (A0A1X2ZAP4_BIFAD); Jul. 5, 2017; 7 pages.

UniProtKB—A0A2G5Q4A6 (A0A2G5Q4A6_9BIFI); Jan. 31, 2018; 8 pages.

UniProtKB—A0A4ROSL12 (A0A4ROSL12_BIFLN); Jul. 31, 2019; 8 pages.

UniProtKB—A0A4ROU1N4 (A0A4ROU1N4_BIFLN); Jul. 31, 2019; 8 pages.

UniProtKB—A0A6A2R535 (A0A6A2R535_BIFAD); Jun. 17, 2020; 7 pages.

(56) References Cited

OTHER PUBLICATIONS

UniProtKB—A0A6B1X5Q7 (A0A6B1X5Q7_9BIFI); Jun. 17, 2020; 6 pages.
UniProtKB—A0A6I1DQE1 (A0A6I1DQE1_BIFLN); Aug. 12, 2020; 8 pages.
UniProtKB—A0A6L4K944 (A0A6L4K944_BIFAD); Oct. 7, 2020; 7 pages.
UniProtKB—A0A6L4V5B5 (A0A6L4V5B5_9BIFI); Oct. 7, 2020; 8 pages.
UniProtKB—A0A7D9N5G4 (A0A7D9N5G4_LACJH); Dec. 2, 2020; 8 pages.
UniProtKB—A0A829LWJ6 (A0A829LWJ6_LIMFE); Sep. 29, 2021; 7 pages.
UniProtKB—A5VKG8 (A5VKG8_LIMRD); Jul. 10, 2007; 8 pages.
UniProtKB—B2GAA1 (B2GAA1_LIMF3); Jun. 10, 2008; 7 pages.
UniProtKB—B2GAA2 (B2GAA2_LIMF3); Jun. 10, 2008; 6 pages.
UniProtKB—D6ZY97 (D6ZY97_BIFLJ); Aug. 10, 2010; 8 pages.
UniProtKB—E4SLB1 (E4SLB1_LACAR); Feb. 8, 2011; 8 pages.
UniProtKB—E8MRV2 (E8MRV2_BIFL1); Apr. 5, 2011; 8 pages.
UniProtKB—F0HTF8 (F0HTF8_LACDL); May 3, 2011; 9 pages.
UniProtKB—F0TG75 (F0TG75_LACAM); May 3, 2011; 8 pages.
UniProtKB—F2M1D8 (F2MID8_LACAL); May 11, 2011; 8 pages.
UniProtKB—F4AFP0 (F4AFP0_LACJH); Jun. 28, 2011; 8 pages.
UniProtKB—F8ASA8 (F8ASA8_BIFLN); Sep. 21, 2011; 8 pages.
UniProtKB—G6F860 (G6F860_LACDE); Jan. 25, 2012; 9 pages.
UniProtKB—I3WJ66 (I3WJ66_BIFBI); Sep. 5, 2012; 8 pages.
UniProtKB—K215J0 (K215J0_BIFBI); Nov. 28, 2012; 8 pages.
UniProtKB—Q5FJD5 (Q5FJD5_LACAC); Mar. 1, 2005; 9 pages.
UniProtKB—Q74KL4 (Q74KL4_LACJO); Jul. 5, 2004; 8 pages.
UnitProtKB—D9ZDZ1 (D9ZDZ1_9ZZZZ); Oct. 5, 2010; 7 pages.
Guo et al., "Protein tolerance to random amino acid change," PNAS, vol. 101, No. 25, pp. 9205-9210 (Jun. 2004).
Keskin et al., "A new, structurally nonredundant, diverse data set of protein-protein interfaces and its implications," Protein Science, vol. 13, pp. 1043-1055 (2004).
Klimova E.V. Advantages of using beta-galactosidase for hydrolysis of lactose and obtaining galactooligosaccharides; prospects for the use of the obtained products in industrial food technologies, Food and processing industry, Abstract journal, No. 4, 2008, p. 1269.
Ogurtsov A.N., Methods of bioinformatic analysis, Textbook, Kharkov, 2011, NTU "KhPI", pp. 4-5, 25.
Singer et al., "Genes & Genomes, A changing Perspective," University Science Books Mill Valley, CA (1998).
UniProt Accession Nos. TrEMBL, A7A6G3_BIFAD, Sep. 11, 2007, Q38UW6_LACSS, 22.11.2005, Q38UW7_LACSS, 22.11.2005, R5YYAO_9LACO, Jul. 24, 2013, FOTG79_LACAM, May 3, 2011, K2MWD3_BIFBI, Nov. 28, 2012, D4QFE8_BIFBI, Jul. 15, 2012, A0A133L394_BIFBR, Jul. 8, 2016, A0A1VSPPN6_9BIFI, Jul. 7, 2017, A0A1Q6ESN3_9BIFI, Apr. 12, 2016, A0A045FVZ6_LACDE, Mar. 16, 2017, 0A1L3JVR5_LACDL, Mar. 15, 2017, FOK2P6_LACD2, May 3, 2011 A0A0D5MI45_LACHE, May 27, 2015, A0A0D5MHU_LACHE, May 27, 2015, A0A1V8RDS6_BIFIN, Jun. 7, 2017, B3XQL8_LACRI, Sep. 23, 2008, B3XQL9_LACRI, Sep. 23, 2008, U6F4Q6_LACHE, Jan. 22, 2014, A8YWAO_LACH4, Jan. 15, 2008, LOCMG0_9LACO, Mar. 6, 2016, A0A0M410A2_STRR, Dec. 9, 2015, A0A0C0RIHO_9LACO, Nov. 11, 2015, 0A174B8K1_BIFAD, Apr. 7, 2016.
Office Action and Search Report issued on May 14, 2021 in Russian Application No. 2019134223/10.
U.S. Appl. No. 17/285,288, filed Apr. 14, 2021, Hans Raj et al.
Banerjee, Goutam et al.; "Is divalent magnesium cation the best cofactor for bacterial β- galactosidase?"; J Biosci, vol. 43, No. 5; Oct. 4, 2018; pp. 941-945.
Kuznetsova, E., "Brackets in Text of Legal Document as a Linguistic and Cognitive Phenomenon"; Institute of Humanities, Severodvinsk branch of Lomonosov Northern (Arctic) Federal University; Vestnik Moskovskogo gosudarstvennogo oblastnogo universiteta: Russian Philology, No. 3; ISSN 2072-8522; 2015; pp. 37-43.
Nguyen, Thao Thi et al.; "Effect of mutations to amino acid A301 and F361 in thermostability and catalytic activity of the β-galactosidase from *Bacillus subtilis* VTCC-DVN-12-01"; BMC Biochemistry (2016) 17:15; Jul. 2016; 11 pages.
Patent Office of the Russian Federation: Federal Institute of Industrial Property; Office Action (Enquiry); Russian Patent Application No. 2021112325/10(026315) (English translation); Jun. 19, 2023; 10 pages.
Seffernick, Jennifer et al.; "Melamine Deaminase and Atrazine Chlorohydrolase: 98 Percent Identical but Functionally Different"; Journal of Bacteriology, vol. 183, No. 8; Apr. 2001; pp. 2405-2410.
Whisstock, James C. et al.; "Prediction of protein function from protein sequence and structure"; Quarterly Review of Biophysics 36, 3; Aug. 2003; pp. 307-340.
"Beta-galactosidase [Bifidobacterium angulatum]"; NCBI Reference Sequence: WP_033508907.1; NCBI; https://www.ncbi.nlm.nih.gov/protein/WP_033508907.1?report=genbank&log$=prottop&blast_rank=1&RID=STY73TRP013; Nov. 7, 2014; 1 page.
"Beta-galactosidase [Bifidobacterium bifidum]"; NCBI Reference Sequence: ALE11829.1; NCBI; https://www.ncbi.nlm.nih.gov/protein/ALE11829.1?report=genbank&log$=prottop&blast_rank=1&RID=STXB9JWN016; Sep. 14, 2015; 2 pages.
"Beta-galactosidase [Bifidobacterium longum]"; NCBI Reference Sequence: WP_013582379.1; NCBI; https://www.ncbi.nlm.nih.gov/protein/WP_013582379.1?report=genbank&log$=prottop&blast_rank=1&RID=STXT9S92016; May 18, 2013; 1 page.
"Beta-galactosidase [Lactobacillus amylovorus]"; NCBI Reference Sequence: WP_013438360.1; NCBI; https://www.ncbi.nlm.nih.gov/protein/WP_013438360.1?report=genbank&log$=prottop&blast_rank=1&RID=STWKFN82013; May 18, 2013; 1 page.
"Beta-galactosidase [Lactobacillus helveticus]"; NCBI Reference Sequence: KRO12099.1; NCBI; https://www.ncbi.nlm.nih.gov/protein/KRO12099.1?report=genbank&log$=prottop&blast_rank=1&RID=STXF1W9301N; Nov. 6, 2015; 2 pages.
"Beta-galactosidase [Limosilactobacillus reuteri]"; NCBI Reference Sequence: WP_003666991.1; NCBI; https://www.ncbi.nlm.nih.gov/protein/WP_003666991.1?report=genbank&log$=prottop&blast_rank=1&RID=STXX2K05013; Jul. 31, 2013; 1 page.
Odamaki, Toshitaka et al.; "Comparative Genomics Revealed Genetic Diversity and Species/Strain-Level Differences in Carbohydrate Metabolism of Three Probiotic Bifidobacterial Species"; International Journal of Genomics, vol. 2015, article ID 567809; Jul. 2015; 12 pages.
UniProt—A0A174B8K1_BIFAD; Sep. 7, 2016; 6 pages.

\* cited by examiner

| G no | pH 6.7 at 4°C | pH 6,7 at 37°C | pH 6,7 at 43°C | % gal inhibition |
|---|---|---|---|---|
| 4 | 9,4 | 118,1 | 84,7 | 34 |
| 11 | 8,4 | 69,2 | 111,3 | 9 |
| 16 | 1,6 | 23,4 | 17,0 | 45 |
| 33 | 12,5 | 130,1 | 173,3 | 3 |
| 35 | 12,5 | 121,0 | 100,9 | 27 |
| 40 | 1,2 | 15,8 | 12,4 | 53 |
| 44 | 24,2 | 331,5 | 295,9 | 35 |
| 51 | 20,7 | 250,6 | 214,3 | 35 |
| 57 | 7,4 | 104,6 | 97,2 | 47 |
| 62 | 5,2 | 48,5 | 37,6 | 83 |
| 66 | 15,2 | 187,2 | 136,8 | 23 |
| 83 | 26,9 | 272,9 | 195,1 | 37 |
| 84 | 15,9 | 161,9 | 118,0 | 31 |
| 95 | 28,8 | 288,1 | 250,7 | 37 |
| 100 | 27,9 | 339,9 | 238,1 | 39 |
| 104 | 12,9 | 90,5 | 112,9 | 1 |
| 108 | 27,2 | 277,9 | 213,1 | 34 |
| 109 | 25,3 | 300,1 | 218,3 | 30 |
| 118 | 16,9 | 113,8 | 122,3 | 14 |
| 145 | 2,4 | 24,1 | 22,6 | 64 |
| 158 | 34,2 | 254,7 | 334,8 | 27 |
| 224 | 11,2 | 389,9 | 131,4 | 48 |
| 256 | 15,5 | 111,3 | 112,8 | 14 |
| 282 | 8,4 | 58,5 | 48,6 | 62 |
| 335 | 4,4 | 42,4 | 30,9 | 50 |
| 500 | 3,9 | 46,9 | 13,1 | 35 |
| 600 | 7,4 | 61,9 | 45,6 | 44 |

Figure 28

| G no | pH 5.5 at 4°C | pH 5.5 at 37°C | pH 5.5 at 43°C |
|---|---|---|---|
| 4 | 1,4 | 44,1 | 29,6 |
| 11 | 7,6 | 57,9 | 75,5 |
| 16 | 0,2 | 0,7 | 0,4 |
| 33 | 10,4 | 88,2 | 89,9 |
| 35 | 1,7 | 51,3 | 40,9 |
| 40 | 3,3 | 21,8 | 15,7 |
| 44 | 4,9 | 111,2 | 80,7 |
| 51 | 4,0 | 84,6 | 58,8 |
| 57 | 0,6 | 17,8 | 13,1 |
| 62 | 6,0 | 60,5 | 49,7 |
| 66 | 0,8 | 63,3 | 42,7 |
| 83 | 6,7 | 108,4 | 57,2 |
| 84 | 8,4 | 99,4 | 62,4 |
| 95 | 7,0 | 121,3 | 64,7 |
| 100 | 5,9 | 128,2 | 55,2 |
| 104 | 10,6 | 60,4 | 60,5 |
| 108 | 7,0 | 116,5 | 69,5 |
| 109 | 5,7 | 116,5 | 62,6 |
| 118 | 14,8 | 76,0 | 65,0 |
| 145 | 4,9 | 28,8 | 15,8 |
| 158 | 18,4 | 129,4 | 126,8 |
| 224 | 4,4 | 21,0 | 7,4 |
| 256 | 14,0 | 62,7 | 57,0 |
| 282 | 6,4 | 50,8 | 24,9 |
| 335 | 0,3 | 9,4 | 3,1 |
| 500 | 0,1 | 0,4 | 0,5 |
| 600 | 4,0 | 32,7 | 26,9 |

Figure 29

| G no | pH 4.5 at 4°C | pH 4.5 at 37°C | pH 4.5 at 43°C |
|---|---|---|---|
| 4 | 1,2 | 2,9 | 2,0 |
| 11 | 1,7 | 18,9 | 3,3 |
| 16 | 0,1 | 0 | 0 |
| 33 | 1,6 | 24,7 | 0,7 |
| 35 | 1,6 | 3,7 | 2,5 |
| 40 | 3,4 | 12,9 | 10,6 |
| 44 | 4,3 | 12,5 | 11,8 |
| 51 | 3,9 | 12,8 | 11,0 |
| 57 | 0,4 | 0,1 | -0,5 |
| 62 | 4,2 | 19,9 | 16,6 |
| 66 | 0,8 | 1,6 | 1,2 |
| 83 | 5,6 | 11,2 | 12,4 |
| 84 | 7,9 | 22,7 | 17,1 |
| 95 | 7,0 | 12,8 | 10,4 |
| 100 | 5,6 | 12,5 | 11,4 |
| 104 | 4,5 | 29,7 | 24,1 |
| 108 | 6,7 | 14,3 | 12,8 |
| 109 | 5,5 | 10,4 | 19,8 |
| 118 | 5,8 | 37,5 | 25,6 |
| 145 | 5,0 | 8,9 | 7,2 |
| 158 | 4,2 | 12,7 | 25,1 |
| 224 | 4,1 | 0,0 | 0,0 |
| 256 | 7,9 | 23,2 | 17,2 |
| 282 | 6,3 | 7,5 | 7,2 |
| 335 | 0,3 | 0 | 0,0 |
| 500 | 0,0 | 0 | 0 |
| 600 | 1,6 | 12,2 | 5,0 |

Figure 30

SEQUENCE LISTING

<160> NUMBER OF SEQ ID NOS: 41

<210> SEQ ID NO 1
<211> LENGTH: 1049
<212> TYPE: PRT
<213> ORGANISM: Bifidobacterium adolescentis

<400> SEQUENCE: 1

```
Met Ala Asp Thr Ala Glu Leu Ala Ile Val His Ala Thr Thr Ala Ser
1               5                   10                  15

Ala Ser Trp Leu Thr Asp Pro Thr Val Phe Ala Ala Asn Arg Lys Pro
            20                  25                  30

Ala His Ser Ser His Arg Tyr Val Ile Gly Glu Thr Ser Glu Pro Lys
        35                  40                  45

Gln Ser Leu Asp Gly Glu Trp Lys Val Arg Ile Glu Gln Ala Arg Asn
    50                  55                  60

Val Asp Val Glu Ser Ala Pro Phe Ala Ala Val Asp Phe Glu Asp Gly
65                  70                  75                  80

Asp Phe Gly Ala Ile Glu Val Pro Gly His Leu Gln Met Ala Gly Tyr
                85                  90                  95

Leu Lys Asn Lys Tyr Val Asn Ile Gln Tyr Pro Trp Asp Gly His Glu
            100                 105                 110

Asp Pro Gln Ala Pro Asn Ile Pro Glu Asn Asn His Val Ala Ile Tyr
        115                 120                 125

Arg Arg Arg Phe Ala Leu Asp Ala Gln Leu Ala Arg Thr Leu Glu Asn
130                 135                 140

Asp Gly Thr Val Ser Leu Thr Phe His Gly Ala Ala Thr Ala Ile Tyr
145                 150                 155                 160

Val Trp Leu Asp Gly Thr Phe Val Gly Tyr Gly Glu Asp Gly Phe Thr
                165                 170                 175

Pro Ser Glu Phe Asp Val Thr Glu Ala Leu Arg Asn Gly Asn Gly Asn
            180                 185                 190

Ala Ala Asp Ser Pro Glu Ala Glu His Thr Leu Thr Val Ala Cys Tyr
        195                 200                 205

Glu Tyr Ser Ser Ala Ser Trp Leu Glu Asp Gln Asp Phe Trp Arg Leu
210                 215                 220

His Gly Leu Phe Arg Thr Val Glu Leu Ala Ala Gln Pro His Thr His
225                 230                 235                 240

Val Glu Thr Val Gln Leu Glu Ala Asp Tyr Thr Ala Ala Asp Thr Ala
                245                 250                 255

Gly Thr Ala Asp Thr Ala Glu Leu Asn Ala Ala Leu Thr Leu Arg Asn
            260                 265                 270

Ser Ala Asp Ala Met Thr Ile Glu Ser Thr Leu Arg Asp Gly Asp Gly
        275                 280                 285

Asn Val Val Trp Glu Ser Thr Gln Ala Cys Asn Gly Glu Ile Ala Leu
            290                 295                 300

Asn Ser Gly Lys Met Thr Asn Ile Ala Pro Trp Ser Ala Glu Ser Pro
305                 310                 315                 320

Thr Leu Tyr Thr Leu Thr Val Arg Val Val Gly His Asp Gly Ala Ile
                325                 330                 335

Ile Glu Thr Val Thr Gln Lys Ile Gly Phe Arg Thr Phe Arg Ile Glu
            340                 345                 350

Asn Gly Ile Met Thr Leu Asn Gly Lys Arg Ile Val Phe Lys Gly Ala
        355                 360                 365
```

-continued

```
Asp Arg His Glu Phe Asp Ala Lys Arg Gly Arg Ala Ile Thr Arg Glu
    370                 375                 380

Asp Met Leu Ser Asp Val Val Phe Cys Lys Arg His Asn Ile Asn Ala
385                 390                 395                 400

Ile Arg Thr Ser His Tyr Pro Asn Gln Glu Tyr Trp Tyr Asp Leu Cys
                405                 410                 415

Asp Glu Tyr Gly Leu Tyr Leu Ile Asp Glu Thr Asn Met Glu Thr His
                420                 425                 430

Gly Thr Trp Val Ala Asn Asn Val Glu Arg Pro Glu Asp Gly Ile Pro
            435                 440                 445

Gly Ser Arg Pro Glu Trp Glu Gly Ala Cys Val Asp Arg Ile Asn Ser
450                 455                 460

Met Met Arg Arg Asp Tyr Asn His Pro Ser Val Leu Ile Trp Ser Leu
465                 470                 475                 480

Gly Asn Glu Ser Ser Ala Gly Glu Val Phe Arg Ala Met Tyr Arg His
                485                 490                 495

Ala His Thr Ile Asp Pro Asn Arg Pro Val His Tyr Glu Gly Ser Val
            500                 505                 510

His Met Arg Glu Phe Glu Asp Val Thr Asp Ile Glu Ser Arg Met Tyr
        515                 520                 525

Ala His Ala Asp Glu Ile Glu Arg Tyr Leu Asn Asp Gly Ser Pro Ala
        530                 535                 540

His Thr Asp Gly Pro Lys Lys Pro Tyr Ile Ser Cys Glu Tyr Met His
545                 550                 555                 560

Ala Met Gly Asn Ser Cys Gly Asn Met Asp Glu Tyr Thr Ala Leu Glu
                565                 570                 575

Arg Tyr Pro Met Tyr Gln Gly Gly Phe Ile Trp Asp Phe Ile Asp Gln
            580                 585                 590

Ala Ile Glu Thr Lys Leu Pro Asp Gly Thr Thr Arg Met Cys Tyr Gly
        595                 600                 605

Gly Asp Phe Gly Asp Arg Pro Ser Asp Tyr Glu Phe Ser Gly Asp Gly
        610                 615                 620

Leu Leu Phe Ala Asp Arg Thr Pro Ser Pro Lys Ala Gln Glu Val Lys
625                 630                 635                 640

Gln Leu Tyr Ala Asn Val Lys Ile Val Val Ser Val Asp Glu Ala Arg
                645                 650                 655

Ile Thr Asn Asp Asn Leu Phe Val Ser Thr Gly Asp Tyr Arg Phe Val
            660                 665                 670

Leu Arg Ile Leu Ala Asp Gly Lys Pro Val Trp Ser Thr Thr Arg Arg
        675                 680                 685

Phe Asp Val Ala Ala Gly Glu Ser Ala Ser Phe Glu Val Asp Trp Pro
690                 695                 700

Val Asp Asp Tyr Arg Ser Asn Ala Glu Glu Leu Val Leu Glu Val Ser
705                 710                 715                 720

Gln Gln Leu Gly Asn Ala Cys Asp Trp Ala Pro Ala Gly Tyr Glu Leu
                725                 730                 735

Ala Phe Gly Gln Cys Val Val Ala Gly Ala Lys Thr Thr Ala Asp Ala
            740                 745                 750

Val Asp Ala Ala Gly Ala Pro Ala Asp Gly Thr Val Thr Leu Gly Arg
        755                 760                 765

Trp Asn Ala Gly Val Arg Gly Gln Gly Arg Glu Ala Leu Phe Ser Arg
770                 775                 780

Thr Gln Gly Gly Met Val Ser Tyr Thr Phe Gly Glu Arg Glu Phe Val
```

```
                785                 790                 795                 800

Leu Arg Arg Pro Ser Ile Thr Thr Phe Arg Pro Leu Thr Asp Asn Asp
                805                 810                 815

Arg Gly Ala Gly His Ala Phe Glu Arg Ala Ala Trp Ala Val Ala Gly
                820                 825                 830

Lys Tyr Ala Arg Cys Val Asp Cys Ala Ile Ala Asn Arg Gly Glu Asn
                835                 840                 845

Ala Val Glu Ala Thr Tyr Thr Tyr Glu Leu Ala Ile Pro Gln Arg Thr
                850                 855                 860

Lys Val Thr Val Arg Tyr Val Ala Asp Thr Ala Gly Leu Val Ser Leu
865                 870                 875                 880

Asp Val Glu Tyr Pro Gly Glu Lys Asn Gly Asp Leu Pro Thr Ile Pro
                885                 890                 895

Ala Phe Gly Ile Glu Trp Ala Leu Pro Val Glu Tyr Ala Asn Leu Arg
                900                 905                 910

Phe Tyr Gly Ala Gly Pro Glu Glu Thr Tyr Ala Asp Arg Arg His Ala
                915                 920                 925

Lys Leu Gly Val Trp Ser Thr Thr Ala Gly Asp Asp Cys Ala Pro Tyr
                930                 935                 940

Leu Leu Pro Gln Glu Thr Gly Asn His Glu Asp Val Arg Trp Ala Glu
945                 950                 955                 960

Ile Thr Asp Asp Ser Gly His Gly Val Arg Val Lys Arg Gly Ala Gly
                965                 970                 975

Ala Lys Pro Phe Ala Met Ser Leu Leu Pro Tyr Ser Ser Thr Met Leu
                980                 985                 990

Glu Glu Ala Leu His Gln Asp Glu Leu Pro Lys Pro Arg His Met Phe
                995                 1000                1005

Leu Arg Leu Leu Ala Ala Gln Met Gly Val Gly Gly Asp Asp Ser
        1010                1015                1020

Trp Met Ser Pro Val His Glu Gln Tyr Gln Leu Pro Ala Asp Gln
        1025                1030                1035

Pro Leu Ser Leu Asn Val Gln Leu Lys Leu Phe
        1040                1045

<210> SEQ ID NO 2
<211> LENGTH: 625
<212> TYPE: PRT
<213> ORGANISM: Lactobacillus sakei

<400> SEQUENCE: 2

Met Gln Pro Asn Ile Gln Trp Leu Asp Thr Pro Ala Val Phe Arg Val
1               5                   10                  15

Gly Gln Leu Pro Ala His Ser Asp His Arg Tyr Tyr Ala Thr Leu Ala
                20                  25                  30

Glu Met Ala Gln Gln Gln Ser Ser Phe Glu Gln Ser Leu Asn Gly Thr
                35                  40                  45

Trp Gln Phe His Tyr Ser Val Asn Ala Ala Ser Arg Pro Lys Ser Phe
                50                  55                  60

Tyr Glu Leu Ala Phe Asp Ala Gln Asp Phe Glu Pro Ile Thr Val Pro
65                  70                  75                  80

Gln His Ile Glu Leu Ala Gly Tyr Glu Gln Leu His Tyr Ile Asn Thr
                85                  90                  95

Met Tyr Pro Trp Glu Gly His Glu Tyr Arg Arg Pro Ala Phe Ser Thr
                100                 105                 110
```

-continued

```
Ser Asp Asp Lys Gln His Leu Gly Met Phe Ser Glu Ala Asp Tyr Asn
            115                 120                 125

Pro Val Gly Ser Tyr Leu His His Phe Asp Leu Thr Pro Ala Leu Arg
130                 135                 140

Asn Gln Arg Val Ile Ile Arg Phe Glu Gly Val Glu Gln Ala Met Tyr
145                 150                 155                 160

Val Trp Leu Asn Gly Gln Phe Ile Gly Tyr Ala Glu Asp Ser Phe Thr
                165                 170                 175

Pro Ser Glu Phe Asp Leu Thr Pro Tyr Leu Lys Glu Thr Asp Asn Cys
            180                 185                 190

Leu Ala Val Glu Val His Lys Arg Ser Ser Ala Ala Phe Ile Glu Asp
            195                 200                 205

Gln Asp Phe Phe Arg Phe Phe Gly Ile Phe Arg Asp Val Lys Leu Leu
210                 215                 220

Ala Lys Pro Arg Thr His Leu Glu Asp Leu Trp Val Ile Pro Glu Tyr
225                 230                 235                 240

Asp Val Val Gln Gln Thr Gly Gln Val Lys Leu Arg Leu Gln Phe Ser
                245                 250                 255

Gly Asp Glu Asn Arg Val His Leu Arg Ile Arg Asp Gln His Gln Ile
            260                 265                 270

Ile Leu Thr Ala Asp Leu Thr Ser Ala Ala Gln Val Asn Gly Leu Tyr
            275                 280                 285

Lys Met Pro Glu Leu Val Gln Ala Trp Ser Asn Gln Thr Pro Asn Leu
            290                 295                 300

Tyr Thr Leu Glu Leu Glu Val Val Asp Gln Ala Gly Glu Thr Ile Glu
305                 310                 315                 320

Ile Ser Gln Gln Pro Phe Gly Phe Arg Lys Ile Glu Ile Lys Asp Lys
                325                 330                 335

Val Met Leu Leu Asn Gly Lys Arg Leu Val Ile Asn Gly Val Asn Arg
            340                 345                 350

His Glu Trp His Pro Glu Thr Gly Arg Thr Ile Thr Ala Glu Asp Glu
            355                 360                 365

Ala Trp Asp Ile Ala Cys Met Gln Arg Asn His Ile Asn Ala Val Arg
370                 375                 380

Thr Ser His Tyr Pro Asp Arg Leu Ser Phe Tyr Asn Gly Cys Asp Gln
385                 390                 395                 400

Ala Gly Ile Tyr Met Met Ala Glu Thr Asn Leu Glu Ser His Gly Ser
                405                 410                 415

Trp Gln Lys Met Gly Ala Val Glu Pro Ser Trp Asn Val Pro Gly Ser
            420                 425                 430

Tyr Asp Glu Trp Glu Ala Ala Thr Leu Asp Arg Ala Arg Thr Asn Phe
            435                 440                 445

Glu Thr Phe Lys Asn His Val Ser Ile Leu Phe Trp Ser Leu Gly Asn
450                 455                 460

Glu Ser Tyr Ala Gly Ser Val Leu Glu Lys Met Asn Ala Tyr Tyr Lys
465                 470                 475                 480

Gln Gln Asp Pro Thr Arg Leu Val His Tyr Glu Gly Val Phe Arg Ala
                485                 490                 495

Pro Glu Tyr Lys Ala Thr Ile Ser Asp Val Glu Ser Arg Met Tyr Ala
            500                 505                 510

Thr Pro Ala Glu Ile Lys Ala Tyr Leu Asp Asn Ala Pro Gln Lys Pro
515                 520                 525

Phe Ile Leu Cys Glu Tyr Met His Asp Met Gly Asn Ser Leu Gly Gly
```

Met Gln Ser Tyr Ile Asp Leu Leu Ser Gln Tyr Asp Met Tyr Gln Gly
545                 550                 555                 560

Gly Phe Ile Trp Asp Phe Ile Asp Gln Ala Leu Leu Val Thr Asp Pro
                565                 570                 575

Val Thr Gly Gln Arg Glu Leu Arg Tyr Gly Gly Asp Phe Asp Asp Arg
            580                 585                 590

Pro Ser Asp Tyr Glu Phe Ser Gly Asp Gly Leu Val Phe Ala Thr Arg
        595                 600                 605

Asp Glu Lys Pro Ala Met Gln Glu Val Arg Tyr Tyr Tyr Gly Glu His
    610                 615                 620

Lys
625

<210> SEQ ID NO 3
<211> LENGTH: 330
<212> TYPE: PRT
<213> ORGANISM: Lactobacillus sakei

<400> SEQUENCE: 3

Met Lys Asn Gln Gln Cys Arg Arg Leu Asp Thr Ile Met Ala Asn Thr
1               5                   10                  15

Asn Lys Arg Leu Ala Val Ile Phe Gly Asp Val Thr Leu Gly Leu Lys
            20                  25                  30

Gly Pro Asp Phe His Tyr Leu Phe Ser Tyr Gln Thr Gly Gly Pro Glu
        35                  40                  45

Ser Leu Arg Ile Gln Gly Lys Glu Trp Leu Tyr Arg Ser Pro Lys Pro
    50                  55                  60

Thr Phe Trp Arg Ala Thr Thr Asp Asn Asp Arg Gly Asn Gln Phe Pro
65                  70                  75                  80

Leu Lys Ser Gly Met Trp Leu Ala Ala Asp Gln Phe Ile Ala Cys Gln
                85                  90                  95

Ser Ile Thr Val Ala Ile Asp Gly Gln Thr Ile Pro Leu Pro Ile Ala
            100                 105                 110

Pro Glu Asn Asn Arg Tyr Ser Gly Gln Glu Thr Ala Gln Glu Val Thr
        115                 120                 125

Val Thr Tyr Thr Tyr Gln Thr Ile Thr Thr Pro Gln Thr Thr Val Glu
    130                 135                 140

Val Ser Tyr Thr Ile Gln Ala Ser Gly Lys Ile Arg Val Ala Val Thr
145                 150                 155                 160

Tyr His Gly Gln Ala Gly Leu Pro Ser Leu Pro Val Phe Gly Leu Arg
                165                 170                 175

Phe Val Met Pro Thr Pro Ala Thr Arg Phe Ile Tyr Gln Gly Leu Ser
            180                 185                 190

Gly Glu Thr Tyr Pro Asp Arg Met Ala Gly Gly Met Ala Gly Glu Tyr
        195                 200                 205

Glu Val Thr Gly Leu Pro Val Thr Pro Tyr Leu Val Pro Gln Asp Cys
    210                 215                 220

Gly Val His Met Ala Thr Asp Trp Val Thr Ile Tyr Arg Gln Ala Val
225                 230                 235                 240

Leu Asp Asn Arg Leu Arg Glu Pro Val Glu Thr Gly Leu Lys Phe Lys
                245                 250                 255

Met Val Asp Gln Pro Phe Ala Phe Ser Cys Leu Pro Tyr Thr Ala Glu
            260                 265                 270

```
Glu Leu Glu Asn Ala Thr His His Ser Glu Leu Pro Ala Pro His Arg
            275                 280                 285

Thr Val Leu Ser Leu Leu Gly Ala Val Arg Gly Val Gly Gly Ile Asp
            290                 295                 300

Ser Trp Gly Ser Asp Val Glu Ala Ala Tyr Gln Ile Asp Ala Thr Gln
305                 310                 315                 320

Asp His His Leu Glu Phe Glu Ile Ser Phe
            325                 330

<210> SEQ ID NO 4
<211> LENGTH: 1049
<212> TYPE: PRT
<213> ORGANISM: Bifidobacterium adolescentis

<400> SEQUENCE: 4

Met Ala Asp Thr Ala Glu Leu Ala Ile Val His Ala Thr Thr Ala Ser
1               5                   10                  15

Ala Ser Trp Leu Thr Asp Pro Thr Val Phe Ala Asn Arg Lys Pro
            20                  25                  30

Ala His Ser Ser His Arg Tyr Val Ile Gly Glu Thr Ser Glu Pro Lys
        35                  40                  45

Gln Ser Leu Asp Gly Glu Trp Lys Val Arg Ile Glu Gln Ala Arg Asn
    50                  55                  60

Val Asp Val Glu Ser Ala Pro Phe Ala Ala Val Asp Phe Glu Asp Gly
65                  70                  75                  80

Asp Phe Gly Ala Ile Glu Val Pro Gly His Leu Gln Met Ala Gly Tyr
                85                  90                  95

Leu Lys Asn Lys Tyr Val Asn Ile Gln Tyr Pro Trp Asp Gly His Glu
            100                 105                 110

Asp Pro Gln Ala Pro Asn Ile Pro Glu Asn Asn His Val Ala Ile Tyr
        115                 120                 125

Arg Arg Arg Phe Ala Leu Asp Ala Gln Leu Ala Arg Thr Leu Glu Asn
    130                 135                 140

Asp Gly Thr Val Ser Leu Thr Phe His Gly Ala Ala Thr Ala Ile Tyr
145                 150                 155                 160

Val Trp Leu Asp Gly Thr Phe Val Gly Tyr Gly Glu Asp Gly Phe Thr
                165                 170                 175

Pro Ser Glu Phe Asp Val Thr Glu Ala Leu Arg Asn Gly Asn Gly Asn
            180                 185                 190

Ala Ala Asp Ser Pro Glu Ala Glu His Thr Leu Thr Val Ala Cys Tyr
        195                 200                 205

Glu Tyr Ser Ser Ala Ser Trp Leu Glu Asp Gln Asp Phe Trp Arg Leu
    210                 215                 220

His Gly Leu Phe Arg Thr Val Glu Leu Ala Ala Gln Pro His Thr His
225                 230                 235                 240

Val Glu Thr Val Gln Leu Glu Ala Asp Tyr Thr Ala Ala Asp Thr Ala
                245                 250                 255

Gly Thr Ala Asp Thr Ala Glu Leu Asn Ala Ala Leu Thr Leu Arg Asn
            260                 265                 270

Pro Ala Asp Ala Met Thr Ile Glu Ser Thr Leu Arg Asp Gly Asp Gly
        275                 280                 285

Asn Val Val Trp Glu Ser Thr Gln Ala Cys Asn Gly Glu Ile Ala Leu
    290                 295                 300

Asn Ser Gly Lys Met Thr Asn Ile Ala Pro Trp Ser Ala Glu Ser Pro
305                 310                 315                 320
```

Thr Leu Tyr Thr Leu Thr Val Arg Val Val Gly His Asp Gly Ala Ile
            325                 330                 335

Ile Glu Thr Val Thr Gln Lys Ile Gly Phe Arg Thr Phe Arg Ile Glu
            340                 345                 350

Asn Gly Ile Met Thr Leu Asn Gly Lys Arg Ile Val Phe Lys Gly Ala
            355                 360                 365

Asp Arg His Glu Phe Asp Ala Lys Arg Gly Arg Ala Ile Thr Arg Glu
            370                 375                 380

Asp Met Leu Ser Asp Val Val Phe Cys Lys Arg His Asn Ile Asn Ala
385                 390                 395                 400

Ile Arg Thr Ser His Tyr Pro Asn Gln Glu Tyr Trp Tyr Asp Leu Cys
            405                 410                 415

Asp Glu Tyr Gly Leu Tyr Leu Ile Asp Glu Thr Asn Met Glu Thr His
            420                 425                 430

Gly Thr Trp Val Ala Asn Asn Val Glu Arg Pro Glu Asp Gly Ile Pro
            435                 440                 445

Gly Ser Arg Pro Glu Trp Glu Gly Ala Cys Val Asp Arg Ile Asn Ser
            450                 455                 460

Met Met Arg Arg Asp Tyr Asn His Pro Ser Val Leu Ile Trp Ser Leu
465                 470                 475                 480

Gly Asn Glu Ser Ser Ala Gly Glu Val Phe Arg Ala Met Tyr Arg His
            485                 490                 495

Ala His Thr Ile Asp Pro Asn Arg Pro Val His Tyr Glu Gly Ser Val
            500                 505                 510

His Met Arg Glu Phe Glu Asp Val Thr Asp Ile Glu Ser Arg Met Tyr
            515                 520                 525

Ala His Ala Asp Glu Ile Glu Arg Tyr Leu Asn Asp Gly Ser Pro Ala
            530                 535                 540

His Thr Asp Gly Pro Lys Lys Pro Tyr Ile Ser Cys Glu Tyr Met His
545                 550                 555                 560

Ala Met Gly Asn Ser Cys Gly Asn Met Asp Glu Tyr Thr Ala Leu Glu
            565                 570                 575

Arg Tyr Pro Met Tyr Gln Gly Gly Phe Ile Trp Asp Phe Ile Asp Gln
            580                 585                 590

Ala Ile Glu Thr Lys Leu Pro Asp Gly Thr Thr Arg Met Cys Tyr Gly
            595                 600                 605

Gly Asp Phe Gly Asp Arg Pro Ser Asp Tyr Glu Phe Ser Gly Asp Gly
            610                 615                 620

Leu Leu Phe Ala Asp Arg Thr Pro Ser Pro Lys Ala Gln Glu Val Lys
625                 630                 635                 640

Gln Leu Tyr Ala Asn Val Lys Ile Ala Val Ser Val Asp Glu Ala Arg
            645                 650                 655

Ile Thr Asn Asp Asn Leu Phe Val Ser Thr Gly Asp Tyr Arg Phe Val
            660                 665                 670

Leu Arg Ile Leu Ala Asp Gly Lys Pro Val Trp Ser Thr Thr Arg Arg
            675                 680                 685

Phe Asp Val Ala Ala Gly Glu Ser Ala Ser Phe Glu Val Asp Trp Pro
            690                 695                 700

Val Asp Asp Tyr Arg Ser Asn Ala Glu Glu Leu Val Leu Glu Val Ser
705                 710                 715                 720

Gln Gln Leu Gly Asn Ala Cys Asp Trp Ala Pro Ala Gly Tyr Glu Leu
            725                 730                 735

```
Ala Phe Gly Gln Cys Val Ala Gly Ala Lys Thr Thr Ala Asp Ala
            740                 745                 750

Val Asp Ala Ala Gly Ala Pro Asp Gly Thr Val Thr Leu Gly Arg
            755                 760                 765

Trp Asn Ala Gly Val Arg Gly Gln Gly Arg Glu Ala Leu Phe Ser Arg
            770                 775                 780

Thr Gln Gly Gly Met Val Ser Tyr Thr Phe Gly Glu Arg Glu Phe Val
785                 790                 795                 800

Leu Arg Arg Pro Ser Ile Thr Thr Phe Arg Pro Leu Thr Asp Asn Asp
                    805                 810                 815

Arg Gly Ala Gly His Ala Phe Glu Arg Ala Ala Trp Ala Val Ala Gly
            820                 825                 830

Lys Tyr Ala Arg Cys Val Asp Cys Ala Ile Ala Asn Arg Gly Glu Asn
            835                 840                 845

Ala Val Glu Ala Thr Tyr Thr Tyr Glu Leu Ala Ile Pro Gln Arg Thr
            850                 855                 860

Lys Val Thr Val Arg Tyr Val Ala Asp Thr Ala Gly Leu Val Ser Leu
865                 870                 875                 880

Asp Val Glu Tyr Pro Gly Glu Lys Asn Gly Asp Leu Pro Thr Ile Pro
                    885                 890                 895

Ala Phe Gly Ile Glu Trp Ala Leu Pro Val Glu Tyr Ala Asn Leu Arg
            900                 905                 910

Phe Tyr Gly Ala Gly Pro Glu Thr Tyr Ala Asp Arg His Ala
            915                 920                 925

Lys Leu Gly Val Trp Ser Thr Thr Ala Gly Asp Cys Ala Pro Tyr
            930                 935                 940

Leu Leu Pro Gln Glu Thr Gly Asn His Glu Asp Val Arg Trp Ala Glu
945                 950                 955                 960

Ile Thr Asp Asp Ser Gly His Gly Val Arg Val Lys Arg Gly Ala Gly
                    965                 970                 975

Ala Lys Pro Phe Ala Met Ser Leu Leu Pro Tyr Ser Ser Thr Met Leu
            980                 985                 990

Glu Glu Ala Leu His Gln Asp Glu  Leu Pro Lys Pro Arg  His Met Phe
            995                 1000                1005

Leu Arg  Leu Leu Ala Ala Gln  Met Gly Val Gly Gly  Asp Asp Ser
    1010                1015                1020

Trp Met  Ser Pro Val His Glu  Gln Tyr Gln Leu Pro  Ala Asp Gln
    1025                1030                1035

Pro Leu  Ser Leu Asn Val Gln  Leu Lys Leu Phe
    1040                1045

<210> SEQ ID NO 5
<211> LENGTH: 626
<212> TYPE: PRT
<213> ORGANISM: Lactobacillus amylovorus

<400> SEQUENCE: 5

Met Lys Ala Asn Ile Lys Trp Leu Asp Asp Pro Glu Val Phe Arg Ile
1               5                   10                  15

Asn Gln Leu Pro Ala His Ser Asp His Pro Phe Tyr Lys Asp Tyr Arg
            20                  25                  30

Glu Trp Gln Asn His Ser Ser Ser Phe Lys Gln Ser Leu Asn Gly Ala
        35                  40                  45

Trp Gln Phe His Phe Ser Lys Asp Pro Gln Ser Arg Pro Ile Asp Phe
    50                  55                  60
```

```
Tyr Lys Arg Ser Phe Asp Ser Ser Phe Asp Thr Ile Pro Val Pro
 65                  70                  75                  80

Ser Glu Ile Glu Leu Asn Gly Tyr Ala Gln Asn Gln Tyr Thr Asn Ile
                 85                  90                  95

Leu Tyr Pro Trp Glu Ser Lys Ile Tyr Arg Lys Pro Ala Tyr Thr Leu
            100                 105                 110

Gly Arg Gly Ile Lys Asp Gly Asp Phe Ser Gln Gly Lys Asp Asn Thr
            115                 120                 125

Val Gly Ser Tyr Leu Lys His Phe Asp Leu Asn Pro Ala Leu Ala Gly
            130                 135                 140

His Asp Ile His Ile Gln Phe Glu Gly Val Glu Arg Ala Met Tyr Val
145                 150                 155                 160

Tyr Leu Asn Gly His Phe Ile Gly Tyr Ala Glu Asp Ser Phe Thr Pro
                165                 170                 175

Ser Glu Phe Asp Leu Thr Pro Tyr Ile Gln Ala Lys Asp Asn Ile Leu
            180                 185                 190

Ala Val Glu Val Phe Lys His Ser Thr Ala Ser Trp Leu Glu Asp Gln
            195                 200                 205

Asp Met Phe Arg Phe Ser Gly Ile Phe Arg Ser Val Glu Leu Leu Ala
210                 215                 220

Leu Pro Arg Thr His Leu Met Asp Leu Asp Ile Lys Pro Thr Val Val
225                 230                 235                 240

Asn Asp Tyr His Asp Gly Val Phe Asn Ala Lys Leu His Phe Met Gly
                245                 250                 255

Lys Thr Ser Gly Asn Val His Val Leu Ile Glu Asp Ile Asp Gly Lys
            260                 265                 270

Thr Leu Leu Asn Lys Lys Leu Pro Leu Lys Ser Thr Val Glu Ile Glu
            275                 280                 285

Asn Glu Thr Phe Ala Asn Val His Leu Trp Asp Asn His Asp Pro Tyr
290                 295                 300

Leu Tyr Gln Leu Ile Ile Glu Val His Asp Gln Asp Gly Lys Leu Val
305                 310                 315                 320

Glu Leu Ile Pro Tyr Gln Phe Gly Phe Arg Lys Ile Glu Ile Thr Lys
                325                 330                 335

Asp His Val Val Leu Leu Asn Gly Lys Arg Leu Ile Ile Asn Gly Val
            340                 345                 350

Asn Arg His Glu Trp Asp Ala Lys Arg Gly Arg Ser Ile Thr Leu Ala
            355                 360                 365

Asp Met Lys Gln Asp Ile Ala Thr Phe Lys His Asn Asn Ile Asn Ala
            370                 375                 380

Val Arg Thr Cys His Tyr Pro Asn Gln Ile Pro Trp Tyr Tyr Leu Cys
385                 390                 395                 400

Asp Gln Asn Gly Ile Tyr Met Met Ala Glu Asn Asn Leu Glu Ser His
                405                 410                 415

Gly Thr Trp Gln Lys Leu Gly Gln Val Glu Ala Thr Ser Asn Val Pro
            420                 425                 430

Gly Ser Ile Pro Glu Trp Arg Glu Val Val Asp Arg Ala Arg Ser
            435                 440                 445

Asn Tyr Glu Thr Phe Lys Asn His Thr Ala Ile Leu Phe Trp Ser Leu
            450                 455                 460

Gly Asn Glu Ser Tyr Ala Gly Ser Asn Ile Ala Ala Met Asn Lys Leu
465                 470                 475                 480
```

```
Tyr Lys Asp His Asp Ser Ser Arg Leu Thr His Tyr Glu Gly Val Phe
                485                 490                 495
His Ala Pro Glu Phe Lys Lys Glu Ile Ser Asp Leu Gly Ser Cys Met
            500                 505                 510
Tyr Leu Pro Pro Lys Glu Ala Glu Glu Tyr Leu Gln Asn Pro Lys Lys
            515                 520                 525
Pro Leu Val Glu Cys Glu Tyr Met His Asp Met Gly Thr Pro Asp Gly
            530                 535                 540
Gly Met Gly Ser Tyr Ile Lys Leu Ile Asp Lys Tyr Pro Gln Tyr Met
545                 550                 555                 560
Gly Gly Phe Ile Trp Asp Phe Ile Asp Gln Ala Leu Leu Val His Asp
                565                 570                 575
Pro Val Ser Gly Gln Asp Val Leu Arg Tyr Gly Gly Asp Phe Asp Asp
            580                 585                 590
Arg His Ser Asp Tyr Glu Phe Ser Gly Asp Gly Leu Met Phe Ala Asp
            595                 600                 605
Arg Thr Pro Lys Pro Ala Met Gln Glu Val Arg Tyr Tyr Tyr Gly Leu
            610                 615                 620
His Lys
625

<210> SEQ ID NO 6
<211> LENGTH: 316
<212> TYPE: PRT
<213> ORGANISM: Lactobacillus amylovorus

<400> SEQUENCE: 6

Met Ala Tyr Thr Asn Asn Leu His Val Val Tyr Gly Glu Ala Ser Leu
1               5                   10                  15
Gly Val Asn Gly Gln Asp Phe Ala Tyr Leu Phe Ser Tyr Glu Arg Gly
                20                  25                  30
Gly Leu Glu Ser Leu Lys Ile Lys Asp Lys Glu Trp Leu Tyr Arg Thr
            35                  40                  45
Pro Thr Pro Thr Phe Trp Arg Ala Thr Thr Asp Asn Asp Arg Gly Ser
        50                  55                  60
Gly Phe Asn Gln Lys Ala Ala Gln Trp Leu Gly Ala Asp Met Phe Thr
65                  70                  75                  80
Lys Cys Val Gly Ile His Val Gln Val Asp Asp His Arg Phe Asp Glu
                85                  90                  95
Leu Pro Val Ala Pro Ile Asn Asn Gln Phe Ser Asn Gln Glu Phe Ala
            100                 105                 110
His Glu Val Lys Val Ala Phe Asp Tyr Glu Thr Leu Thr Thr Pro Ala
            115                 120                 125
Thr Lys Val Lys Ile Ile Tyr Asn Ile Asn Asp Phe Gly His Met Thr
        130                 135                 140
Ile Thr Met His Tyr Phe Gly Lys Lys Gly Leu Pro Pro Leu Pro Val
145                 150                 155                 160
Ile Gly Met Arg Phe Ile Met Pro Thr Lys Ala Lys Ser Phe Asp Tyr
                165                 170                 175
Thr Gly Leu Ser Gly Glu Thr Tyr Pro Asp Arg Met Ala Gly Ala Glu
            180                 185                 190
Arg Gly Thr Phe His Ile Asp Gly Leu Pro Val Thr Lys Tyr Leu Val
            195                 200                 205
Pro Gln Glu Asn Gly Met His Met Gln Thr Asn Glu Leu Val Ile Thr
        210                 215                 220
```

```
Arg Asn Ser Thr Gln Asn Asn Ala Asp Lys Asp Gly Asp Phe Ser Leu
225                 230                 235                 240

Lys Ile Thr Gln Thr Lys Gln Pro Phe Asn Phe Ser Leu Leu Pro Tyr
                245                 250                 255

Thr Ala Glu Glu Leu Glu Asn Ala Thr His Ile Glu Glu Leu Pro Leu
            260                 265                 270

Ala Arg Arg Ser Val Leu Val Ile Ala Gly Ala Val Arg Gly Val Gly
        275                 280                 285

Gly Ile Asp Ser Trp Gly Ser Asp Val Glu Glu Gln Tyr His Ile Asp
    290                 295                 300

Pro Glu Gln Asp His Glu Phe Ser Phe Thr Leu Asn
305                 310                 315

<210> SEQ ID NO 7
<211> LENGTH: 1052
<212> TYPE: PRT
<213> ORGANISM: Bifidobacterium bifidum

<400> SEQUENCE: 7

Met Asn Thr Thr Asp Asp Gln Arg Lys Asn Gly Asp Pro Ile Val Ser
1               5                   10                  15

Pro Ser Ile Pro Thr Thr Ala Trp Leu Ala Asp Pro Arg Val Tyr Ala
                20                  25                  30

Val His Arg Leu Asp Ala His Ser Asp His Ala Cys Trp Ser Arg Ser
            35                  40                  45

Pro Val Asp Gly Glu Ser Thr Asp Leu Arg Gln Ser Leu Asp Gly Glu
        50                  55                  60

Trp Arg Val Arg Val Glu Thr Ala Pro Thr Gly Arg Phe Pro Asp Gly
65                  70                  75                  80

Thr Ser Asp Gly Pro Asp Trp Ile Ser Asp Val Ser Pro Leu Phe Ala
                85                  90                  95

Ala Pro Gly Phe Asp Asp Ser Ser Phe Ser Arg Val Gln Val Pro Ser
            100                 105                 110

His Leu Glu Thr Ala Gly Leu Leu Ala Pro Gln Tyr Val Asn Val Gln
        115                 120                 125

Tyr Pro Trp Asp Gly His Glu Asp Pro Lys Ala Pro Ala Ile Pro Glu
    130                 135                 140

His Gly His Val Ala Val Tyr Arg Arg Glu Phe Asp Ala Asp Gly Glu
145                 150                 155                 160

Val Ala Gln Ala Val Arg Glu Gly Arg Pro Val Thr Leu Thr Phe Gln
                165                 170                 175

Gly Ala Ala Thr Ala Ile Tyr Val Trp Leu Asn Gly Ser Phe Ile Gly
            180                 185                 190

Tyr Ala Glu Asp Ser Phe Thr Pro Ser Glu Phe Asp Val Thr Asp Ala
        195                 200                 205

Ile Lys Val Asp Gly Asn Val Leu Ala Val Ala Cys Tyr Glu Tyr Ser
    210                 215                 220

Ser Ala Ser Trp Leu Glu Asp Gln Asp Phe Trp Arg Leu His Gly Leu
225                 230                 235                 240

Phe Arg Ser Val Glu Leu Asn Ala Arg Pro Ala Ala His Val Ala Asp
                245                 250                 255

Leu His Ala Asp Ala Asp Trp Asp Leu Ala Thr Ser Arg Gly Ser Leu
            260                 265                 270

Ser Leu Asp Val Leu Ile Asp Gly Ala Ala Asn Ala Ala Thr Ala Asp
```

```
                275                 280                 285
Phe Ala Leu Arg Asp Lys Asn Gly Thr Ile Val Trp Arg Thr Ala Thr
290                 295                 300
Lys Ala Asp Gly Thr Leu His Ala Glu Ala Glu Ile Asp Asp Ala Ala
305                 310                 315                 320
Pro Trp Ser Ala Glu Arg Pro Asp Leu Tyr Glu Leu Ser Val Thr Leu
                325                 330                 335
Leu Asp Ala Asp Gly Lys Val Leu Glu Thr Ala Arg Thr Arg Ile Gly
                340                 345                 350
Phe Arg His Val Ala Ile Glu Asp Gly Ile Leu Lys Leu Asn Gly Lys
                355                 360                 365
Arg Leu Val Phe Arg Gly Val Asn Arg His Glu Phe Asp Cys Arg Arg
370                 375                 380
Gly Arg Ala Ile Thr Glu Glu Asp Met Leu Trp Asp Ile Arg Phe Met
385                 390                 395                 400
Lys Arg His Asn Ile Asn Ala Val Arg Thr Ser His Tyr Pro Asn Gln
                405                 410                 415
Ser Arg Trp Tyr Glu Leu Cys Asp Glu Tyr Gly Ile Tyr Leu Ile Asp
                420                 425                 430
Glu Thr Asn Leu Glu Thr His Gly Ser Trp Asn Ser Pro Gly Asp Ile
                435                 440                 445
Pro Val Gly Thr Ser Val Pro Gly Asp Asp Glu Ala Trp Leu Gly Ala
450                 455                 460
Cys Ile Asp Arg Leu Asp Ser Met Ile Leu Arg Asp Arg Asn His Pro
465                 470                 475                 480
Ser Val Leu Val Trp Ser Leu Gly Asn Glu Ser Tyr Ala Gly Glu Val
                485                 490                 495
Leu Lys Ala Met Ser Ala His Ala His Gln Leu Asp Pro Gly Arg Pro
                500                 505                 510
Val His Tyr Glu Gly Val Asn Trp Asn His Ala Tyr Asp Gly Ile Ser
                515                 520                 525
Asp Phe Glu Ser Arg Met Tyr Ala Lys Pro Ala Glu Ile Gln Asp Trp
530                 535                 540
Leu Glu His Gly Asp Glu Arg Gly Glu Ala Ser Lys Pro Phe Val Ser
545                 550                 555                 560
Cys Glu Tyr Met His Ala Met Gly Asn Ser Cys Gly Gly Leu Ser Glu
                565                 570                 575
Phe Ile Asp Leu Glu Arg Tyr Glu Arg Tyr Ser Gly Gly Phe Ile Trp
                580                 585                 590
Asp Tyr Ile Asp Gln Gly Leu Val Gln Arg Leu Pro Asp Gly Ser Glu
                595                 600                 605
Arg Leu Ser Val Gly Gly Glu Trp Gly Asp Arg Pro Thr Asp Tyr Glu
                610                 615                 620
Phe Val Gly Asn Gly Ile Val Phe Ala Asp Arg Thr Pro Ser Pro Lys
625                 630                 635                 640
Ala Gln Glu Val Lys Gln Leu Tyr Ser Pro Val Lys Leu Ala Pro Asp
                645                 650                 655
Gly His Gly Val Thr Ile Glu Asn Arg Asn Leu Phe Ala Gly Thr Asp
                660                 665                 670
Gly Tyr Val Phe Ala Ala Arg Leu Leu Glu Asp Gly His Glu Ile Trp
                675                 680                 685
His Ala Asp Tyr Arg Phe Asp Val Ala Ala Gly Asp Thr Gln His His
690                 695                 700
```

Asp Ile Ala Phe Pro Asp Ile Asp Ala Asp Gly Asp Thr Arg Glu Val
705                 710                 715                 720

Thr Tyr Glu Val Asp Leu Leu Ala Glu Ala Thr Ala Trp Ala Pro
            725                 730                 735

Ala Gly Tyr Glu Leu Ala Phe Gly Gln Leu Thr Gly Thr Leu Asn Pro
            740                 745                 750

Glu Gln Asp Ile Thr Glu Thr Ser His Asp Asp Gly Arg Ala Thr
            755                 760                 765

Arg Thr Leu Ser Arg Trp Asn Ala Gly Ile Arg Arg Asp Asp Glu Glu
770                 775                 780

Ile Leu Leu Ser Arg Thr Gln Gly Gly Ile Val Ser Trp Lys Arg Asp
785                 790                 795                 800

Asp Arg Glu Met Val Ile Arg Arg Pro Glu Leu Val Thr Phe Arg Pro
                805                 810                 815

Leu Thr Asp Asn Asp Arg Gly Asn His Ser Gly Phe Asp Arg Ala Ala
                820                 825                 830

Trp Phe Ala Ala Gly Arg Tyr Ala Ile Val Thr Glu Thr Lys Ile His
                835                 840                 845

Glu Ser Asp Asp Gly Leu Val Ala Glu Tyr Gln Tyr Glu Leu Ala Asp
850                 855                 860

Pro Asn His Thr Pro Val Ser Val Thr Tyr His Val Asn Ser Asp Met
865                 870                 875                 880

Arg Met Gln Leu Thr Val Glu Tyr Pro Gly Asn Ala Thr Asp Met Ala
                885                 890                 895

Ser Leu Pro Ala Phe Gly Ile Glu Trp Glu Leu Pro Gly Glu Tyr Asp
                900                 905                 910

Arg Leu Arg Tyr Tyr Gly Pro Gly Pro Glu Glu Thr Tyr Arg Asp Arg
                915                 920                 925

Lys Gln Gly Gly Lys Leu Gly Ile Trp Asp Ala Thr Ala Lys Ala Ser
930                 935                 940

Met Ala Pro Tyr Leu Met Val Gln Glu Thr Gly Ser His Glu Asp Val
945                 950                 955                 960

Arg Trp Leu Glu Ala Thr Asp Ile Gln Gly His Gly Leu Arg Val Thr
                965                 970                 975

Gln Arg Gly Asp Arg His Phe Thr Ala Ser Leu Leu Pro Trp Asn Thr
                980                 985                 990

Tyr Thr Ile Glu Ala Ala Arg Arg His Glu Asp Leu Pro Lys Pro Arg
                995                 1000                1005

His Asn Tyr Leu Arg Leu Leu Ala Ala Gln Met Gly Val Gly Gly
        1010                1015                1020

Asp Asp Ser Trp Gly Ala Pro Val His Thr Ala Tyr Gln Leu Pro
        1025                1030                1035

Ala Gly Arg Pro Leu Thr Leu Asp Val Asn Leu Glu Leu Ile
        1040                1045                1050

<210> SEQ ID NO 8
<211> LENGTH: 1052
<212> TYPE: PRT
<213> ORGANISM: Bifidobacterium bifidum

<400> SEQUENCE: 8

Met Asn Thr Thr Asp Asp Gln Arg Lys Asn Gly Asp Pro Ile Val Ser
1               5                   10                  15

Pro Ser Ile Pro Thr Thr Ala Trp Leu Ala Asp Pro Arg Val Tyr Ala

```
            20                  25                  30
Val His Arg Leu Asp Ala His Ser Asp His Ala Cys Trp Ser Arg Ser
             35                  40                  45

Pro Val Asp Gly Glu Ser Thr Asp Leu Arg Gln Ser Leu Asp Gly Glu
 50                  55                  60

Trp Arg Val Arg Val Glu Thr Ala Pro Thr Gly Arg Phe Pro Asp Gly
 65                  70                  75                  80

Thr Ser Asp Gly Pro Asp Trp Ile Ser Asp Val Ser Pro Leu Phe Ala
                 85                  90                  95

Ala Pro Gly Phe Asp Asp Ser Ser Phe Ser Arg Val Gln Val Pro Ser
                100                 105                 110

His Leu Glu Thr Ala Gly Leu Leu Ala Pro Gln Tyr Val Asn Val Gln
                115                 120                 125

Tyr Pro Trp Asp Gly His Glu Asp Pro Lys Ala Pro Ala Ile Pro Glu
                130                 135                 140

His Gly His Val Ala Val Tyr Arg Arg Glu Phe Asp Ala Asp Gly Glu
145                 150                 155                 160

Val Ala Gln Ala Val Arg Glu Gly Arg Pro Val Thr Leu Thr Phe Gln
                165                 170                 175

Gly Ala Ala Thr Ala Ile Tyr Val Trp Leu Asn Gly Ser Phe Ile Gly
                180                 185                 190

Tyr Ala Glu Asp Ser Phe Thr Pro Ser Glu Phe Asp Val Thr Asp Ala
                195                 200                 205

Ile Lys Val Asp Gly Asn Val Leu Ala Val Ala Cys Tyr Glu Tyr Ser
                210                 215                 220

Ser Ala Ser Trp Leu Glu Asp Gln Asp Phe Trp Arg Leu His Gly Leu
225                 230                 235                 240

Phe Arg Ser Val Glu Leu Asn Ala Arg Pro Ala Ala His Val Ala Asp
                245                 250                 255

Leu His Ala Asp Ala Asp Trp Asp Leu Ala Thr Ser Arg Gly Ser Leu
                260                 265                 270

Ser Leu Asp Val Leu Ile Asp Gly Ala Ala Asn Ala Ala Thr Ala Asp
                275                 280                 285

Phe Ala Leu Trp Asp Lys Asn Gly Thr Ile Val Trp His Ile Val Thr
                290                 295                 300

Lys Ala Asp Gly Thr Leu His Ala Glu Ala Glu Ile Asp Asp Ala Ala
305                 310                 315                 320

Pro Trp Ser Ala Glu Arg Pro Asp Leu Tyr Glu Leu Ser Val Thr Leu
                325                 330                 335

Leu Asp Ala Asp Gly Lys Val Leu Glu Thr Ala Arg Thr Arg Ile Gly
                340                 345                 350

Phe Arg His Val Ala Ile Glu Asp Gly Ile Leu Lys Leu Asn Gly Lys
                355                 360                 365

Arg Leu Val Phe Arg Gly Val Asn Arg His Glu Phe Asp Cys Arg Arg
                370                 375                 380

Gly Arg Ala Ile Thr Glu Glu Asp Met Leu Trp Asp Ile Arg Phe Met
385                 390                 395                 400

Lys Arg His Asn Ile Asn Ala Val Arg Thr Ser His Tyr Pro Asn Gln
                405                 410                 415

Ser Arg Trp Tyr Glu Leu Cys Asp Glu Tyr Gly Ile Tyr Leu Ile Asp
                420                 425                 430

Glu Thr Asn Leu Glu Thr His Gly Ser Trp Asn Ser Pro Gly Asp Ile
                435                 440                 445
```

```
Pro Val Gly Thr Ser Val Pro Gly Asp Asp Glu Ala Trp Leu Gly Ala
    450                 455                 460

Cys Ile Asp Arg Leu Asp Ser Met Ile Leu Arg Asp Arg Asn His Pro
465                 470                 475                 480

Ser Val Leu Val Trp Ser Leu Gly Asn Glu Ser Tyr Ala Gly Glu Val
                485                 490                 495

Leu Lys Ala Met Ser Ala His Ala His Arg Leu Asp Pro Gly Arg Pro
                500                 505                 510

Val His Tyr Glu Gly Val Asn Trp Asn His Ala Tyr Asp Gly Ile Ser
            515                 520                 525

Asp Phe Glu Ser Arg Met Tyr Ala Lys Pro Ala Glu Ile Gln Asp Trp
        530                 535                 540

Leu Glu His Gly Asp Glu Arg Gly Glu Ala Ser Lys Pro Phe Val Ser
545                 550                 555                 560

Cys Glu Tyr Met His Ala Met Gly Asn Ser Cys Gly Gly Leu Ser Glu
                565                 570                 575

Phe Ile Asp Leu Glu Arg Tyr Glu Arg Tyr Ser Gly Gly Phe Ile Trp
                580                 585                 590

Asp Tyr Ile Asp Gln Gly Leu Val Gln Arg Leu Pro Asp Gly Ser Glu
            595                 600                 605

Arg Leu Ser Val Gly Gly Glu Trp Gly Asp Arg Pro Thr Asp Tyr Glu
    610                 615                 620

Phe Val Gly Asn Gly Ile Val Phe Ala Asp Arg Thr Pro Ser Pro Lys
625                 630                 635                 640

Ala Gln Glu Val Lys Gln Leu Tyr Ser Pro Val Lys Leu Ala Pro Asp
                645                 650                 655

Gly His Gly Val Thr Ile Glu Asn Arg Asn Leu Phe Ala Gly Thr Asp
                660                 665                 670

Gly Tyr Val Phe Ala Ala Arg Leu Leu Glu Asp Gly His Glu Ile Trp
            675                 680                 685

His Ala Asp Tyr Arg Phe Asp Val Ala Ala Gly Asp Thr Gln His His
        690                 695                 700

Asp Ile Ala Phe Pro Asp Ile Asp Ala Asp Gly Asp Thr Arg Glu Val
705                 710                 715                 720

Thr Tyr Glu Val Asp Leu Leu Leu Ala Glu Ala Thr Ala Trp Ala Pro
                725                 730                 735

Ala Gly Tyr Glu Leu Ala Phe Gly Gln Leu Thr Gly Thr Leu Asn Pro
                740                 745                 750

Glu Gln Asp Ile Thr Glu Thr Ser His Asp Asp Gly Arg Ala Thr
            755                 760                 765

Arg Thr Leu Ser Arg Trp Asn Ala Gly Ile Arg Arg Asp Asp Lys Glu
    770                 775                 780

Ile Leu Leu Ser Arg Thr Gln Gly Gly Ile Val Ser Trp Lys Arg Asp
785                 790                 795                 800

Asp Arg Glu Met Val Ile Arg Arg Pro Glu Leu Val Thr Phe Arg Pro
                805                 810                 815

Leu Thr Asp Asn Asp Arg Gly Asn His Ser Gly Phe Asp Arg Ala Ala
                820                 825                 830

Trp Phe Ala Ala Gly Arg Tyr Ala Ile Val Thr Glu Thr Lys Ile His
        835                 840                 845

Glu Ser Asp Asp Gly Leu Val Ala Glu Tyr Gln Tyr Glu Leu Ala Asp
    850                 855                 860
```

```
Pro Asn His Thr Pro Val Ser Val Thr Tyr His Val Asn Ser Asp Met
865                 870                 875                 880

Arg Met Gln Leu Thr Val Glu Tyr Pro Gly Asn Ala Thr Asp Met Ala
            885                 890                 895

Ser Leu Pro Ala Phe Gly Ile Glu Trp Glu Leu Pro Gly Glu Tyr Asp
        900                 905                 910

Arg Leu Arg Tyr Tyr Gly Pro Gly Glu Glu Thr Tyr Arg Asp Arg
    915                 920                 925

Lys Gln Gly Gly Lys Leu Gly Ile Trp Asp Ala Thr Ala Lys Ala Ser
930                 935                 940

Met Ala Pro Tyr Leu Met Val Gln Glu Thr Gly Ser His Glu Asp Val
945                 950                 955                 960

Arg Trp Leu Glu Ala Thr Asp Ile Gln Gly His Gly Leu Arg Val Thr
            965                 970                 975

Gln Arg Gly Asp Arg His Phe Thr Ala Ser Leu Leu Pro Trp Asn Thr
        980                 985                 990

Tyr Met Ile Glu Ala Ala Arg Arg His Glu Asp Leu Pro Glu Pro Arg
    995                 1000                1005

His Asn Tyr Leu Arg Leu Leu Ala Ala Gln Met Gly Val Gly Gly
    1010                1015                1020

Asp Asp Ser Trp Gly Ala Pro Val His Thr Ala Tyr Gln Leu Pro
    1025                1030                1035

Ala Gly Arg Pro Leu Thr Leu Asp Val Asn Leu Glu Leu Ile
    1040                1045                1050
```

<210> SEQ ID NO 9
<211> LENGTH: 1055
<212> TYPE: PRT
<213> ORGANISM: Bifidobacterium breve

<400> SEQUENCE: 9

```
Met Thr Asn Ser Met Gln Gly Lys Ala Lys Thr Ile Met Thr Asn Leu
1               5                   10                  15

Gln Ser Ala Gln Gln Phe Ser Gln Ala Trp Leu Thr Asp Pro Arg Val
            20                  25                  30

Phe Ala Val Asn Arg Leu Ala Ala His Ser Ser His Lys Phe Tyr Asp
        35                  40                  45

His Ser Pro Gln Cys Gly Glu Ala Met Asp Leu Lys Gln Ser Leu Asp
    50                  55                  60

Gly Gln Trp Arg Val Gln Met Leu Asp Leu Ala Asp Leu Ala Asp Asn
65                  70                  75                  80

Glu Leu Ala Glu Ala Ala Phe Ala Gln Pro Gly Tyr Asp Ala Ala Gly
            85                  90                  95

Phe Ser Pro Ile Glu Val Pro Ser Ala Leu Glu Thr Lys Gly Phe Leu
        100                 105                 110

Asn His Gln Tyr Val Asn Gln Gln Tyr Pro Trp Ser Gly His Glu Ser
    115                 120                 125

Pro Val Ala Pro Asp Val Pro Lys His Asn His Val Ala Leu Tyr Arg
    130                 135                 140

His Glu Phe Ser Leu Glu Pro Lys Ala Ala Val Leu Glu Ala Asn
145                 150                 155                 160

Lys Thr Ala Ala Asp Asp Ala Ala Lys Arg Arg Val Thr Leu Thr Phe
            165                 170                 175

Gln Gly Ala Ala Thr Ala Ile Val Val Trp Leu Asn Gly Ala Phe Ile
        180                 185                 190
```

```
Gly Tyr Ala Glu Asp Ser Phe Thr Pro Ser Glu Phe Asp Val Thr Asp
        195                 200                 205

Val Leu Arg Asp Gly Val Asn Thr Leu Ala Val Ala Cys Phe Glu Phe
210                 215                 220

Ser Ser Ala Ser Trp Leu Glu Asp Gln Asp Phe Trp Arg Leu His Gly
225                 230                 235                 240

Ile Phe Arg Ser Val Glu Leu Glu Ala Gln Pro Leu Val His Val Asn
                245                 250                 255

Asp Leu Arg Val Leu Ala Asp Tyr Asp His Thr Thr Gly Glu Gly Ser
            260                 265                 270

Leu Asp Val Val Ala Leu Leu Arg Asn Ala Gly Thr Ala Ala Ala Val
        275                 280                 285

Ala Ala Thr Val Leu Asp Ala Ala Gly Asn Thr Val Trp His Ser Lys
    290                 295                 300

Leu Thr Ala Gly Ala Asp Ala Glu Thr Leu Thr Val Lys Ala Asn Val
305                 310                 315                 320

Gly Lys Val Asn Pro Trp Ser Ala Glu Glu Pro Thr Leu Tyr Thr Leu
                325                 330                 335

Gln Val Val Ala Thr Asp Ala Ala Gly Gln Val Ile Glu Ala Ala Leu
            340                 345                 350

Gln Arg Ile Gly Phe Arg His Phe Ala Ile Glu Asp Gly Leu Met Lys
        355                 360                 365

Leu Asn Gly Lys Arg Ile Val Phe Lys Gly Val Asp Arg His Glu Phe
    370                 375                 380

Asp Ala Arg Thr Gly Arg Thr Ile Ala Glu Ala Asp Met Ile Glu Asp
385                 390                 395                 400

Ile His Ser Phe Lys Arg Leu Asn Ile Asn Ala Val Arg Thr Ser His
                405                 410                 415

Tyr Pro Asn Glu Thr Arg Trp Tyr Glu Leu Cys Asp Glu Tyr Gly Ile
            420                 425                 430

Tyr Val Leu Asp Glu Thr Asn Leu Glu Thr His Gly Ser Trp Thr Asp
        435                 440                 445

Pro Gly Asp Val Phe Gln Pro Ala Arg Ala Ile Pro Gly Ser Lys Asp
    450                 455                 460

Glu Trp Arg Ala Ala Cys Val Asp Arg Thr Ala Ser Met Val Arg Arg
465                 470                 475                 480

Asp Tyr Asn His Pro Ser Val Ile Trp Ser Leu Gly Asn Glu Ala
                485                 490                 495

Phe Gly Gly Asp Val Phe Tyr Ser Met Arg Asp Phe Val His Glu Asn
            500                 505                 510

Asp Pro Phe Arg Pro Val His Tyr Glu Gly Thr Phe Asn Asp Pro Glu
        515                 520                 525

Phe Ser Ala Ala Thr Asp Ile Met Ser Arg Met Tyr Ala Lys Pro Asp
    530                 535                 540

Glu Ile Val Lys Leu Tyr Leu Gly Glu Asp Gly Lys Lys Pro Tyr Ile
545                 550                 555                 560

Ser Cys Glu Tyr Ser His Ser Met Gly Asn Ser Thr Gly Gly Leu His
                565                 570                 575

Leu Tyr Thr Glu Leu Glu Arg Tyr Pro Leu Tyr Gln Gly Gly Phe Ile
            580                 585                 590

Trp Asp Tyr Val Asp Gln Ala Leu Trp Gln Asp Cys Gly Asn Gly Thr
        595                 600                 605
```

-continued

```
Glu Arg Leu Ala Tyr Gly Gly Asp Phe Glu Asp Arg Pro Asn Asp Tyr
    610                 615                 620

Glu Phe Ser Gly Asp Gly Val Met Phe Ala Asp Arg Thr Pro Ser Pro
625                 630                 635                 640

Lys Ala Gln Glu Val Lys Gln Leu Tyr Ala Asn Val Lys Leu Val Pro
                645                 650                 655

Asp Glu Ser Gly Val Thr Ile Thr Asn Asp Asn Leu Phe Ile Ser Thr
                660                 665                 670

Ala Ser Ser Leu Phe Thr Ala Arg Val Leu Val Asp Gly Ala Glu Arg
            675                 680                 685

Trp His Ala Asn Tyr Arg Phe Asp Val Pro Ala Gly Glu Thr Val Arg
690                 695                 700

Glu Pro Ile Ala Phe Pro Lys Val Thr Asp Leu Val Ala Leu Ser Gly
705                 710                 715                 720

Ser Ala Glu Val Thr Tyr Glu Val Asp Gln Arg Leu Ala Glu Ala Thr
                725                 730                 735

Asp Trp Ala Pro Ala Gly Tyr Glu Leu Thr Phe Gly Gln Tyr Val Ala
            740                 745                 750

Ala Val Ser Phe Asp Asp Gly Ala Asp Ala Val Val Ala Gly Asp
            755                 760                 765

Ala Glu Val Ala Ala Asp Gly Phe Asn Ala Gly Ile His Thr Asp Phe
770                 775                 780

Gly Glu Val Leu Leu Ser Lys Thr Gln Gly Gly Met Val Ser Phe Lys
785                 790                 795                 800

Arg Asp Gly Arg Glu Met Val Ile Arg Arg Pro Asn Leu Thr Thr Phe
                805                 810                 815

Arg Ala Leu Thr Asp Asn Asp Arg Gly Asn Gly Ser Gly Phe Glu Arg
            820                 825                 830

Ala Gln Trp Met Ala Ala Gly Arg Tyr Ala Arg Val Thr Gly Thr Ser
835                 840                 845

Val Glu Glu Thr Ala Asp Gly Lys Gly Leu Lys Ala Thr Tyr Ser Tyr
850                 855                 860

Glu Leu Ala Asp Ala Lys His Thr Pro Val Thr Val His Tyr Glu Val
865                 870                 875                 880

Asp Ala Ala Leu Arg Val His Leu Thr Val Glu Tyr Pro Gly Glu Ala
                885                 890                 895

Asp Ala Ala Thr Leu Pro Ala Phe Gly Leu Glu Trp Ile Leu Pro Lys
            900                 905                 910

Gln Tyr Asp Arg Leu Arg Phe Tyr Gly Leu Gly Pro Glu Glu Thr Tyr
            915                 920                 925

Ala Asp Arg Leu His Gly Ala Lys Leu Gly Val Phe Ser Arg Thr Ala
930                 935                 940

Ala Glu Asp Cys Ala Pro Tyr Leu Leu Pro Gln Glu Thr Gly Asn His
945                 950                 955                 960

Glu Gln Val Arg Trp Ala Glu Ile Thr Asp Glu Tyr Gly His Gly Met
                965                 970                 975

Arg Val Thr Ala Ala Gly Gly Thr Arg Phe Ala Thr Ser Leu Leu Pro
            980                 985                 990

Tyr Ser Ser Leu Met Phe Glu Asp Ala Leu His Gln Asn Glu Leu Pro
            995                1000                1005

Lys Pro Arg His Thr Phe Leu Arg Leu Leu Ala Ala Gln Met Gly
           1010                1015                1020

Val Gly Gly Asp Asp Thr Trp Gly Ala Pro Val His Asp Glu Phe
```

```
           1025                1030                1035
Gln Val Pro Ala Asp Gln Pro Leu Lys Leu Asp Val Thr Leu Glu
        1040                1045                1050

Leu Ile
    1055

<210> SEQ ID NO 10
<211> LENGTH: 689
<212> TYPE: PRT
<213> ORGANISM: Bifidobacterium catenulatum

<400> SEQUENCE: 10

Met Thr Gln Arg Arg Ser Tyr Arg Trp Pro Gln Pro Leu Ala Gly Gln
1               5                   10                  15

Gln Ala Arg Ile Trp Tyr Gly Gly Asp Tyr Asn Pro Asp Gln Trp Pro
            20                  25                  30

Glu Glu Val Trp Asp Asp Val Arg Leu Met Lys Lys Ala Gly Val
        35                  40                  45

Asn Leu Val Ser Val Gly Ile Phe Ser Trp Ala Lys Ile Glu Thr Ser
    50                  55                  60

Glu Gly Val Tyr Asp Phe Asp Trp Leu Asp Arg Ile Ile Asp Lys Leu
65                  70                  75                  80

Gly Glu Ala Gly Ile Ala Val Asp Leu Ala Ser Ala Thr Ala Ser Pro
                85                  90                  95

Pro Met Trp Leu Thr Gln Ala His Pro Glu Val Leu Trp Lys Asp Tyr
            100                 105                 110

Arg Gly Asp Val Cys Gln Pro Gly Ala Arg Gln His Trp Arg Pro Thr
        115                 120                 125

Ser Pro Val Phe Arg Glu Tyr Ala Leu Lys Leu Cys Arg Ala Met Ala
130                 135                 140

Glu His Tyr Lys Gly Asn Pro Tyr Val Val Ala Trp His Val Ser Asn
145                 150                 155                 160

Glu Tyr Gly Cys His Asn Arg Phe Asp Tyr Ser Glu Asp Ala Glu Arg
                165                 170                 175

Ala Phe Arg Lys Trp Cys Glu Glu Arg Tyr Gly Thr Ile Asp Ala Val
            180                 185                 190

Asn Asp Ala Trp Gly Thr Ala Phe Trp Ala Gln Arg Met Asn Asp Phe
        195                 200                 205

Thr Glu Ile Val Pro Pro Arg Phe Ile Gly Asp Gly Asn Phe Met Asn
    210                 215                 220

Pro Gly Lys Leu Leu Asp Phe Lys Arg Phe Ser Ser Asp Ala Leu Lys
225                 230                 235                 240

Ala Phe Tyr Val Ala Glu Arg Asp Ala Leu Ala Glu Ile Thr Pro Asp
                245                 250                 255

Leu Pro Leu Thr Thr Asn Phe Met Val Ser Ala Ala Gly Ser Val Leu
            260                 265                 270

Asp Tyr Asp Asp Trp Gly Arg Glu Val Asp Phe Val Ser Asn Asp His
        275                 280                 285

Tyr Phe Ile Pro Gly Glu Ala His Leu Asp Glu Leu Ala Phe Ser Ala
    290                 295                 300

Ser Leu Val Asp Gly Ile Ala Arg Lys Asp Pro Trp Phe Leu Met Glu
305                 310                 315                 320

His Ser Thr Ser Ala Val Asn Trp Arg Pro Val Asn Tyr Arg Lys Glu
                325                 330                 335
```

```
Pro Gly Gln Leu Val Arg Asp Ser Leu Ala His Val Ala Met Gly Ala
            340                 345                 350

Asp Ala Val Cys Tyr Phe Gln Trp Arg Gln Ser Lys Ala Gly Ala Glu
        355                 360                 365

Lys Phe His Ser Ala Met Val Pro His Thr Gly Glu Asp Ser Ala Val
    370                 375                 380

Phe Arg Asp Val Cys Glu Leu Gly Ala Asp Leu Asn Thr Leu Ala Asp
385                 390                 395                 400

Asn Gly Leu Leu Gly Thr Lys Leu Ala Lys Ser Lys Val Ala Val Val
                405                 410                 415

Phe Asp Tyr Glu Ser Glu Trp Ala Thr Glu His Thr Ala Thr Pro Thr
            420                 425                 430

Gln Lys Val His His Val Asp Glu Pro Leu Gln Trp Phe Arg Ala Leu
        435                 440                 445

Ala Asp His Gly Val Thr Ala Asp Val Val Pro Val Ser Ser Asn Trp
    450                 455                 460

Asp Glu Tyr Glu Val Val Leu Pro Ser Val Tyr Ile Leu Ser Glu
465                 470                 475                 480

Glu Thr Thr Arg Arg Val Arg Asp Tyr Val Asn Gly Gly Arg Leu
                485                 490                 495

Ile Val Thr Tyr Tyr Thr Gly Leu Ser Asp Glu Lys Asp His Val Trp
            500                 505                 510

Leu Gly Gly Tyr Pro Gly Ser Ile Arg Asp Val Val Gly Val Arg Val
        515                 520                 525

Glu Glu Phe Met Pro Met Gly Asp Asp Phe Pro Gly Val Pro Asp Cys
    530                 535                 540

Leu Gly Leu Ser Asn Gly Ala Val Ala His Asp Ile Ala Asp Val Ile
545                 550                 555                 560

Gly Ser Val Asp Gly Thr Ala Thr Val Leu Glu Thr Phe Arg Asp Asp
                565                 570                 575

Pro Trp Thr Gly Met Asp Gly Ala Pro Ala Ile Val Ala Asn Thr Phe
            580                 585                 590

Gly Glu Gly Arg Ser Val Tyr Val Gly Ala Arg Leu Gly Arg Asp Gly
        595                 600                 605

Ile Ala Lys Ser Leu Pro Glu Ile Phe Glu Ser Leu Gly Met Ala Glu
    610                 615                 620

Thr Gly Glu Asn Asp Ser Arg Val Leu Arg Val Glu Arg Glu Gly Ser
625                 630                 635                 640

Asp Gly Ser Arg Phe Val Phe Ser Phe Asn Arg Thr His Glu Ala Val
                645                 650                 655

Gln Ile Pro Phe Glu Gly Lys Ile Val Val Ser Ser Phe Ala Glu Val
            660                 665                 670

Ser Gly Glu Asn Val Ser Ile Lys Pro Asn Gly Val Ile Val Thr Lys
        675                 680                 685

Gln

<210> SEQ ID NO 11
<211> LENGTH: 1023
<212> TYPE: PRT
<213> ORGANISM: Bifidobacterium catenulatum

<400> SEQUENCE: 11

Met Ala Asn Ser Asn Arg Val Glu His Ala Ser Glu Thr Trp Leu Thr
1               5                   10                  15
```

```
Asp Ala Thr Val Phe Glu Val Asn Arg Thr Pro Ala His Ser Asn His
            20                  25                  30

Lys Cys Phe Thr His Asp Pro Gln Ser Gly Glu His Ser Asp Leu Thr
        35                  40                  45

Gln Ser Leu Asp Gly Glu Trp Arg Val Glu Ile Val Gln Ala Ser Asp
    50                  55                  60

Ile Asp Phe Asn Glu Glu Pro Phe Val Ala Glu Asn Phe Asp Asp Ser
65                  70                  75                  80

Ser Phe Cys Arg Ala Gln Val Pro Gly His Leu Gln Met Ala Gly Leu
                85                  90                  95

Leu Lys Asn Lys Tyr Val Asn Ile Gln Tyr Pro Trp Asp Gly His Glu
            100                 105                 110

Asn Pro Leu Glu Pro Asn Val Pro Glu Asn Asn His Val Ala Leu Tyr
        115                 120                 125

Arg Arg Lys Phe Val Val Ser Lys Arg Leu Ala Asp Thr Lys Glu Ser
    130                 135                 140

Glu Gly Ser Val Ser Ile Val Phe His Gly Met Ala Thr Ala Ile Tyr
145                 150                 155                 160

Val Trp Val Asn Gly Leu Phe Ala Gly Tyr Gly Glu Asp Gly Phe Thr
                165                 170                 175

Pro Asn Glu Phe Asp Ile Thr Asp Leu Leu His Asp Gly Glu Asn Val
            180                 185                 190

Val Ala Val Ala Cys Tyr Glu Tyr Ser Ser Ala Ser Trp Leu Glu Asp
        195                 200                 205

Gln Asp Phe Trp Arg Leu His Gly Leu Phe Arg Ser Val Glu Leu Thr
    210                 215                 220

Ala Gln Pro His Val His Val Glu Asn Met Gln Leu Glu Ala Asp Trp
225                 230                 235                 240

Asp Ala Glu Ser Gly Thr Ala Ser Leu Asp Ala Ala Leu Ser Val Arg
                245                 250                 255

Asn Ala Ser Asp Ala Ala Thr Ile Ser Ala Thr Leu Lys Asp Ser Glu
            260                 265                 270

Gly Asn Val Val Trp Glu Ala Ser Thr Asn Ala Asp Ala Asn Thr Thr
        275                 280                 285

Phe Ala Ser Gly Ser Leu Gln Gly Leu Glu Pro Trp Ser Ala Glu Ser
    290                 295                 300

Pro Ser Leu Tyr Glu Leu Glu Val Asn Val Ile Asp Gln Ala Gly Asn
305                 310                 315                 320

Ile Val Glu Ala Ala Val Gln Lys Val Gly Phe Arg Arg Phe Arg Ile
                325                 330                 335

Glu Asn Gly Ile Met Thr Leu Asn Gly Lys Arg Ile Val Phe Lys Gly
            340                 345                 350

Ala Asp Arg His Glu Phe Asp Ala Lys Arg Gly Arg Ser Ile Thr Glu
        355                 360                 365

Gln Asp Met Ile Asp Asp Val Ile Phe Cys Lys Arg His Asn Ile Asn
    370                 375                 380

Ala Ile Arg Thr Ser His Tyr Pro Asn Gln Glu Arg Trp Tyr Asp Leu
385                 390                 395                 400

Cys Asp Glu Tyr Gly Ile Tyr Leu Ile Asp Glu Thr Asn Leu Glu Thr
                405                 410                 415

His Gly Ser Trp Cys Leu Pro Gly Asp Val Val Thr Ala Glu Thr Ala
            420                 425                 430

Val Pro Gly Ser Lys Ala His Trp Glu Gly Ala Cys Val Asp Arg Val
```

-continued

```
              435                 440                 445
Asn Ser Met Val Arg Arg Asp Tyr Asn His Pro Ser Val Val Ile Trp
450                 455                 460

Ser Leu Gly Asn Glu Ser Tyr Thr Gly Asp Val Phe Arg Ala Met Tyr
465                 470                 475                 480

Lys His Val His Asp Ile Asp Pro Asn Arg Pro Val His Tyr Glu Gly
                485                 490                 495

Val Thr Lys Asn Arg Asp Tyr Asp Val Thr Asp Ile Glu Thr Arg
                500                 505                 510

Met Tyr Glu His Ala Asp Val Val Glu Glu Tyr Leu Lys Asn Asp Pro
            515                 520                 525

Gln Lys Pro Tyr Ile Ser Cys Glu Tyr Met His Ala Met Gly Asn Ser
        530                 535                 540

Val Gly Asn Leu Asp Glu Tyr Thr Ala Leu Glu Arg Tyr Pro His Tyr
545                 550                 555                 560

Gln Gly Gly Phe Ile Trp Asp Phe Ile Asp Gln Ala Ile Tyr Ala Thr
                565                 570                 575

Gln Pro Asp Gly Ser Thr Arg Leu Cys Tyr Gly Gly Asp Phe Gly Asp
            580                 585                 590

Arg Pro Ser Asp Tyr Glu Phe Ser Gly Asn Gly Leu Val Phe Ala Asp
        595                 600                 605

Arg Thr Pro Thr Pro Lys Ala Gln Glu Val Lys Gln Leu Tyr Ser Asn
610                 615                 620

Val His Ile Asp Val Thr Asp Arg Ser Val Ser Ile Lys Asn Asp Asn
625                 630                 635                 640

Leu Phe Ile Ser Thr Gly Gly Tyr Gln Phe Val Leu Arg Ile Leu Ala
                645                 650                 655

Asp Gly Glu Pro Val Trp Gln Ser Glu Arg Arg Phe Asp Val Pro Ala
            660                 665                 670

Asp Ser Ala Cys Thr Phe Asp Val Glu Trp Pro Val Asp Leu Tyr Arg
        675                 680                 685

Ala Asn Ala Asp Glu Leu Val Leu Glu Val Ser Gln Arg Leu Ala Glu
    690                 695                 700

Ala Thr Asp Trp Ala Pro Ala Gly Tyr Glu Leu Ala Phe Gly Gln Thr
705                 710                 715                 720

Ile Val Ala Gly Thr Lys Ala Glu Asp Ala Ala Leu Pro Ala Asp
                725                 730                 735

Gly Ile Val Thr Val Gly Arg Trp Asn Ala Gly Val Gln Gly Ser Gly
            740                 745                 750

Arg Glu Ile Leu Leu Ser Arg Thr Gln Gly Gly Leu Val Ser Tyr Thr
        755                 760                 765

Phe Asp Gly His Glu Phe Val Leu Arg Arg Pro Ala Ile Thr Thr Phe
    770                 775                 780

Arg Ala Leu Thr Asp Asn Asp Arg Gly Ala Gly His Gly Phe Glu Arg
785                 790                 795                 800

Ala Gln Trp Met Val Ala Gly Arg Tyr Ala Arg Cys Val Asp Asn Val
                805                 810                 815

Ile Glu Gln Val Asp Glu Asp Thr Leu Lys Ala Val Tyr Thr Tyr Glu
            820                 825                 830

Leu Ala Thr Pro Gln Cys Thr Lys Val Thr Val Gly Tyr Thr Ala Asp
        835                 840                 845

Thr Thr Gly Arg Leu Asn Leu His Val Glu Tyr Pro Gly Glu Ser Gly
    850                 855                 860
```

```
Glu Leu Pro Thr Ile Pro Ala Phe Gly Ile Glu Trp Thr Leu Pro Val
865                 870                 875                 880

Gln Tyr Ser Asn Leu Arg Phe Phe Gly Ala Gly Pro Glu Glu Thr Tyr
                885                 890                 895

Gln Asp Arg Lys His Ala Lys Leu Gly Val Trp Ser Thr Asp Ala Phe
            900                 905                 910

Lys Asp His Ala Pro Tyr Leu Met Pro Gln Glu Thr Gly Asn His Glu
        915                 920                 925

Glu Val Arg Trp Ala Glu Ile Thr Asp Glu Asn Gly His Gly Leu Arg
    930                 935                 940

Val Ser Arg Ala Asn Gly Ala Ala Pro Phe Ala Val Ser Leu Gln Pro
945                 950                 955                 960

Tyr Ser Ser Phe Met Ile Glu Glu Ala Gln His Gln Asp Glu Leu Pro
                965                 970                 975

Ala Pro Lys His Met Phe Leu Arg Val Leu Ala Ala Gln Met Gly Val
            980                 985                 990

Gly Gly Asp Asp Ser Trp Met Ser Pro Val His Ser Gln Tyr His Ile
        995                 1000                1005

Thr Ala Asp Gln Pro Ile Ser Leu Asp Val Asn Leu Glu Leu Ile
    1010                1015                1020

<210> SEQ ID NO 12
<211> LENGTH: 1008
<212> TYPE: PRT
<213> ORGANISM: Lactobacillus delbrueckii

<400> SEQUENCE: 12

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Leu Glu Glu Gly
        35                  40                  45

Lys Ser Ser Leu Val Gln Ser Leu Asp Gly Asp Trp Leu Ile Asp Tyr
50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
            100                 105                 110

Ser Glu Glu Ile Phe Pro Pro Gln Ile Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Met Ser Gly Leu Phe Arg Ser Val Thr Leu Gln Ala Lys Pro
```

```
              210                 215                 220
Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Leu Gly Pro Ile Arg Ser Glu Gln Leu Glu Phe Thr
                275                 280                 285

Leu Ala Asp Leu Pro Val Ala Ala Trp Ser Ala Glu Lys Pro Asn Leu
290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Ala Asn Arg His
                340                 345                 350

Glu Phe Asp Ser Lys Leu Gly Arg Ala Ile Thr Glu Glu Asp Met Ile
                355                 360                 365

Trp Asp Ile Lys Thr Met Lys Arg Ser Asn Ile Asn Ala Val Arg Cys
370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
                420                 425                 430

Asp Gln His Trp Leu Gly Ala Ser Leu Ser Arg Val Lys Asn Met Met
                435                 440                 445

Ala Arg Asp Lys Asn His Ala Ser Ile Leu Ile Trp Ser Leu Gly Asn
450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
                500                 505                 510

Ala Lys Val Ile Glu Glu Tyr Leu Thr Asn Lys Pro Ala Lys Pro Phe
                515                 520                 525

Ile Ser Val Glu Tyr Ala His Ala Met Gly Asn Ser Val Gly Asp Leu
530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
                565                 570                 575

Tyr Gly Gly Asp Phe Asp Asp Arg Pro Thr Asp Tyr Glu Phe Cys Gly
                580                 585                 590

Asn Gly Leu Val Phe Ala Asp Arg Thr Glu Ser Pro Lys Leu Ala Asn
                595                 600                 605

Val Lys Ala Leu Tyr Ala Asn Leu Lys Leu Glu Val Lys Asp Gly Gln
610                 615                 620

Leu Phe Leu Lys Asn Asp Asn Leu Phe Thr Asn Ser Ser Ser Tyr Tyr
625                 630                 635                 640
```

Phe Leu Thr Ser Leu Leu Val Asp Gly Lys Leu Thr Tyr Gln Ser Arg
            645                 650                 655

Pro Leu Thr Phe Gly Leu Glu Pro Glu Ser Gly Thr Phe Ala Leu
            660                 665                 670

Pro Trp Pro Glu Val Ala Asp Glu Lys Gly Glu Val Val Tyr Arg Val
            675                 680                 685

Thr Ala His Leu Lys Glu Asp Leu Pro Trp Ala Asp Glu Gly Phe Thr
    690                 695                 700

Val Ala Glu Ala Glu Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
            725                 730                 735

Gly Asn Asn Phe Gln Ile Leu Phe Ser Lys Val Lys Gly Trp Pro Val
            740                 745                 750

Ser Leu Lys Tyr Ala Gly Arg Glu Tyr Leu Lys Arg Leu Pro Glu Phe
            755                 760                 765

Thr Phe Trp Arg Ala Leu Thr Asp Asn Asp Arg Gly Ala Gly Tyr Gly
            770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
            805                 810                 815

Phe Thr Leu Pro Val Ala Leu Lys Gly Asp Leu Thr Val Thr Tyr Glu
            820                 825                 830

Val Asp Gly Arg Gly Lys Ile Ala Val Thr Ala Asp Phe Pro Gly Ala
            835                 840                 845

Glu Glu Ala Gly Leu Leu Pro Ala Phe Gly Leu Asn Leu Ala Leu Pro
            850                 855                 860

Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
            885                 890                 895

Val Lys Lys Asn Phe Ser Pro Tyr Leu Arg Pro Gln Glu Thr Gly Asn
            900                 905                 910

Arg Ser Lys Val Arg Trp Tyr Gln Leu Phe Asp Glu Lys Gly Gly Leu
            915                 920                 925

Glu Phe Thr Ala Asn Gly Ala Asp Leu Asn Leu Ser Ala Leu Pro Tyr
    930                 935                 940

Ser Ala Ala Gln Ile Glu Ala Ala Asp His Ala Phe Asp Leu Thr Asn
945                 950                 955                 960

Asn Tyr Thr Trp Val Arg Ala Leu Ser Ala Gln Met Gly Val Gly Gly
            965                 970                 975

Asp Asp Ser Trp Gly Gln Lys Val His Pro Glu Phe Cys Leu Asp Ala
            980                 985                 990

Gln Lys Ala Arg Gln Leu Arg Leu Val Ile Gln Pro Leu Leu Leu Lys
            995                 1000                1005

<210> SEQ ID NO 13
<211> LENGTH: 1007
<212> TYPE: PRT
<213> ORGANISM: Lactobacillus delbrueckii

<400> SEQUENCE: 13

Met Ser Asn Lys Leu Val Lys Glu Lys Arg Val Asp Gln Ala Asp Leu

-continued

```
1               5                   10                  15
Ala Trp Leu Thr Asp Pro Glu Val Tyr Glu Val Asn Thr Ile Pro Pro
                20                  25                  30

His Ser Asp His Glu Ser Phe Gln Ser Gln Glu Leu Glu Glu Gly
                35                  40                  45

Lys Ser Ser Leu Val Gln Ser Leu Asp Gly Asn Trp Leu Ile Asp Tyr
                50                  55                  60

Ala Glu Asn Gly Gln Gly Pro Ile Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Ile Gln Tyr Pro Trp Asp Gly
                100                 105                 110

Ser Glu Glu Ile Phe Pro Pro Gln Val Pro Ser Lys Asn Pro Leu Ala
                115                 120                 125

Ser Tyr Val Arg Tyr Phe Asp Leu Asp Glu Ala Leu Trp Asp Lys Glu
                130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Gly Asn Arg Leu Ala Val
                180                 185                 190

Ala Leu Tyr Lys Tyr Ser Ser Ala Ser Trp Leu Glu Asp Gln Asp Phe
                195                 200                 205

Trp Arg Leu Ser Gly Leu Phe Arg Ser Val Thr Leu Glu Ala Lys Pro
                210                 215                 220

Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Val Gly Pro Ile Arg Ser Glu Lys Leu Gly Phe Ser
                275                 280                 285

Leu Ala Asp Leu Pro Val Ala Ala Trp Ser Ala Glu Lys Pro Asn Leu
                290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
                340                 345                 350

Glu Phe Asp Ser Lys Leu Gly Arg Ala Ile Thr Glu Ala Asp Met Ile
                355                 360                 365

Trp Asp Ile Lys Thr Met Lys Gln Ser Asn Ile Asn Ala Val Arg Cys
                370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly His Glu Asp Pro Ser Phe Asn Val Pro Gly Asp Asp
                420                 425                 430
```

```
Gln His Trp Leu Gly Ala Ser Leu Ser Arg Val Lys Asn Met Met Ala
        435                 440                 445

Arg Asp Lys Asn His Ala Ser Ile Leu Ile Trp Ser Leu Gly Asn Glu
    450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
                500                 505                 510

Lys Glu Ile Glu Glu Tyr Leu Thr Lys Lys Pro Ala Lys Pro Phe Ile
        515                 520                 525

Ser Val Glu Tyr Ala His Ala Met Gly Asn Ser Val Gly Asp Leu Ala
    530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Asp Phe Asp Asp Arg Pro Thr Asp Tyr Glu Phe Cys Gly Asp
                580                 585                 590

Gly Leu Val Phe Ala Asp Arg Thr Thr Ser Pro Lys Leu Ala Asn Val
        595                 600                 605

Lys Ala Leu Tyr Ser Asn Leu Lys Leu Glu Val Lys Asp Gly Gln Leu
    610                 615                 620

Phe Ile Lys Asn Asp Asn Leu Phe Thr Asn Ser Ser Ala Tyr Tyr Phe
625                 630                 635                 640

Leu Ala Ser Leu Leu Val Asp Gly Lys Leu Thr Tyr Gln Ser Gln Pro
                645                 650                 655

Leu Thr Phe Gly Leu Glu Pro Gly Glu Ser Gly Thr Phe Val Leu Pro
                660                 665                 670

Trp Pro Glu Val Glu Asp Glu Lys Gly Glu Ile Val Tyr Gln Val Thr
        675                 680                 685

Ala His Leu Lys Glu Asp Leu Pro Trp Ala Asp Glu Gly Phe Thr Val
    690                 695                 700

Ala Glu Ala Glu Ala Val Thr Lys Leu Pro Glu Phe Tyr Pro Ala
705                 710                 715                 720

Gly Arg Pro Glu Leu Val Asp Ser Asp Phe Asn Leu Gly Leu Lys Gly
                725                 730                 735

Asn Gly Phe Arg Ile Leu Phe Ser Lys Ala Lys Gly Trp Pro Val Ser
                740                 745                 750

Ile Lys Tyr Ala Gly Arg Glu Tyr Leu Lys Arg Leu Pro Glu Phe Thr
        755                 760                 765

Phe Trp Arg Ala Leu Thr Asp Asn Asp Arg Gly Ala Gly Tyr Gly Tyr
    770                 775                 780

Asp Leu Ala Lys Trp Glu Asn Ala Gly Lys Tyr Ala Arg Leu Gln Asp
785                 790                 795                 800

Ile Ser Tyr Glu Ile Lys Glu Asn Ser Ala Leu Val Lys Thr Thr Phe
                805                 810                 815

Thr Leu Pro Val Ala Leu Lys Gly Asp Leu Thr Ile Thr Tyr Glu Val
                820                 825                 830

Asp Ser Leu Gly Lys Ile Ala Val Thr Ala Asn Phe Pro Gly Ala Val
        835                 840                 845
```

```
Glu Asn Gly Leu Leu Pro Ala Phe Gly Leu Asn Phe Ala Leu Pro Lys
    850                 855                 860

Glu Leu Ser Asp Tyr Arg Tyr Tyr Gly Leu Gly Pro Asn Glu Ser Tyr
865                 870                 875                 880

Ala Asp Arg Leu Glu Gly Ser Tyr Leu Gly Ile Tyr Gln Gly Ala Val
                885                 890                 895

Glu Lys Asn Phe Thr Pro Tyr Leu Arg Pro Gln Ala Gly Asn Arg
                900                 905                 910

Ser Lys Val Arg Tyr Tyr Gln Leu Phe Asp Glu Gly Gly Leu Glu
                915                 920                 925

Phe Thr Ala Asn Gly Ala Asp Leu Asn Leu Ser Ala Leu Pro Tyr Ser
930                 935                 940

Ala Ala Gln Ile Glu Ala Asp His Ala Phe Glu Leu Thr Asn Asn
945                 950                 955                 960

Tyr Thr Trp Val Arg Ala Leu Ala Ala Gln Met Gly Val Gly Gly Asp
                965                 970                 975

Asp Ser Trp Gly Gln Lys Val His Pro Glu Phe Cys Leu Asp Ala Gln
                980                 985                 990

Glu Ala Arg Gln Leu Lys Leu Val Ile Gln Pro Leu Leu Leu Lys
                995                 1000                1005

<210> SEQ ID NO 14
<211> LENGTH: 1008
<212> TYPE: PRT
<213> ORGANISM: Lactobacillus delbrueckii

<400> SEQUENCE: 14

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
                20                  25                  30

His Phe Asp His Glu Ser Phe Gln Ser Gln Glu Glu Leu Glu Glu Gly
            35                  40                  45

Lys Ser Ser Leu Val Gln Ser Leu Asp Gly Asp Trp Leu Ile Asp Tyr
50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
                100                 105                 110

Ser Glu Glu Ile Phe Pro Pro Gln Ile Pro Ser Lys Asn Pro Leu Ala
            115                 120                 125

Ser Tyr Val Arg Tyr Phe Asp Leu Asp Glu Ala Phe Trp Asp Lys Glu
            130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
                180                 185                 190

Ala Leu Tyr Lys Tyr Ser Ser Ala Ser Trp Leu Glu Asp Gln Asp Phe
            195                 200                 205

Trp Arg Met Ser Gly Leu Phe Arg Ser Val Thr Leu Gln Ala Lys Pro
210                 215                 220
```

-continued

```
Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Gly Asp Leu
        260                 265                 270

Val Ala Glu Lys Leu Gly Pro Ile Arg Ser Glu Gln Leu Glu Phe Thr
        275                 280                 285

Leu Ala Asp Leu Pro Val Ala Ala Trp Ser Ala Glu Lys Pro Asn Leu
        290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Ala Asn Arg His
                340                 345                 350

Glu Phe Asp Ser Lys Leu Gly Arg Ala Ile Thr Glu Asp Met Ile
        355                 360                 365

Trp Asp Ile Lys Thr Met Lys Arg Ser Asn Ile Asn Ala Val Arg Cys
370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
                420                 425                 430

Asp Gln His Trp Leu Gly Ala Ser Leu Ser Arg Val Lys Asn Met Met
                435                 440                 445

Ala Arg Asp Lys Asn His Ala Ser Ile Leu Ile Trp Ser Leu Gly Asn
450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
                500                 505                 510

Ala Lys Val Ile Glu Glu Tyr Leu Thr Asn Lys Pro Ala Lys Pro Phe
                515                 520                 525

Ile Ser Val Glu Tyr Ala His Ala Met Gly Asn Ser Val Gly Asp Leu
                530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
                565                 570                 575

Tyr Gly Gly Asp Phe Asp Asp Arg Pro Thr Asp Tyr Glu Phe Cys Gly
                580                 585                 590

Asn Gly Leu Val Phe Ala Asp Arg Thr Glu Ser Pro Lys Leu Ala Asn
                595                 600                 605

Val Lys Ala Leu Tyr Ala Asn Leu Lys Leu Glu Val Lys Asp Gly Gln
        610                 615                 620

Leu Phe Leu Lys Asn Asp Asn Leu Phe Thr Asn Ser Ser Ser Tyr Tyr
625                 630                 635                 640
```

```
Phe Leu Thr Ser Leu Leu Val Asp Gly Lys Leu Thr Tyr Gln Ser Arg
                645                 650                 655

Pro Leu Thr Phe Gly Leu Glu Pro Gly Glu Ser Gly Thr Phe Ala Leu
            660                 665                 670

Pro Trp Pro Glu Val Ala Asp Glu Lys Gly Glu Val Val Tyr Arg Val
        675                 680                 685

Thr Ala His Leu Lys Glu Asp Leu Pro Trp Ala Asp Glu Gly Phe Thr
    690                 695                 700

Val Ala Glu Ala Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
                725                 730                 735

Gly Asn Asn Phe Gln Ile Leu Phe Ser Lys Val Lys Gly Trp Pro Val
            740                 745                 750

Ser Leu Lys Tyr Ala Gly Arg Glu Tyr Leu Lys Arg Leu Pro Glu Phe
        755                 760                 765

Thr Phe Trp Arg Ala Leu Thr Asp Asn Asp Arg Gly Ala Gly Tyr Gly
    770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
                805                 810                 815

Phe Thr Leu Pro Val Ala Leu Lys Gly Asp Leu Thr Val Thr Tyr Glu
            820                 825                 830

Val Asp Gly Arg Gly Lys Ile Ala Val Thr Ala Asp Phe Pro Gly Ala
        835                 840                 845

Glu Glu Ala Gly Leu Leu Pro Ala Phe Gly Leu Asn Leu Ala Leu Pro
    850                 855                 860

Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
                885                 890                 895

Val Lys Lys Asn Phe Ser Pro Tyr Leu Arg Pro Gln Glu Thr Gly Asn
            900                 905                 910

Arg Ser Lys Val Arg Trp Tyr Gln Leu Phe Asp Glu Lys Gly Gly Leu
        915                 920                 925

Glu Phe Thr Ala Asn Gly Ala Asp Leu Asn Leu Ser Ala Leu Pro Tyr
    930                 935                 940

Ser Ala Ala Gln Ile Glu Ala Ala Asp His Ala Phe Glu Leu Thr Asn
945                 950                 955                 960

Asn Tyr Thr Trp Val Arg Ala Leu Ser Ala Gln Met Gly Val Gly Gly
                965                 970                 975

Asp Asp Ser Trp Gly Gln Lys Val His Pro Glu Phe Cys Leu Asp Ala
            980                 985                 990

Gln Lys Ala Arg Gln Leu Arg Leu Val Ile Gln Pro Leu Leu Leu Lys
        995                 1000                1005

<210> SEQ ID NO 15
<211> LENGTH: 1008
<212> TYPE: PRT
<213> ORGANISM: Lactobacillus delbrueckii

<400> SEQUENCE: 15

Met Ser Asn Lys Leu Val Lys Glu Lys Arg Val Asp Gln Ala Asp Leu
1               5                   10                  15
```

```
Ala Trp Leu Thr Asp Pro Glu Val Tyr Glu Val Asn Thr Ile Pro Pro
            20                  25                  30

His Ser Asp His Glu Ser Phe Gln Ser Gln Glu Leu Glu Glu Gly
        35                  40                  45

Lys Ser Ser Leu Val Gln Ser Leu Asp Gly Asp Trp Leu Ile Asp Tyr
50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
                100                 105                 110

Ser Glu Glu Ile Phe Pro Pro Gln Ile Pro Ser Lys Asn Pro Leu Ala
            115                 120                 125

Ser Tyr Val Arg Tyr Phe Asp Leu Asp Glu Ala Phe Trp Asp Lys Glu
130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
            195                 200                 205

Trp Arg Met Ser Gly Leu Phe Arg Ser Val Thr Leu Gln Ala Lys Pro
            210                 215                 220

Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Leu Gly Pro Ile Arg Ser Gln Leu Glu Phe Thr
            275                 280                 285

Leu Ala Asp Leu Pro Val Ala Ala Trp Ser Ala Glu Lys Pro Asn Leu
290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Ala Asn Arg His
                340                 345                 350

Glu Phe Asp Ser Lys Leu Gly Arg Ala Ile Thr Glu Glu Asp Met Ile
            355                 360                 365

Trp Asp Ile Lys Thr Met Lys Arg Ser Asn Ile Asn Ala Val Arg Cys
            370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
            420                 425                 430
```

-continued

```
Asp Gln His Trp Leu Gly Ala Ser Leu Ser Arg Val Lys Asn Met Met
            435                 440                 445
Ala Arg Asp Lys Asn His Ala Ser Ile Leu Ile Trp Ser Leu Gly Asn
450                 455                 460
Glu Ser Tyr Ala Gly Thr Val Phe Ala Gln Met Ala Asp Tyr Val Arg
465                 470                 475                 480
Lys Ala Asp Pro Thr Arg Val Gln His Tyr Glu Gly Val Thr His Asn
                485                 490                 495
Arg Lys Phe Asp Asp Ala Thr Gln Ile Glu Ser Arg Met Tyr Ala Pro
                500                 505                 510
Ala Lys Val Ile Glu Glu Tyr Leu Thr Asn Lys Pro Ala Lys Pro Phe
            515                 520                 525
Ile Ser Val Glu Tyr Ala His Ala Met Gly Asn Ser Val Gly Asp Leu
530                 535                 540
Ala Ala Tyr Thr Ala Leu Glu Lys Tyr Pro His Tyr Gln Gly Gly Phe
545                 550                 555                 560
Ile Trp Asp Trp Ile Asp Gln Gly Leu Glu Lys Asp Gly His Leu Leu
                565                 570                 575
Tyr Gly Gly Asp Phe Asp Asp Arg Pro Thr Asp Tyr Glu Phe Cys Gly
                580                 585                 590
Asn Gly Leu Val Phe Ala Asp Arg Thr Glu Ser Pro Lys Leu Ala Asn
            595                 600                 605
Val Lys Ala Leu Tyr Ala Asn Leu Lys Leu Glu Val Lys Asp Gly Gln
            610                 615                 620
Leu Phe Leu Lys Asn Asp Asn Leu Phe Thr Asn Ser Ser Ser Tyr Tyr
625                 630                 635                 640
Phe Leu Thr Ser Leu Leu Val Asp Gly Lys Leu Thr Tyr Gln Ser Arg
                645                 650                 655
Pro Leu Thr Phe Gly Leu Glu Pro Gly Glu Ser Gly Thr Phe Ala Leu
                660                 665                 670
Pro Trp Pro Glu Val Ala Asp Glu Lys Gly Glu Val Val Tyr Arg Val
            675                 680                 685
Thr Ala His Leu Lys Glu Asp Leu Pro Trp Ala Asp Glu Gly Phe Thr
690                 695                 700
Val Ala Glu Ala Glu Glu Val Ala Gln Lys Leu Pro Glu Phe Lys Pro
705                 710                 715                 720
Glu Gly Arg Pro Asp Leu Val Asp Ser Asp Tyr Asn Leu Gly Leu Lys
                725                 730                 735
Gly Asn Asn Phe Gln Ile Leu Phe Ser Lys Val Lys Gly Trp Pro Val
            740                 745                 750
Ser Leu Lys Tyr Ala Gly Arg Glu Tyr Leu Lys Arg Leu Pro Glu Phe
            755                 760                 765
Thr Phe Trp Arg Ala Leu Thr Asp Asn Asp Arg Gly Ala Gly Tyr Gly
            770                 775                 780
Tyr Asp Leu Ala Arg Trp Glu Asn Ala Gly Lys Tyr Ala Arg Leu Lys
785                 790                 795                 800
Asp Ile Ser Cys Glu Val Lys Glu Asp Ser Val Leu Val Lys Thr Ala
                805                 810                 815
Phe Thr Leu Pro Val Ala Leu Lys Gly Asp Leu Thr Val Thr Tyr Glu
                820                 825                 830
Val Asp Gly Arg Gly Lys Ile Ala Val Thr Ala Asp Phe Pro Gly Ala
            835                 840                 845
Glu Glu Ala Gly Leu Leu Pro Ala Phe Gly Leu Asn Leu Ala Leu Pro
```

```
            850                 855                 860
Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
                    885                 890                 895

Val Lys Lys Asn Phe Ser Pro Tyr Leu Arg Pro Gln Glu Thr Gly Asn
                900                 905                 910

Arg Ser Lys Val Arg Trp Tyr Gln Leu Phe Asp Glu Lys Gly Gly Leu
            915                 920                 925

Glu Phe Thr Ala Asn Gly Ala Asp Leu Asn Leu Ser Ala Leu Pro Tyr
        930                 935                 940

Ser Ala Ala Gln Ile Glu Ala Asp His Ala Phe Glu Leu Thr Asn
945                 950                 955                 960

Asn Tyr Thr Trp Val Arg Ala Leu Ser Ala Gln Met Gly Val Gly Gly
                    965                 970                 975

Asp Asp Ser Trp Gly Gln Lys Val His Pro Glu Phe Cys Leu Asp Ala
                980                 985                 990

Gln Lys Ala Arg Gln Leu Arg Leu  Val Ile Gln Pro Leu  Leu Leu Lys
            995                 1000                1005

<210> SEQ ID NO 16
<211> LENGTH: 1008
<212> TYPE: PRT
<213> ORGANISM: Lactobacillus delbrueckii

<400> SEQUENCE: 16

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
                20                  25                  30

His Ser Asp His Glu Ser Phe Gln Ser Gln Glu Glu Leu Glu Glu Gly
            35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Ile Gln Tyr Pro Trp Asp Gly
            100                 105                 110

Ser Glu Glu Ile Phe Pro Pro Gln Val Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Leu Ser Gly Leu Phe Arg Ser Val Thr Leu Gln Ala Lys Pro
    210                 215                 220
```

```
Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
            245                 250                 255

Pro Asn Ala Ser Phe Lys Leu Glu Val Arg Asp Ser Glu Gly Asp Leu
            260                 265                 270

Val Ala Glu Lys Leu Gly Pro Ile Arg Ser Glu Gln Leu Glu Phe Thr
            275                 280                 285

Leu Ala Asp Leu Pro Val Ala Ala Trp Ser Ala Glu Lys Pro Asn Leu
            290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
                340                 345                 350

Glu Phe Asp Ser Lys Leu Gly Arg Ala Ile Thr Glu Glu Asp Met Ile
            355                 360                 365

Trp Asp Ile Lys Thr Met Lys Arg Ser Asn Ile Asn Ala Val Arg Cys
370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly His Glu Asp Pro Ser Phe Asn Val Pro Gly Asp Asp
            420                 425                 430

Gln His Trp Leu Gly Ala Ser Leu Ser Arg Val Lys Asn Met Met Ala
            435                 440                 445

Arg Asp Lys Asn His Ala Ser Ile Leu Ile Trp Ser Leu Gly Asn Glu
            450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
            500                 505                 510

Lys Glu Ile Glu Glu Tyr Leu Thr Lys Lys Pro Ala Lys Pro Phe Ile
            515                 520                 525

Ser Val Glu Tyr Ala His Ala Met Gly Asn Ser Val Gly Asp Leu Ala
            530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Gly Asp Phe Asp Asp Arg Pro Thr Asp Tyr Glu Phe Cys Gly
            580                 585                 590

Asn Gly Leu Val Phe Ala Asp Arg Thr Thr Ser Pro Lys Leu Ala Asn
            595                 600                 605

Val Lys Ala Leu Tyr Ser Asn Leu Lys Leu Glu Val Lys Asp Gly Gln
            610                 615                 620

Leu Phe Leu Lys Asn Asp Asn Leu Phe Thr Asn Ser Ser Ala Tyr Tyr
625                 630                 635                 640

Phe Leu Thr Ser Leu Leu Val Asp Gly Lys Leu Thr Tyr Gln Ser Gln
```

```
                645                 650                 655
Pro Leu Thr Phe Gly Leu Glu Pro Gly Glu Ser Gly Thr Phe Val Leu
            660                 665                 670

Pro Trp Pro Glu Val Glu Asp Glu Lys Gly Glu Ile Val Tyr Gln Val
        675                 680                 685

Thr Ala His Leu Lys Glu Asp Leu Pro Trp Ala Asp Glu Gly Phe Thr
    690                 695                 700

Val Ala Glu Ala Glu Ala Val Thr Lys Leu Pro Glu Phe Tyr Pro
705                 710                 715                 720

Ala Gly Arg Pro Glu Leu Val Asp Ser Asp Phe Asn Leu Gly Leu Lys
                725                 730                 735

Gly Asn Gly Phe Arg Ile Leu Phe Ser Lys Ala Lys Gly Trp Pro Val
            740                 745                 750

Ser Ile Lys Tyr Ala Gly Arg Glu Tyr Leu Lys Arg Leu Pro Glu Phe
        755                 760                 765

Thr Phe Trp Arg Ala Leu Thr Asp Asn Asp Arg Gly Ala Gly Tyr Gly
    770                 775                 780

Tyr Asp Leu Ala Lys Trp Glu Asn Ala Gly Lys Tyr Ala Arg Leu Gln
785                 790                 795                 800

Asp Ile Ser Tyr Glu Ile Lys Glu Asn Ser Val Leu Val Lys Thr Ala
                805                 810                 815

Phe Thr Leu Pro Val Ala Leu Lys Gly Asp Leu Thr Ile Thr Tyr Glu
            820                 825                 830

Val Asp Ser Leu Gly Lys Ile Ala Val Thr Ala Asn Phe Pro Gly Ala
        835                 840                 845

Val Glu Asn Gly Leu Leu Pro Ala Phe Gly Leu Asn Phe Ala Leu Pro
    850                 855                 860

Lys Glu Leu Ser Asp Tyr Arg Tyr Tyr Gly Leu Gly Pro Asn Glu Ser
865                 870                 875                 880

Tyr Ala Asp Arg Leu Glu Gly Ser Tyr Leu Gly Ile Tyr Gln Gly Ala
                885                 890                 895

Val Glu Lys Asn Phe Thr Pro Tyr Leu Arg Pro Gln Glu Ala Gly Asn
            900                 905                 910

Arg Ser Lys Val Arg Tyr Tyr Gln Leu Phe Asp Glu Glu Ser Gly Leu
        915                 920                 925

Glu Phe Thr Ala Asn Gly Ala Asp Leu Asn Leu Ser Ala Leu Pro Tyr
    930                 935                 940

Ser Ala Ala Gln Ile Glu Ala Asp His Ala Phe Glu Leu Ser Asn
945                 950                 955                 960

Asn Tyr Thr Trp Val Arg Ala Leu Ala Ala Gln Met Gly Val Gly Gly
                965                 970                 975

Asp Asp Ser Trp Gly Gln Lys Val His Pro Glu Phe Cys Leu Asp Ala
            980                 985                 990

Gln Glu Ala Arg Gln Leu Lys Leu Val Ile Gln Pro Leu Leu Leu Lys
        995                 1000                1005

<210> SEQ ID NO 17
<211> LENGTH: 1008
<212> TYPE: PRT
<213> ORGANISM: Lactobacillus delbrueckii

<400> SEQUENCE: 17

Met Ser Asn Lys Leu Val Lys Glu Lys Arg Val Asp Gln Ala Asp Leu
1               5                   10                  15
```

```
Ala Trp Leu Thr Asp Pro Glu Val Tyr Glu Val Asn Thr Ile Pro Pro
             20                  25                  30

His Ser Asp His Glu Ser Phe Gln Ser Gln Glu Leu Glu Gly
         35                  40                  45

Lys Ser Ser Leu Val Gln Ser Leu Asp Gly Asp Trp Leu Ile Asp Tyr
         50                  55                  60

Ala Glu Asn Gly Gln Gly Pro Val Asn Phe Tyr Ala Glu Asp Phe Asp
 65              70                  75                  80

Asp Ser Asn Phe Lys Ser Val Lys Val Pro Gly Asn Leu Glu Leu Gln
                 85                  90                  95

Gly Phe Gly Gln Pro Gln Tyr Val Asn Val Gln Tyr Pro Trp Asp Gly
            100                 105                 110

Ser Glu Glu Ile Phe Pro Pro Gln Ile Pro Ser Lys Asn Pro Leu Ala
            115                 120                 125

Ser Tyr Val Arg Tyr Phe Asp Leu Asp Glu Ala Phe Trp Asp Lys Glu
        130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Met Ser Gly Leu Phe Arg Ser Val Thr Leu Gln Ala Lys Pro
210                 215                 220

Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Leu Gly Pro Ile Arg Ser Glu Gln Leu Glu Phe Thr
            275                 280                 285

Leu Ala Asp Leu Pro Val Ala Ala Trp Ser Ala Glu Lys Pro Asn Leu
290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
            340                 345                 350

Glu Phe Asp Ser Lys Leu Gly Arg Ala Ile Thr Glu Glu Asp Met Ile
        355                 360                 365

Trp Asp Ile Lys Thr Ile Lys Arg Ser Asn Ile Asn Ala Val Arg Cys
        370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
            420                 425                 430

Asp Gln His Trp Leu Gly Ala Ser Leu Ser Arg Val Lys Asn Met Met
```

-continued

```
                435                 440                 445
Ala Arg Asp Lys Asn His Ala Ser Ile Leu Ile Trp Ser Leu Gly Asn
450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
                500                 505                 510

Ala Lys Val Ile Glu Glu Tyr Leu Thr Asn Lys Pro Ala Lys Pro Phe
515                 520                 525

Ile Ser Val Glu Tyr Ala His Ala Met Gly Asn Ser Val Gly Asp Leu
530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
                565                 570                 575

Tyr Gly Gly Asp Phe Asp Asp Arg Pro Thr Asp Tyr Glu Phe Cys Gly
                580                 585                 590

Asn Gly Leu Val Phe Ala Asp Arg Thr Glu Ser Pro Lys Leu Ala Asn
                595                 600                 605

Val Lys Ala Leu Tyr Ala Asn Leu Lys Leu Glu Val Lys Asp Gly Gln
610                 615                 620

Leu Phe Leu Lys Asn Asp Asn Leu Phe Thr Asn Ser Ser Ser Tyr Tyr
625                 630                 635                 640

Phe Leu Thr Ser Leu Leu Val Asp Gly Lys Leu Thr Tyr Gln Ser Arg
                645                 650                 655

Pro Leu Thr Phe Gly Leu Glu Pro Gly Glu Ser Gly Thr Phe Ala Leu
                660                 665                 670

Pro Trp Pro Glu Val Ala Asp Glu Lys Gly Glu Val Val Tyr Arg Val
                675                 680                 685

Thr Ala His Leu Lys Glu Asp Leu Pro Trp Ala Asp Glu Gly Phe Thr
690                 695                 700

Val Ala Glu Ala Glu Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
                725                 730                 735

Gly Asn Asn Phe Gln Ile Leu Phe Ser Lys Val Lys Gly Trp Pro Val
                740                 745                 750

Ser Leu Lys Tyr Ala Gly Arg Glu Tyr Leu Lys Arg Leu Pro Glu Phe
                755                 760                 765

Thr Phe Trp Arg Ala Leu Thr Asp Asn Asp Arg Gly Ala Gly Tyr Gly
                770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
                805                 810                 815

Phe Thr Leu Pro Val Ala Leu Lys Gly Asp Leu Thr Val Thr Tyr Glu
                820                 825                 830

Val Asp Gly Arg Gly Lys Ile Ala Val Thr Ala Asp Phe Pro Gly Ala
                835                 840                 845

Glu Glu Ala Gly Leu Leu Pro Ala Phe Gly Leu Asn Leu Ala Leu Pro
850                 855                 860
```

```
Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
            885                 890                 895

Val Lys Lys Asn Phe Ser Pro Tyr Leu Arg Pro Gln Glu Thr Gly Asn
        900                 905                 910

Arg Ser Lys Val Arg Trp Tyr Gln Leu Phe Asp Glu Lys Gly Gly Leu
            915                 920                 925

Glu Phe Thr Ala Asn Gly Ala Asp Leu Asn Leu Ser Ala Leu Pro Tyr
        930                 935                 940

Ser Ala Ala Gln Ile Glu Ala Ala Asp His Ala Phe Asp Leu Thr Asn
945                 950                 955                 960

Asn Tyr Thr Trp Val Arg Ala Leu Ser Ala Gln Met Gly Val Gly Gly
            965                 970                 975

Asp Asp Ser Trp Gly Gln Lys Val His Pro Glu Phe Cys Leu Asp Ala
            980                 985                 990

Gln Lys Ala Arg Gln Leu Arg Leu Val Ile Gln Pro Leu Leu Leu Lys
            995                 1000                1005

<210> SEQ ID NO 18
<211> LENGTH: 1008
<212> TYPE: PRT
<213> ORGANISM: Lactobacillus delbrueckii

<400> SEQUENCE: 18

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
            100                 105                 110

Ser Glu Glu Ile Phe Pro Pro Gln Ile Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Met Ser Gly Leu Phe Arg Ser Val Thr Leu Gln Ala Lys Pro
    210                 215                 220

Arg Leu His Leu Glu Asp Leu Lys Leu Thr Ala Ser Leu Thr Asp Asn
```

```
            225                 230                 235                 240
        Tyr Gln Lys Gly Lys Leu Glu Val Glu Ala Asn Ile Ala Tyr Arg Leu
                        245                 250                 255

Pro Asn Ala Ser Phe Lys Leu Glu Val Arg Asp Ser Glu Gly Asp Leu
                        260                 265                 270

Val Ala Glu Lys Leu Gly Pro Ile Gly Ser Glu Gln Leu Glu Phe Thr
                        275                 280                 285

Leu Ala Asp Leu Pro Val Ala Ala Trp Ser Ala Glu Lys Pro Asn Leu
                        290                 295                 300

Tyr Gln Val Arg Leu Tyr Leu Tyr Gln Ala Gly Ser Leu Leu Glu Val
        305                 310                 315                 320

Ser Arg Gln Glu Val Gly Phe Arg Asn Phe Glu Leu Lys Asp Gly Ile
                        325                 330                 335

Met Tyr Leu Asn Gly Gln Arg Ile Val Phe Lys Gly Val Asn Arg His
                        340                 345                 350

Glu Phe Asp Ser Lys Leu Gly Arg Ala Ile Thr Glu Glu Asp Met Ile
                        355                 360                 365

Trp Asp Ile Lys Thr Ile Lys Arg Ser Asn Ile Asn Ala Val Arg Cys
        370                 375                 380

Ser His Tyr Pro Asn Gln Ser Leu Phe Tyr Arg Leu Cys Asp Lys Tyr
        385                 390                 395                 400

Gly Leu Tyr Val Ile Asp Glu Ala Asn Leu Glu Ser His Gly Thr Trp
                        405                 410                 415

Glu Lys Val Gly Gly His Glu Asp Pro Ser Phe Asn Val Pro Gly Asp
                        420                 425                 430

Asp Gln His Trp Leu Gly Ala Ser Leu Ser Arg Val Lys Asn Met Met
                        435                 440                 445

Ala Arg Asp Lys Asn His Ala Ser Ile Leu Ile Trp Ser Leu Gly Asn
                        450                 455                 460

Glu Ser Tyr Ala Gly Thr Val Phe Ala Gln Met Ala Asp Tyr Val Arg
        465                 470                 475                 480

Lys Ala Asp Pro Thr Arg Val Gln His Tyr Glu Gly Val Thr His Asn
                        485                 490                 495

Arg Lys Phe Asp Asp Ala Thr Gln Ile Glu Ser Arg Met Tyr Ala Pro
                        500                 505                 510

Ala Lys Val Ile Glu Glu Tyr Leu Thr Asn Lys Pro Ala Lys Pro Phe
                        515                 520                 525

Ile Ser Val Glu Tyr Ala His Ala Met Gly Asn Ser Val Gly Asp Leu
                        530                 535                 540

Ala Ala Tyr Thr Ala Leu Glu Lys Tyr Pro His Tyr Gln Gly Gly Phe
        545                 550                 555                 560

Ile Trp Asp Trp Ile Asp Gln Gly Leu Glu Lys Asp Gly His Leu Leu
                        565                 570                 575

Tyr Gly Gly Asp Phe Asp Asp Arg Pro Thr Asp Tyr Glu Phe Cys Gly
                        580                 585                 590

Asn Gly Leu Val Phe Ala Asp Arg Thr Glu Ser Pro Lys Leu Ala Asn
                        595                 600                 605

Val Lys Ala Leu Tyr Ala Asn Leu Lys Leu Glu Val Lys Asp Gly Gln
                        610                 615                 620

Leu Phe Leu Lys Asn Asp Asn Leu Phe Thr Asn Ser Ser Ser Tyr Tyr
        625                 630                 635                 640

Phe Leu Thr Ser Leu Leu Val Asp Gly Lys Leu Thr Tyr Gln Ser Arg
                        645                 650                 655
```

Pro Leu Thr Phe Gly Leu Glu Pro Gly Glu Ser Gly Thr Phe Ala Leu
            660                 665                 670

Pro Trp Pro Glu Val Ala Asp Glu Lys Gly Glu Val Val Tyr Arg Val
            675                 680                 685

Thr Ala His Leu Lys Glu Asp Leu Pro Trp Ala Asp Glu Gly Phe Thr
690                 695                 700

Val Ala Glu Ala Glu Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
                725                 730                 735

Gly Asn Asn Phe Gln Ile Leu Phe Ser Lys Val Lys Gly Trp Pro Val
            740                 745                 750

Ser Leu Lys Tyr Ala Gly Arg Glu Tyr Leu Lys Arg Leu Pro Glu Phe
            755                 760                 765

Thr Phe Trp Arg Ala Leu Thr Asp Asn Asp Arg Gly Ala Gly Tyr Gly
            770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
                805                 810                 815

Phe Thr Leu Pro Val Ala Leu Lys Gly Asp Leu Thr Val Thr Tyr Glu
            820                 825                 830

Val Asp Gly Arg Gly Lys Ile Ala Val Thr Ala Asp Phe Pro Gly Ala
            835                 840                 845

Glu Glu Ala Gly Leu Leu Pro Ala Phe Gly Leu Asn Leu Ala Leu Pro
850                 855                 860

Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
                885                 890                 895

Val Lys Lys Asn Phe Ser Pro Tyr Leu Arg Pro Gln Glu Thr Gly Asn
            900                 905                 910

Arg Ser Lys Val Arg Trp Tyr Gln Leu Phe Asp Glu Lys Gly Gly Leu
            915                 920                 925

Glu Phe Thr Ala Asn Gly Ala Asp Leu Asn Leu Ser Ala Leu Pro Tyr
930                 935                 940

Ser Ala Ala Gln Ile Glu Ala Asp His Ala Phe Glu Leu Thr Asn
945                 950                 955                 960

Asn Tyr Thr Trp Val Arg Ala Leu Ser Ala Gln Met Gly Val Gly Gly
                965                 970                 975

Asp Asp Ser Trp Gly Gln Lys Val His Pro Glu Phe Cys Leu Asp Ala
            980                 985                 990

Gln Lys Ala Arg Gln Leu Arg Leu Val Ile Gln Pro Leu Leu Leu Lys
            995                 1000                1005

<210> SEQ ID NO 19
<211> LENGTH: 1007
<212> TYPE: PRT
<213> ORGANISM: Lactobacillus delbrueckii

<400> SEQUENCE: 19

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro

```
            20                  25                  30
His Ser Asp His Glu Ser Phe Gln Ser Gln Glu Glu Leu Glu Glu Gly
            35                  40                  45

Lys Ser Ser Leu Val Gln Ser Leu Asp Gly Asn Trp Leu Ile Asp Tyr
 50                  55                  60

Ala Glu Asn Gly Gln Gly Pro Ile Asn Phe Tyr Ala Glu Asp Phe Asp
 65                  70                  75                  80

Asp Ser Asn Phe Lys Ser Val Lys Val Pro Gly Asn Leu Glu Leu Gln
                 85                  90                  95

Gly Phe Gly Gln Pro Gln Tyr Val Asn Ile Gln Tyr Pro Trp Asp Gly
                100                 105                 110

Ser Glu Glu Ile Phe Pro Pro Gln Val Pro Ser Lys Asn Pro Leu Ala
                115                 120                 125

Ser Tyr Val Arg Tyr Phe Asp Leu Asp Glu Ala Leu Trp Asp Lys Glu
                130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Gly Asn Arg Leu Ala Val
                180                 185                 190

Ala Leu Tyr Lys Tyr Ser Ser Ala Ser Trp Leu Glu Asp Gln Asp Phe
                195                 200                 205

Trp Arg Leu Ser Gly Leu Phe Arg Ser Val Thr Leu Glu Ala Lys Pro
                210                 215                 220

Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Val Gly Pro Ile Arg Ser Glu Lys Leu Asp Phe Ser
                275                 280                 285

Leu Ala Asp Leu Pro Val Ala Ala Trp Ser Ala Glu Lys Pro Asn Leu
                290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
                340                 345                 350

Glu Phe Asp Ser Lys Leu Gly Arg Ala Ile Thr Glu Ala Asp Met Ile
                355                 360                 365

Trp Asp Ile Lys Thr Met Lys Gln Ser Asn Ile Asn Ala Val Arg Cys
                370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly His Glu Asp Pro Ser Phe Asn Val Pro Gly Asp Asp
                420                 425                 430

Gln His Trp Leu Gly Ala Ser Leu Ser Arg Val Lys Asn Met Met Ala
                435                 440                 445
```

-continued

Arg Asp Lys Asn His Ala Ser Ile Leu Ile Trp Ser Leu Gly Asn Glu
450                     455                     460

Ser Tyr Ala Gly Thr Val Phe Ala Gln Met Ala Asp Tyr Val Arg Lys
465                     470                     475                     480

Ala Asp Pro Thr Arg Val Gln His Tyr Glu Gly Val Thr His Asn Arg
                485                     490                     495

Lys Phe Asp Asp Ala Thr Gln Ile Glu Ser Arg Met Tyr Ala Pro Ala
                500                     505                     510

Lys Glu Ile Glu Glu Tyr Leu Thr Lys Lys Pro Ala Lys Pro Phe Ile
            515                     520                     525

Ser Val Glu Tyr Ala His Ala Met Gly Asn Ser Val Gly Asp Leu Ala
        530                     535                     540

Ala Tyr Thr Ala Leu Glu Lys Tyr Pro His Tyr Gln Gly Gly Phe Ile
545                     550                     555                     560

Trp Asp Trp Ile Asp Gln Gly Leu Glu Lys Asp Gly His Leu Leu Tyr
                565                     570                     575

Gly Gly Asp Phe Asp Asp Arg Pro Thr Asp Tyr Glu Phe Cys Gly Asp
                580                     585                     590

Gly Leu Val Phe Ala Asp Arg Thr Thr Ser Pro Lys Leu Ala Asn Val
        595                     600                     605

Lys Ala Leu Tyr Ser Asn Leu Lys Leu Glu Val Lys Asp Gly Gln Leu
610                     615                     620

Phe Ile Lys Asn Asp Asn Leu Phe Thr Asn Ser Ser Ala Tyr Tyr Phe
625                     630                     635                     640

Leu Thr Ser Leu Leu Val Asp Gly Lys Leu Thr Tyr Gln Ser Gln Pro
                645                     650                     655

Leu Thr Phe Gly Leu Glu Pro Gly Glu Ser Gly Thr Phe Ala Leu Pro
                660                     665                     670

Trp Pro Glu Val Glu Asp Glu Lys Gly Glu Ile Val Tyr Gln Val Thr
            675                     680                     685

Ala His Leu Lys Glu Asp Leu Pro Trp Ala Asp Glu Gly Phe Thr Val
        690                     695                     700

Ala Glu Ala Glu Glu Ala Val Thr Lys Leu Pro Glu Phe Tyr Pro Ala
705                     710                     715                     720

Gly Arg Pro Glu Leu Val Asp Ser Asp Phe Asn Leu Gly Leu Lys Gly
                725                     730                     735

Asn Gly Phe Arg Ile Leu Phe Ser Lys Ala Lys Gly Trp Pro Val Ser
                740                     745                     750

Ile Lys Tyr Ala Gly Arg Glu Tyr Leu Lys Arg Leu Pro Glu Phe Thr
            755                     760                     765

Phe Trp Arg Ala Leu Thr Asp Asn Asp Arg Gly Ala Gly Tyr Gly Tyr
        770                     775                     780

Asp Leu Ala Lys Trp Glu Asn Ala Gly Lys Tyr Ala Arg Leu Gln Asp
785                     790                     795                     800

Ile Ser Tyr Glu Ile Lys Glu Asn Ser Ala Leu Val Lys Thr Ala Phe
                805                     810                     815

Thr Leu Pro Val Ala Leu Lys Gly Asp Leu Thr Ile Thr Tyr Glu Val
                820                     825                     830

Asp Ser Leu Gly Lys Ile Ala Val Thr Ala Asn Phe Pro Gly Ala Val
            835                     840                     845

Glu Asn Gly Leu Leu Pro Ala Phe Gly Leu Asn Phe Ala Leu Pro Lys
850                     855                     860

Glu Leu Ser Asp Tyr Arg Tyr Tyr Gly Leu Gly Pro Asn Glu Ser Tyr
865                 870                 875                 880

Ala Asp Arg Leu Glu Gly Ser Tyr Leu Gly Ile Tyr Gln Gly Met Val
            885                 890                 895

Glu Lys Asn Phe Thr Pro Tyr Leu Arg Pro Gln Glu Ala Gly Asn Arg
            900                 905                 910

Ser Lys Val Arg Tyr Tyr Gln Leu Phe Asp Glu Glu Gly Gly Leu Glu
            915                 920                 925

Phe Thr Ala Asn Gly Ala Asp Leu Asn Leu Ser Ala Leu Pro Tyr Ser
            930                 935                 940

Ala Ala Gln Ile Glu Ala Ala Asp His Ala Phe Glu Leu Thr Asn Asn
945                 950                 955                 960

Tyr Thr Trp Val Arg Ala Leu Ala Ala Gln Met Gly Val Gly Gly Asp
            965                 970                 975

Asp Ser Trp Gly Gln Lys Val His Pro Glu Phe Cys Leu Asp Ala Gln
            980                 985                 990

Glu Ala Arg Gln Leu Lys Leu Val Ile Gln Pro Leu Leu Leu Lys
            995                 1000                1005

<210> SEQ ID NO 20
<211> LENGTH: 628
<212> TYPE: PRT
<213> ORGANISM: Lactobacillus helveticus

<400> SEQUENCE: 20

Met Gln Ala Asn Ile Asn Trp Leu Asp Asn Pro Glu Val Phe Arg Val
1               5                   10                  15

Asn Gln Leu Pro Ala His Ser Asp His Pro Phe Phe Arg Asp Tyr Arg
            20                  25                  30

Glu Trp Gln Lys Gln His Ser Ser Tyr Gln Gln Ser Leu Asn Gly Lys
            35                  40                  45

Trp Lys Phe His Phe Ser Ala Asn Pro Met Asp Arg Pro Gln Asp Phe
        50                  55                  60

Tyr Gln Arg Asp Phe Asp Ser Ser Asn Phe Asp Ser Ile Pro Val Pro
65                  70                  75                  80

Ser Glu Ile Glu Leu Ser Asn Tyr Thr Gln Asn Gln Tyr Ile Asn Val
                85                  90                  95

Leu Phe Pro Trp Glu Gly Lys Ile Phe Arg Arg Pro Ala Tyr Ala Leu
            100                 105                 110

Asp Pro Asn Asp His Glu Glu Gly Ser Phe Ser Lys Gly Ala Asp Asn
            115                 120                 125

Thr Val Gly Ser Tyr Leu Lys Arg Phe Asp Leu Ser Ser Ala Leu Ile
        130                 135                 140

Gly Lys Asp Val His Ile Lys Phe Glu Gly Val Glu Gln Ala Met Tyr
145                 150                 155                 160

Val Trp Leu Asn Gly His Phe Val Gly Tyr Ala Glu Asp Ser Phe Thr
                165                 170                 175

Pro Ser Glu Phe Asp Leu Thr Pro Tyr Ile Gln Asp Lys Asp Asn Leu
            180                 185                 190

Leu Ala Val Glu Val Phe Lys Ser Thr Ala Ser Trp Leu Glu Asp
            195                 200                 205

Gln Asp Met Phe Arg Phe Ser Gly Ile Phe Arg Ser Val Glu Leu Leu
        210                 215                 220

Gly Ile Pro Ala Thr His Leu Met Asp Met Asp Leu Lys Pro Arg Val
225                 230                 235                 240

```
Ala Asp Asn Tyr Gln Asp Gly Ile Phe Asn Leu Lys Leu His Phe Ile
            245                 250                 255

Gly Lys Lys Ala Gly Ser Phe His Leu Leu Val Lys Asp Ile Lys Gly
            260                 265                 270

His Thr Leu Leu Glu Lys Asn Glu Asp Ile Lys Glu Asn Val Gln Ile
            275                 280                 285

Asn Asn Glu Lys Phe Glu Asn Val His Leu Trp Asn Asn His Asp Pro
    290                 295                 300

Tyr Leu Tyr Gln Leu Leu Ile Glu Val Tyr Asp Gln Gln Asn Leu
305                 310                 315                 320

Leu Glu Leu Ile Pro Phe Gln Phe Gly Phe Arg Arg Ile Glu Ile Ser
                325                 330                 335

Pro Glu Lys Val Val Leu Leu Asn Gly Lys Arg Leu Ile Ile Asn Gly
            340                 345                 350

Val Asn Arg His Glu Trp Asp Ala Lys Arg Gly Arg Ser Ile Thr Met
            355                 360                 365

Ser Asp Met Thr Thr Asp Ile Asn Thr Phe Lys Glu Asn Asn Ile Asn
    370                 375                 380

Ala Val Arg Thr Cys His Tyr Pro Asn Gln Ile Pro Trp Tyr Tyr Leu
385                 390                 395                 400

Cys Asp Gln Asn Gly Ile Tyr Val Met Ala Glu Asn Asn Leu Glu Ser
                405                 410                 415

His Gly Thr Trp Gln Lys Met Gly Glu Ile Glu Pro Ser Asp Asn Val
            420                 425                 430

Pro Gly Ser Ile Pro Gln Trp Lys Glu Ala Val Ile Asp Arg Ala Arg
            435                 440                 445

Asn Asn Tyr Glu Thr Phe Lys Asn His Thr Ser Ile Leu Phe Trp Ser
    450                 455                 460

Leu Gly Asn Glu Ser Tyr Ala Gly Asp Asn Ile Ile Ala Met Asn Glu
465                 470                 475                 480

Phe Tyr Lys Ser His Asp Asp Thr Arg Leu Val His Tyr Glu Gly Val
                485                 490                 495

Val His Arg Pro Glu Leu Lys Asp Lys Ile Ser Asp Val Glu Ser Cys
            500                 505                 510

Met Tyr Leu Pro Pro Lys Lys Val Glu Glu Tyr Leu Gln Asn Asp Pro
            515                 520                 525

Pro Lys Pro Phe Met Glu Cys Glu Tyr Met His Asp Met Gly Asn Ser
    530                 535                 540

Asp Gly Gly Met Gly Ser Tyr Ile Lys Leu Leu Asp Lys Tyr Pro Gln
545                 550                 555                 560

Tyr Phe Gly Gly Phe Ile Trp Asp Phe Ile Asp Gln Ala Leu Leu Val
                565                 570                 575

His Asp Glu Ile Ser Gly His Asp Val Leu Arg Tyr Gly Gly Asp Phe
            580                 585                 590

Asp Asp Arg His Ser Asp Tyr Glu Phe Ser Gly Asp Gly Leu Met Phe
    595                 600                 605

Ala Asp Arg Thr Pro Lys Pro Ala Met Gln Glu Val Arg Tyr Tyr Tyr
610                 615                 620

Gly Leu His Lys
625

<210> SEQ ID NO 21
<211> LENGTH: 318
```

<212> TYPE: PRT
<213> ORGANISM: Lactobacillus helveticus

<400> SEQUENCE: 21

Met Asp Tyr Thr Asn Asn Gln Leu His Ile Ile Tyr Gly Asp Ala Thr
1               5                   10                  15

Phe Gly Val Asn Gly Lys Asp Phe Gln Tyr Ile Phe Ser Tyr Glu Arg
            20                  25                  30

Gly Gly Leu Glu Ser Leu Lys Val His Gly Lys Glu Trp Leu Tyr Arg
        35                  40                  45

Val Pro Thr Pro Thr Phe Trp Arg Ala Thr Thr Asp Asn Asp Arg Gly
50                  55                  60

Ser Gly Phe Asn Leu Lys Ala Ala Gln Trp Leu Gly Ala Asp Met Phe
65                  70                  75                  80

Thr Lys Cys Thr Asp Ile His Leu Lys Val Asp Arg His Asp Phe Ala
                85                  90                  95

Glu Leu Pro Ile Ala Pro Phe Asn Asn Lys Phe Ser Asn His Glu Tyr
            100                 105                 110

Ala Lys Ser Ala Glu Ile Ser Phe Thr Tyr Gln Thr Leu Thr Thr Pro
        115                 120                 125

Ala Thr Asn Ala Lys Ile Ile Tyr Asn Ile Asp Asp Val Gly His Ile
130                 135                 140

Lys Val Thr Met Arg Tyr Tyr Gly Lys Lys Gly Leu Pro Pro Leu Pro
145                 150                 155                 160

Val Ile Gly Ile Arg Leu Ile Met Pro Thr Ala Ala Thr Gly Phe Asp
                165                 170                 175

Tyr Glu Gly Leu Ser Gly Glu Thr Tyr Pro Asp Arg Met Ala Gly Ala
            180                 185                 190

Lys Glu Gly Lys Phe His Ile Asp Gly Leu Pro Val Thr Glu Tyr Leu
        195                 200                 205

Val Pro Gln Glu Asn Gly Met His Met Gln Thr Lys Lys Leu Thr Ile
210                 215                 220

Asn Arg Glu Thr Thr Gln Asn Asn Val Asp Arg Thr Asn Glu Lys Phe
225                 230                 235                 240

Ser Leu Ser Ile Gln Gln Ala Glu Lys Pro Phe Asn Phe Ser Cys Leu
                245                 250                 255

Pro Tyr Thr Ala Glu Glu Leu Glu Asn Ala Thr His Ile Glu Glu Leu
            260                 265                 270

Pro Leu Val Arg Arg Thr Val Leu Val Ile Ala Gly Ala Val Arg Gly
        275                 280                 285

Val Gly Gly Ile Asp Ser Trp Gly Thr Asp Val Glu Ser Ala Tyr His
290                 295                 300

Ile Asn Pro Glu Leu Asp His Glu Phe Ser Phe Ile Leu Asn
305                 310                 315

<210> SEQ ID NO 22
<211> LENGTH: 1023
<212> TYPE: PRT
<213> ORGANISM: Bifidobacterium longum

<400> SEQUENCE: 22

Met Thr Asp Val Thr His Val Asp Arg Ala Ser Gln Ala Trp Leu Thr
1               5                   10                  15

Asp Pro Thr Val Phe Glu Val Asn Arg Thr Pro Ala His Ser Ser His
            20                  25                  30

```
Lys Trp Tyr Ala Arg Asp Pro Gln Ser Gly Gln Trp Ser Asp Leu Lys
             35                  40                  45

Gln Ser Leu Asp Gly Glu Trp Arg Val Glu Val Gln Ala Ala Asp
 50                  55                  60

Ile Asn Leu Glu Glu Glu Pro Ala Thr Ala Glu Ser Phe Asp Ser
 65                  70                  75                  80

Ser Phe Glu Arg Ile Gln Val Pro Gly His Leu Gln Thr Ala Gly Leu
                 85                  90                  95

Met Asn His Lys Tyr Val Asn Val Gln Tyr Pro Trp Asp Gly His Glu
                100                 105                 110

Asn Pro Leu Glu Pro Asn Ile Pro Glu Asn Asn His Val Ala Leu Tyr
                115                 120                 125

Arg Arg Lys Phe Thr Val Ser Ala Pro Val Ala Asn Ala Lys Gln Ala
130                 135                 140

Gly Gly Ser Val Ser Ile Val Phe His Gly Met Ala Thr Ala Ile Tyr
145                 150                 155                 160

Val Trp Val Asn Gly Ala Phe Val Gly Tyr Gly Glu Asp Gly Phe Thr
                165                 170                 175

Pro Asn Glu Phe Asp Ile Thr Glu Leu Leu His Asp Gly Glu Asn Val
                180                 185                 190

Val Ala Val Ala Cys Tyr Glu Tyr Ser Ser Ala Ser Trp Leu Glu Asp
                195                 200                 205

Gln Asp Phe Trp Arg Leu His Gly Leu Phe Arg Ser Val Glu Leu Ala
                210                 215                 220

Ala Arg Pro His Val His Ile Glu Asn Thr Gln Ile Glu Ala Asp Trp
225                 230                 235                 240

Asp Pro Glu Ala Gly Thr Ala Ser Leu Asp Ala Ala Leu Thr Val Leu
                245                 250                 255

Asn Ala Ala Asp Ala Ala Thr Val Arg Ala Thr Leu Lys Asp Ala Asp
                260                 265                 270

Gly Asn Thr Val Trp Gln Thr Gly Asp Ala Glu Ala Gln Thr Ala
                275                 280                 285

Ile Ser Ser Gly Pro Leu Gln Gly Ile Ala Pro Trp Ser Ala Glu Ser
290                 295                 300

Pro Thr Leu Tyr Glu Leu Asp Val Asp Val Ile Asp Gln Ala Gly Asp
305                 310                 315                 320

Val Ile Glu Cys Thr Ser Gln Lys Val Gly Phe Arg Phe Arg Ile
                325                 330                 335

Glu Asp Gly Ile Leu Thr Ile Asn Gly Lys Arg Ile Val Phe Lys Gly
                340                 345                 350

Ala Asp Arg His Glu Phe Asp Ala Glu Gln Gly Arg Ala Ile Thr Glu
                355                 360                 365

Gln Asp Met Ile Asp Asp Val Val Phe Cys Lys Arg His Asn Ile Asn
                370                 375                 380

Ser Ile Arg Thr Ser His Tyr Pro Asn Gln Glu Arg Trp Tyr Glu Leu
385                 390                 395                 400

Cys Asp Glu Tyr Gly Ile Tyr Leu Ile Asp Glu Ala Asn Leu Glu Ala
                405                 410                 415

His Gly Ser Trp Ser Leu Pro Gly Asp Val Leu Thr Glu Asp Thr Ile
                420                 425                 430

Val Pro Gly Ser Lys Arg Glu Trp Glu Gly Ala Cys Val Asp Arg Val
                435                 440                 445

Asn Ser Met Met Arg Arg Asp Tyr Asn His Pro Ser Val Leu Ile Trp
```

```
                450              455              460
Ser Leu Gly Asn Glu Ser Tyr Val Gly Asp Val Phe Arg Ala Met Tyr
465              470              475              480

Lys His Val His Asp Ile Asp Pro Asn Arg Pro Val His Tyr Glu Gly
                485              490              495

Val Thr His Asn Arg Asp Tyr Asp Val Thr Asp Ile Glu Thr Arg
                500              505              510

Met Tyr Ser His Ala Asp Glu Ile Glu Lys Tyr Leu Lys Asp Asp Pro
            515              520              525

Lys Lys Pro Tyr Leu Ser Cys Glu Tyr Met His Ala Met Gly Asn Ser
            530              535              540

Val Gly Asn Met Asp Glu Tyr Thr Ala Leu Glu Arg Tyr Pro Lys Tyr
545              550              555              560

Gln Gly Gly Phe Ile Trp Asp Phe Ile Asp Gln Ala Ile Tyr Ala Thr
                565              570              575

Gln Pro Asp Gly Thr Arg Ser Leu Arg Tyr Gly Gly Asp Phe Gly Asp
                580              585              590

Arg Pro Ser Asp Tyr Glu Phe Ser Gly Asp Gly Leu Leu Phe Ala Asn
                595              600              605

Arg Lys Pro Ser Pro Lys Ala Gln Glu Val Lys Gln Leu Tyr Ser Asn
            610              615              620

Val His Ile Asp Val Thr Lys Asp Ser Val Ser Val Lys Asn Asp Asn
625              630              635              640

Leu Phe Thr Ala Thr Gly Asp Tyr Val Phe Val Leu Ser Val Leu Ala
                645              650              655

Asp Gly Lys Pro Val Trp Gln Ser Thr Arg Arg Phe Asp Val Pro Ala
                660              665              670

Gly Glu Thr Arg Thr Phe Asp Val Ala Trp Pro Val Ala Ala Tyr Arg
                675              680              685

Ala Asp Ala Arg Glu Leu Val Leu Gln Val Ser Gln Arg Leu Ala Lys
            690              695              700

Ala Thr Asp Trp Ala Glu Ser Gly Tyr Glu Leu Ala Phe Gly Gln Thr
705              710              715              720

Val Val Pro Ala Asp Ala Thr Ala Thr Pro Asp Thr Lys Pro Ala Asp
                725              730              735

Gly Thr Ile Thr Val Gly Arg Trp Asn Ala Gly Val Arg Gly Ala Gly
                740              745              750

Arg Glu Val Leu Leu Ser Arg Thr Gln Gly Gly Met Val Ser Tyr Thr
            755              760              765

Phe Ala Gly Asn Glu Phe Val Leu Arg Arg Pro Ala Ile Thr Thr Phe
770              775              780

Arg Pro Leu Thr Asp Asn Asp Arg Gly Ala Gly His Gly Phe Glu Arg
785              790              795              800

Val Gln Trp Leu Gly Ala Gly Arg Tyr Ala Arg Cys Val Asp Asn Val
                805              810              815

Leu Glu Gln Ile Asp Asp Ser Thr Leu Lys Gly Thr Tyr Thr Tyr Glu
                820              825              830

Leu Ala Thr Ala Gln Arg Thr Lys Val Thr Val Ser Tyr Thr Ala His
            835              840              845

Thr Asp Gly Arg Val Asn Leu His Val Glu Tyr Pro Gly Glu Gln Gly
            850              855              860

Asp Leu Pro Thr Ile Pro Ala Phe Gly Ile Glu Trp Thr Leu Pro Val
865              870              875              880
```

-continued

```
Gln Tyr Thr Asn Leu Arg Phe Gly Thr Gly Pro Ala Glu Thr Tyr
                885                 890                 895

Leu Asp Arg Lys His Ala Lys Leu Gly Val Trp Ser Thr Asn Ala Phe
            900                 905                 910

Ala Asp His Ala Pro Tyr Leu Met Pro Gln Glu Thr Gly Asn His Glu
            915                 920                 925

Asp Val Arg Trp Ala Glu Ile Thr Asp Asp His Gly His Gly Met Arg
        930                 935                 940

Val Ser Arg Ala Asp Gly Ala Ala Pro Phe Ala Val Ser Leu Leu Pro
945                 950                 955                 960

Tyr Ser Ser Phe Met Leu Glu Glu Ala Gln His Gln Asp Glu Leu Pro
                965                 970                 975

Lys Pro Lys His Met Phe Leu Arg Val Leu Ala Ala Gln Met Gly Val
            980                 985                 990

Gly Gly Asp Asp Ser Trp Met Ser  Pro Val His Pro Gln  Tyr His Ile
            995                 1000                1005

Pro Ala  Asp Lys Pro Ile Ser  Leu Asp Val Asp Leu  Glu Leu Ile
    1010                1015                1020
```

<210> SEQ ID NO 23
<211> LENGTH: 628
<212> TYPE: PRT
<213> ORGANISM: Lactobacillus reuteri

<400> SEQUENCE: 23

```
Met Asp Ala Asp Ile Lys Trp Leu Asp Glu Pro Glu Thr Phe Arg Val
1               5                   10                  15

Asn Gln Leu Pro Ala His Ser Asp His Tyr Tyr Gly Asn Tyr Asp
                20                  25                  30

Glu Trp Arg His Asn Asn Ser Arg Phe Ala Gln Asn Leu Asp Gly Gln
            35                  40                  45

Trp Gln Phe Asn Phe Ala Glu Asn Leu Arg Glu Arg Glu Asn Asp Phe
        50                  55                  60

Tyr Lys Met Asp Tyr Asp Ser Ser Phe Gly Thr Ile Glu Val Pro
65                  70                  75                  80

Ser Glu Ile Glu Leu Asn Asn Tyr Ala Gln Asn Asn Tyr Ile Asn Thr
                85                  90                  95

Leu Ile Pro Trp Glu Gly Lys Ile Tyr Arg Arg Pro Ala Tyr Thr Leu
            100                 105                 110

Ser Pro Asp Asp Ala Gln Glu Gly Ser Phe Ser Asp Gly Asp Asn
        115                 120                 125

Thr Ile Gly Glu Tyr Leu Lys His Phe Asp Leu Asp Pro Ser Leu Arg
    130                 135                 140

Gly Lys Gln Val Arg Ile Arg Phe Asp Gly Val Glu Arg Ala Met Tyr
145                 150                 155                 160

Val Trp Leu Asn Gly His Phe Ile Gly Tyr Ala Glu Asp Ser Phe Thr
                165                 170                 175

Pro Ser Glu Phe Asp Leu Thr Pro Tyr Ile Gln Asp Glu Gly Asn Val
            180                 185                 190

Leu Ala Val Glu Val Phe Lys His Ser Thr Ala Ser Trp Ile Glu Asp
        195                 200                 205

Gln Asp Met Phe Arg Phe Ser Gly Ile Phe Arg Ser Val Asn Leu Leu
    210                 215                 220

Ala Gln Pro Leu Val His Val Glu Asp Leu Asn Ile Arg Pro Ile Val
```

```
            225                 230                 235                 240
        Thr Asp Asn Tyr Gln Asp Gly Ile Phe Asn Val Glu Leu Gln Leu His
                        245                 250                 255
        Gly Glu Lys Thr Gly Asn Val Asn Val Arg Val Ile Asp Asn Asp Gly
                        260                 265                 270
        Asn Thr Leu Val Asn Glu Thr His Pro Val Asp Ser Thr Val Lys Val
                        275                 280                 285
        Gln Asp Gln Phe Leu Glu Asn Val His Leu Trp Asp Asn His Asp Pro
                        290                 295                 300
        Tyr Leu Tyr Gln Leu Leu Ile Glu Ile Arg Asp Asp Glu Gly Asn Leu
        305                 310                 315                 320
        Val Glu Leu Val Pro Tyr Arg Phe Gly Phe Arg Ile Glu Ile Asn
                        325                 330                 335
        Lys Asp His Val Val Leu Leu Asn Gly Gln Arg Leu Ile Ile Asn Gly
                        340                 345                 350
        Val Asn Arg His Glu Trp Asp Ala Arg Arg Gly Arg Ala Ile Thr Met
                        355                 360                 365
        Asp Asp Met Thr Ser Asp Ile His Thr Phe Lys Glu Asn Asn Ile Asn
        370                 375                 380
        Ala Val Arg Thr Cys His Tyr Pro Asp Gln Ile Pro Trp Tyr Tyr Leu
        385                 390                 395                 400
        Cys Asp Asp Asn Gly Ile Tyr Met Met Ala Glu Asn Asn Leu Glu Ser
                        405                 410                 415
        His Ala Thr Trp Gln Lys Met Gly Ala Ile Glu Pro Ser Tyr Asn Val
                        420                 425                 430
        Pro Gly Ser Val Pro Gln Trp Arg Asp Val Val Asp Arg Ala Arg
                        435                 440                 445
        Thr Asn Tyr Glu Thr Phe Lys Asn His Pro Ser Ile Leu Phe Trp Ser
                        450                 455                 460
        Leu Gly Asn Glu Ser Tyr Ala Gly Asp Asn Ile Val Lys Met Asn Glu
        465                 470                 475                 480
        Phe Tyr Lys Lys His Asp Asp Ser Arg Leu Val His Tyr Glu Gly Val
                        485                 490                 495
        Cys His Thr Pro Glu Tyr Arg Asp Arg Ile Ser Asp Val Glu Ser Trp
                        500                 505                 510
        Met Tyr Leu Pro Pro Lys Glu Val Glu Glu Tyr Leu Lys Asn Asn Pro
                        515                 520                 525
        Asp Lys Pro Phe Met Glu Cys Glu Tyr Met His Asp Met Gly Asn Ser
                        530                 535                 540
        Asp Gly Gly Met Gly Ser Tyr Ile Ser Leu Leu Asp Lys Tyr Pro Gln
        545                 550                 555                 560
        Tyr Phe Gly Gly Phe Ile Trp Asp Phe Ile Asp Gln Ala Leu Leu Val
                        565                 570                 575
        Lys Asp Pro Val Ser Gly Gln Glu Val Met Arg Tyr Gly Gly Asp Phe
                        580                 585                 590
        Asp Asp Arg His Ser Asp Tyr Glu Phe Ser Gly Asp Gly Leu Met Phe
                        595                 600                 605
        Ala Asp Arg Thr Pro Lys Pro Ala Met Gln Glu Val Arg Tyr Tyr Tyr
        610                 615                 620
        Gly Leu His Lys
        625

<210> SEQ ID NO 24
```

<211> LENGTH: 319
<212> TYPE: PRT
<213> ORGANISM: Lactobacillus reuteri

<400> SEQUENCE: 24

```
Met Ala Tyr Thr Asn Lys Leu Arg Val Ile Tyr Gly Asp Ala Thr Leu
1               5                   10                  15
Gly Leu Ser Gly Asp Gly Phe His Tyr Ile Phe Ser Tyr Glu Arg Gly
            20                  25                  30
Gly Leu Glu Ser Leu Lys Leu Asn Gly Lys Glu Trp Leu Tyr Arg Glu
        35                  40                  45
Pro Met Pro Thr Phe Trp Arg Ala Thr Thr Asp Asn Asp Arg Gly Ser
50                  55                  60
Gly Phe Asn Ile Arg Ser Ala Gln Trp Leu Ala Ala Asp Thr Phe His
65                  70                  75                  80
Lys Cys Val Gly Ile Asp Leu Thr Val Asp Asn Gln His Phe Ala Glu
                85                  90                  95
Leu Pro Ile Ala Pro Ile Thr Asn Glu Phe Ser Asp Pro Val Ser Ala
            100                 105                 110
Glu Ser Val Lys Ile Lys Tyr Thr Phe Ala Thr Leu Thr Val Pro Ala
        115                 120                 125
Thr Gln Val Thr Val Ile Tyr Glu Val Asn Gly Gln Gly Glu Ile Lys
130                 135                 140
Val Thr Met His Tyr Tyr Gly His Glu Asp Leu Pro Gly Leu Pro Val
145                 150                 155                 160
Val Gly Met Arg Phe Ile Met Pro Thr Val Ala Thr Gly Phe Asp Tyr
                165                 170                 175
Gln Gly Leu Ser Gly Glu Thr Tyr Pro Asp Arg Met Ala Gly Ala Thr
            180                 185                 190
Glu Gly Thr Phe His Val Asp Gly Leu Pro Val Thr Lys Tyr Leu Val
        195                 200                 205
Pro Gln Glu Asn Gly Met His Met Ala Thr His Ala Leu Thr Ile Thr
210                 215                 220
Arg Asp Ser Thr Gln Asn Asn Ala Asp His Ser Arg Glu Pro Phe Ser
225                 230                 235                 240
Leu Thr Val Lys Gln Asp Ala Gln Pro Phe Ala Phe Ser Cys Leu Pro
                245                 250                 255
Tyr Thr Ala Glu Glu Leu Glu Asn Ala Thr His Ile Glu Glu Leu Pro
            260                 265                 270
Leu Ala Arg Arg Thr Val Leu Val Val Ala Gly Ala Val Arg Gly Val
        275                 280                 285
Gly Gly Ile Asp Ser Trp Gly Ala Asp Val Glu Glu Gln Tyr His Ile
290                 295                 300
Pro Ala Asp Arg Asp Val Glu Phe Ser Phe Val Leu Asn Ala Lys
305                 310                 315
```

<210> SEQ ID NO 25
<211> LENGTH: 1007
<212> TYPE: PRT
<213> ORGANISM: Lactobacillus delbrueckii

<400> SEQUENCE: 25

```
Met Ser Asn Lys Leu Val Lys Glu Lys Arg Val Asp Gln Ala Asp Leu
1               5                   10                  15
Ala Trp Leu Thr Asp Pro Glu Val Tyr Glu Val Asn Thr Ile Pro Pro
            20                  25                  30
```

```
His Ser Asp His Glu Ser Phe Gln Ser Gln Glu Glu Leu Glu Glu Gly
         35                  40                  45

Lys Ser Ser Leu Val Gln Ser Leu Asp Gly Asn Trp Leu Ile Asp Tyr
 50                  55                  60

Ala Glu Asn Gly Gln Gly Pro Ile Asn Phe Tyr Ala Glu Asp Phe Asp
 65                  70                  75                  80

Asp Ser Asn Phe Lys Ser Val Lys Val Pro Gly Asn Leu Glu Leu Gln
                 85                  90                  95

Gly Phe Gly Gln Pro Gln Tyr Val Asn Ile Gln Tyr Pro Trp Asp Gly
                100                 105                 110

Ser Glu Glu Ile Phe Pro Pro Gln Val Pro Ser Lys Ile Pro Leu Ala
                115                 120                 125

Ser Tyr Val Arg Tyr Phe Asp Leu Asp Glu Ala Leu Trp Asp Lys Glu
        130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Gly Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Leu Ser Gly Leu Phe Arg Ser Val Thr Leu Glu Ala Lys Pro
        210                 215                 220

Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Val Gly Pro Ile Arg Ser Glu Lys Leu Asp Phe Ser
            275                 280                 285

Leu Ala Asp Leu Pro Val Ala Ala Trp Ser Ala Glu Lys Pro Asn Leu
        290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
                340                 345                 350

Glu Phe Asp Ser Lys Leu Gly Arg Ala Ile Thr Glu Ala Asp Met Ile
            355                 360                 365

Trp Asp Ile Lys Thr Met Lys Gln Ser Asn Ile Asn Ala Val Arg Cys
        370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly His Glu Asp Pro Ser Phe Asn Val Pro Gly Asp Asp
            420                 425                 430

Gln His Trp Leu Gly Ala Ser Leu Ser Arg Val Lys Asn Met Met Ala
        435                 440                 445
```

Arg Asp Lys Asn His Ala Ser Ile Leu Ile Trp Ser Leu Gly Asn Glu
450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
            500                 505                 510

Lys Glu Ile Glu Glu Tyr Leu Thr Lys Lys Pro Ala Lys Pro Phe Ile
        515                 520                 525

Ser Val Glu Tyr Ala His Ala Met Gly Asn Ser Val Gly Asp Leu Ala
530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Asp Phe Asp Asp Arg Pro Thr Asp Tyr Glu Phe Cys Gly Asp
            580                 585                 590

Gly Leu Val Phe Ala Asp Arg Thr Thr Ser Pro Lys Leu Ala Asn Val
        595                 600                 605

Lys Ala Leu Tyr Ser Asn Leu Lys Leu Glu Val Lys Asp Gly Gln Leu
610                 615                 620

Phe Ile Lys Asn Asp Asn Leu Phe Thr Asn Ser Ser Ala Tyr Tyr Phe
625                 630                 635                 640

Leu Thr Ser Leu Leu Val Asp Gly Lys Leu Thr Tyr Gln Ser Gln Pro
                645                 650                 655

Leu Thr Phe Gly Leu Glu Pro Gly Glu Ser Gly Thr Phe Ala Leu Pro
            660                 665                 670

Trp Pro Glu Val Glu Asp Glu Lys Gly Glu Ile Val Tyr Gln Val Thr
        675                 680                 685

Ala His Leu Lys Glu Asp Leu Pro Trp Ala Asp Glu Gly Phe Thr Val
690                 695                 700

Ala Glu Ala Glu Glu Ala Val Thr Lys Leu Pro Glu Phe Tyr Pro Ala
705                 710                 715                 720

Gly Arg Pro Glu Leu Val Asp Ser Asp Phe Asn Leu Gly Leu Lys Gly
                725                 730                 735

Asn Gly Phe Arg Ile Leu Phe Ser Lys Ala Lys Gly Trp Pro Val Ser
            740                 745                 750

Ile Lys Tyr Ala Gly Arg Glu Tyr Leu Lys Arg Leu Pro Glu Phe Thr
        755                 760                 765

Phe Trp Arg Ala Leu Thr Asp Asn Asp Arg Gly Ala Gly Tyr Gly Tyr
770                 775                 780

Asp Leu Ala Lys Trp Glu Asn Ala Gly Lys Tyr Ala Arg Leu Gln Asp
785                 790                 795                 800

Ile Ser Tyr Glu Ile Lys Glu Asn Ser Ala Leu Val Lys Thr Thr Phe
                805                 810                 815

Thr Leu Pro Val Ala Leu Lys Gly Asp Leu Thr Ile Thr Tyr Glu Val
            820                 825                 830

Asp Ser Leu Gly Lys Ile Ala Val Thr Ala Asn Phe Pro Gly Ala Val
        835                 840                 845

Glu Asn Gly Leu Leu Pro Ala Phe Gly Leu Asn Phe Ala Leu Pro Lys
850                 855                 860

Glu Leu Ser Asp Tyr Arg Tyr Tyr Gly Leu Gly Pro Asn Glu Ser Tyr

```
865                 870                 875                 880
Ala Asp Arg Leu Glu Gly Ser Tyr Leu Gly Ile Tyr Gln Gly Met Val
                885                 890                 895

Glu Lys Asn Phe Thr Pro Tyr Leu Arg Pro Gln Glu Ala Gly Asn Arg
                900                 905                 910

Ser Lys Val Arg Tyr Tyr Gln Leu Phe Asp Glu Glu Gly Gly Leu Glu
                915                 920                 925

Phe Thr Ala Asn Gly Ala Asp Leu Asn Leu Ser Ala Leu Pro Tyr Ser
                930                 935                 940

Ala Ala Gln Ile Glu Ala Ala Asp His Ala Phe Glu Leu Thr Asn Asn
945                 950                 955                 960

Tyr Thr Trp Val Arg Ala Leu Ala Ala Gln Met Gly Val Gly Gly Asp
                965                 970                 975

Asp Ser Trp Gly Gln Lys Val His Pro Glu Phe Cys Leu Asp Ala Gln
                980                 985                 990

Glu Ala Arg Gln Leu Lys Leu Val Ile Gln Pro Leu Leu Leu Lys
                995                1000                1005

<210> SEQ ID NO 26
<211> LENGTH: 628
<212> TYPE: PRT
<213> ORGANISM: Lactobacillus helveticus

<400> SEQUENCE: 26

Met Gln Ala Asn Ile Asn Trp Leu Asp Asn Pro Glu Val Phe Arg Val
1               5                   10                  15

Asn Gln Leu Pro Ala His Ser Asp His Pro Phe Phe Arg Asp Tyr Arg
                20                  25                  30

Glu Trp Gln Lys Gln His Ser Ser Tyr Gln Gln Ser Leu Asn Gly Lys
            35                  40                  45

Trp Lys Phe His Phe Ser Ala Asn Pro Met Asp Arg Pro Gln Asp Phe
50                  55                  60

Tyr Gln Arg Asp Phe Asp Ser Ser Asn Phe Asp Ser Ile Pro Val Pro
65                  70                  75                  80

Ser Glu Ile Glu Leu Ser Asn Tyr Thr Gln Asn Gln Tyr Ile Asn Val
                85                  90                  95

Leu Phe Pro Trp Glu Gly Lys Ile Phe Arg Arg Pro Ala Tyr Ala Leu
                100                 105                 110

Asp Pro Asn Asp His Glu Glu Gly Ser Phe Ser Lys Gly Ala Asp Asn
                115                 120                 125

Thr Val Gly Ser Tyr Leu Lys Arg Phe Asp Leu Ser Ser Ala Leu Ile
                130                 135                 140

Gly Lys Asp Val His Ile Lys Phe Glu Gly Val Glu Gln Ala Met Tyr
145                 150                 155                 160

Val Trp Leu Asn Gly His Phe Val Gly Tyr Ala Glu Asp Ser Phe Thr
                165                 170                 175

Pro Ser Glu Phe Asp Leu Thr Pro Tyr Ile Gln Glu Lys Asp Asn Leu
                180                 185                 190

Leu Ala Val Glu Val Phe Lys His Ser Thr Ala Ser Trp Leu Glu Asp
                195                 200                 205

Gln Asp Met Phe Arg Phe Ser Gly Ile Phe Arg Ser Val Glu Leu Leu
                210                 215                 220

Gly Ile Pro Ala Thr His Leu Met Asp Met Asp Leu Lys Pro Arg Val
225                 230                 235                 240
```

```
Ala Asp Asn Tyr Gln Asp Gly Ile Phe Asn Leu Lys Leu His Phe Ile
                245                 250                 255

Gly Lys Lys Ala Gly Ser Phe His Leu Leu Val Lys Asp Ile Lys Gly
            260                 265                 270

His Thr Leu Leu Glu Lys Asn Glu Asp Ile Lys Glu Asn Val Gln Ile
        275                 280                 285

Asn Asn Glu Lys Phe Glu Asn Val His Leu Trp Asn Asn His Asp Pro
290                 295                 300

Tyr Leu Tyr Gln Leu Leu Ile Glu Val Tyr Asp Glu Gln Gln Asn Leu
305                 310                 315                 320

Leu Glu Leu Ile Pro Phe Gln Phe Gly Phe Arg Arg Ile Glu Ile Ser
                325                 330                 335

Pro Glu Lys Val Val Leu Leu Asn Gly Lys Arg Leu Ile Ile Asn Gly
            340                 345                 350

Val Asn Arg His Glu Trp Asp Ala Lys Arg Gly Arg Ser Ile Thr Met
        355                 360                 365

Ser Asp Met Thr Thr Asp Ile Asn Thr Phe Lys Glu Asn Asn Ile Asn
370                 375                 380

Ala Val Arg Thr Cys His Tyr Pro Asn Gln Ile Pro Trp Tyr Tyr Leu
385                 390                 395                 400

Cys Asp Gln Asn Gly Ile Tyr Val Met Ala Glu Asn Asn Leu Glu Ser
                405                 410                 415

His Gly Thr Trp Gln Lys Met Gly Glu Ile Glu Pro Ser Asp Asn Val
            420                 425                 430

Pro Gly Ser Ile Pro Gln Trp Lys Glu Ala Val Ile Asp Arg Ala Arg
        435                 440                 445

Asn Asn Tyr Glu Thr Phe Lys Asn His Thr Ser Ile Leu Phe Trp Ser
450                 455                 460

Leu Gly Asn Glu Ser Tyr Ala Gly Asp Asn Ile Ile Ala Met Asn Glu
465                 470                 475                 480

Phe Tyr Lys Ser His Asp Asp Thr Arg Leu Val His Tyr Glu Gly Val
                485                 490                 495

Val His Arg Pro Glu Leu Lys Asp Lys Ile Ser Asp Val Glu Ser Cys
            500                 505                 510

Met Tyr Leu Pro Pro Lys Lys Val Glu Glu Tyr Leu Gln Asn Asp Pro
        515                 520                 525

Pro Lys Pro Phe Met Glu Cys Glu Tyr Met His Asp Met Gly Asn Ser
530                 535                 540

Asn Gly Gly Met Asp Ser Tyr Ile Lys Leu Leu Asp Lys Tyr Pro Gln
545                 550                 555                 560

Tyr Phe Gly Gly Phe Ile Trp Asp Phe Ile Asp Gln Ala Leu Leu Val
                565                 570                 575

His Asp Glu Ile Ser Gly His Asp Val Leu Arg Tyr Gly Gly Asp Phe
            580                 585                 590

Asp Asp Arg His Ser Asp Tyr Glu Phe Ser Gly Asp Gly Leu Met Phe
        595                 600                 605

Ala Asp Arg Lys Pro Lys Pro Ala Met Gln Glu Val Arg Tyr Tyr Tyr
610                 615                 620

Gly Leu His Lys
625

<210> SEQ ID NO 27
<211> LENGTH: 318
<212> TYPE: PRT
```

<213> ORGANISM: Lactobacillus helveticus

<400> SEQUENCE: 27

Met Asp Tyr Thr Asn Asn Gln Leu His Ile Ile Tyr Gly Asp Ala Thr
1               5                   10                  15

Phe Gly Val Asn Gly Lys Asp Phe Gln Tyr Ile Phe Ser Tyr Glu Arg
            20                  25                  30

Gly Gly Leu Glu Ser Leu Lys Val His Gly Lys Glu Trp Leu Tyr Arg
        35                  40                  45

Val Pro Thr Pro Thr Phe Trp Arg Ala Thr Thr Asp Asn Asp Arg Gly
    50                  55                  60

Ser Gly Phe Asn Leu Lys Ala Ala Gln Trp Leu Gly Ala Asp Met Phe
65                  70                  75                  80

Thr Lys Cys Thr Asp Ile His Leu Lys Val Asp Arg His Asp Phe Ala
                85                  90                  95

Glu Leu Pro Ile Ala Pro Phe Asn Asn Lys Phe Ser Asn His Glu Tyr
            100                 105                 110

Ala Lys Ser Ala Glu Ile Ser Phe Thr Tyr Gln Thr Leu Thr Thr Pro
        115                 120                 125

Ala Thr Asn Ala Lys Ile Ile Tyr Asn Ile Asp Asp Gly Gly His Ile
    130                 135                 140

Lys Val Thr Met Arg Tyr Tyr Gly Lys Lys Gly Leu Pro Pro Leu Pro
145                 150                 155                 160

Val Ile Gly Ile Arg Leu Ile Met Pro Thr Ala Ala Thr Gly Phe Asp
                165                 170                 175

Tyr Glu Gly Leu Ser Gly Glu Thr Tyr Pro Asp Arg Met Ala Gly Ala
            180                 185                 190

Lys Glu Gly Lys Phe His Ile Asp Gly Leu Pro Val Thr Glu Tyr Leu
        195                 200                 205

Val Pro Gln Glu Asn Gly Met His Met Gln Thr Lys Lys Leu Thr Ile
    210                 215                 220

Asn Arg Glu Thr Thr Gln Asn Asn Val Asp Arg Thr Asn Glu Lys Phe
225                 230                 235                 240

Ser Leu Ser Ile Gln Gln Ala Glu Lys Pro Phe Asn Phe Ser Cys Leu
                245                 250                 255

Pro Tyr Thr Ala Glu Glu Leu Glu Asn Ala Thr His Ile Glu Glu Leu
            260                 265                 270

Pro Leu Val Arg Arg Thr Val Leu Val Ile Ala Gly Ala Val Arg Gly
        275                 280                 285

Val Gly Gly Ile Asp Ser Trp Gly Thr Asp Val Glu Ser Ala Tyr His
    290                 295                 300

Ile Asn Pro Asp Leu Asp His Glu Phe Ser Phe Ile Leu Asn
305                 310                 315

<210> SEQ ID NO 28
<211> LENGTH: 626
<212> TYPE: PRT
<213> ORGANISM: Lactobacillus crispatus

<400> SEQUENCE: 28

Met Lys Ala Asn Ile Lys Trp Leu Asp Asp Pro Glu Val Phe Arg Ile
1               5                   10                  15

Asn Gln Leu Pro Ala His Ser Asp His Pro Phe Tyr Lys Asp Tyr Arg
            20                  25                  30

Glu Trp Gln Lys His Ser Ser Ser Phe Lys Gln Ser Leu Asn Gly Ala

```
                35                  40                  45
Trp Gln Phe His Phe Ser Lys Asp Pro Gln Ser Arg Pro Ile Asp Phe
 50                  55                  60

Tyr Lys Leu Ser Phe Asp Ser Ser Phe Asp Thr Ile Pro Val Pro
65                  70                  75                  80

Ser Glu Ile Glu Leu Asn Gly Tyr Ala Gln Asn Gln Tyr Thr Asn Ile
                85                  90                  95

Leu Tyr Pro Trp Glu Ser Lys Ile Tyr Arg Lys Pro Ala Tyr Thr Leu
                100                 105                 110

Gly Arg Gly Ile Lys Asp Gly Asp Phe Ser Gln Gly Lys Asp Asn Thr
                115                 120                 125

Val Gly Ser Tyr Leu Lys His Phe Asp Leu Asn Pro Ala Leu Ala Gly
                130                 135                 140

His Asp Ile His Ile Gln Phe Glu Gly Val Glu Arg Ala Met Tyr Val
145                 150                 155                 160

Tyr Leu Asn Gly His Phe Ile Gly Tyr Ala Glu Asp Ser Phe Thr Pro
                165                 170                 175

Ser Glu Phe Asp Leu Thr Pro Tyr Ile Gln Ala Lys Asp Asn Ile Leu
                180                 185                 190

Ala Val Glu Val Phe Lys His Ser Thr Ala Ser Trp Leu Glu Asp Gln
                195                 200                 205

Asp Met Phe Arg Phe Ser Gly Ile Phe Arg Ser Val Glu Leu Leu Ala
210                 215                 220

Leu Pro Arg Thr His Leu Met Asp Leu Asp Ile Lys Pro Thr Val Val
225                 230                 235                 240

Asn Asp Tyr His Asp Gly Val Phe Asn Ala Lys Leu His Phe Met Gly
                245                 250                 255

Lys Thr Ser Gly Asn Val His Val Leu Ile Glu Asp Ile Asp Gly Lys
                260                 265                 270

Thr Leu Leu Asn Lys Lys Leu Pro Leu Lys Ser Thr Val Glu Ile Glu
                275                 280                 285

Asn Glu Thr Phe Ala Asn Val His Leu Trp Asp Asn His Asp Pro Tyr
290                 295                 300

Leu Tyr Gln Leu Ile Ile Glu Val His Asp Gln Asp Gly Lys Leu Val
305                 310                 315                 320

Glu Leu Ile Pro Tyr Gln Phe Gly Phe Arg Lys Ile Glu Ile Thr Lys
                325                 330                 335

Asp His Val Val Leu Leu Asn Gly Lys Arg Leu Ile Ile Asn Gly Val
                340                 345                 350

Asn Arg His Glu Trp Asp Ala Lys Arg Gly Arg Ser Ile Thr Leu Ala
                355                 360                 365

Asp Met Lys Gln Asp Ile Ala Thr Phe Lys His Asn Asn Ile Asn Ala
                370                 375                 380

Val Arg Thr Cys His Tyr Pro Asn Gln Ile Pro Trp Tyr Tyr Leu Cys
385                 390                 395                 400

Asp Gln Asn Gly Ile Tyr Met Met Ala Glu Asn Asn Leu Glu Ser His
                405                 410                 415

Gly Thr Trp Gln Lys Leu Gly Val Glu Ala Thr Ser Asn Val Pro
                420                 425                 430

Gly Ser Ile Pro Glu Trp Arg Glu Val Val Asp Arg Ala Arg Ser
                435                 440                 445

Asn Tyr Glu Thr Phe Lys Asn His Thr Ala Ile Leu Phe Trp Ser Leu
450                 455                 460
```

-continued

```
Gly Asn Glu Ser Tyr Ala Gly Ser Asn Ile Ala Ala Met Asn Lys Leu
465                 470                 475                 480

Tyr Lys Asp His Asp Ser Ser Arg Leu Thr His Tyr Glu Gly Val Phe
            485                 490                 495

His Ala Pro Glu Phe Lys Lys Glu Ile Ser Asp Leu Gly Ser Cys Met
        500                 505                 510

Tyr Leu Pro Pro Lys Glu Ala Glu Glu Tyr Leu Gln Asn Pro Lys Lys
    515                 520                 525

Pro Leu Val Glu Cys Glu Tyr Met His Asp Met Gly Asn Ser Asp Gly
530                 535                 540

Gly Ile Gly Ser Tyr Ile Lys Leu Ile Asp Lys Tyr Pro Gln Tyr Met
545                 550                 555                 560

Gly Gly Phe Ile Trp Asp Phe Ile Asp Gln Ala Leu Leu Val His Asp
                565                 570                 575

Pro Val Ser Gly Gln Asp Val Leu Arg Tyr Gly Gly Asp Phe Asp Asp
            580                 585                 590

Arg His Ser Asp Tyr Glu Phe Ser Gly Asp Gly Leu Met Phe Ala Asp
        595                 600                 605

Arg Thr Pro Lys Pro Ala Met Gln Glu Val Arg Tyr Tyr Tyr Gly Leu
    610                 615                 620

His Lys
625

<210> SEQ ID NO 29
<211> LENGTH: 316
<212> TYPE: PRT
<213> ORGANISM: Lactobacillus crispatus

<400> SEQUENCE: 29

Met Ala Tyr Thr Asn Asn Leu His Val Val Tyr Gly Glu Ala Ser Leu
1               5                   10                  15

Gly Val Asn Gly Gln Asp Phe Ala Tyr Leu Phe Ser Tyr Glu Arg Gly
            20                  25                  30

Val Leu Glu Ser Leu Lys Ile Lys Asp Lys Glu Trp Leu Tyr Arg Thr
        35                  40                  45

Pro Thr Pro Thr Phe Trp Arg Ala Thr Thr Asp Asn Asp Arg Gly Ser
    50                  55                  60

Gly Phe Asn Gln Lys Ala Ala Gln Trp Leu Gly Ala Asp Met Phe Thr
65                  70                  75                  80

Lys Cys Val Gly Ile His Val Gln Val Asp Asp His Gln Phe Asp Glu
                85                  90                  95

Leu Pro Ile Ala Pro Ile Asn Asn Gln Phe Ser Asn Gln Glu Phe Ala
            100                 105                 110

His Glu Val Lys Val Ala Phe Asp Tyr Glu Thr Leu Thr Thr Pro Ala
        115                 120                 125

Thr Lys Val Lys Ile Ile Tyr Asn Ile Asn Asp Ala Gly His Met Thr
    130                 135                 140

Ile Thr Met His Tyr Phe Gly Lys Lys Gly Leu Pro Pro Leu Pro Val
145                 150                 155                 160

Ile Gly Met Arg Phe Ile Met Pro Thr Lys Ala Lys Ser Phe Asp Tyr
                165                 170                 175

Thr Gly Leu Ser Gly Glu Thr Tyr Pro Asp Arg Met Ala Gly Ala Glu
            180                 185                 190

Arg Gly Thr Phe His Ile Asp Gly Leu Pro Val Thr Lys Tyr Leu Val
```

```
            195                 200                 205
Pro Gln Glu Asn Gly Met His Met Gln Thr Asn Glu Leu Val Ile Thr
210                 215                 220

Arg Asn Ser Thr Gln Asn Asn Ala Asp Lys Asp Gly Asp Phe Ser Leu
225                 230                 235                 240

Lys Ile Thr Gln Thr Lys Gln Pro Phe Asn Phe Ser Leu Leu Pro Tyr
                245                 250                 255

Thr Ala Glu Glu Leu Glu Asn Ala Thr His Ile Glu Glu Leu Pro Leu
            260                 265                 270

Ala Arg Arg Ser Val Leu Val Ile Ala Gly Ala Val Arg Gly Val Gly
        275                 280                 285

Gly Ile Asp Ser Trp Gly Ser Asp Val Glu Glu Gln Tyr His Ile Asp
    290                 295                 300

Pro Glu Gln Asp His Glu Phe Ser Phe Thr Leu Asn
305                 310                 315

<210> SEQ ID NO 30
<211> LENGTH: 1025
<212> TYPE: PRT
<213> ORGANISM: Streptococcus thermophilus

<400> SEQUENCE: 30

Met Asn Met Thr Lys Ile Gln Thr Tyr Leu Asn Asp Pro Lys Ile Val
1               5                   10                  15

Ser Val Asn Thr Val Asp Ala His Ser Asp His Lys Tyr Phe Glu Ser
            20                  25                  30

Leu Glu Glu Phe Ser Glu Gly Glu Met Lys Leu Arg Gln Ser Leu Asn
        35                  40                  45

Gly Lys Trp Lys Ile His Tyr Ala Gln Asn Thr Asn Gln Val Leu Lys
    50                  55                  60

Asp Phe Tyr Lys Thr Glu Phe Asp Glu Thr Asp Leu Asn Phe Ile Asn
65                  70                  75                  80

Val Pro Gly His Leu Glu Leu Gln Gly Phe Gly Ser Pro Gln Tyr Val
                85                  90                  95

Asn Thr Gln Tyr Pro Trp Asp Gly Lys Glu Phe Leu Arg Pro Pro Gln
            100                 105                 110

Val Pro Gln Glu Ser Asn Ala Val Ala Ser Tyr Val Lys His Phe Thr
        115                 120                 125

Leu Asn Asp Ala Leu Lys Asp Lys Val Phe Ile Ser Phe Gln Gly
130                 135                 140

Val Ala Thr Ser Ile Phe Val Trp Val Asn Gly Asn Phe Val Gly Tyr
145                 150                 155                 160

Ser Glu Asp Ser Phe Thr Pro Ser Glu Phe Glu Ile Ser Asp Tyr Leu
                165                 170                 175

Val Glu Gly Asp Asn Lys Leu Ala Val Ala Val Tyr Arg Tyr Ser Thr
            180                 185                 190

Ala Ser Trp Leu Glu Asp Gln Asp Phe Trp Arg Leu Tyr Gly Ile Phe
        195                 200                 205

Arg Asp Val Tyr Leu Tyr Ala Ile Pro Lys Val His Val Gln Asp Leu
210                 215                 220

Phe Val Lys Gly Asp Tyr Asp Tyr Gln Thr Lys Ala Gly Gln Leu Asp
225                 230                 235                 240

Ile Asp Leu Lys Thr Val Gly Asp Tyr Glu Asp Lys Lys Ile Lys Tyr
                245                 250                 255
```

-continued

Val Leu Ser Asp Tyr Glu Gly Ile Val Thr Glu Gly Asp Ala Ser Val
            260                 265                 270

Asn Gly Asp Gly Glu Leu Ser Val Ser Leu Glu Asn Leu Lys Ile Lys
        275                 280                 285

Pro Trp Ser Ala Glu Ser Pro Lys Leu Tyr Asp Leu Ile Leu His Val
    290                 295                 300

Leu Asp Asp Asp Gln Val Val Glu Val Pro Val Lys Val Gly Phe
305                 310                 315                 320

Arg Arg Phe Glu Ile Lys Asp Lys Leu Met Leu Leu Asn Gly Lys Arg
                325                 330                 335

Ile Val Phe Lys Gly Val Asn Arg His Glu Phe Asn Ala Arg Thr Gly
            340                 345                 350

Arg Cys Ile Thr Glu Glu Asp Met Leu Trp Asp Ile Lys Val Met Lys
        355                 360                 365

Gln His Asn Ile Asn Ala Val Arg Thr Ser His Tyr Pro Asn Gln Thr
    370                 375                 380

Arg Trp Tyr Glu Leu Cys Asp Glu Tyr Gly Leu Tyr Val Ile Asp Glu
385                 390                 395                 400

Ala Asn Leu Glu Thr His Gly Thr Trp Gln Lys Leu Gly Leu Cys Glu
                405                 410                 415

Pro Ser Trp Asn Ile Pro Ala Ser Glu Pro Glu Trp Leu Pro Ala Cys
            420                 425                 430

Leu Asp Arg Ala Asn Asn Met Phe Gln Arg Asp Lys Asn His Ala Ser
        435                 440                 445

Val Ile Ile Trp Ser Cys Gly Asn Glu Ser Tyr Ala Gly Lys Asp Ile
    450                 455                 460

Ala Asp Met Ala Asp Tyr Phe Arg Ser Val Asn Thr Arg Pro Val
465                 470                 475                 480

His Tyr Glu Gly Val Ala Trp Cys Arg Glu Phe Asp Tyr Ile Thr Asp
                485                 490                 495

Ile Glu Ser Arg Met Tyr Ala Lys Pro Ala Asp Ile Glu Glu Tyr Leu
            500                 505                 510

Thr Thr Gly Lys Leu Val Asp Leu Ser Ser Val Ser Asp Lys His Phe
        515                 520                 525

Ala Ser Gly Asn Leu Thr Asn Lys Pro Gln Lys Pro Tyr Ile Ser Cys
    530                 535                 540

Glu Tyr Met His Thr Met Gly Asn Ser Gly Gly Leu Gln Leu Tyr
545                 550                 555                 560

Thr Asp Leu Glu Lys Tyr Pro Glu Tyr Gln Gly Gly Phe Ile Trp Asp
                565                 570                 575

Phe Ile Asp Gln Ala Ile Tyr Lys Thr Leu Pro Asn Gly Ser Glu Phe
            580                 585                 590

Leu Ser Tyr Gly Gly Asp Trp His Asp Arg Pro Ser Asp Tyr Glu Phe
        595                 600                 605

Cys Gly Asn Gly Ile Val Phe Ala Asp Arg Thr Leu Thr Pro Lys Leu
    610                 615                 620

Gln Thr Val Lys His Leu Tyr Ser Asn Ile Lys Ile Ala Val Asp Glu
625                 630                 635                 640

Lys Ser Val Thr Ile Lys Asn Asp Asn Leu Phe Glu Asp Leu Ser Ala
                645                 650                 655

Tyr Thr Phe Leu Ala Arg Val Tyr Glu Asp Gly Arg Lys Val Ser Glu
            660                 665                 670

Ser Glu Tyr His Phe Asp Val Lys Pro Gly Glu Glu Ala Thr Phe Pro 675                 680                 685
Val Asn Phe Val Val Glu Ala Ser Asn Ser Glu Gln Ile Tyr Glu Val
            690                 695                 700

Ala Cys Val Leu Arg Glu Ala Thr Lys Trp Ala Pro Lys Gly His Glu
705                 710                 715                 720

Ile Val Arg Gly Gln Tyr Val Val Glu Lys Ile Ser Thr Glu Thr Pro
                725                 730                 735

Val Lys Ala Pro Leu Asn Val Val Glu Gly Asp Phe Asn Ile Gly Ile
            740                 745                 750

Gln Gly Gln Asn Phe Ser Ile Leu Leu Ser Arg Ala Gln Asn Thr Leu
                755                 760                 765

Val Ser Ala Lys Tyr Asn Gly Val Glu Phe Ile Glu Lys Gly Pro Lys
            770                 775                 780

Leu Ser Phe Thr Arg Ala Tyr Thr Asp Asn Asp Arg Gly Ala Gly Tyr
785                 790                 795                 800

Pro Phe Glu Met Ala Gly Trp Lys Val Ala Gly Asn Tyr Ser Lys Val
                805                 810                 815

Thr Asp Thr Gln Ile Gln Ile Glu Asp Asp Ser Val Lys Val Thr Tyr
            820                 825                 830

Val His Glu Leu Pro Gly Leu Ser Asp Val Glu Val Lys Val Thr Tyr
            835                 840                 845

Gln Val Asp Tyr Lys Gly Arg Ile Phe Val Thr Ala Asn Tyr Asp Gly
850                 855                 860

Lys Ala Gly Leu Pro Asn Phe Pro Glu Phe Gly Leu Glu Phe Ala Ile
865                 870                 875                 880

Gly Ser Gln Phe Thr Asn Leu Ser Tyr Tyr Gly Tyr Gly Ala Glu Glu
                885                 890                 895

Ser Tyr Arg Asp Lys Leu Pro Gly Ala Tyr Leu Gly Arg Tyr Glu Thr
            900                 905                 910

Ser Val Glu Lys Thr Phe Ala Pro Tyr Leu Met Pro Gln Glu Ser Gly
            915                 920                 925

Asn His Tyr Gly Thr Arg Glu Phe Thr Val Ser Asp Asp Asn His Asn
930                 935                 940

Gly Leu Lys Phe Thr Ala Leu Asn Lys Ala Phe Glu Phe Ser Ala Leu
945                 950                 955                 960

Arg Asn Ser Thr Glu Gln Ile Glu Asn Ala Arg His Gln Tyr Glu Leu
                965                 970                 975

Gln Glu Ser Asp Ala Thr Trp Ile Lys Val Leu Ala Ala Gln Met Gly
            980                 985                 990

Val Gly Gly Asp Asp Ser Trp Gly Ala Pro Val His Asp Glu Phe Leu
            995                 1000                1005

Leu Ser Ser Ala Asp Ser Tyr Gln Leu Ser Phe Met Ile Glu Pro
    1010                1015                1020

Leu Asn
    1025

<210> SEQ ID NO 31
<211> LENGTH: 1008
<212> TYPE: PRT
<213> ORGANISM: Lactobacillus delbrueckii

<400> SEQUENCE: 31

Met Asn Asn Lys Leu Ala Gln Val Lys Arg Val Asp Gln Ala Asp Leu
1               5                   10                  15

-continued

Ala Trp Leu Thr Asp Pro Glu Ile Tyr Glu Val Asn Thr Ile Pro Pro
         20                  25                  30

His Ser Asp His Glu Ser Phe Gln Ser Leu Glu Leu Glu Glu Gly
     35                  40                  45

Lys Ser Ser Leu Val Gln Ser Leu Asp Gly Asp Trp Leu Ile Asp Tyr
 50                  55                  60

Ala Glu Asn Gly Glu Gly Pro Ala Asn Phe Tyr Glu Asn Phe Asp
 65                  70                  75                  80

Asp Ser Ser Phe Lys Ser Val Lys Val Pro Gly Asn Leu Glu Leu Gln
                 85                  90                  95

Gly Phe Gly Gln Pro Gln Tyr Val Asn Val Gln Tyr Pro Trp Asp Gly
             100                 105                 110

Ser Asp Glu Ile Phe Pro Pro Met Ile Pro Ser Lys Asn Pro Val Ala
         115                 120                 125

Ser Tyr Val Arg Tyr Phe Asp Leu Glu Glu Ala Phe Trp Asp Lys Glu
     130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                 165                 170                 175

Phe Met Val Thr Lys Phe Leu Lys Lys Glu Gly Asn Arg Leu Ala Val
             180                 185                 190

Ala Leu Tyr Lys Tyr Ser Ser Ala Ser Trp Leu Glu Asp Gln Asp Phe
         195                 200                 205

Trp Arg Met Ser Gly Leu Phe Arg Ser Val Thr Leu Glu Ala Lys Pro
210                 215                 220

Leu Leu His Leu Gln Asp Leu Lys Leu Thr Ala Ser Leu Thr Asn Asp
225                 230                 235                 240

Tyr Gln Lys Gly Ser Leu Gln Val Glu Ala Asp Ile Asp Tyr Arg Leu
                 245                 250                 255

Pro Asn Ser Ser Phe Lys Leu Glu Leu Arg Asp Ser Ala Gly Glu Leu
             260                 265                 270

Val Ala Glu Lys Val Gly Pro Ile Arg Ser Glu Lys Leu Asp Phe Ser
         275                 280                 285

Leu Ala Asp Leu Pro Val Ala Ala Trp Ser Ala Glu Glu Pro Asn Leu
     290                 295                 300

Tyr Gln Val Arg Leu Ser Leu Tyr Gln Gln Gly Ser Leu Leu Glu Val
305                 310                 315                 320

Ser Arg Gln Glu Val Gly Phe Arg Asn Phe Glu Leu Lys Asp Gly Ile
                 325                 330                 335

Met Tyr Leu Asn Gly Lys Arg Ile Val Phe Lys Gly Val Asn Arg His
             340                 345                 350

Glu Phe Asp Ser Lys Leu Gly Arg Ala Ile Thr Glu Ala Asp Met Ile
         355                 360                 365

Trp Asp Ile Lys Thr Met Lys Gln Ser Asn Ile Asn Ala Val Arg Cys
     370                 375                 380

Ser His Tyr Pro Asn Gln Ser Ile Phe Tyr His Leu Cys Asp Lys Tyr
385                 390                 395                 400

Gly Leu Tyr Val Ile Asp Glu Ala Asn Leu Glu Ser His Gly Thr Trp
                 405                 410                 415

Glu Lys Val Gly Gly His Glu Asp Pro Ser Phe Asn Val Pro Gly Asp
             420                 425                 430

Asp Gln Arg Trp Leu Gly Ala Ser Leu Ser Arg Val Lys Asn Met Met

```
                   435                 440                 445
Ala Arg Asp Lys Asn His Ala Ser Ile Leu Ile Trp Ser Leu Gly Asn
450                 455                 460

Glu Ser Tyr Ala Gly Lys Val Phe Ala Gln Met Ala Asp Tyr Val Arg
465                 470                 475                 480

Gln Ala Asp Pro Thr Arg Val Gln His Tyr Glu Gly Val Thr His Asn
                    485                 490                 495

Arg Lys Phe Asp Asp Ala Thr Gln Ile Glu Ser Arg Met Tyr Ala Pro
                500                 505                 510

Ala Lys Glu Ile Glu Glu Tyr Leu Thr Lys Lys Pro Ala Lys Pro Phe
            515                 520                 525

Val Ser Cys Glu Tyr Ala His Ala Met Gly Asn Ser Val Gly Asp Leu
530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Glu Gly His Leu Leu
                    565                 570                 575

Tyr Gly Gly Asp Phe Asp Asp Arg Pro Ser Asp Tyr Glu Phe Cys Gly
                580                 585                 590

Asp Gly Leu Val Phe Ala Asp Arg Thr Thr Ser Pro Lys Leu Ala Asn
            595                 600                 605

Val Lys Ala Leu Tyr Ser Asn Leu Lys Leu Glu Leu Lys Asp Gly Gln
610                 615                 620

Leu Phe Leu Lys Asn Asp Asn Leu Phe Thr Asn Ser Ser Ala Tyr Tyr
625                 630                 635                 640

Phe Leu Thr Ser Leu Leu Val Asp Gly Lys Leu Thr Tyr Gln Ser Gln
                    645                 650                 655

Pro Leu Thr Phe Ala Leu Glu Pro Gly Glu Ser Gly Thr Phe Ala Leu
                660                 665                 670

Pro Trp Pro Glu Val Glu Asp Glu Lys Gly Glu Ile Val Tyr Gln Val
            675                 680                 685

Thr Ala His Leu Lys Glu Asp Leu Pro Trp Ala Asp Glu Gly Phe Thr
690                 695                 700

Val Ala Glu Ala Glu Glu Ala Val Thr Lys Leu Pro Glu Phe Tyr Pro
705                 710                 715                 720

Ala Gly Arg Pro Glu Leu Val Asp Ser Asp Tyr Asn Leu Gly Ile Lys
                    725                 730                 735

Gly Asn Gly Phe Arg Ile Leu Phe Ser Lys Ala Lys Gly Trp Pro Val
                740                 745                 750

Ser Ile Lys Tyr Ala Gly Arg Glu Tyr Leu Lys Arg Leu Pro Glu Phe
            755                 760                 765

Thr Phe Trp Arg Ala Leu Thr Asp Asn Asp Arg Gly Ala Gly Tyr Gly
770                 775                 780

Tyr Asp Leu Ala Lys Trp Glu Asn Ala Gly Lys Tyr Ala Arg Leu Gln
785                 790                 795                 800

Asp Ile Ser Tyr Glu Ile Lys Glu Asn Ser Val Leu Val Lys Thr Ala
                    805                 810                 815

Phe Thr Leu Pro Val Ala Leu Lys Gly Asp Leu Thr Ile Thr Tyr Glu
                820                 825                 830

Val Asp Ser Leu Gly Lys Ile Ala Val Thr Ala Asn Phe Pro Gly Ala
            835                 840                 845

Val Glu Asn Gly Leu Leu Pro Ala Phe Gly Leu Asn Phe Ala Leu Pro
850                 855                 860
```

Lys Glu Leu Ser Asp Tyr Arg Tyr Tyr Gly Leu Gly Pro Asn Glu Ser
865                 870                 875                 880

Tyr Ala Asp Arg Leu Glu Gly Ser Tyr Leu Gly Ile Tyr Gln Gly Ala
                885                 890                 895

Val Glu Lys Asn Phe Thr Pro Tyr Leu Arg Pro Gln Glu Val Gly Asn
            900                 905                 910

Arg Ser Lys Val Arg Tyr Tyr Gln Leu Phe Asp Glu Glu Gly Gly Leu
        915                 920                 925

Glu Phe Thr Ala Asn Gly Ala Asn Leu Asn Leu Ser Ala Leu Pro Tyr
    930                 935                 940

Ser Ala Ala Gln Ile Glu Ala Ala Asp His Ala Phe Glu Leu Thr Asn
945                 950                 955                 960

Asn Tyr Thr Trp Val Arg Ala Leu Ala Ala Gln Met Gly Val Gly Gly
                965                 970                 975

Asp Asp Ser Trp Gly Gln Lys Val His Pro Glu Phe Cys Leu Asp Ala
            980                 985                 990

Gln Glu Ala Arg Gln Leu Lys Leu Val Ile Gln Pro Leu Phe Thr Glu
        995                 1000                1005

<210> SEQ ID NO 32
<211> LENGTH: 1049
<212> TYPE: PRT
<213> ORGANISM: Bifidobacterium adolescentis

<400> SEQUENCE: 32

Met Ala Asp Thr Ala Glu Leu Ala Ile Val His Ala Thr Thr Ala Ser
1               5                   10                  15

Ala Ser Trp Leu Thr Asp Pro Thr Val Phe Ala Ala Asn Arg Lys Pro
            20                  25                  30

Ala His Ser Ser His Arg Tyr Val Ile Gly Glu Thr Ser Glu Pro Lys
        35                  40                  45

Gln Ser Leu Asp Gly Glu Trp Lys Val Arg Ile Glu Gln Ala Arg Asn
    50                  55                  60

Val Asp Val Glu Ser Ala Pro Phe Ala Ala Val Asp Phe Glu Asp Gly
65                  70                  75                  80

Asp Phe Gly Ala Ile Glu Val Pro Gly His Leu Gln Met Ala Gly Tyr
                85                  90                  95

Leu Lys Asn Lys Tyr Val Asn Ile Gln Tyr Pro Trp Asp Gly His Glu
            100                 105                 110

Asp Pro Gln Ala Pro Asn Ile Pro Glu Asn Asn His Val Ala Ile Tyr
        115                 120                 125

Arg Arg Arg Phe Ala Leu Asp Ala Gln Leu Ala Arg Thr Leu Glu Asn
    130                 135                 140

Asp Gly Thr Val Ser Leu Thr Phe His Gly Ala Ala Thr Ala Ile Tyr
145                 150                 155                 160

Val Trp Leu Asp Gly Thr Phe Val Gly Tyr Gly Glu Asp Gly Phe Thr
                165                 170                 175

Pro Ser Glu Phe Asp Val Thr Glu Ala Leu Arg Asn Gly Asn Gly Asn
            180                 185                 190

Ala Ala Asp Ser Pro Glu Ala Glu His Thr Leu Thr Val Ala Cys Tyr
        195                 200                 205

Glu Tyr Ser Ser Ala Ser Trp Leu Glu Asp Gln Asp Phe Trp Arg Leu
    210                 215                 220

His Gly Leu Phe Arg Thr Val Glu Leu Ala Ala Gln Pro His Thr His

```
            225                 230                 235                 240
Val Glu Thr Val Gln Leu Glu Ala Asp Tyr Thr Ala Ala Asp Thr Ala
                245                 250                 255
Gly Thr Ala Asp Thr Ala Glu Leu Asn Ala Ala Leu Thr Leu Arg Asn
                260                 265                 270
Pro Ala Asp Ala Met Thr Ile Glu Ser Thr Leu Arg Asp Gly Asp Gly
                275                 280                 285
Asn Val Val Trp Glu Ser Thr Gln Ala Cys Asn Gly Glu Ile Ala Leu
                290                 295                 300
Asn Ser Gly Lys Met Thr Asn Ile Ala Pro Trp Ser Ala Glu Ser Pro
305                 310                 315                 320
Thr Leu Tyr Thr Leu Thr Val Arg Val Val Gly His Asp Gly Ala Ile
                325                 330                 335
Ile Glu Thr Val Thr Gln Lys Ile Gly Phe Arg Thr Phe Arg Ile Glu
                340                 345                 350
Asn Gly Ile Met Thr Leu Asn Gly Lys Arg Ile Val Phe Lys Gly Ala
                355                 360                 365
Asp Arg His Glu Phe Asp Ala Lys Arg Gly Arg Ala Ile Thr Arg Glu
                370                 375                 380
Asp Met Leu Ser Asp Val Val Phe Cys Lys Arg His Asn Ile Asn Ala
385                 390                 395                 400
Ile Arg Thr Ser His Tyr Pro Asn Gln Glu Tyr Trp Tyr Asp Leu Cys
                405                 410                 415
Asp Glu Tyr Gly Leu Tyr Leu Ile Asp Glu Thr Asn Met Glu Thr His
                420                 425                 430
Gly Thr Trp Val Ala Asn Asn Val Glu Arg Pro Glu Asp Gly Ile Pro
                435                 440                 445
Gly Ser Arg Pro Glu Trp Glu Asp Ala Cys Val Asp Arg Ile Asn Ser
                450                 455                 460
Met Met Arg Arg Asp Tyr Asn His Pro Ser Val Leu Ile Trp Ser Leu
465                 470                 475                 480
Gly Asn Glu Ser Ser Ala Gly Glu Val Phe Arg Ala Met Tyr Arg His
                485                 490                 495
Ala His Thr Ile Asp Pro Asn Arg Pro Val His Tyr Glu Gly Ser Val
                500                 505                 510
His Met Arg Glu Phe Glu Asp Val Thr Asp Ile Glu Ser Arg Met Tyr
                515                 520                 525
Ala His Ala Asp Glu Ile Glu Arg Tyr Leu Asn Asp Gly Ser Pro Ala
                530                 535                 540
His Thr Asp Gly Pro Lys Lys Pro Tyr Ile Ser Cys Glu Tyr Met His
545                 550                 555                 560
Ala Met Gly Asn Ser Cys Gly Asn Met Asp Glu Tyr Thr Ala Leu Glu
                565                 570                 575
Arg Tyr Pro Met Tyr Gln Gly Gly Phe Ile Trp Asp Phe Ile Asp Gln
                580                 585                 590
Ala Ile Glu Thr Lys Leu Pro Asp Gly Thr Thr Arg Met Cys Tyr Gly
                595                 600                 605
Gly Asp Phe Gly Asp Arg Pro Ser Asp Tyr Glu Phe Ser Gly Asp Gly
                610                 615                 620
Leu Leu Phe Ala Asp Arg Thr Pro Ser Pro Lys Ala Gln Glu Val Lys
625                 630                 635                 640
Gln Leu Tyr Ala Asn Val Lys Ile Ala Val Ser Val Asp Glu Ala Arg
                645                 650                 655
```

Ile Thr Asn Asp Asn Leu Phe Val Ser Thr Gly Asp Tyr Arg Phe Val
            660                 665                 670

Leu Arg Ile Leu Ala Asp Gly Lys Pro Val Trp Ser Thr Arg Arg
        675                 680                 685

Phe Asp Val Ala Ala Gly Glu Ser Ala Ser Phe Glu Val Asp Trp Pro
690                 695                 700

Val Asp Tyr Arg Ser Asn Ala Glu Glu Leu Val Leu Glu Val Ser
705                 710                 715                 720

Gln Gln Leu Gly Asn Ala Cys Asp Trp Ala Pro Ala Gly Tyr Glu Leu
                725                 730                 735

Ala Phe Gly Gln Cys Val Val Ala Gly Ala Lys Thr Thr Ala Asp Ala
            740                 745                 750

Val Asp Ala Ala Gly Ala Pro Ala Asp Gly Thr Val Thr Leu Gly Arg
        755                 760                 765

Trp Asn Ala Gly Val Arg Gly Gln Gly Arg Glu Ala Leu Phe Ser Arg
    770                 775                 780

Thr Gln Gly Gly Met Val Ser Tyr Thr Phe Gly Glu Arg Glu Phe Val
785                 790                 795                 800

Leu Arg Arg Pro Ser Ile Thr Thr Phe Arg Pro Leu Thr Asp Asn Asp
                805                 810                 815

Arg Gly Ala Gly His Ala Phe Glu Arg Ala Ala Trp Ala Val Ala Gly
            820                 825                 830

Lys Tyr Ala Arg Cys Val Asp Cys Ala Ile Ala Asn Arg Gly Glu Asn
        835                 840                 845

Ala Val Glu Ala Thr Tyr Thr Tyr Glu Leu Ala Ile Pro Gln Arg Thr
    850                 855                 860

Lys Val Thr Val Arg Tyr Val Ala Asp Thr Ala Gly Leu Val Ser Leu
865                 870                 875                 880

Asp Val Glu Tyr Pro Gly Glu Lys Asn Gly Asp Leu Pro Thr Ile Pro
                885                 890                 895

Ala Phe Gly Ile Glu Trp Ala Leu Pro Val Glu Tyr Ala Asn Leu Arg
            900                 905                 910

Phe Tyr Gly Ala Gly Pro Glu Glu Thr Tyr Ala Asp Arg Arg His Ala
        915                 920                 925

Lys Leu Gly Val Trp Ser Thr Thr Ala Gly Asp Asp Cys Ala Pro Tyr
    930                 935                 940

Leu Leu Pro Gln Glu Thr Gly Asn His Glu Asp Val Arg Trp Ala Glu
945                 950                 955                 960

Ile Thr Asp Asp Ser Gly His Gly Val Arg Val Lys Arg Gly Ala Gly
                965                 970                 975

Ala Lys Pro Phe Ala Met Ser Leu Leu Pro Tyr Ser Ser Thr Met Leu
            980                 985                 990

Glu Glu Ala Leu His Gln Asp Glu Leu Pro Lys Pro Arg His Met Phe
        995                 1000                1005

Leu Arg Leu Leu Ala Ala Gln Met Gly Val Gly Gly Asp Asp Ser
    1010                1015                1020

Trp Met Ser Pro Val His Glu Gln Tyr Gln Leu Pro Ala Asp Gln
    1025                1030                1035

Pro Leu Ser Leu Asn Val Gln Leu Lys Leu Phe
    1040                1045

<210> SEQ ID NO 33
<211> LENGTH: 1023

<212> TYPE: PRT
<213> ORGANISM: Bifidobacterium adolescentis

<400> SEQUENCE: 33

```
Met Ala Asn Glu Thr Arg Ile Glu His Ala Ser Glu Thr Trp Leu Ala
1               5                   10                  15

Asp Ser Thr Val Phe Glu Val Asn Arg Val Pro Ala His Ser Asp His
            20                  25                  30

Lys Cys Tyr Ala His Asp Ser Gln Thr Asn Glu Trp Ser Asp Leu Arg
        35                  40                  45

Gln Ser Leu Asp Gly Glu Trp Arg Val Glu Val Val Gln Ala Ser Asp
    50                  55                  60

Ile Glu Phe Asn Glu Glu Pro Phe Val Arg Glu Asn Phe Asp Asp Ser
65                  70                  75                  80

Ala Phe Glu Arg Ile Gln Val Pro Gly His Leu Gln Met Ala Gly Leu
                85                  90                  95

Met Asn Asn Lys Tyr Val Asn Ile Gln Tyr Pro Trp Asp Gly His Glu
            100                 105                 110

Asn Pro Ala Glu Pro Asn Ile Pro Glu Asn Asn His Val Ala Leu Tyr
        115                 120                 125

Arg Lys Thr Phe Thr Met Ala Asn Arg Leu Ala Asp Thr Lys Asn Ala
    130                 135                 140

Gly Gly Thr Val Ser Ile Val Phe His Gly Met Ala Thr Ala Ile Tyr
145                 150                 155                 160

Val Trp Val Asn Gly Met Phe Val Gly Tyr Gly Glu Asp Gly Phe Thr
                165                 170                 175

Pro Asn Glu Phe Asp Ile Thr Glu Met Leu His Asp Gly Glu Asn Val
            180                 185                 190

Val Ala Val Ala Cys Tyr Glu Tyr Ser Ser Ala Ser Trp Leu Glu Asp
        195                 200                 205

Gln Asp Phe Trp Arg Leu His Gly Leu Phe Arg Ser Val Glu Leu Ala
    210                 215                 220

Ala Gln Pro His Val His Ile Glu Asn Met Gln Ile Glu Ser Asp Trp
225                 230                 235                 240

Asp Pro Glu Ser Gly Ser Ala Ser Leu Asp Ala Ala Leu Thr Val Arg
                245                 250                 255

Asn Ala Ala Asp Ala Ala Thr Ile Ser Ala Thr Leu Lys Asp Ser Asp
            260                 265                 270

Gly Asn Val Val Trp Glu Thr Ala Asn Cys Ala Asp Pro Asp Thr Ser
        275                 280                 285

Ile Ser Thr Gly Ser Leu Asn Gly Ile Arg Pro Trp Ser Ala Glu Asp
    290                 295                 300

Pro Val Leu Tyr Glu Phe Glu Val Thr Val Ile Asp His Ala Gly Asn
305                 310                 315                 320

Ile Ala Glu Val Ala Val Gln Lys Val Gly Phe Arg Arg Phe Arg Ile
                325                 330                 335

Glu Asp Gly Ile Met Thr Ile Asn Gly Lys Arg Ile Val Phe Lys Gly
            340                 345                 350

Ala Asp Arg His Glu Phe Asp Pro Lys Arg Gly Arg Ala Ile Thr Glu
        355                 360                 365

Gln Asp Met Ile Asp Asp Val Val Phe Cys Lys Arg His Asn Leu Asn
    370                 375                 380

Ala Ile Arg Thr Ser His Tyr Pro Asn Gln Glu Arg Trp Tyr Glu Leu
385                 390                 395                 400
```

```
Cys Asp Glu Tyr Gly Ile Tyr Leu Ile Asp Glu Thr Asn Leu Glu Thr
                405                 410                 415

His Gly Ser Trp Cys Leu Pro Gly Asp Val Leu Thr Glu Thr Ala
        420                 425                 430

Val Pro Gly Ser Lys Ala His Trp Glu Gly Ala Cys Val Asp Arg Val
        435                 440                 445

Asn Ser Met Val Arg Arg Asp Tyr Asn His Pro Ser Val Leu Ile Trp
450                 455                 460

Ser Leu Gly Asn Glu Ser Tyr Thr Gly Asp Val Phe Arg Ala Met Tyr
465                 470                 475                 480

Lys Arg Val His Asp Ile Asp Pro Asn Arg Pro Val His Tyr Glu Gly
                485                 490                 495

Val Thr His Asn Arg Asp Tyr Asn Asp Val Thr Asp Ile Glu Thr Arg
                500                 505                 510

Met Tyr Ala His Ala Asp Ala Ile Glu Glu Tyr Leu Lys Asn Asp Pro
            515                 520                 525

Gln Lys Pro Tyr Ile Ser Cys Glu Tyr Met His Ala Met Gly Asn Ser
            530                 535                 540

Cys Gly Asn Met Asp Glu Tyr Thr Ala Leu Glu Arg Tyr Pro Lys Tyr
545                 550                 555                 560

Gln Gly Gly Phe Ile Trp Asp Phe Ile Asp Gln Ala Ile Tyr Ala Thr
                565                 570                 575

Gln Pro Asp Gly Thr Thr Ser Leu Arg Tyr Gly Gly Asp Phe Gly Asp
            580                 585                 590

Arg Pro Ser Asp Tyr Glu Phe Ser Gly Asn Gly Leu Val Phe Ala Asp
        595                 600                 605

Arg Lys Pro Thr Pro Lys Ala Gln Glu Val Lys Gln Leu Tyr Ser Asn
610                 615                 620

Val His Ile Asp Val Ala Glu Asp Ser Val Thr Ile Lys Asn Asp Asn
625                 630                 635                 640

Leu Phe Thr Ser Thr Gly Glu Tyr Thr Phe Val Leu Arg Val Leu Ala
                645                 650                 655

Asp Gly Glu Pro Val Trp Gln Ser Glu Arg Arg Phe Asp Val Pro Ala
            660                 665                 670

Gly Ser Thr Glu Lys Leu Asp Val Asp Trp Pro Leu Asp Leu Tyr Arg
        675                 680                 685

Asp Gly Ala Ser Glu Leu Val Leu Glu Val Ser Gln Arg Leu Ala Lys
        690                 695                 700

Ala Thr Asn Trp Ala Val Ala Gly Tyr Glu Leu Ala Phe Gly Gln Thr
705                 710                 715                 720

Val Val Ala Gly Ser Lys Lys Ala Ser Ala Pro Val Lys Pro Val Asp
                725                 730                 735

Gly Ile Val Thr Val Gly Arg Trp Asn Val Gly Val Gln Gly Ser Gly
            740                 745                 750

Arg Glu Val Leu Leu Ser Arg Thr Gln Gly Gly Leu Val Ser Tyr Thr
        755                 760                 765

Phe Asn Asn Arg Glu Phe Val Leu Arg Arg Pro Ala Val Thr Thr Phe
770                 775                 780

Arg Ala Leu Thr Asp Asn Asp Arg Gly Ala Gly His Gly Phe Glu Arg
785                 790                 795                 800

Ala Gln Trp Leu Gly Ala Gly Arg Tyr Ala Arg Cys Ile Gly Asn Glu
                805                 810                 815
```

```
Ile Glu Gln Ile Asp Glu Asn Thr Val Lys Ala Ser Tyr Thr Tyr Glu
            820                 825                 830

Leu Ala Thr Pro Gln Arg Thr Lys Val Thr Val Ser Tyr Thr Ala Asp
            835                 840                 845

Thr Thr Gly Arg Val Asn Leu His Val Glu Tyr Pro Gly Glu Pro Gly
            850                 855                 860

Asp Leu Pro Thr Ile Pro Ala Phe Gly Ile Glu Trp Thr Leu Pro Val
865                 870                 875                 880

Gln Tyr Ser Asn Leu Arg Phe Phe Gly Ala Gly Pro Glu Glu Thr Tyr
            885                 890                 895

Gln Asp Arg Lys His Ala Lys Leu Gly Val Trp Ser Thr Asp Ala Phe
            900                 905                 910

Lys Asp His Ala Pro Tyr Leu Met Pro Gln Glu Thr Gly Asn His Glu
            915                 920                 925

Asp Val Arg Trp Ala Glu Ile Thr Asp Glu Lys Gly His Gly Leu Arg
            930                 935                 940

Ile Ser Arg Ala Glu Gly Ala Glu Pro Phe Ala Met Ser Leu Gln Pro
945                 950                 955                 960

Tyr Ser Ser Phe Met Leu Glu Glu Ala Gln His Gln Asp Glu Leu Pro
            965                 970                 975

Ala Pro Lys His Met Phe Leu Arg Val Leu Ala Glu Gln Met Gly Val
            980                 985                 990

Gly Gly Asp Asp Ser Trp Met Ser Pro Val His Pro Gln Tyr His Ile
            995                 1000                1005

Pro Ala Asp Gln Pro Ile Ser Leu Asp Val Asp Leu Asp Leu Ile
            1010                1015                1020

<210> SEQ ID NO 34
<211> LENGTH: 1305
<212> TYPE: PRT
<213> ORGANISM: Bifidobacterium bifidum

<400> SEQUENCE: 34

Met Val Glu Asp Ala Thr Arg Ser Asp Ser Thr Thr Gln Met Ser Ser
1               5                   10                  15

Thr Pro Glu Val Val Tyr Ser Ser Ala Val Asp Ser Lys Gln Asn Arg
            20                  25                  30

Thr Ser Asp Phe Asp Ala Asn Trp Lys Phe Met Leu Ser Asp Ser Val
        35                  40                  45

Gln Ala Gln Asp Pro Ala Phe Asp Asp Ser Ala Trp Gln Gln Val Asp
    50                  55                  60

Leu Pro His Asp Tyr Ser Ile Thr Gln Lys Tyr Ser Gln Ser Asn Glu
65                  70                  75                  80

Ala Glu Ser Ala Tyr Leu Pro Gly Gly Thr Gly Trp Tyr Arg Lys Ser
            85                  90                  95

Phe Thr Ile Asp Arg Asp Leu Ala Gly Lys Arg Ile Ala Ile Asn Phe
            100                 105                 110

Asp Gly Val Tyr Met Asn Ala Thr Val Trp Phe Asn Gly Val Lys Leu
        115                 120                 125

Gly Thr His Pro Tyr Gly Tyr Ser Pro Phe Ser Phe Asp Leu Thr Gly
    130                 135                 140

Asn Ala Lys Phe Gly Gly Glu Asn Thr Ile Val Val Lys Val Glu Asn
145                 150                 155                 160

Arg Leu Pro Ser Ser Arg Trp Tyr Ser Gly Ser Gly Ile Tyr Arg Asp
            165                 170                 175
```

```
Val Thr Leu Thr Val Thr Asp Gly Val His Val Gly Asn Asn Gly Val
            180                 185                 190

Ala Ile Lys Thr Pro Ser Leu Ala Thr Gln Asn Gly Gly Asn Val Thr
            195                 200                 205

Met Asn Leu Thr Thr Lys Val Ala Asn Asp Thr Glu Ala Ala Ala Asn
            210                 215                 220

Ile Thr Leu Lys Gln Thr Val Phe Pro Lys Gly Gly Lys Thr Asp Ala
225                 230                 235                 240

Ala Ile Gly Thr Val Thr Thr Ala Ser Lys Ser Ile Ala Ala Gly Ala
                245                 250                 255

Ser Ala Asp Val Thr Ser Thr Ile Thr Ala Ala Ser Pro Lys Leu Trp
                260                 265                 270

Ser Ile Lys Asn Pro Asn Leu Tyr Thr Val Arg Thr Glu Val Leu Asn
            275                 280                 285

Gly Asp Thr Val Leu Asp Thr Tyr Asp Thr Glu Tyr Gly Phe Arg Trp
            290                 295                 300

Thr Gly Phe Asp Ala Thr Ser Gly Phe Ser Leu Asn Gly Glu Lys Val
305                 310                 315                 320

Lys Leu Lys Gly Val Ser Met His His Asp Gln Gly Ser Leu Gly Ala
                325                 330                 335

Val Ala Asn Arg Arg Ala Ile Glu Arg Gln Val Glu Ile Leu Gln Lys
                340                 345                 350

Met Gly Val Asn Ser Ile Arg Thr Thr His Asn Pro Ala Ala Lys Ala
            355                 360                 365

Leu Ile Asp Val Cys Asn Glu Lys Gly Val Leu Val Val Glu Glu Val
            370                 375                 380

Phe Asp Met Trp Asn Arg Ser Lys Asn Gly Asn Thr Glu Asp Tyr Gly
385                 390                 395                 400

Lys Trp Phe Gly Gln Thr Ile Ala Gly Asp Asn Ala Val Leu Gly Gly
                405                 410                 415

Asp Lys Asp Glu Thr Trp Ala Lys Phe Asp Leu Thr Ser Thr Ile Asn
            420                 425                 430

Arg Asp Arg Asn Ala Pro Ser Val Ile Met Trp Ser Leu Gly Asn Glu
            435                 440                 445

Met Met Glu Gly Ile Ser Gly Ser Val Ser Asp Phe Pro Ala Thr Ser
450                 455                 460

Ala Lys Leu Val Ala Trp Thr Lys Ala Ala Asp Ser Thr Arg Pro Met
465                 470                 475                 480

Thr Tyr Gly Asp Asn Lys Ile Lys Ala Asn Trp Asn Glu Ser Asn Thr
                485                 490                 495

Met Gly Asp Asn Leu Thr Ala Asn Gly Gly Val Val Gly Thr Asn Tyr
            500                 505                 510

Ser Asp Gly Ala Asn Tyr Asp Lys Ile Arg Thr Thr His Pro Ser Trp
            515                 520                 525

Ala Ile Tyr Gly Ser Glu Thr Ala Ser Ala Ile Asn Ser Arg Gly Ile
            530                 535                 540

Tyr Asn Arg Thr Thr Gly Gly Ala Gln Ser Ser Asp Lys Gln Leu Thr
545                 550                 555                 560

Ser Tyr Asp Asn Ser Ala Val Gly Trp Gly Ala Val Ala Ser Ser Ala
                565                 570                 575

Trp Tyr Asp Val Val Gln Arg Asp Phe Val Ala Gly Thr Tyr Val Trp
                580                 585                 590
```

```
Thr Gly Phe Asp Tyr Leu Gly Glu Pro Thr Pro Trp Asn Gly Thr Gly
            595                 600                 605

Ser Gly Ala Val Gly Ser Trp Pro Ser Pro Lys Asn Ser Tyr Phe Gly
610                 615                 620

Ile Val Asp Thr Ala Gly Phe Pro Lys Asp Thr Tyr Tyr Phe Tyr Gln
625                 630                 635                 640

Ser Gln Trp Asn Asp Asp Val His Thr Leu His Ile Leu Pro Ala Trp
                645                 650                 655

Asn Glu Asn Val Val Ala Lys Gly Ser Gly Asn Lys Val Pro Val Val
                660                 665                 670

Val Tyr Thr Asp Ala Ala Lys Val Lys Leu Tyr Phe Thr Pro Lys Gly
            675                 680                 685

Ser Thr Glu Lys Arg Leu Ile Gly Glu Lys Ser Phe Thr Lys Lys Thr
            690                 695                 700

Thr Ala Ala Gly Tyr Thr Tyr Gln Val Tyr Glu Gly Thr Asp Lys Asp
705                 710                 715                 720

Ser Thr Ala His Lys Asn Met Tyr Leu Thr Trp Asn Val Pro Trp Ala
                725                 730                 735

Glu Gly Thr Ile Ser Ala Glu Ala Tyr Asp Glu Asn Asn Arg Leu Ile
            740                 745                 750

Pro Glu Gly Ser Thr Glu Gly Asn Ala Ser Val Thr Thr Gly Lys
            755                 760                 765

Ala Ala Lys Leu Lys Ala Asp Ala Arg Lys Thr Ile Thr Ala Asp
770                 775                 780

Gly Lys Asp Leu Ser Tyr Ile Glu Val Asp Val Thr Asp Ala Asn Gly
785                 790                 795                 800

His Ile Val Pro Asp Ala Ala Asn Arg Val Thr Phe Asp Val Lys Gly
                805                 810                 815

Ala Gly Lys Leu Val Gly Val Asp Asn Gly Ser Ser Pro Asp His Asp
                820                 825                 830

Ser Tyr Gln Ala Asp Asn Arg Lys Ala Phe Ser Gly Lys Val Leu Ala
            835                 840                 845

Ile Val Gln Ser Thr Lys Glu Ala Gly Glu Ile Thr Val Thr Ala Lys
850                 855                 860

Ala Asp Gly Leu Gln Ser Ser Thr Val Lys Ile Ala Thr Thr Ala Val
865                 870                 875                 880

Pro Gly Thr Ser Thr Glu Lys Thr Val Arg Ser Phe Tyr Tyr Ser Arg
                885                 890                 895

Asn Tyr Tyr Val Lys Thr Gly Asn Lys Pro Ile Leu Pro Ser Asp Val
                900                 905                 910

Glu Val Arg Tyr Ser Asp Gly Thr Ser Asp Arg Gln Asn Val Thr Trp
            915                 920                 925

Asp Ala Val Ser Asp Asp Gln Ile Ala Lys Ala Gly Ser Phe Ser Val
930                 935                 940

Ala Gly Thr Val Ala Gly Gln Lys Ile Ser Val Arg Val Thr Met Ile
945                 950                 955                 960

Asp Glu Ile Gly Ala Leu Leu Asn Tyr Ser Ala Ser Thr Pro Val Gly
                965                 970                 975

Thr Pro Ala Val Leu Pro Gly Ser Arg Pro Ala Val Leu Pro Asp Gly
            980                 985                 990

Thr Val Thr Ser Ala Asn Phe Ala Val His Trp Thr Lys Pro Ala Asp
            995                1000                1005

Thr Val Tyr Asn Thr Ala Gly Thr Val Lys Val Pro Gly Thr Ala
```

```
                1010                1015                1020

Thr Val Phe Gly Lys Glu Phe Lys Val Thr Ala Thr Ile Arg Val
            1025                1030                1035

Gln Arg Ser Gln Val Thr Ile Gly Ser Ser Val Ser Gly Asn Ala
            1040                1045                1050

Leu Arg Leu Thr Gln Asn Ile Pro Ala Asp Lys Gln Ser Asp Thr
            1055                1060                1065

Leu Asp Ala Ile Lys Asp Gly Ser Thr Thr Val Asp Ala Asn Thr
            1070                1075                1080

Gly Gly Gly Ala Asn Pro Ser Ala Trp Thr Asn Trp Ala Tyr Ser
            1085                1090                1095

Lys Ala Gly His Asn Thr Ala Glu Ile Thr Phe Glu Tyr Ala Thr
            1100                1105                1110

Glu Gln Gln Leu Gly Gln Ile Val Met Tyr Phe Phe Arg Asp Ser
            1115                1120                1125

Asn Ala Val Arg Phe Pro Asp Ala Gly Lys Thr Lys Ile Gln Ile
            1130                1135                1140

Ser Ala Asp Gly Lys Asn Trp Thr Asp Leu Ala Ala Thr Glu Thr
            1145                1150                1155

Ile Ala Ala Gln Glu Ser Ser Asp Arg Val Lys Pro Tyr Thr Tyr
            1160                1165                1170

Asp Phe Ala Pro Val Gly Ala Thr Phe Val Lys Val Thr Val Thr
            1175                1180                1185

Asn Ala Asp Thr Thr Thr Pro Ser Gly Val Val Cys Ala Gly Leu
            1190                1195                1200

Thr Glu Ile Glu Leu Lys Thr Ala Thr Ser Lys Phe Val Thr Asn
            1205                1210                1215

Thr Ser Ala Ala Leu Ser Ser Leu Thr Val Asn Gly Thr Lys Val
            1220                1225                1230

Ser Asp Ser Val Leu Ala Ala Gly Ser Tyr Asn Thr Pro Ala Ile
            1235                1240                1245

Ile Ala Asp Val Lys Ala Glu Gly Glu Gly Asn Ala Ser Val Thr
            1250                1255                1260

Val Leu Pro Ala His Asp Asn Val Ile Arg Val Ile Thr Glu Ser
            1265                1270                1275

Glu Asp His Val Thr Arg Lys Thr Phe Thr Ile Asn Leu Gly Thr
            1280                1285                1290

Glu Gln Glu Phe Pro Ala Asp Ser Asp Glu Arg Asp
            1295                1300                1305

<210> SEQ ID NO 35
<211> LENGTH: 1025
<212> TYPE: PRT
<213> ORGANISM: Kluyveromyces lactis

<400> SEQUENCE: 35

Met Ser Cys Leu Ile Pro Glu Asn Leu Arg Asn Pro Lys Lys Val His
1               5                   10                  15

Glu Asn Arg Leu Pro Thr Arg Ala Tyr Tyr Tyr Asp Gln Asp Ile Phe
            20                  25                  30

Glu Ser Leu Asn Gly Pro Trp Ala Phe Ala Leu Phe Asp Ala Pro Leu
        35                  40                  45

Asp Ala Pro Asp Ala Lys Asn Leu Asp Trp Glu Thr Ala Lys Lys Trp
    50                  55                  60
```

```
Ser Thr Ile Ser Val Pro Ser His Trp Glu Leu Gln Glu Asp Trp Lys
 65                  70                  75                  80

Tyr Gly Lys Pro Ile Tyr Thr Asn Val Gln Tyr Pro Ile Pro Ile Asp
                 85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
        115                 120                 125

Phe Glu Gly Val Asp Asn Cys Tyr Glu Leu Tyr Val Asn Gly Gln Tyr
    130                 135                 140

Val Gly Phe Asn Lys Gly Ser Arg Asn Gly Ala Glu Phe Asp Ile Gln
145                 150                 155                 160

Lys Tyr Val Ser Glu Gly Glu Asn Leu Val Val Lys Val Phe Lys
                165                 170                 175

Trp Ser Asp Ser Thr Tyr Ile Glu Asp Gln Asp Gln Trp Trp Leu Ser
                180                 185                 190

Gly Ile Tyr Arg Asp Val Ser Leu Leu Lys Leu Pro Lys Lys Ala His
            195                 200                 205

Ile Glu Asp Val Arg Val Thr Thr Thr Phe Val Asp Ser Gln Tyr Gln
    210                 215                 220

Asp Ala Glu Leu Ser Val Lys Val Asp Val Gln Gly Ser Ser Tyr Asp
225                 230                 235                 240

His Ile Asn Phe Thr Leu Tyr Glu Pro Glu Asp Gly Ser Lys Val Tyr
                245                 250                 255

Asp Ala Ser Ser Leu Leu Asn Glu Glu Asn Gly Asn Thr Thr Phe Ser
            260                 265                 270

Thr Lys Glu Phe Ile Ser Phe Ser Thr Lys Lys Asn Glu Glu Thr Ala
    275                 280                 285

Phe Lys Ile Asn Val Lys Ala Pro Glu His Trp Thr Ala Glu Asn Pro
290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
                325                 330                 335

Asp Gly Asn Ile Thr Val Asn Gly Lys Asp Ile Leu Phe Arg Gly Val
            340                 345                 350

Asn Arg His Asp His His Pro Arg Phe Gly Arg Ala Val Pro Leu Asp
    355                 360                 365

Phe Val Val Arg Asp Leu Ile Leu Met Lys Lys Phe Asn Ile Asn Ala
370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
                405                 410                 415

Gly Val Gln Glu Pro Phe Asn Arg His Thr Asn Leu Glu Ala Glu Tyr
            420                 425                 430

Pro Asp Thr Lys Asn Lys Leu Tyr Asp Val Asn Ala His Tyr Leu Ser
    435                 440                 445

Asp Asn Pro Glu Tyr Glu Val Ala Tyr Leu Asp Arg Ala Ser Gln Leu
450                 455                 460

Val Leu Arg Asp Val Asn His Pro Ser Ile Ile Trp Ser Leu Gly
465                 470                 475                 480

Asn Glu Ala Cys Tyr Gly Arg Asn His Lys Ala Met Tyr Lys Leu Ile
```

-continued

```
                485                 490                 495
Lys Gln Leu Asp Pro Thr Arg Leu Val His Tyr Glu Gly Asp Leu Asn
                500                 505                 510

Ala Leu Ser Ala Asp Ile Phe Ser Phe Met Tyr Pro Thr Phe Glu Ile
                515                 520                 525

Met Glu Arg Trp Arg Lys Asn His Thr Asp Glu Asn Gly Lys Phe Glu
                530                 535                 540

Lys Pro Leu Ile Leu Cys Glu Tyr Gly His Ala Met Gly Asn Gly Pro
545                 550                 555                 560

Gly Ser Leu Lys Glu Tyr Gln Glu Leu Phe Tyr Lys Glu Lys Phe Tyr
                565                 570                 575

Gln Gly Gly Phe Ile Trp Glu Trp Ala Asn His Gly Ile Glu Phe Glu
                580                 585                 590

Asp Val Ser Thr Ala Asp Gly Lys Leu His Lys Ala Tyr Ala Tyr Gly
                595                 600                 605

Gly Asp Phe Lys Glu Glu Val His Asp Gly Val Phe Ile Met Asp Gly
                610                 615                 620

Leu Cys Asn Ser Glu His Asn Pro Thr Pro Gly Leu Val Glu Tyr Lys
625                 630                 635                 640

Lys Val Ile Glu Pro Val His Ile Lys Ile Ala His Gly Ser Val Thr
                645                 650                 655

Ile Thr Asn Lys His Asp Phe Ile Thr Thr Asp His Leu Leu Phe Ile
                660                 665                 670

Asp Lys Asp Thr Gly Lys Thr Ile Asp Val Pro Ser Leu Lys Pro Glu
                675                 680                 685

Glu Ser Val Thr Ile Pro Ser Asp Thr Thr Tyr Val Val Ala Val Leu
                690                 695                 700

Lys Asp Asp Ala Gly Val Leu Lys Ala Gly His Glu Ile Ala Trp Gly
705                 710                 715                 720

Gln Ala Glu Leu Pro Leu Lys Val Pro Asp Phe Val Thr Glu Thr Ala
                725                 730                 735

Glu Lys Ala Ala Lys Ile Asn Asp Gly Lys Arg Tyr Val Ser Val Glu
                740                 745                 750

Ser Ser Gly Leu His Phe Ile Leu Asp Lys Leu Leu Gly Lys Ile Glu
                755                 760                 765

Ser Leu Lys Val Lys Gly Lys Glu Ile Ser Ser Lys Phe Glu Gly Ser
770                 775                 780

Ser Ile Thr Phe Trp Arg Pro Pro Thr Asn Asn Asp Glu Pro Arg Asp
785                 790                 795                 800

Phe Lys Asn Trp Lys Lys Tyr Asn Ile Asp Leu Met Lys Gln Asn Ile
                805                 810                 815

His Gly Val Ser Val Glu Lys Gly Ser Asn Gly Ser Leu Ala Val Val
                820                 825                 830

Thr Val Asn Ser Arg Ile Ser Pro Val Val Phe Tyr Tyr Gly Phe Glu
                835                 840                 845

Thr Val Gln Lys Tyr Thr Ile Phe Ala Asn Lys Ile Asn Leu Asn Thr
                850                 855                 860

Ser Met Lys Leu Thr Gly Glu Tyr Gln Pro Pro Asp Phe Pro Arg Val
865                 870                 875                 880

Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
                900                 905                 910
```

```
Phe Gly Leu Tyr Asp Ser Lys Asp Val Glu Glu Phe Val Asp Tyr
        915                 920                 925

Pro Gln Glu Asn Gly Asn His Thr Asp Thr His Phe Leu Asn Ile Lys
    930                 935                 940

Phe Glu Gly Ala Gly Lys Leu Ser Ile Phe Gln Lys Gly Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
            980                 985                 990

Ile His Gly Val Gly Ser Glu Ala  Cys Gly Pro Ala Val  Leu Asp Gln
        995                 1000                1005

Tyr Arg  Leu Lys Ala Gln Asp  Phe Asn Phe Glu Phe  Asp Leu Ala
    1010                1015                1020

Phe Glu
    1025

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(9)
<223> OTHER INFORMATION: deoxyuracil

<400> SEQUENCE: 36
attaaccaug cgacgcaact tcgaatggcc                                    30

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(9)
<223> OTHER INFORMATION: deoxyuracil

<400> SEQUENCE: 37
atcttctcut taccgcctta ccacgagcac g                                  31

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(9)
```

```
<223> OTHER INFORMATION: deoxyuracil

<400> SEQUENCE: 38
agagaagaut tcagcctga tacagattaa atc                                33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(9)
<223> OTHER INFORMATION: deoxyuracil

<400> SEQUENCE: 39
atggttaaut cctcctgtta gcccaaaaaa cgg                                33

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cggcgtcaca ctttgctatg cc                                             22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccgcgctact gccgccaggc                                                20
```

LACTASE ENZYMES WITH IMPROVED ACTIVITY AT LOW TEMPERATURES

CROSS-REFERENCE TO RELATED APPLICATIONS

The present application is the U.S. National Stage of International Application No. PCT/EP2018/059289, filed Apr. 11, 2018, and claims priority to European Patent Application Nos. 17166021.0, filed Apr. 11, 2017, and 17188732.6, filed Aug. 31, 2017.

SEQUENCE LISTING

The instant application contains a Sequence Listing which has been filed electronically in ASCII format and is hereby incorporated by reference in its entirety. Said ASCII copy, created on Apr. 3, 2020, is named 030427-0310_SL.txt and is 253,448 bytes in size.

FIELD OF THE INVENTION

The present invention relates to methods for producing a dairy product and methods for reducing the lactose content of a dairy product using new peptides or dimeric peptides exhibiting beta-galactosidase enzyme activity with improved activity at low temperatures.

BACKGROUND OF THE INVENTION

In order to grow on milk, lactose hydrolysis is a good way for lactic acid bacteria to obtain glucose and galactose as carbon source. Lactase (beta-galactosidase; EC 3.2.1.23) is the enzyme that performs the hydrolysis step of the milk sugar lactose into monosaccharides. The commercial use of lactase is to break down lactose in dairy products. Lactose intolerant people have difficulties to digest dairy products with high lactose levels. It is estimated that about 70% of the world's population has a limited ability to digest lactose. Accordingly, there is a growing demand for dairy food products that contain no or only low levels of lactose.

Lactases have been isolated from a large variety of organisms, including microorganisms like *Kluyveromyces* and *Bacillus*. *Kluyveromyces*, especially *K. fragilis* and *K. lactis*, and other fungi such as those of the genera *Candida*, *Torula* and *Torulopsis*, are a common source of fungal lactases, whereas *B. coagulans* and *B. circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so-called neutral lactases having a pH optimum between pH 6 and pH 8, as well as a temperature optimum around 37° C. When such lactases are used in the production of, e.g. low-lactose yoghurt, the enzyme treatment will either have to be done in a separate step before fermentation or rather high enzyme dosages have to be used because their activity will drop as the pH decreases during fermentation.

A typical process for production of pasteurized milk with reduced lactose comprises addition of the lactase enzyme to the milk followed by prolonged incubation (10-48 h, often 24 h) at temperatures around 6° C. Because the Ha-Lactase and NOLA® Fit activity is in the range of 45-70 µmol per min per mg of enzyme, enzyme doses in the range of 55-70 mg/L and 45-60 mg/L respectively for pasteurized milk are required to achieve the desired residual lactose level. The Ha-Lactase and NOLA® Fit enzymes have temperature optimum around 37° C. Longer incubation of milk at 37° C. can result in microbial growth.

Also, these lactases are not suitable for hydrolysis of lactose in milk performed at high or low temperatures, which would in some cases be beneficial in order to keep the microbial count low and thus ensure high milk quality. Furthermore, the known lactases would not be suitable for use in a desired process for the production of ultra-heat treated (UHT) milk, wherein enzymes were added prior to the UHT treatment.

WO92/13068 relates to compositions comprising lactase activity obtained from sonication of microbial cells of bacteria or yeast. WO2010092057 and WO0104276 relate to cold-active beta-galactosidases. WO07110619 relates to beta-galactosidase with high transgalactosylating activity, whereas WO2009071539 relates to beta-galactosidase with lower transgalactosylating activity.

OBJECT OF THE INVENTION

It is an object of embodiments of the invention to provide methods using beta-galactosidases that enable the production of improved lactose-free or low-lactose products at low temperatures.

It is a further object of embodiments of the invention to provide methods using beta-galactosidases with properties that improve the lowering of lactose in a product, such as lactose-free or low-lactose products.

SUMMARY OF THE INVENTION

The present inventor(s) have identified beta-galactosidases with properties not previously described that enable the production of improved lactose-free or low-lactose products as well as enabling improved production methods for such lactose-free or low-lactose products. In particular these beta-galactosidases have been shown to be very stable with relatively high activity at a very broad range of both temperatures as well as pH values. They are also useable at specific temperatures, such as at high temperatures and pH values not normally seen with these enzymes. First of all, this enables to the use of beta-galactosidases at specific pH values and temperatures that were not known to be possible. It also enables the use of the same specific enzyme in several different applications, which is highly requested in the industry.

In a first aspect the present invention provides methods for producing a dairy product comprising:
  (a) mixing a milk-based substrate comprising lactose in a concentration of at least 10 g/L and a peptide or a dimeric peptide exhibiting beta-galactosidase activity in a concentration of 10 to 55 mg/L, such as e.g. 20 to 55 mg/L;
  (b) incubating the mixture at a temperature from 1° C.-10° C. for a period of time sufficient to reduce the lactose concentration in the mixture to less than 0.2 g/L.

In a related embodiment the present invention provides methods for reducing the lactose content in a milk-based substrate comprising:
  (a) mixing a milk-based substrate comprising lactose in a concentration of at least 10 g/L and a peptide or a dimeric peptide exhibiting beta-galactosidase activity in a concentration of 10 to 55 mg/L, such as e.g. 20 to 55 mg/L;

(b) incubating the mixture at a temperature from 1° C.-10° C. for a period of time sufficient to reduce the lactose concentration in the mixture to less than 0.2 g/L.

The methods as described above can be carried out with a peptide or dimeric peptide exhibiting beta-galactosidase activity which may be further be characterized as:

(i) a peptide having an amino acid sequence selected from SEQ ID NO: 22, 33, 14, 7, 9, 11, 30 and 1 or a peptide having an amino acid sequence identity of more than 85% to any of these sequences;

(ii) a peptide having an amino acid sequence selected from SEQ ID NO: 22, 33, 14, 13, 19, 7, 9, 11, 26 and 27, 30 and 1 or a peptide having an amino acid sequence identity of more than 85% to any of these sequences;

(iii) a peptide having an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

The methods of the present invention are advantageous as they only require a low concentration of the peptide or dimeric peptide exhibiting beta-galactosidase activity and still significantly reduce the lactose concentration. In a preferred alternative, the peptide or dimeric peptide exhibiting beta-galactosidase activity is added in a concentration of 35 to 52 mg/L, in a concentration of 40 to 52 mg/L or in a concentration of 45 to 52 mg/L.

The milk-based substrate can be any substrate containing milk. In one aspect the above methods use a milk-based substrate which is:

(i) cow milk, sheep milk, goat milk, buffalo milk, camel milk, or a pasteurized and/or filtered form thereof; or (ii) a fermented dairy product obtained from (i) by fermentation.

In a particularly preferred embodiment, the above methods use cow milk comprising lactose in a concentration of about 37 to 50 g/L or a heat treated, pasteurized, raw and/or filtered form thereof as the milk-based substrate.

The above methods provide for a significant reduction of the concentration of lactose in a short period of time. In certain embodiments, the concentration is reduced to a value of less than 0.2 g/l lactose after incubation for at least 4 hours, at least 8 hours, at least 12 hours or at least 24 hours.

One of the advantages of the methods of the present invention resides in reduction of the concentration of lactose at low temperatures. For example the incubation temperature in step (b) of the above methods can be in the range of from 2° C.-7° C. or in the range of from 3° C.-6° C.

The methods provide a significant reduction of the concentration of lactose and preferably the incubation in step (b) reduces the lactose concentration in the mixture to less than 0.05 g/L, to less than 0.02 g/L, or to less than 0.01 g/L.

Specific the peptide or dimeric peptide exhibiting beta-galactosidase activity to be used in the methods of the invention are not only highly active at low temperatures, but also at high temperatures. In one aspect the invention thus provides method as described above, wherein the mixture comprising the milk-based substrate and the peptide or dimeric peptide exhibiting beta-galactosidase activity is heated to a temperature of at least 60° C. for at least four seconds before or after incubating the mixture at a temperature from 1° C.-10° C. In particular, the method may comprise a heating step including heating to a temperature of 72° C. for about 15 seconds before or after incubating the mixture at low temperatures in step (b) or heated to a temperature of 140° C. for about four seconds before or after incubating the mixture at a temperature from 1° C.-10° C.

In one alternative, the methods of the present invention are used for producing a dairy product. These methods may further comprise a step of fermenting the milk-based substrate with lactic acid bacteria. The fermentation step is carried out before or after the incubation with a peptide or dimeric peptide exhibiting beta-galactosidase activity.

The methods are particularly suitable for producing dairy products, such as a fermented milk product, cheese, yoghurt, butter, dairy spread, butter milk, acidified milk drink, sour cream, whey based drink, ice cream, condensed milk, dulce de leche or a flavored milk drink.

In a particularly preferred embodiment the present invention provides methods for producing milk or a dairy product comprising:

(a) mixing a milk-based substrate comprising lactose in a concentration of at least 10 g/L and a peptide exhibiting beta-galactosidase activity in a concentration of 35 to 52 mg/L, wherein the peptide has an amino acid sequence selected from SEQ ID NO: 22, 33, 14, 7, 9, 11, 30 and 1 or an amino acid sequence identity of more than 85% to any of these sequences;

(b) incubating the mixture at a temperature from 1° C.-10° C. for 12 hours under conditions sufficient to reduce the lactose concentration in the mixture to less than 0.02 g/L.

In a further preferred embodiment the present invention provides methods for producing milk or a dairy product comprising:

(a) mixing a milk-based substrate comprising lactose in a concentration of at least 10 g/L and a peptide exhibiting beta-galactosidase activity in a concentration of 35 to 52 mg/L, wherein the peptide has an amino acid sequence selected from SEQ ID NO: 22, 33, 14, 7, 9, 11, 30 and 1 or an amino acid sequence identity of more than 85% to any of these sequences;

(b) incubating the mixture at a temperature from 1° C.-10° C. for 12 hours under conditions sufficient to reduce the lactose concentration in the mixture to less than 0.02 g/L, wherein the mixture comprising the milk-based substrate and the peptide exhibiting beta-galactosidase activity is heated to a temperature of at least 60° C. for at least four seconds before or after incubating the mixture at a temperature from 1° C.-10° C.

In a further embodiment the present invention relates to the use of a peptide or dimeric peptide exhibiting beta-galactosidase activity for producing a dairy product with reduced lactose content at a temperature from 1° C.-10° C. for a period of time sufficient to reduce the lactose concentration in the mixture to less than 0.2 g/L, wherein the peptide or dimeric peptide exhibiting beta-galactosidase activity is:

(i) a peptide having an amino acid sequence selected from SEQ ID NO: 22, 33, 14, 7, 9, 11, 30 and 1 or a peptide having an amino acid sequence identity of more than 85% to any of these sequences;

(ii) a peptide having an amino acid sequence selected from SEQ ID NO: 22, 33, 14, 13, 19, 7, 9, 11, 26 and 27, 30 and 1 or a peptide having an amino acid sequence identity of more than 85% to any of these sequences;

(iii) a peptide having an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

LEGENDS TO THE FIGURES

FIG. 1. The specific activity of the purified enzymes determined at pH 6.7 at 37° C. with lactose as substrate, described as SUAL-1, discussed in example 6. The measured standard deviation at the given condition was less than 6%.

Figure 2:
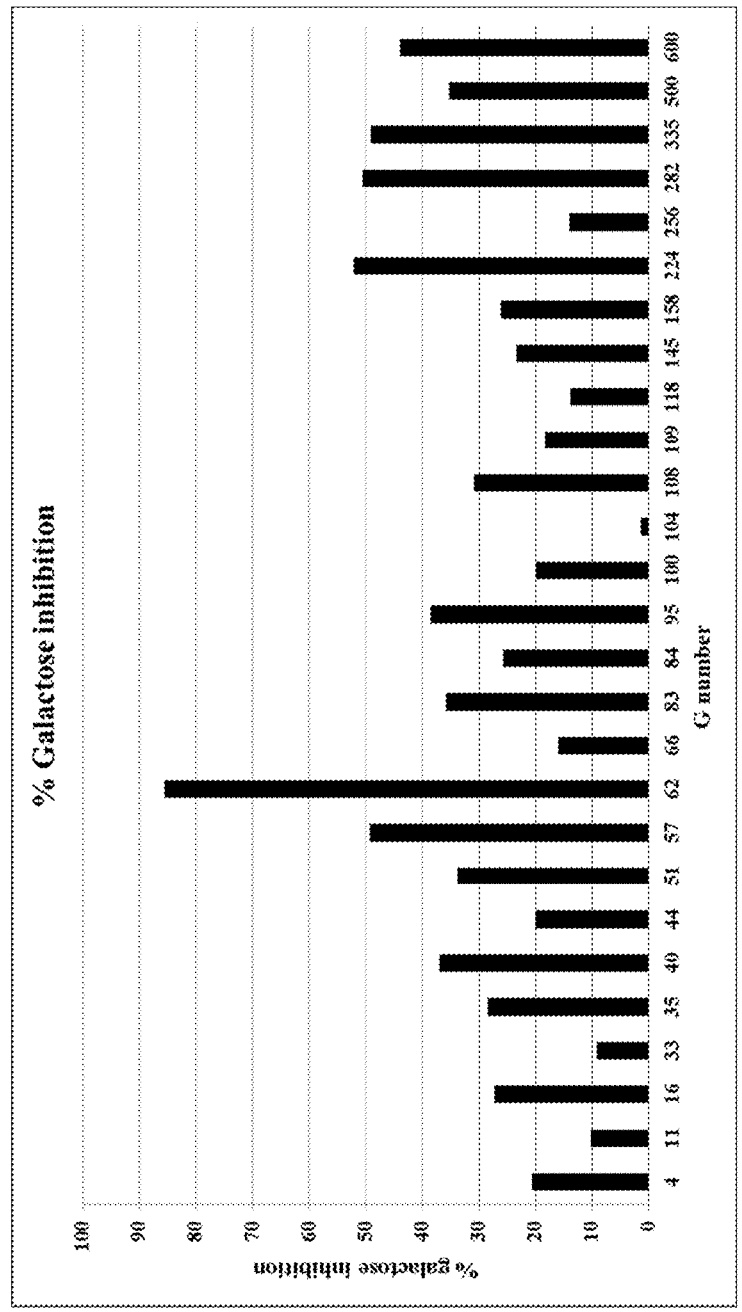

FIG. 2. The specific activity of the purified enzymes determined at pH 6.7 at 37° C. in presence of galactose, described as SUAG, discussed in example 7. The measured standard deviation at the given condition was less than 15%.

Figure 3:
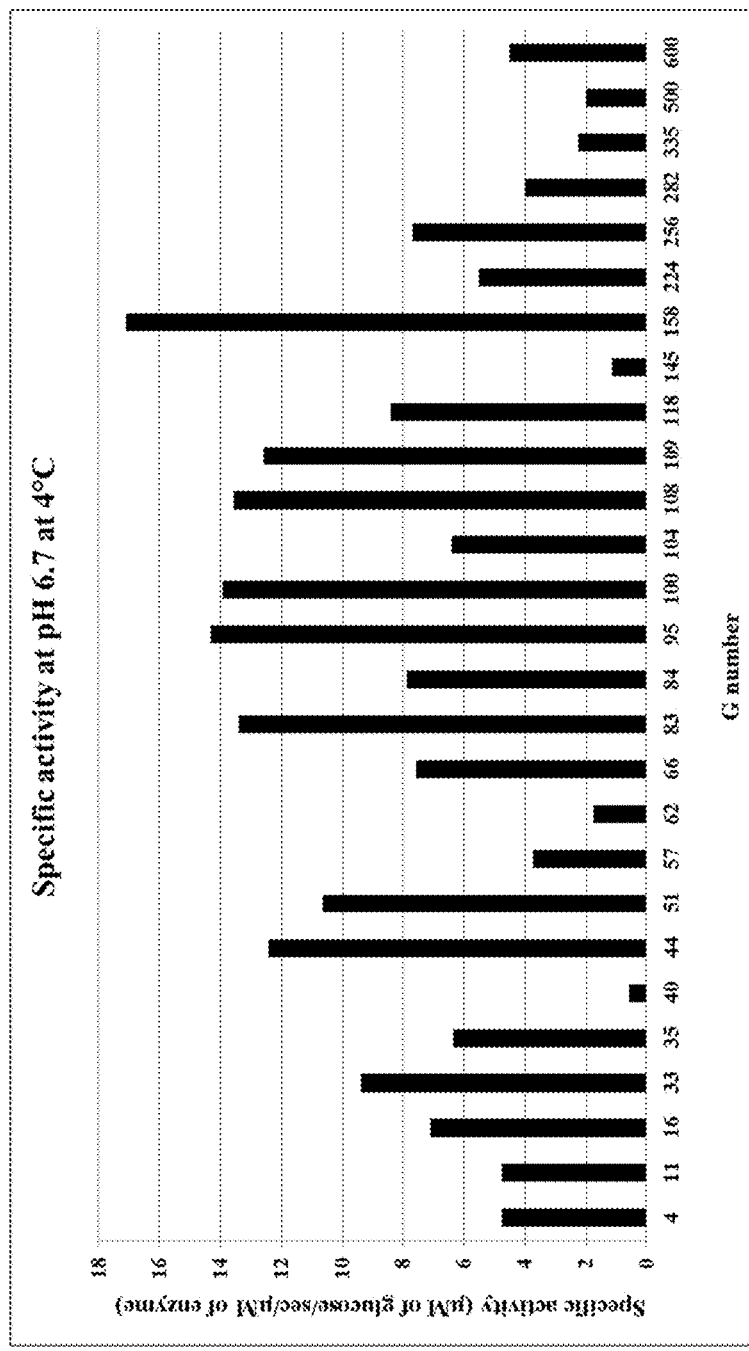

FIG. 3. The specific activity of the purified enzymes determined at pH 6.7 at 4° C. with lactose as substrate, described as SUAL-2, discussed in example 8. The measured standard deviation at the given condition was less than 5%.

Figure 4:
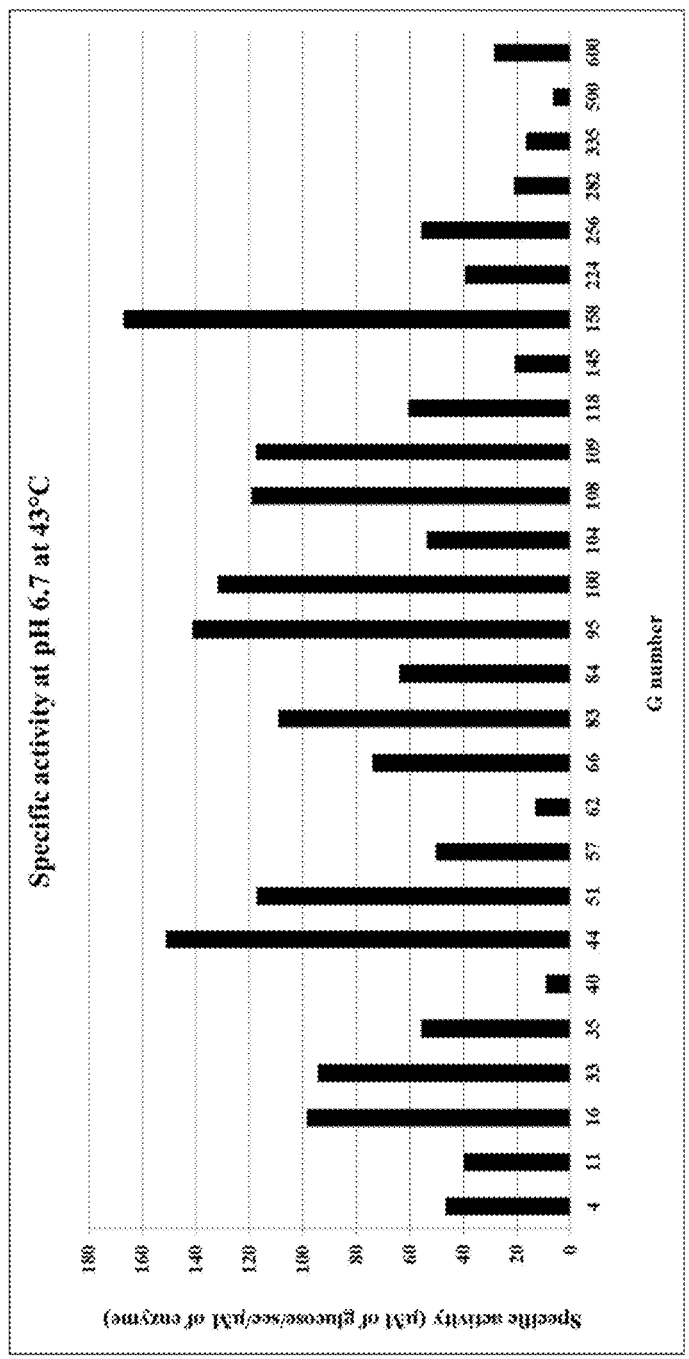

FIG. 4. The specific activity of the purified enzymes determined at pH 6.7 at 43° C. with lactose as substrate, described as SUAL-3, discussed in example 9. The measured standard deviation at the given condition was less than 5%.

Figure 5:
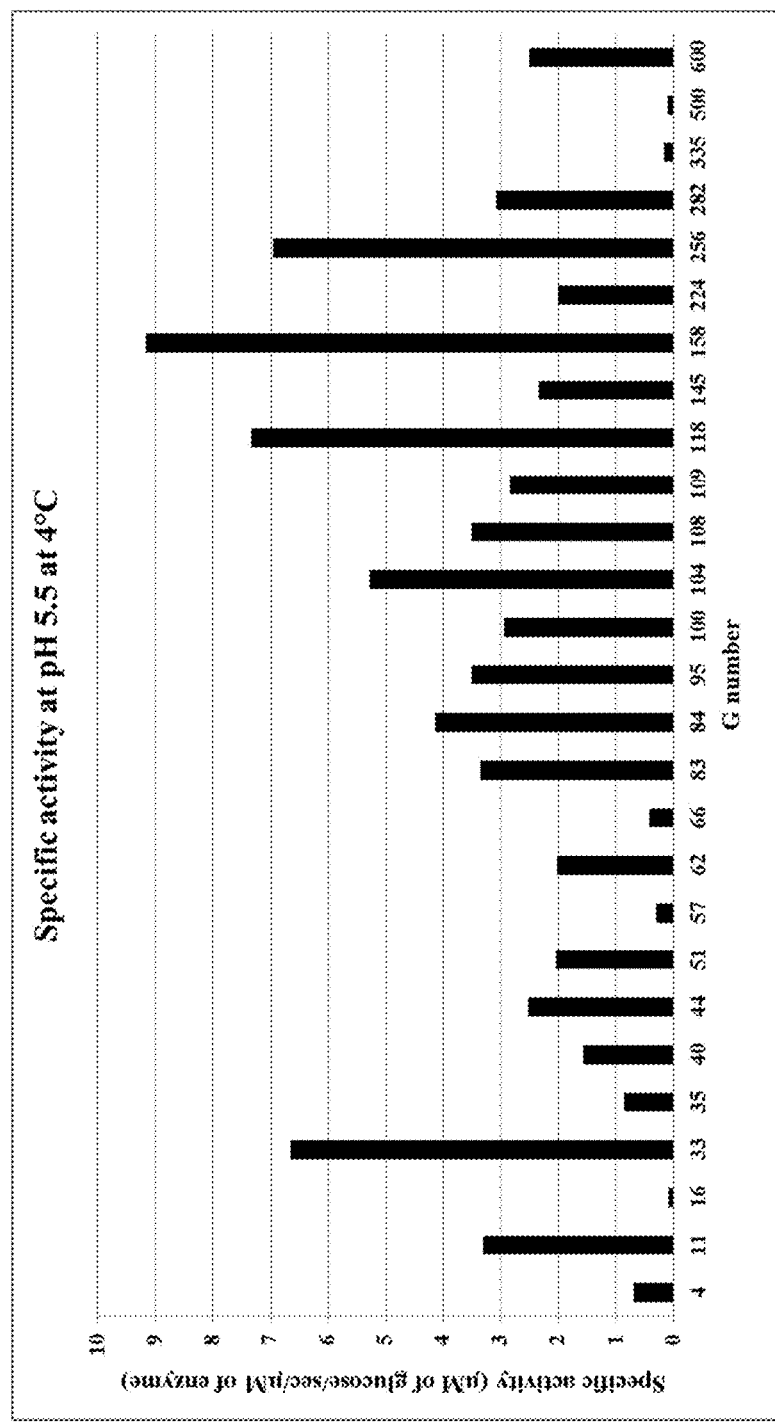

FIG. 5. The specific activity of the purified enzymes determined at pH 5.5 at 4° C. with lactose as substrate, described as SUAL-4, discussed in example 10. The measured standard deviation at the given condition was less than 5%.

Figure 6:
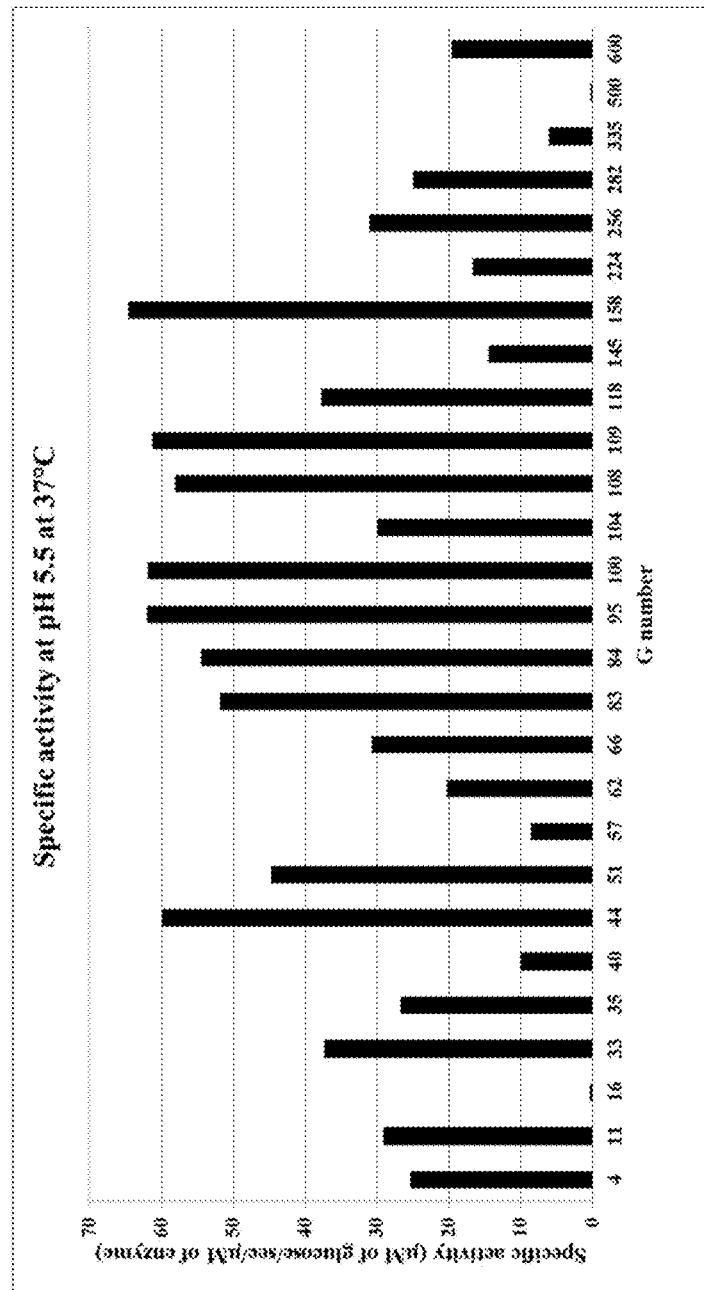

FIG. 6. The specific activity of the purified enzymes determined at pH 5.5 at 37° C. with lactose as substrate, described as SUAL-5, discussed in example 11. The measured standard deviation at the given condition was less than 5%.

Figure 7:
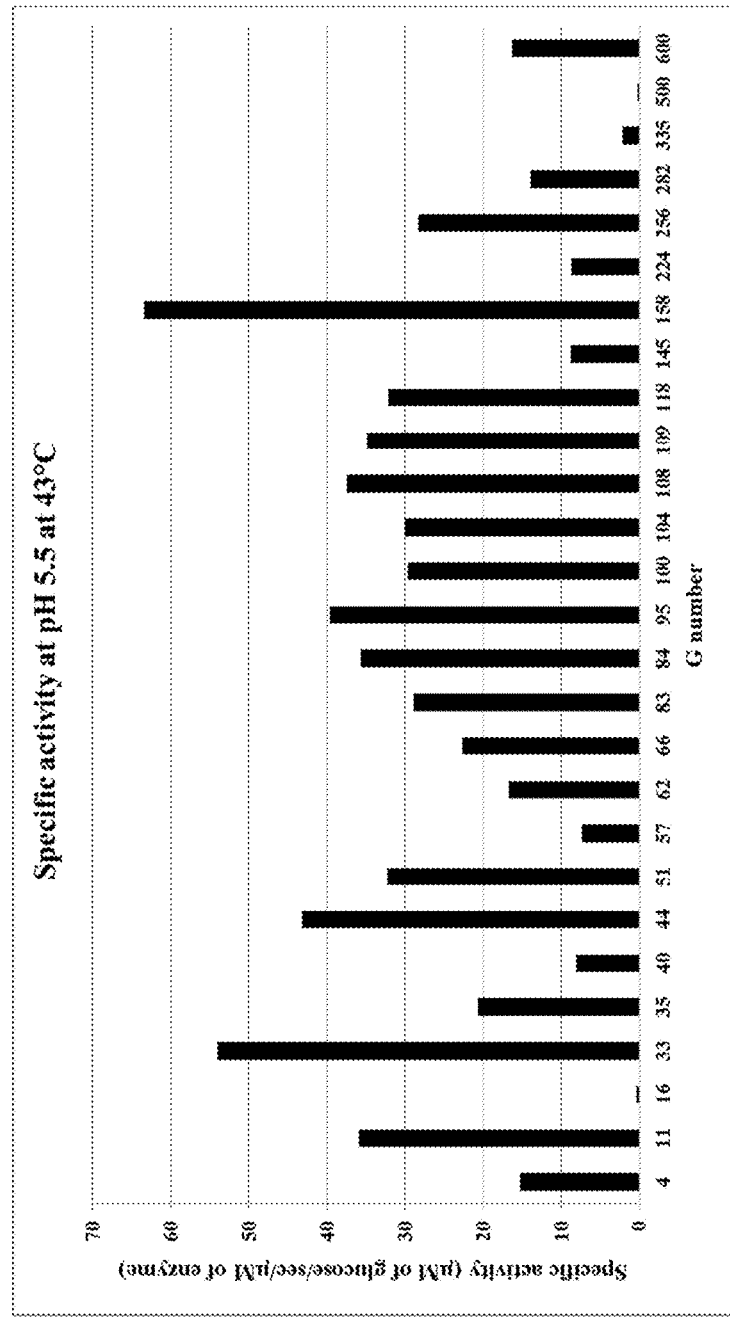

FIG. 7. The specific activity of the purified enzymes determined at pH 5.5 at 43° C. with lactose as substrate, described as SUAL-6, discussed in example 12. The measured standard deviation at the given condition was less than 5%.

Figure 8:
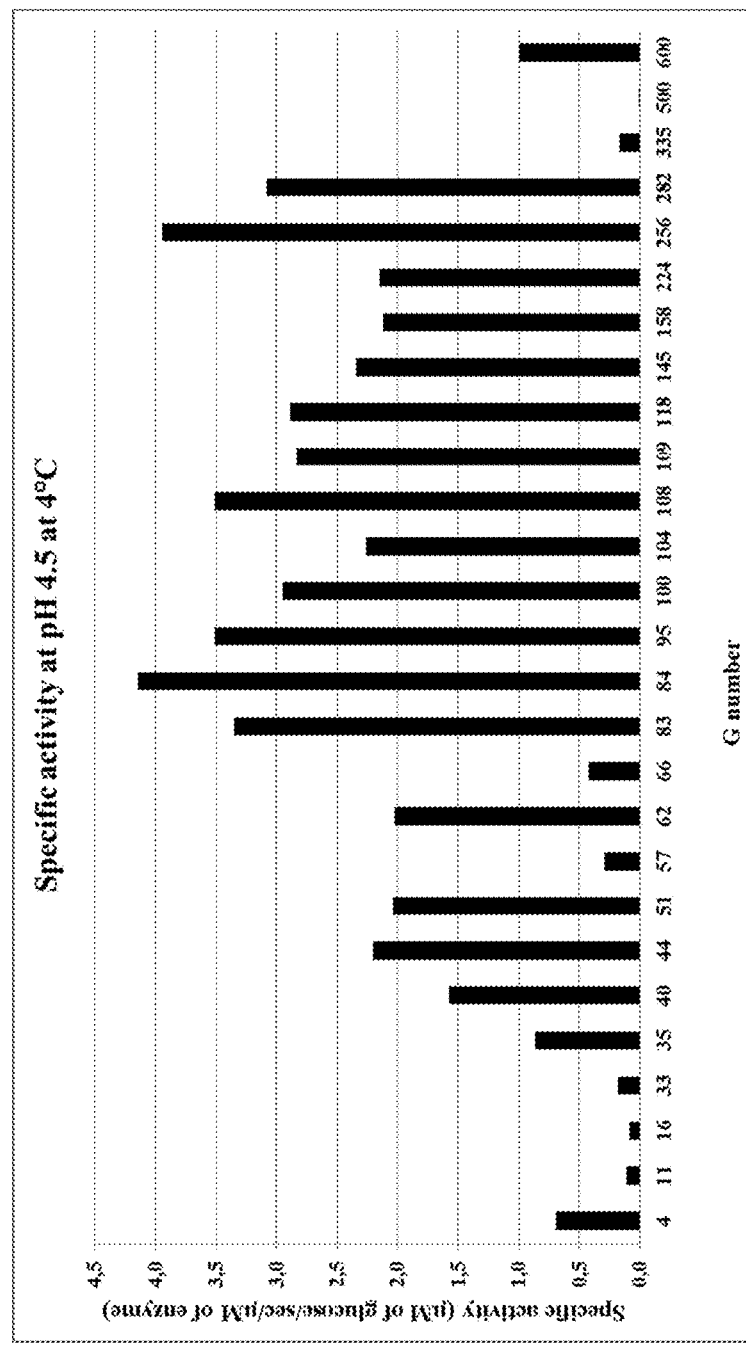

FIG. 8. The specific activity of the purified enzymes determined at pH 4.5 at 4° C. with lactose as substrate, described as SUAL-7, discussed in example 13. The measured standard deviation at the given condition was less than 5%.

Figure 9:
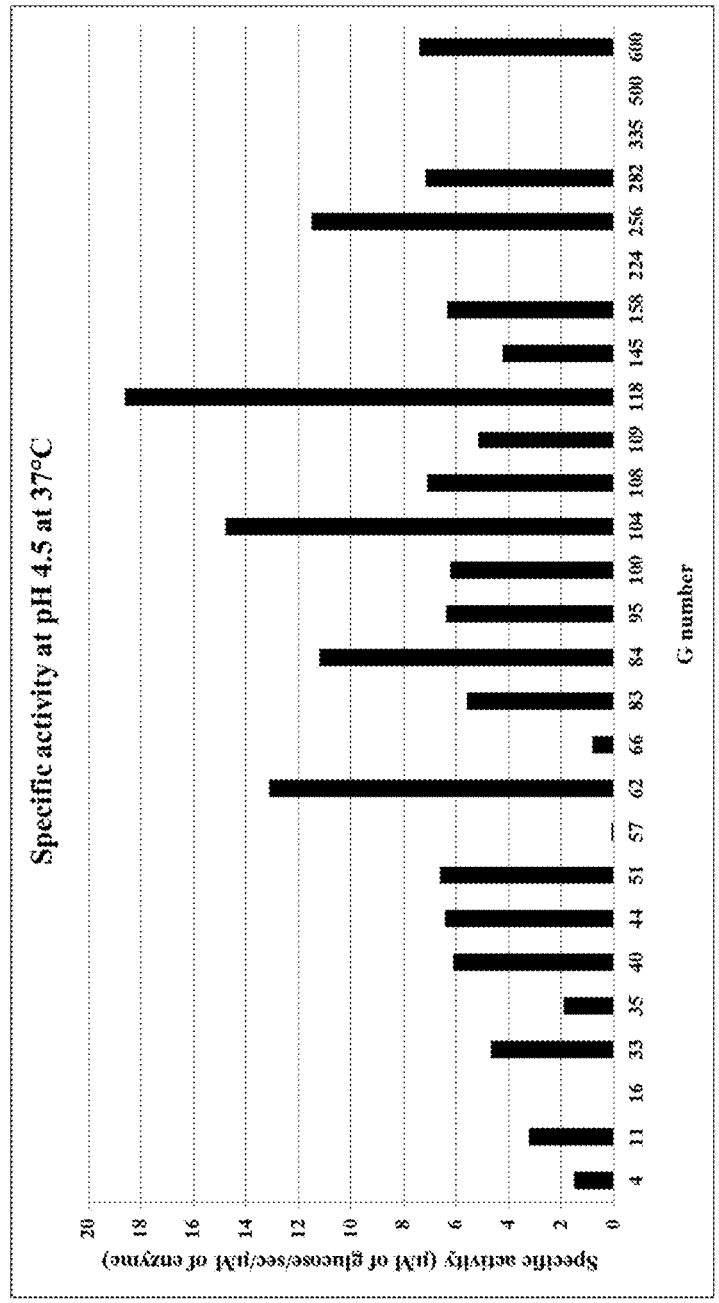

FIG. 9. The specific activity of the purified enzymes determined at pH 4.5 at 37° C. with lactose as substrate, described as SUAL-8, discussed in example 14. The measured standard deviation at the given condition was less than 5%.

Figure 10:
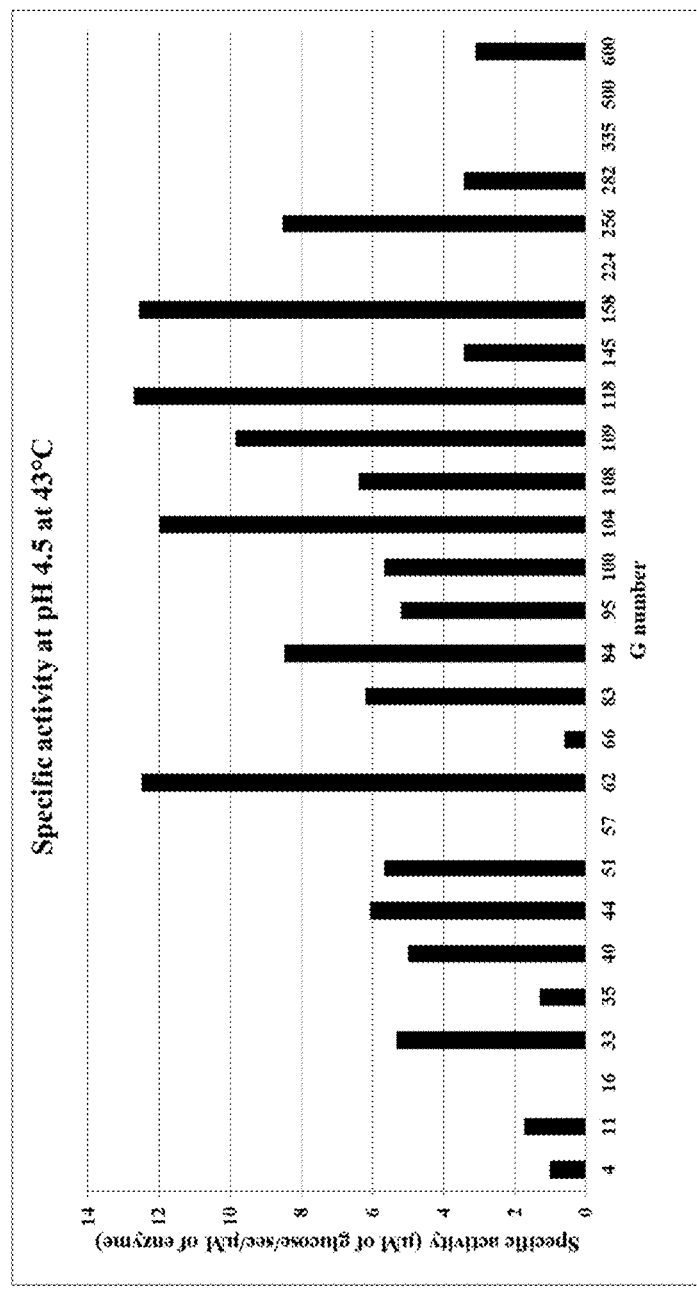

FIG. 10. The specific activity of the purified enzymes determined at pH 4.5 at 43° C. with lactose as substrate, described as SUAL-9, discussed in example 15. The measured standard deviation at the given condition was less than 5%.

Figure 11:
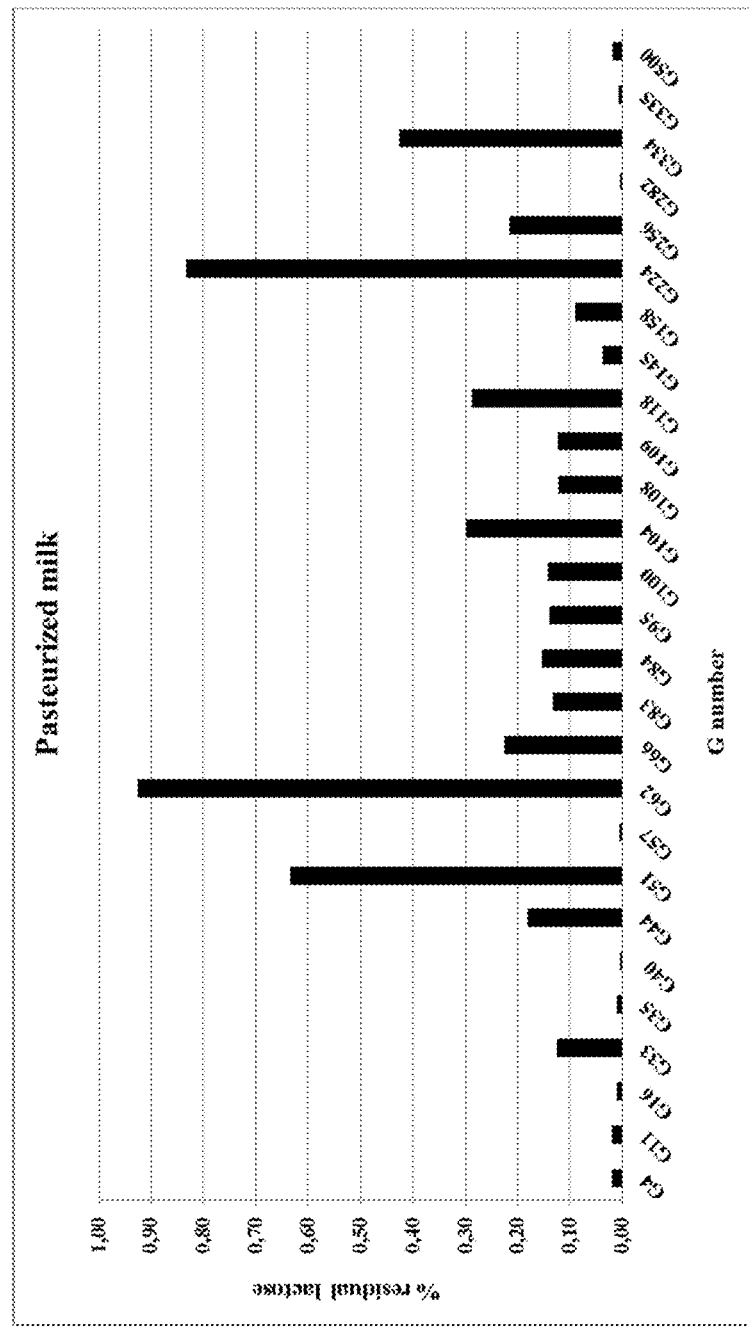

FIG. 11. The percentage residual lactose in the pasteurized milk, after the treatment with a fixed amount of the enzyme, after 24 hr at 5° C. determined using HPLC.

Figure 12:
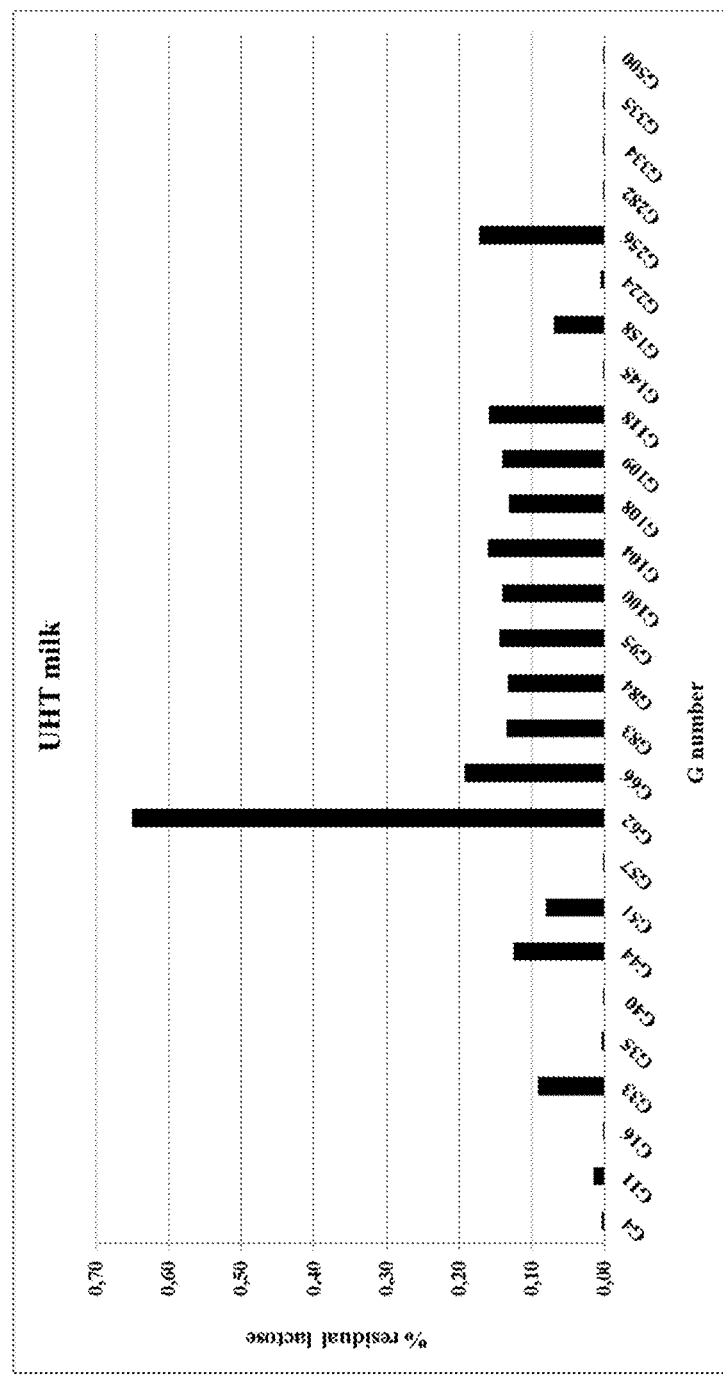

FIG. 12. The percentage residual lactose in the UHT milk, after the treatment with a fixed amount of the enzyme, after 24 hr at 25° C. determined using HPLC.

Figure 13:
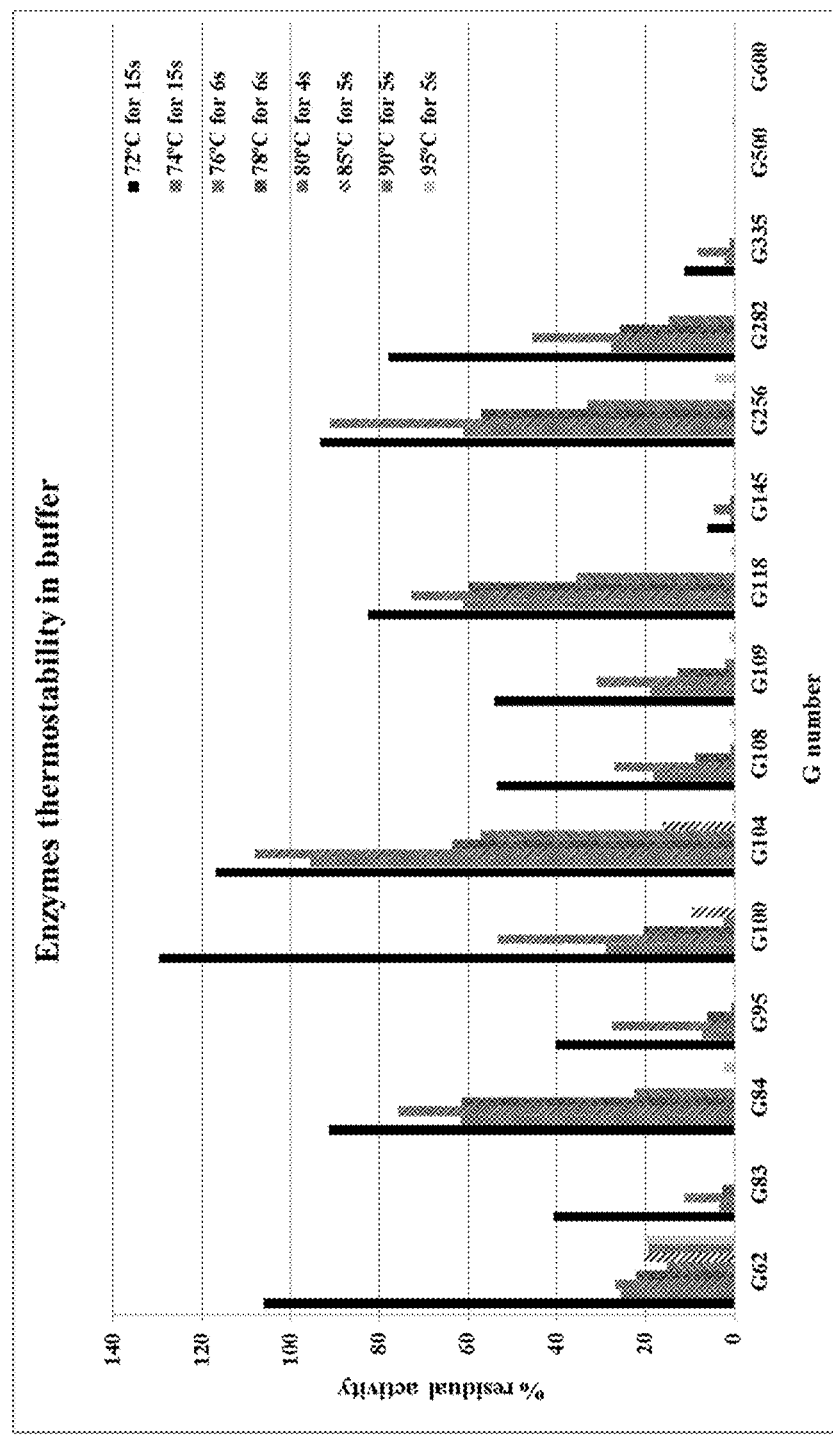

FIG. 13. The percentage residual activity of the purified enzymes at elevated temperatures, determined using lactose as substrate. The activity at pH 6.7 at 37° C. was considered as 100%.

Figure 14:
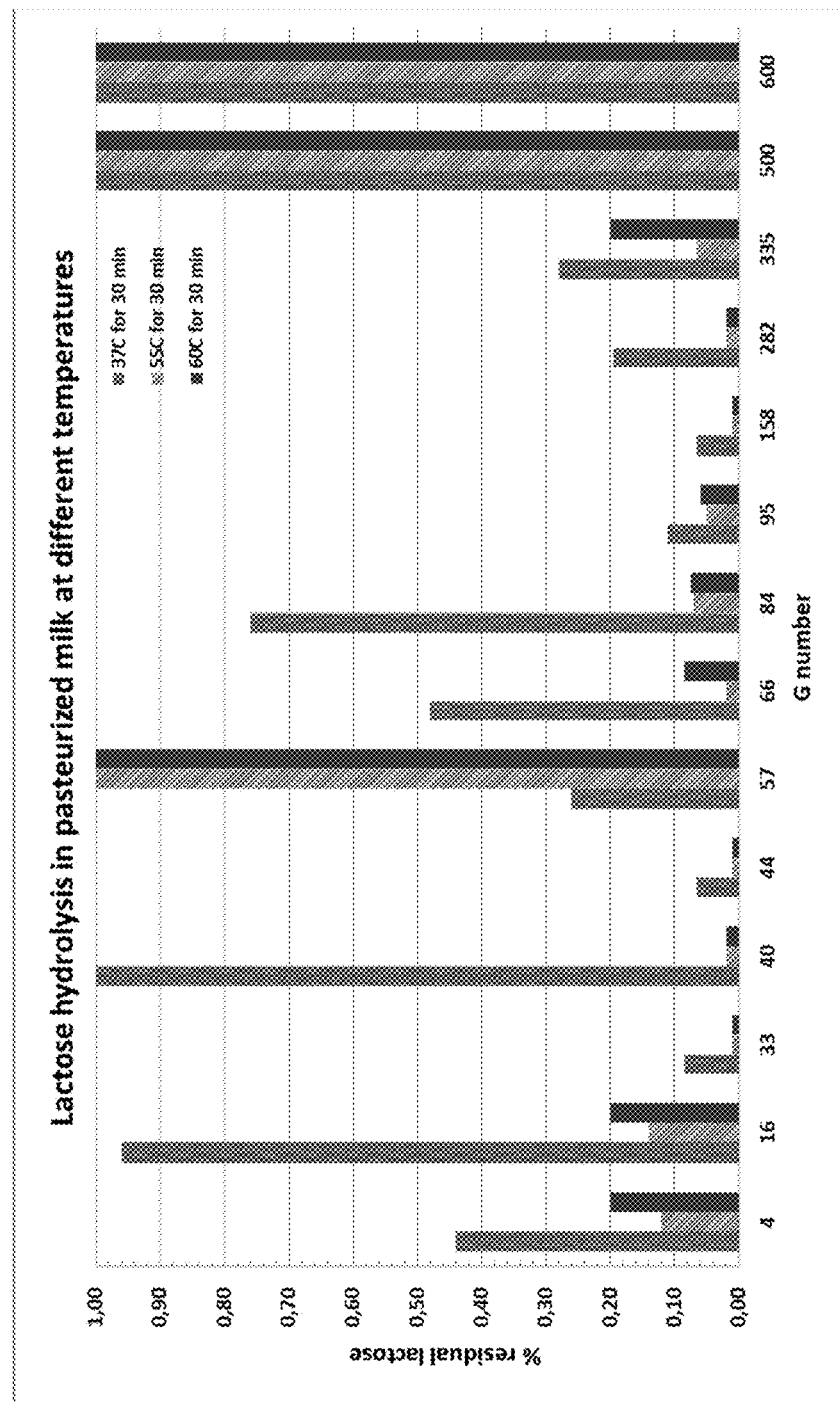

FIG. 14. The percentage residual lactose present in pasteurized milk after incubation with lactase enzymes at different temperatures, at 37° C., 55° C. or 60° C. The detection limit of the LactoSens® kit used in the assay is either 0.01% to 0.2% or 0.02%-1.0% lactose.

Figure 15:
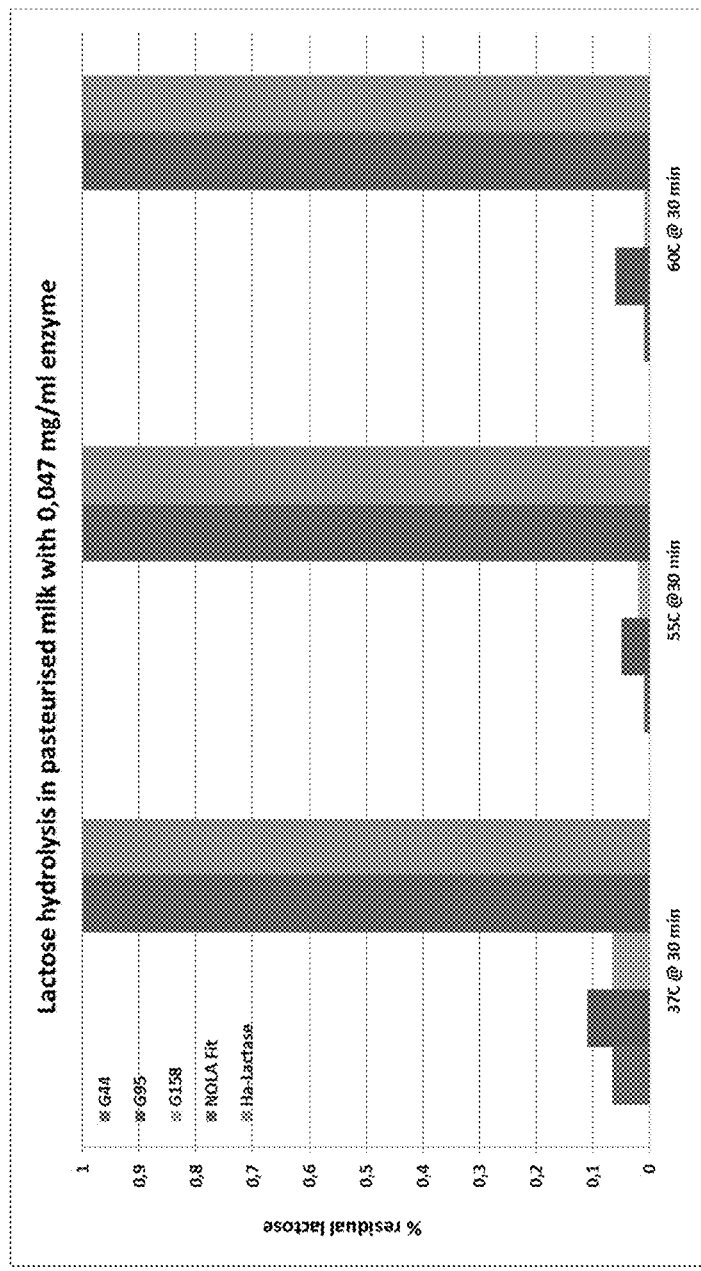

FIG. 15. The percentage residual lactose present in pasteurized milk after incubation with lactase enzymes in a concentration of 0.047 mg/ml. The detection limit of the LactoSens® kit used in the assay is either 0.01% to 0.2% or 0.02%-1.0% lactose.

Figure 16:
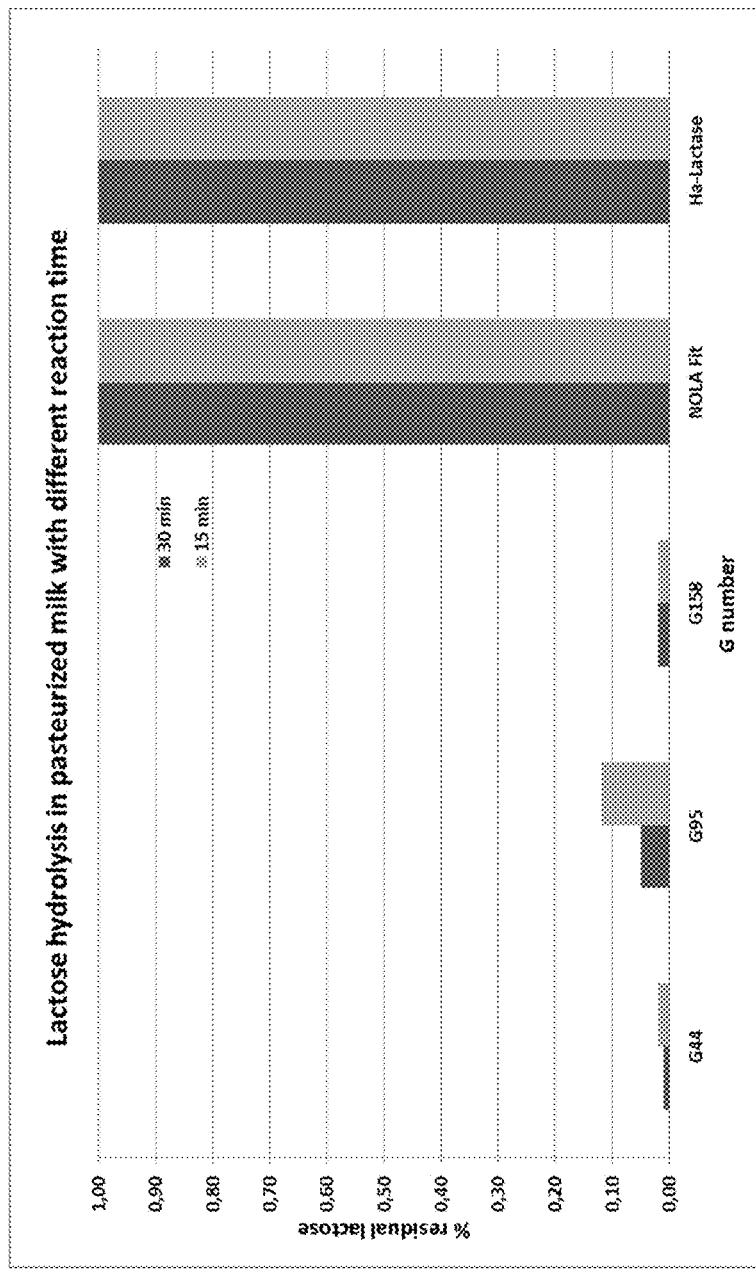

FIG. 16. The percentage residual lactose present in pasteurized milk incubated with lactase enzymes for a different reaction time, namely 15 or 30 minutes. The detection limit of the LactoSens® kit used in the assay is either 0.01% to 0.2% or 0.02%-1.0% lactose.

Figure 17:
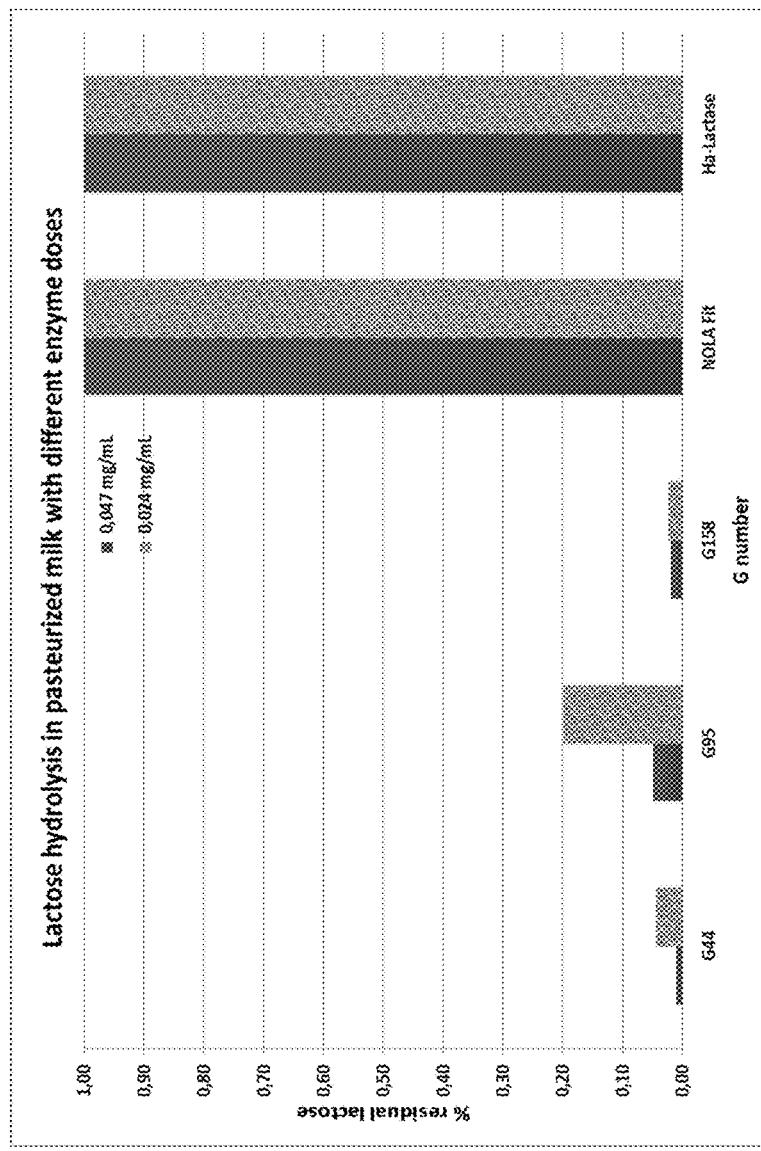

FIG. 17. The percentage residual lactose present in pasteurized milk incubated with lactase enzymes at different enzyme doses, namely 0.047 mg/ml or 0.024 mg/ml. The detection limit of the LactoSens® kit used in the assay is either 0.01% to 0.2% or 0.02%-1.0% lactose.

Figure 18:
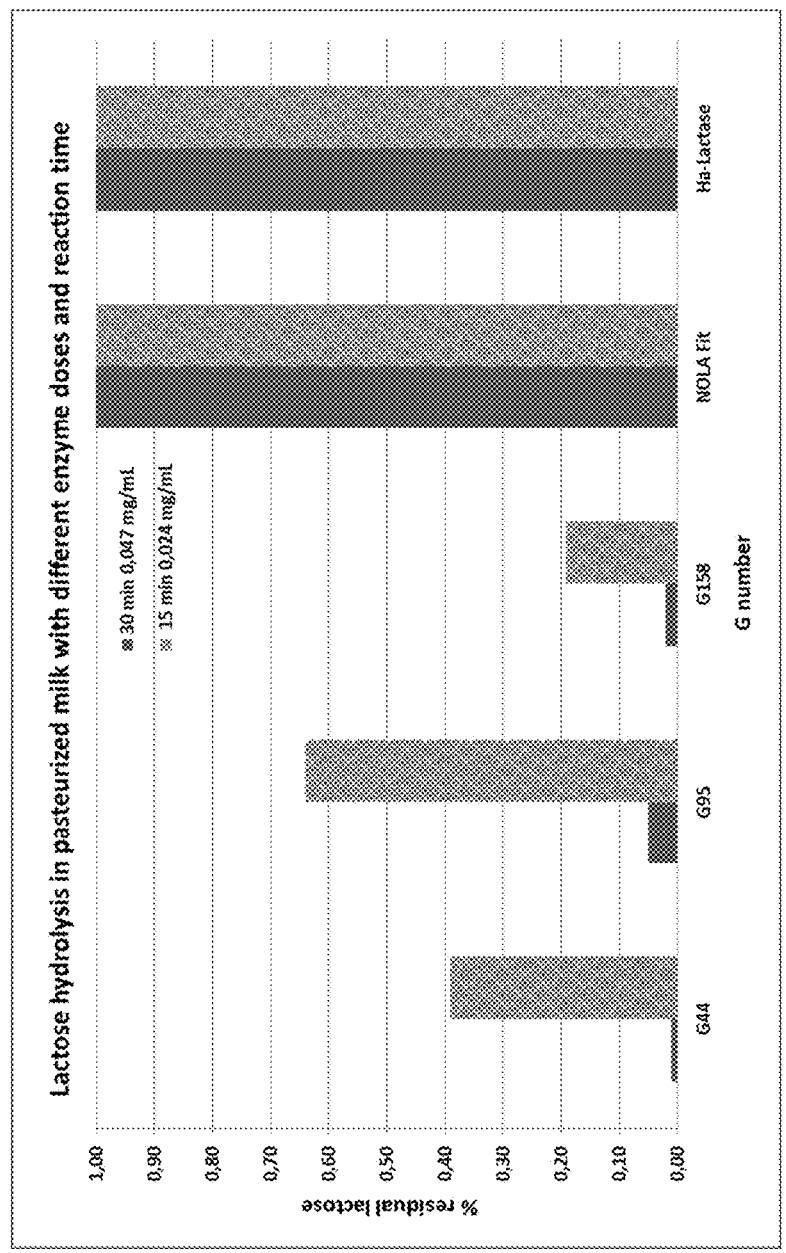

FIG. 18. The percentage residual lactose present in pasteurized milk incubated with lactase enzymes using a different dose and a different reaction time. The detection limit of the LactoSens® kit used in the assay is either 0.01% to 0.2% or 0.02%-1.0% lactose.

Figure 19:
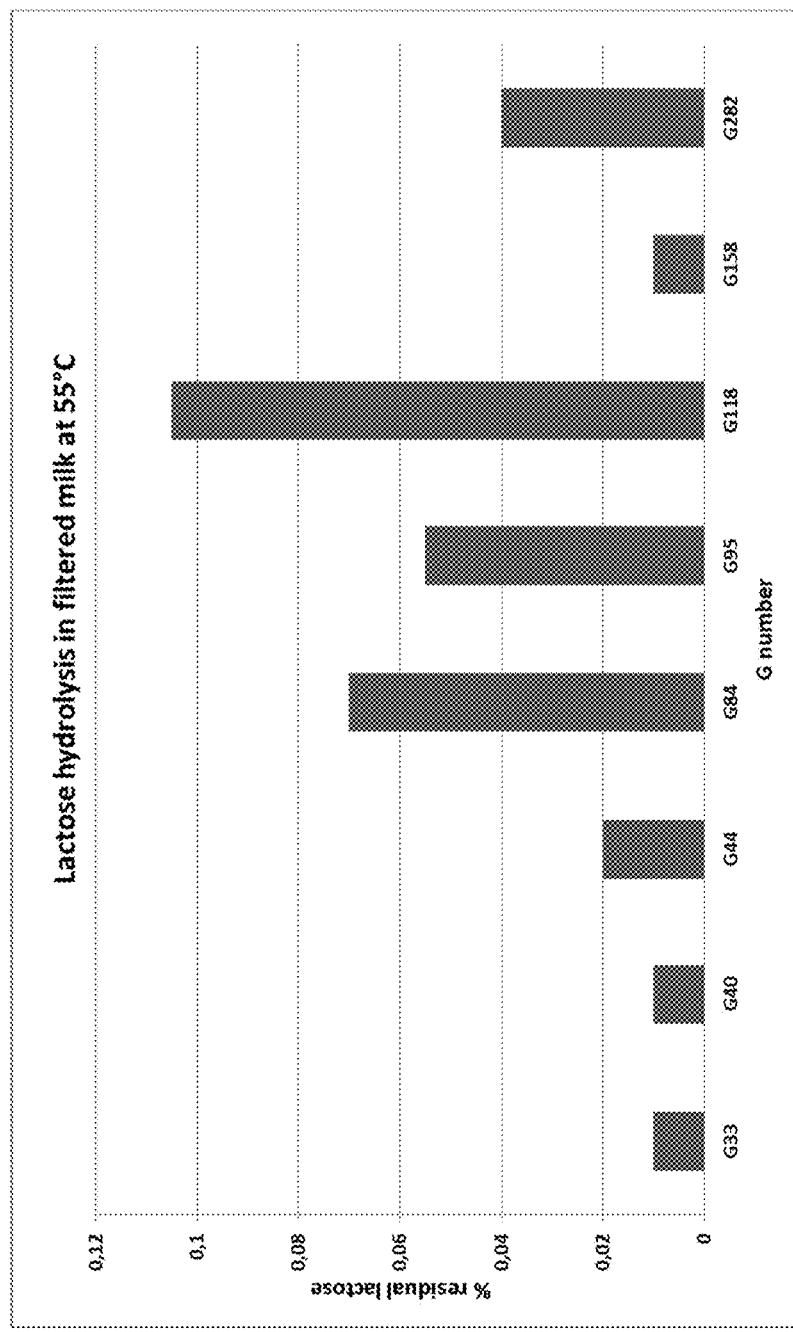

FIG. 19. The percentage residual lactose present in filtered milk incubated with lactase enzymes at 55° C. The detection limit of the LactoSens® kit used in the assay is either 0.01% to 0.2% or 0.02%-1.0% lactose.

Figure 20:
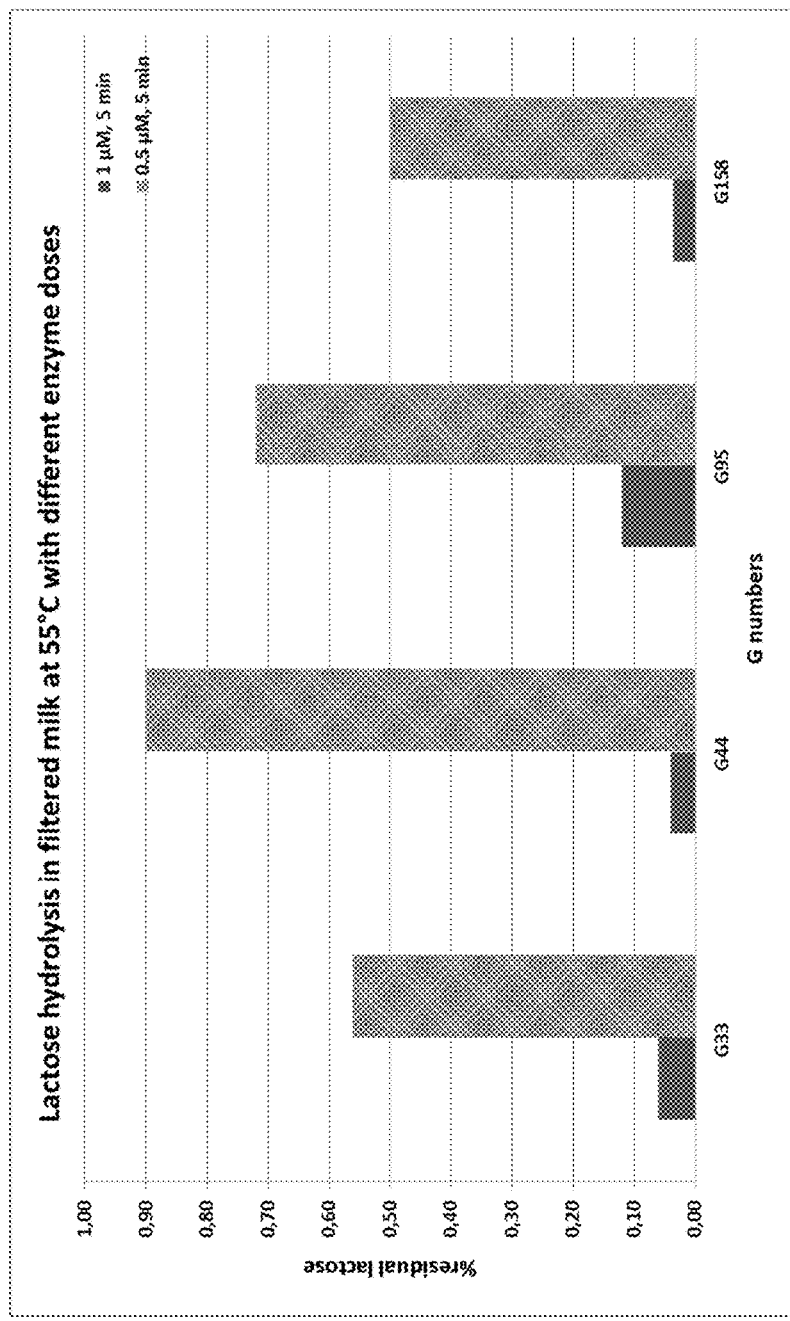

FIG. 20. The percentage residual lactose present in filtered milk incubated with lactase enzymes at 55° C. and at different enzyme doses. The detection limit of the LactoSens® kit used in the assay is either 0.01% to 0.2% or 0.02%-1.0% lactose.

Figure 21:
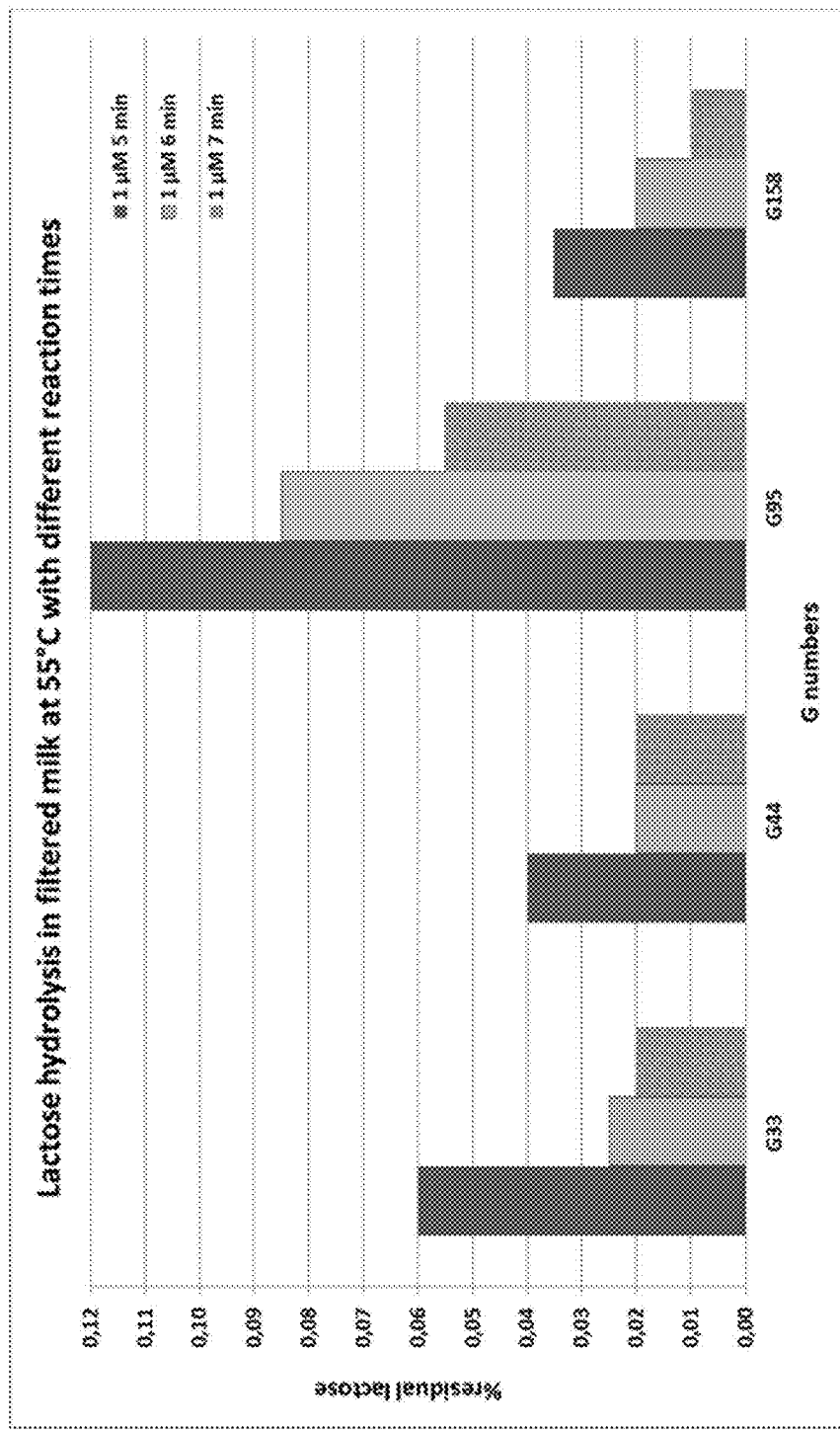

FIG. 21. The percentage residual lactose present in filtered milk incubated with lactase enzymes at 55° C. for a different reaction time. The detection limit of the LactoSens® kit used in the assay is either 0.01% to 0.2% or 0.02%-1.0% lactose.

Figure 22:
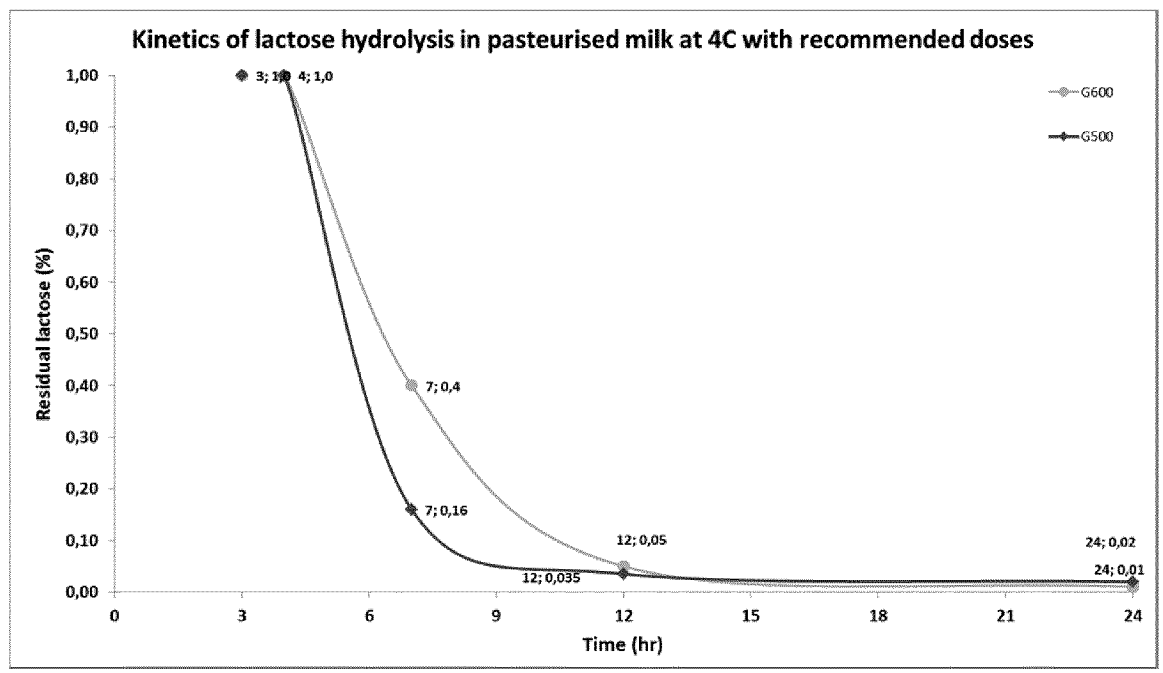

FIG. 22. The kinetics of lactose hydrolysis in pasteurized milk at 4° C. with Ha-Lactase and NOLA® Fit with 50 mg/L dose. The enzyme was mixed in milk and stored at 4° C. for different time interval. The residual lactose was determined using LactoSens® assay kit (Chr. Hansen, Denmark). The detection limit of the LactoSens® kit used in the assay is either 0.01% to 0.2% or 0.02%-1.0% lactose.

Figure 23:
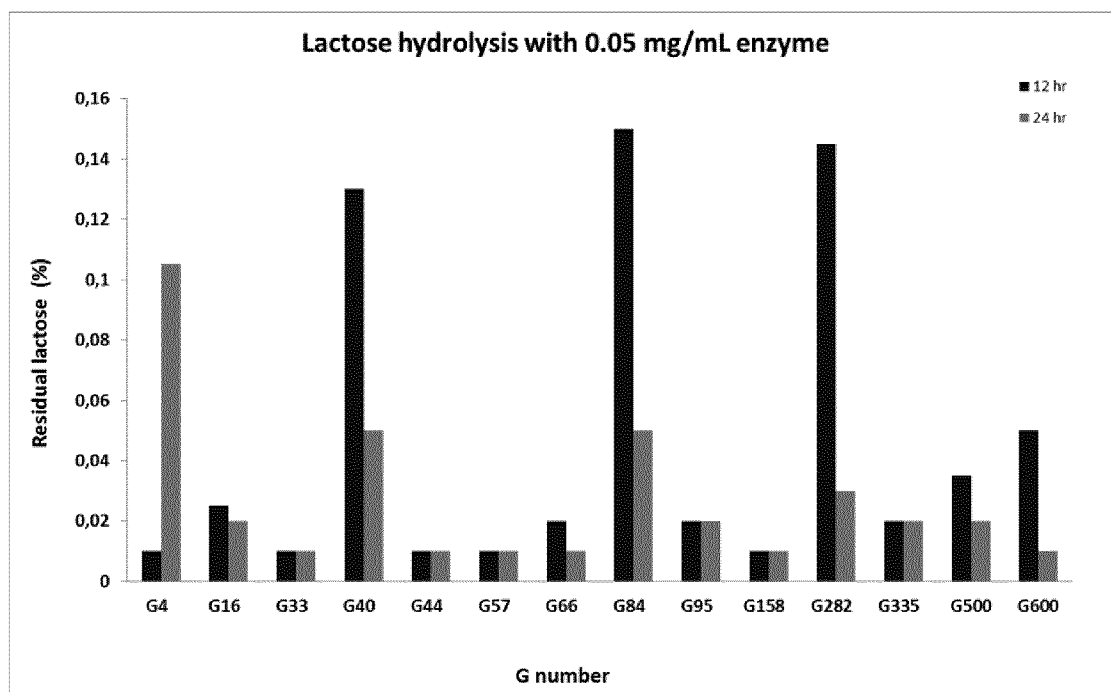

FIG. 23. The percentage residual lactose measured after 12 hr and 24 hr of enzymes addition. The enzyme was mixed in milk and stored at 4° C. for different time interval. The residual lactose was determined using LactoSens® assay kit (Chr. Hansen, Denmark). The detection limit of the LactoSens® kit used in the assay is either 0.01% to 0.2% or 0.02%-1.0% lactose.

Figure 24:
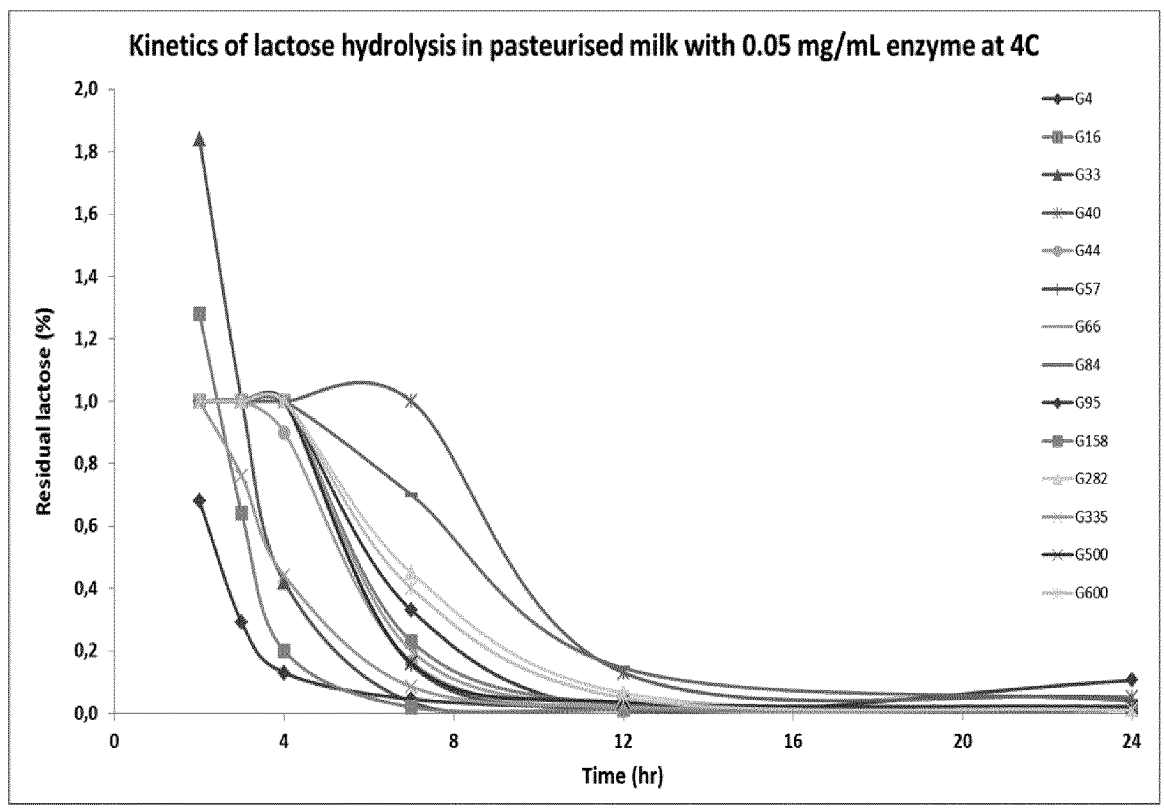

FIG. 24. The kinetics of lactose hydrolysis in pasteurized milk at 4° C. with novel lactases with 0.050 mg/mL dose. The enzyme was mixed in milk and stored at 4° C. for different time interval. The residual lactose was determined using LactoSens® assay kit (Chr. Hansen, Denmark). The NOLA® Fit and Ha-Lactase were used as controls. The detection limit of the LactoSens® kit used in the assay is either 0.01% to 0.2% or 0.02%-1.0% lactose.

Figure 25:
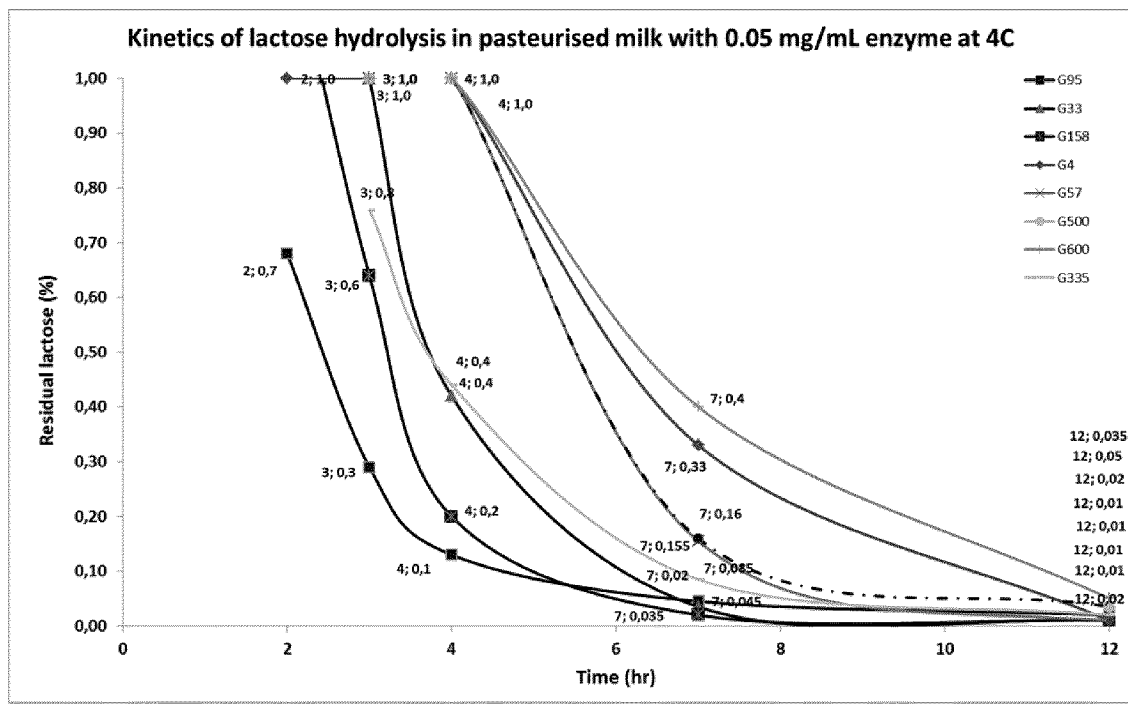

FIG. 25. The kinetics of lactose hydrolysis in pasteurized milk at 4° C. with selected novel lactases with 0.050 mg/L dose. The measured residual lactose values are shown in the graph. The enzyme was mixed in milk and stored at 4° C. for different time interval. The residual lactose was determined using LactoSens® assay kit (Chr. Hansen, Denmark). The NOLA® Fit and Ha-Lactase were used as controls. The measured residual lactose values are shown in the graph. The detection limit of the LactoSens® kit used in the assay is either 0.01% to 0.2% or 0.02%-1.0% lactose.

Figure 26:
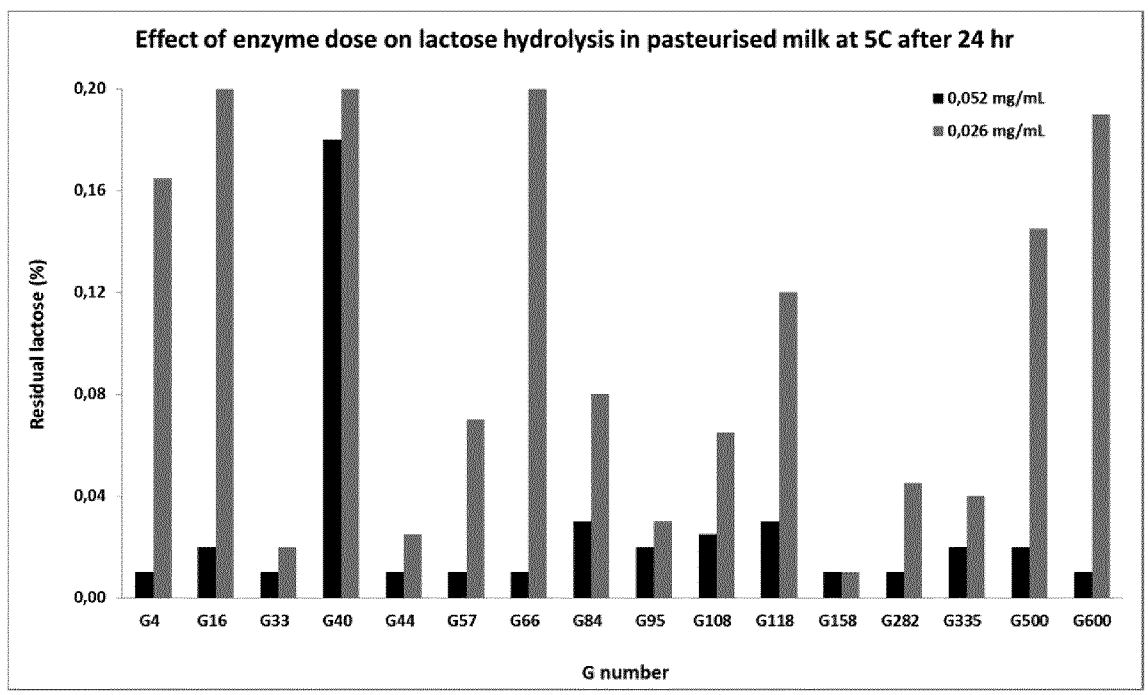

FIG. 26. The effect of enzyme dose on lactose hydrolysis. The milk was incubated with different enzyme doses, mixed and stored at 4° C. for 24 hr. The residual lactose was determined using LactoSens® assay kit (Chr. Hansen, Denmark). The detection limit of the LactoSens® kit used in the assay is either 0.01% to 0.2% or 0.02%-1.0% lactose.

Figure 27:
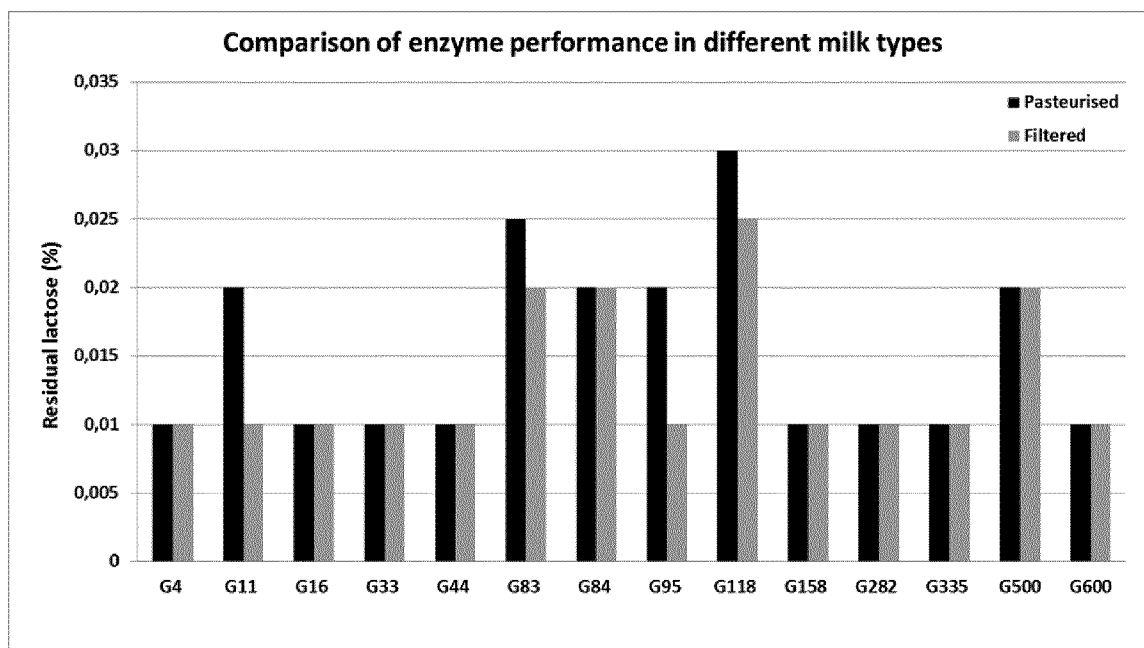

FIG. 27. Comparison of enzyme performance in different milk types. The milk was incubated with 0.052 mg/L in pasteurized and filtered milk, mixed and stored at 4° C. for 24 hr. The residual lactose was determined using LactoSens® assay kit (Chr. Hansen, Denmark). The detection limit of the LactoSens® kit used in the assay is either 0.01% to 0.2% lactose.

FIG. 28. The measured specific activity of purified enzymes determined at pH 6.7 at different temperatures. The specific activity values were defined as μmole of glucose formed per minute per milligram of enzyme under a given condition. The measured standard deviations at the given conditions were between 5-20%.

FIG. 29. The measured specific activity of purified enzymes determined at pH 5.5 at different temperatures. The specific activity values were defined as μmole of glucose formed per minute per milligram of enzyme under a given condition. The measured standard deviations at the given conditions were around 5%.

FIG. 30. The measured specific activity of purified enzymes determined at pH 4.5 at different temperatures. The specific activity values were defined as μmole of glucose formed per minute per milligram of enzyme under a given condition. The measured standard deviations at the given conditions were around 5%.

DETAILED DISCLOSURE OF THE INVENTION

The present inventors have found that certain peptides and dimeric peptides exhibiting beta-galactosidase enzyme activity are surprisingly stabile at many different physical conditions giving a relatively high activity outside of the ranges normally seen to be optimal for this class of enzymes.

Accordingly, these by the present inventors identified enzymes have a relatively high activity around 4° C. or 5° C. and may thus be used for lactose hydrolysis in the production of e.g. fresh milk. The novel enzymes are thus particularly suitable for reducing the lactose content of milk-based products, such as dairy products, at low temperatures.

A further advantage of these novel improved peptides exhibiting beta-galactosidase enzyme activity is that they have a relatively low degree of galactose inhibition. The lower galactose inhibition of these novel enzymes is highly relevant for applications wherein very low lactose concentrations are desired.

In terms of applicability for fermented products it is highly advantageous that the enzymes as described herein have a high beta-galactosidase enzymatic activity at a relatively broad temperature range of between 4° C. and 43° C., such as around 37° C., where fermentation would normally be optimal, but also that this activity of the beta-galactosidase enzyme is present at low pH, such as down to 4.5, or down to 4.0, or down to 3.5, or even down to pH 3.

In summary, it has been found by the present inventors that some peptides exhibiting beta-galactosidase enzyme activity is active over wide range of temperature, active over wide range of pH, has a general high hydrolytic activity without side activities, that these peptides have no or little galactose inhibition, such as less than 60%, and that they are stable over long-term storage.

The beta-galactosidase activity may be determined by measuring the amount of released glucose after incubation with lactose at set conditions. Released glucose can be detected by a coloring reaction.

Definitions

The term "milk", as used herein and in the context of the present invention, is to be understood as the lacteal secretion obtained by milking any mammal, such as cow, sheep, goats, buffalo or camel.

The term "composition containing lactose" as used herein refers to any composition, such as any liquid that contain lactose in significant measurable degree, such as a lactose content higher than 0.002% (0.002 g/100 ml). Encompassed within this term are milk and milk-based substrates.

The term "milk-based substrate", in the context of the present invention, may be any raw and/or processed milk material. Useful milk-based substrates include, but are not limited to solutions/suspensions of any milk or milk like products comprising lactose, such as whole or low fat milk, skim milk, buttermilk, low-lactose milk, reconstituted milk powder, condensed milk, solutions of dried milk, UHT milk, whey, whey permeate, acid whey, cream, fermented milk products, such as yoghurt, cheese, dietary supplement and probiotic dietary products. Typically the term milk-based substrate refers to a raw or processed milk material that is processed further in order to produce a dairy product.

The term "pasteurization" as used herein refers to the process of reducing or eliminating the presence of live organisms, such as microorganisms in a milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.

The term "dairy product" as used herein may be any food product wherein one of the major constituents is milk-based. Usually the major constituent is milk-based and in some embodiments, the major constituent is a milk-based substrate which has been treated with an enzyme having beta-galactosidase activity according to a method of the present invention.

A dairy product according to the invention may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavored milk drink.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavoring agents, microbial cultures such as probiotic cultures, salts, sweeteners, sugars, acids, fruit, fruit prep, fruit juices, or any other component known in the art as a component of, or additive to, a dairy product.

The terms "fermented dairy product" or "fermented milk product" as used herein is to be understood as any dairy product wherein any type of fermentation forms part of the production process. Examples of fermented dairy products are products like yoghurt, buttermilk, creme fraiche, quark and fromage frais. A fermented dairy product may be produced by or include steps of any method known in the art.

The term "fermentation" as used herein refers to the conversion of carbohydrates into alcohols or acids through the action of a microorganism. In some embodiments fermentation according to the present invention comprises the conversion of lactose to lactic acid. In the context of the present invention, "microorganism" may include any bacterium or fungus being able to ferment the milk substrate.

The term "increased beta-galactosidase enzyme activity" as used herein refers to a relatively higher specific activity of a beta-galactosidase enzyme in comparison to a reference sequence.

The term "peptide exhibiting beta-galactosidase enzyme activity" as used herein refers to any peptide, which has enzymatic activity to catalyze the hydrolysis of the disaccharide lactose into its component monosaccharides glucose and galactose. This peptide may also be referred to as a lactase or simply a beta-galactosidase (EC: 3.2.1.23).

In a preferred embodiment the beta-galactosidase activity is determined by incubating 13 µl of a solution comprising a known amount of a purified lactase enzyme with a solution comprising 140 mM of lactose at pH 6.7 and 37° C. for 10 min, terminating the lactase reaction by increasing the temperature to 95° C. for 10 min. The amount of glucose formed was determined by incubating the reaction product at 30° C. for 40 min with a 80 µL solution of glucose oxidase (0.6 g/L), 2,2'-azino-bis(3-ethylbenzothiazoline-6-sulfonic acid diammonium salt) (1.0 g/L ABTS) and horseradish peroxidase (0.02 g/L) and determining the absorbance at 610 nm using a FLUOphotometer. The absorbance is correlated to the concentration of glucose formed per minute and the maximum value determined (in pmol of glucose formed/min) is determined as the Unit of Lactase Activity 1 (also designated herein UAL-1). The Specific Activity of Lactase (also herein designated SUAL-1) at pH 6.7 at 37° C. is defined as µmol of glucose formed/min/mg of enzyme and is determined by dividing UAL-1 by the lactase protein concentration in mg. Full details of a preferred alternative of carrying out this assay are illustrated in Example 6.

While characterizing beta-galactosidase activity by reference to values of the unit µmol of glucose formed/min/mg of enzyme represents the standard approach for the determination of the activity, other units may equally be used to characterize the activity of the lactase enzymes using the above test. Accordingly, some of the examples characterize the lactase enzyme activity by reference to µM of glucose formed per second per µM of enzyme.

In alternative embodiments the assay can be carried out using a different temperature or different pH values for the lactase incubation.

The terms "peptide" and "oligopeptide" as used in the context of this present application are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All peptide and polypeptide formulas or sequences herein are written from left to right and in the direction from amino terminus to carboxy terminus. "Proteins" as used herein refers to peptide sequences as they are produced by some host organism and may include posttranslational modification, such as added glycans.

The terms "amino acid" or "amino acid sequence," as used herein, refer to an oligopeptide, peptide, polypeptide, or protein sequence, or a fragment of any of these, and to naturally occurring or synthetic molecules. In this context, "fragment" refer to fragments of a peptide exhibiting beta-galactosidase enzyme activity, which retain some enzymatic activity. Where "amino acid sequence" is recited herein to refer to an amino acid sequence of a naturally occurring protein molecule, "amino acid sequence" and like terms are not meant to limit the amino acid sequence to the complete native amino acid sequence associated with the recited peptide molecule.

Exemplary peptides of the invention also include fragments of at least about 50,100,150, 200, 250, 300, 350, 400, 450, 500, 550, 600, 650, 700, 750, 800 or more residues in length, or over the full length of an enzyme. Accordingly a "peptide fragment" or "enzymatically active fragment" of the invention are fragments that retain at least some functional enzymatic activity. Typically a peptide fragment of the invention will still contain the functional catalytic domain or other essential active sites of the peptide exhibiting beta-galactosidase enzyme activity. Other domains may be deleted.

Typically, the specific beta-galactosidase enzyme activity will be measured and indicated as µmol of glucose formed/min/mg of enzyme used. This specific value however will vary depending on conditions applied, such as temperature, and pH. Accordingly, values for beta-galactosidase enzyme activity may also be referred to as relative to a reference known enzyme, such as the beta-galactosidase enzyme defined by SEQ ID NO:34 OR SEQ ID NO:35.

Unless otherwise stated the term "Sequence identity" for amino acids as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences.

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

A peptide with a specific amino acid sequence as described herein may vary from a reference peptide sequence by any of amino acid substitutions, additions/insertions, or deletions.

Some embodiments according to the present invention refer to the use of a peptide with an amino acid sequence represented by SEQ ID NO: 1-33 or a sequence with at least 80% sequence identity to any one of said sequences. In some embodiments this sequence identity may be at least about 81%, 82%, 83%, 84%, 85%, 86%, 87%, 88%, 89%, 90%, 91%, 92%, 93%, 94%, 95%, 96%, 97%, 98%, or 99%, such as a peptide with not more than 1, 2, 3, 4, 5, 6, 7, 8, 9, 10, 11, 12, 13, 14, 15, 16, 17, 18, 19, 20, 21, or 22 amino acid substitutions, additions or deletions as compared to any one reference amino acid sequence represented by SEQ ID NO:1-33. The invention also features biologically active fragments of the peptides according to the invention. Biologically active fragments of a peptide of the invention include peptides comprising amino acid sequences sufficiently identical to or derived from the amino acid sequence of peptide of the invention which include fewer amino acids than the full length protein but which exhibit a substantial part of the biological activity of the corresponding full-length peptide. Typically, biologically active fragments comprise a domain or motif with at least one activity of a variant protein of the invention. A biologically active fragment of a peptide of the invention can be a peptide which is, for example, 100, 200, 300, 400, 500, 600, 700, 800, 900, 1000 or more amino acids in length.

The term "host cell", as used herein, includes any cell type which is susceptible to transformation, transfection, transduction, and the like with a nucleic acid construct or expression vector comprising a polynucleotide encoding the peptides of the present invention. A host cell may be the cell type, where a specific enzyme is derived from or it may be an alternative cell type susceptible to the production of a specific enzyme. The term includes both wild type and attenuated strains.

Suitable host cell may be any bacteria including lactic acid within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Also included are lactic acid producing bacteria belonging to the group of anaerobic bacteria, bifidobacteria, i.e. *Bifidobacterium* spp., which are frequently used as food cultures alone or in combination with lactic acid bacteria. Also included within this definition are *Lactococcus lactis*, *Lactococcus lactis* subsp. *cremoris*, *Leuconostoc mesenteroides* subsp. *cremoris*, *Pseudoleuconostoc mesenteroides* subsp. *cremoris*, *Pediococcus pentosaceus*, *Lactococcus lactis* subsp. *lactis biovar. diacetylactis*, *Lactobacillus casei* subsp. *casei* and *Lactobacillus paracasei* subsp. *Paracasei* and thermophilic lactic acid bacterial species include as examples *Streptococcus thermophilus*, *Enterococcus faecium*, *Lactobacillus delbrueckii* subsp. *lactis*, *Lactobacillus helveticus*, *Lactobacillus delbrueckii* subsp. *bulgaricus* and *Lactobacillus acidophilus*. Other specific bacteria within this definition includes bacteria of the family Bifidobacteriaceae, such as from the genus *Bifidobacterium*, such as from a strain of *Bifidobacterium animalis* or *Bifidobacterium longum*, *Bifidobacterium adolescentis*, *bifidobacterium bifodum*, *Bifidobacterium breve*, *Bifidobacterium catenulatum*, *Bifidobacterium infantus* or from the genus *Lactobacillus*, such as *L. sakei*, *L. amylovorus*, *L. delbrueckii* subsp. *Lactis*, and *L. helveticus*.

Also included within this definition of host cells include strain of *Agaricus*, e.g. *A. bisporus*; *Ascovaginospora*; *Aspergillus*, e.g. *A. niger, A. awamori, A. foetidus, A. japonicus, A. oryzae*; *Candida*; *Chaetomium*; *Chaetotomastia*; *Dictyostelium*, e.g. *D. discoideum*; *Kluveromyces*, e.g. *K. fragilis, K. lactis*; *Mucor*, e.g. *M. javanicus, M. mucedo, M. subtilissimus*; *Neurospora*, e.g. *N. crassa*; *Rhizomucor*, e.g. *R. pusillus*; *Rhizopus*, e.g. *R. arrhizus, R. japonicus, R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans, B. circulans, B. megaterium, B. novalis, B. subtilis, B. pumilus, B. stearothermophilus, B. thuringiensis*; *Bifidobacterium*, e.g. *B. longum, B. bifidum, B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. aerogenes, E. cloacae*; *Edwardsiella, E. tarda*; *Erwinia*, e.g. *E. herbicola*; *Escherichia*, e.g. *E. coli*; *Klebsiella*, e.g. *K. pneumoniae*; Miriococcum; Myrothesium; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus, Pycnoporus sanguineus*; *Ruminococcus*, e.g. *R. torques*; *Salmonella*, e.g. *S. typhimurium*; *Serratia*, e.g. *S. liquefasciens, S. marcescens*; *Shigella*, e.g. *S. flexneri*; *Streptomyces*, e.g. *S. antibioticus, S. castaneoglobisporus, S. violeceoruber*; *Trametes*; *Trichoderma*, e.g. *T. reesei, T. viride*; *Yersinia*, e.g. *Y. enterocolitica*.

To produce lactose free milk pasteurized milk (<0.01% residual lactose level) at cold temperatures (4-5° C.) in 24 hr, the recommended dose of the Ha-Lactase and NOLA® are 55-70 mg/L (10000 NLU/L) and 45-60 mg/L respectively (10000 BLU/L), respectively. The enzymes of the present invention provided very low residual lactose concentrations at low temperatures (<0.01% to 0.2%). The specific activity measurements shows that the novel enzymes have 2-5 higher activity than Ha-Lactase and NOLA® Fit, therefore they will require lesser time to produce the lactose free milk.

The Examples below show that the novel lactases are faster than Ha-Lactase and NOLA® Fit and results in lactose free pasteurized milk in significantly shorter time. These new enzymes can reduce the overall process time. Additionally, with novel enzymes it is possible to further reduce the enzyme dose between 25-50% to produce lactose free/reduced pasteurized milk.

TABLE 1

The gene numbers with corresponding sequence identification number.

| Gene number | Sequence Identity number | Species name |
| --- | --- | --- |
| G4 | SEQ ID No 1 | *Bifidobacterium adolescentis* |
| G16 | SEQ ID No 2 (domain a) SEQ ID No 3 (domain b) | *Lactobacillus sakei* |
| G35 | SEQ ID No 4 | *Bifidobacterium adolescentis* |
| G40 | SEQ ID No 5 (domain a) SEQ ID No 6 (domain b) | *Lactobacillus amylovorus* |
| G44 | SEQ ID No 7 | *Bifidobacterium bifidum* |
| G51 | SEQ ID No 8 | *Bifidobacterium bifidum* |
| G57 | SEQ ID No 9 | *Bifidobacterium breve* |
| G62 | SEQ ID No 10 | *Bifidobacterium catenulatum* |
| G66 | SEQ ID No 11 | *Bifidobacterium catenulatum* |
| G83 | SEQ ID No 12 | *Lactobacillus delbrueckii* subsp. *bulgaricus* |
| G84 | SEQ ID No 13 | *Lactobacillus delbrueckii* subsp. *lactis* |
| G95 | SEQ ID No 14 | *Lactobacillus delbrueckii* subsp. *bulgaricus* |
| G100 | SEQ ID No 15 | *Lactobacillus delbrueckii* subsp. *bulgaricus* |
| G104 | SEQ ID No 16 | *Lactobacillus delbrueckii* subsp. *lactis* |
| G108 | SEQ ID No 17 | *Lactobacillus delbrueckii* subsp. *bulgaricus* |
| G109 | SEQ ID No 18 | *Lactobacillus delbrueckii* subsp. *bulgaricus* |
| G118 | SEQ ID No 19 | *Lactobacillus delbrueckii* subsp. *lactis* |
| G145 | SEQ ID No 20 (domain a) SEQ ID No 21 (domain b) | *Lactobacillus helvaticus* |
| G158 | SEQ ID No 22 | *Bifidobacterium longum* |
| G224 | SEQ ID No 23 (domain a) SEQ ID No 24 (domain b) | *Lactobacillus reuteri* |
| G256 | SEQ ID No 25 | *Lactobacillus delbrueckii* subsp. *lactis* |
| G282 | SEQ ID No 26 (domain a) SEQ ID No 27 (domain b) | *Lactobacillus helvaticus* |
| G334 | SEQ ID No 28 (domain a) SEQ ID No 29 (domain b) | *Lactobacillus crispatus* |
| G335 | SEQ ID No 30 | *Streptococcus thermophilus* |
| G336 | SEQ ID No 31 | *Lactobacillus delbrueckii* subsp. *indicus* |

TABLE 1-continued

The gene numbers with corresponding sequence identification number.

| Gene number | Sequence Identity number | Species name |
|---|---|---|
| G11 | SEQ ID No 32 | Bifidobacterium adolescentis |
| G33 | SEQ ID No 33 | Bifidobacterium adolescentis |
| G600 | SEQ ID No 34 | Bifidobacterium bifidum |
| G500 | SEQ ID No 35 | Kluyveromyces lactis |

EXAMPLES

General Material and Methods

Molecular Cloning and Genetic Techniques

Techniques for restriction enzyme digestions, ligation, transformation and other standard molecular biology manipulations were based on methods described in the literature (Maniatis et al. "Molecular cloning: a laboratory manual, 2nd edition" Cold Spring Harbor Laboratory Press, Cold Spring Harbor, NY, 1989; Sambrook and Russell "Molecular Cloning: A Laboratory Manual, 3rd edition" Cold Spring Harbor Laboratory Press, Cold Spring Harbor, NY 2001; Miller "Experiment in molecular genetics" Cold Spring Harbor Laboratory Press, 1972); or as suggested by the manufacturer. The PCR was carried out in a DNA thermal cycler obtained from (Bio-Rad, USA). DNA sequencing was performed by LGC, Berlin, Germany. Proteins were analyzed by polyacrylamide gel electrophoresis (PAGE) under the denaturation conditions using sodium dodecyl sulphate on gels containing 10% SDS (Mini-PROTEAN® TGX stain-free™ gel, Biorad, USA). Protein concentrations were determined using BCA method by following the protocol supplied with the kit.

Bacterial Strains, Plasmid and Growth Conditions

Escherichia coli strain TOP10 (Invitrogen) was used for the cloning and isolation of plasmids. The beta-galactosidase deficient E. coli strain BW25113 (Δ(araD-araB)567, AlacZ4787(::rrnB-3), λ-, rph-1, Δ(rhaD-rhaB)568, hsdR514) (Datsenko K A, Wanner B L; 2000, Proc Natl Acad Sci U.S.A. 97: 6640-6645) was used in combination with the pBAD/His vector (obtained from Invitrogen™ Life Technologies Corporation Europe BV) for recombinant protein production.

Growth Media for Protein Expression

2xPY medium containing (16 g/L BD BBL™ Phyton™ Peptone, 10 g/L Yeast Extract, 5 g/L NaCl) was used for the recombinant protein production. The growth medium was supplemented with ampicillin (100 μg/ml) to maintain the plasmid. Protein production was initiated by adding 0.05% of arabinose in to the culture medium.

Example 1: Construction of the Expression Vector for the Production of Lactases

The genomic DNA of the lactic acid bacteria or bifidobacteria was extracted using commercial genomic extraction kit by following the supplied protocol (DNeasy, Qaigen, Germany). The lactase gene was amplified by PCR using two synthetic primers, using the purified genomic DNA source as biomass, and the PCR reagents were supplied in the Phusion U Hot start DNA polymerase (Thermo Scientific, USA) kit. The lactase gene was cloned into the start codon of the expression vector pBAD/His using the USER cloning method (Nour-Eldin H H, Geu-Flores F, Halkier B A, Plant Secondary Metabolism Engineering, Methods in Molecular Biology, 643; 2010), resulting in the expression construct. With the USER cloning method long, complementary overhangs in both PCR product and destination vector were generated. These overhangs can anneal to each other to form a stable hybridization product which was used to transform into E. coli without ligation. For the generation of overhangs in the PCR product, a single deoxyuradine residue is included in the upstream region of each primer to amplify target DNA. The lactase gene was amplified using the forward primer (5'-ATTAAC-CAUGCGACGCAACTTCGAATGGCC-3' (SEQ ID NO: 36)) and reverse primer (ATCTTCTCUTTACCGCCTTAC-CACGAGCACG (SEQ ID NO: 37)) containing a uridine at 9th position (as shown in bold), followed by the lactase gene sequence. In parallel, the vector DNA was PCR amplified using the forward (5'-AGAGAAGAUTTTCAGCCTGATA-CAGATTAAATC-3' (SEQ ID NO: 38)) and reverse primer (5'-ATGGTTAAUTCCTCCTGTTAGCCCAAAAAACGG-3' (SEQ ID NO: 39)) pair containing single deoxyuracil residue at 9th positions (as highlighted in bold) followed by vector DNA sequence. The PCR products were purified using the commercial PCR purification kit (Qiagen, Denmark). The purified PCR products (lactase gene and the vector DNA) were mixed in equimolar amount and incubated with a commercial USER enzyme mix (New England Biolabs, USA) by following the supplied protocol. These enzymes remove the uracil residue and also the short fragment upstream of the uridine, thereby creating complementary overhang in the PCR products. These complementary overhangs anneal with each other resulting in the pBAD-lactase expression vector. Aliquots of the ligation mixture were transformed into chemically competent E. coli TOP 10 cells. Transformants were selected at 37° C. on LB-Amp plates (LB; Luria-Bertani, Amp; 100 μg/ml ampicillin). The following day, colony PCR was carried out using a small biomass from the overnight grown transformant using the vector primers (primer 1; 5'-CGGCGTCACACTTTGC-TATGCC-3' (SEQ ID NO: 40) and primer 2; 5'-CCGCGC-TACTGCCGCCAGGC-3' (SEQ ID NO: 41)). The positive clones from the colony PCR were cultured in 5 mL LB-Amp medium and plasmid DNA was isolated from the cells. The cloned lactase gene was sequenced to verify that no additional mutations had been introduced during the amplification of the gene. The plasmid DNA was transformed in to the expression host E. coli strain BW25113.

Example 2: Expression of Lactases in E. coli Expression Host the Lactase Enzyme was Produced in E. coli BW25113 Using the pBAD Expression System Freshly transformed E. coli BW25113 cells carrying the plasmid DNA were collected from a Lb-Amp plate using a sterile loop and used to inoculate 5 mL of Lb-Amp medium. The overnight grown culture (200 μL) was used to inoculate 50 mL 2xPY medium (containing 100 μg/mL ampicillin) in a 250 mL flask in a shaker (Innova® 42). The culture was grown at 37° C. at 220 rpm until the OD600 reached between 0.6-0.8. The lactase expression was initiated by adding 0.05% arabinose into the culture medium and the cells were cultured for additional 16-20 hours at 18° C. at 180 rpm. Cells were harvested by centrifugation (5000 rpm, 10 min at 4° C.) and were stored at −20° C. until further use.

Example 3: Protein Purification Using Immobilized Metal Affinity Chromatography

Cells from 50 mL culture was thawed on ice and the cells were lysed using 10 mL mixture of lysis buffer (BugBuster®

(Novagen) containing 2 mg/mL Lysozyme (Sigma Aldrich), 1 unit Benzonase (Sigma Aldrich), and 1× Complete Protease inhibitor cocktail (EDTA-free, Roche)) by incubating the cells at room temperature for 30 min. After 30 min, the cell debris was removed by centrifugation at 16000 rpm for 20 min at 4° C. The obtained supernatant was filtered through 0.45 µm pore diameter filter. A gravity flow Ni-Sepharose (GE Healthcare) column was prepared with 1 mL slurry by washing out the ethanol and water. The column was then equilibrated with washing buffer (50 mM of $NaH_2PO_4$, pH 8.0 containing 300 mM of NaCl and 20 mM of Imidazole). The cell-free extract was applied to the column and the non-bound proteins were eluted from the column. The column was washed with 20 mL of washing buffer and the retained proteins were eluted with 3.5 mL of elution buffer (50 mM of $NaH_2PO_4$, pH 8.0 containing 300 mM of NaCl and 250 mM of imidazole). The collected fractions were analyzed by SDS-PAGE on gels containing 10% acrylamide and those contained the purified lactase enzymes combined together. The buffer was exchanged against the storage buffer (50 mM $KH_2PO_4$ buffer pH 7.0 containing 10 mM NaCl, 1 mM $MgCl_2$), using a prepacked PD-10 desalting G-25 gel filtration column (GE Healthcare). The purified enzymes were stored at 4° C. until further use.

Example 4: Protein Purification Using Gel Filtration Chromatography

Cells from 50 mL culture was thawed on ice and the cells were lysed using 10 mL mixture of lysis buffer (BugBuster® (Novagen) containing 2 mg/ml lysozyme, 1 unit Benzonase (Sigma Aldrich), and 1× Complete Protease inhibitor cocktail (EDTA-free, Roche)) by incubating the cells at room temperature (25° C.) for 30 min. After 30 min, the cell debris was removed by centrifugation at 16000 rpm for 20 min at 4° C. The obtained supernatant was filtered through 0.45 µm pore diameter filter. The clear cell-free extract was concentrated by filtering through a 30000 Dalton filter (Vivaspin 20, GE Healthcare) by following the supplied protocol. A gravity flow Sephadex G50 superfine (Pharmacia Chemicals, Sweden) column was prepared with 1 g of column material (prepared by boiling in 100 mL water for 1 hour, cooled to room temperature). A column was prepared by applying 20 mL of the cooled slurry on a 30 mL filtration column. The column was washed with MilliQ water and equilibrated with wash buffer B (50 mM of $NaH_2PO_4$ buffer, pH 7.0). 500 µL of the concentrated supernatant was applied on the column and allowed the supernatant to enter in the column bed. The wash buffer (50 mM of $NaH_2PO_4$ buffer, pH 7.0) was applied on top of the column and the eluent fractions were collected individually. The collected fractions were analyzed on SDS-PAGE gel (containing 10% acrylamide). The protein fractions were combined together and buffer was exchanged against the storage buffer (50 mM $KH_2PO_4$ buffer pH 7.0 containing 10 mM NaCl, 1 mM $MgCl_2$) with the desalting column as described in earlier section. The purified enzymes were stored at 4° C. until further use.

Example 5: Protein Concentration Measurement Using BCA Assay

The concentration of purified lactases was determined using Pierce™ BCA protein assay kit (Thermo Fisher Scientific, Germany) by following the protocol supplied with the kit.

Example 6: Activity Determination Using Purified Enzymes on Lactose as Substrate at pH 6.7 at 37° C.

To measure the beta-galactosidase activity, the purified lactases were diluted to 40× in buffer A (50 mM $NaH_2PO_4$ buffer pH 6.7 containing 100 µM of $MgSO_4$). In a separate reaction, the diluted enzyme was incubated with lactose solution prepared in buffer B (140 mM of lactose prepared in 100 mM sodium-citrate buffer of pH 6.7, containing 100 µM of $MgSO_4$). The reaction mixture was prepared by mixing 13 µL of diluted enzyme and 37 µL of lactose solution in a PCR tube. The reaction mixture was incubated in a DNA thermal cycler with the following incubation parameters (reaction time; 10 min at 37° C., enzyme inactivation; 10 min at 95° C., cooling; 4° C.). The reaction mixtures were stored at −20° C. until further use. To determine the amount of glucose formed during the reaction, 10 µL of the reaction mixture was transferred to one well of standard microtiter plate (Thermo Fischer Scientific, Denmark) containing 80 µL of buffer C (100 mM of $NaH_2PO_4$ buffer, pH 7.0, containing glucose oxidase; 0.6 g/L (Sigma Aldrich), 2,2'-azino-bis(3-ethylbenzothiazoline-6-sulfonic acid diammonium salt); ABTS: 1.0 g/L (Sigma Aldrich), horseradish peroxidase; 0.02 g/L (Sigma Adrich)) and incubated at 30° C. for 40 min. After 40 min, the absorbance was determined at 610 nm using FLUOStar Omega UV-plate reader (BMG Labtech, Germany). The absorbance values between 0.1 and 1.5 were used for calculations, if the A610 nm value >1.5, the reaction mixture was diluted up to 10× with buffer A. With each purified enzyme, the reactions were carried out in triplicate and the mean value of the triplicate measurement was used for calculation. The protein purification performed with the E. coli cells transformed with the empty pBAD/His was used for normalization. Using a known concentration of glucose (0-2.5 mM), a standard curve was drawn and the slope of the curve was used to calculate the glucose formed during the reaction. The maximum absorbance value for each lactase was used to determine µmol of glucose formed per min (for example by correlating the absorbance value to the glucose concentration formed using a standard or calibration curve) and is also designated Unit of Lactase Activity 1 (or UAL-1) at pH 6.7 at 37° C. The Specific Activity (designated as SUAL-1) at pH 6.7 at 37° C. is defined as µmol of glucose formed per m per mg of enzyme (µmol of glucose/min/mg of enzyme) and is determined by dividing UAL-1 by the protein concentration in mg. The specific activity of SEQ ID NO: 34 and SEQ ID NO: 35 were determined under essentially the same conditions. The high specific activity at pH 6.7 is highly desired for robustness for the enzyme in fresh and fermented milk applications. The detailed results of the specific activity of enzymes at pH 6.7 at 37° C. are described in FIG. 28. Additionally the activity was described as µM of glucose formed per second per µM of enzyme added. The results are shown in FIG. 1.

The specific activity of the enzymes was determined at pH 6.7 and at 37° C. and used to calculate the approximate time required for hydrolysis of lactose using a fixed enzyme dose based activity units at pH 6.7 at 37° C. and 140 mM lactose as substrate (SUAL-1). The results in terms of time calculated for lactose hydrolysis are shown in Table 2:

TABLE 2

Specific activity of purified enzymes determined at pH 6.7 at 37° C. with lactose as substrate, described SUAL-1, discussed in example 6. The calculated time required in seconds for the complete lactose hydrolysis. The measured standard deviation at the given condition was less than 6%. The theoretical time required to hydrolyze the 140 mmol of lactose is calculated by assuming that reaction rate stay unchanged over the entire reaction period

| | | Time required for complete lactose hydrolysis using | | |
|---|---|---|---|---|
| G No. | SUAL-1 | 1 mg enzyme per liter (m in) | 100 mg enzyme per liter (sec) | 47 mg enzyme per liter (sec) |
| 4 | 118.1 | 1185 | 711 | 1508 |
| 11 | 69.2 | 2023 | 1214 | 2573 |
| 16 | 23.4 | 5996 | 3597 | 7626 |
| 33 | 130.1 | 1076 | 646 | 1369 |
| 40 | 15.8 | 8874 | 5324 | 11287 |
| 44 | 331.5 | 422 | 253 | 537 |
| 57 | 104.6 | 1339 | 803 | 1703 |
| 66 | 187.2 | 748 | 449 | 951 |
| 83 | 272.9 | 513 | 308 | 653 |
| 84 | 161.9 | 865 | 519 | 1100 |
| 95 | 288.1 | 486 | 292 | 618 |
| 104 | 90.5 | 1548 | 929 | 1969 |
| 108 | 277.9 | 504 | 302 | 641 |
| 118 | 113.8 | 1230 | 738 | 1565 |
| 158 | 254.7 | 550 | 330 | 699 |
| 282 | 58.5 | 2392 | 1435 | 3042 |
| 335 | 42.4 | 3298 | 1979 | 4195 |
| 500 | 46.9 | 2983 | 1790 | 3794 |
| 600 | 61.9 | 2263 | 1358 | 2879 |

Note*
Complete lactose hydrolysis is defined as the time required for the enzyme to hydrolyze 140 mmol of lactose using a fixed enzyme concentration based on specific activity units at pH 6.7 at 37° C. with 140 mmol lactose as substrate (SUAL).

Example 7: Activity Determination Using Purified Enzymes in the Presence of Galactose at pH 6.7 at 37° C.

The purified lactases were diluted to 40× in buffer A (50 mM $NaH_2PO_4$ buffer pH 6.7 containing 100 μM of $MgSO_4$). In separate reactions, the diluted enzymes were incubated with buffer D (140 mM of lactose and 140 mM of galactose prepared in 100 mM sodium-citrate buffer of pH 6.7, containing 100 μM of $MgSO_4$). The reaction mixture consists of 13 μL of the diluted enzyme and 37 μL of buffer D in a PCR tube. The reaction mixture was incubated in thermal cycler with the following incubation parameters (reaction time: 10 min at 37° C., enzyme inactivation: 10 min at 95° C., cooling: 4° C.). The reaction mixtures were stored at −20° C. until further use. To determine the amount of glucose formed during the reaction, 10 μL of the reaction mixture was transferred to one well of standard microtiter plate (Thermo Fischer Scientific, Denmark) containing 80 μL of buffer C (100 mM of $NaH_2PO_4$ buffer, pH 7.0, containing glucose oxidase; 0.6 g/L (Sigma Aldrich), 2,2'-azino-bis(3-ethylbenzothiazoline-6-sulfonic acid diammonium salt); ABTS: 1.0 g/L (Sigma Aldrich), horseradish peroxidase; 0.02 g/L (Sigma Adrich)) and incubated at 30° C. for 40 min. After 40 min, the absorbance was determined at 610 nm using FLUOStar Omega UV-plate reader (BMG Labtech, Germany). The absorbance values between 0.1 and 1.5 were used for calculations, if the A610 nm value >1.5, the reaction mixture was diluted up to 10× with buffer A. With each purified enzyme, the reactions were carried out in triplicate and the mean value of the triplicate measurement was used for calculation. The protein purification performed with the E. coli cells transformed with the empty pBAD/His was used for normalization. Using a known concentration of glucose (0-2.5 mM), a standard curve was drawn and the slope of the curve was used to calculate the absorbance corresponding to 1 μM of glucose formed during the reaction. The maximum absorbance value for each lactase was used to determine μM of glucose formed per sec, described as 1 Unit of Activity with Galactose at pH 6.7 at 37° C. (UAG). The specific activity at pH 6.7 at 37° C. in presence of galactose is defined as μM of glucose formed per second per μM of enzyme (μM of glucose/sec/μM of enzyme) and determined by dividing UAG by the protein concentration in μM, described as SUAG.

The percentage inhibition of enzymes with galactose is calculated by using the formula $$\% \text{ inhibition} = 100*(A-B)/A$$

Where A is specific activity in of enzymes with lactose at pH 6.7 at 37° C. (SUAL) as described in the example 6, and B stand for the specific activity of enzymes in presence of galactose at pH 6.7 at 37° C. (SUAG) as described in the example 7. The detail results of the % galactose inhibition are described the FIG. 2 and FIG. 28. The lower galactose inhibition is highly relevant for the applications where very low lactose concentration is desired.

Additionally the activity was described as μmole of glucose formed per minute per milligram of enzyme added. The results are shown in FIG. 28.

Note: relatively high standard deviations in galactose inhibition measurement are due to trace amounts of glucose impurities in purchased galactose.

Example 8: Activity Determination Using Purified Enzymes on Lactose as Substrate at pH 6.7 at 4° C.

The purified lactases were diluted up to 40× in buffer A (50 mM $NaH_2PO_4$ buffer pH 6.7 containing 100 μM of $MgSO_4$). In a separate reaction, the diluted enzyme was incubated with lactose solution prepared in buffer B (140 mM of lactose prepared in 100 mM sodium-citrate buffer of pH 6.7, containing 100 μM of $MgSO_4$). The reaction mixture was prepared by mixing 13 μL of diluted purified enzyme and 37 μL of lactose solution in a PCR tube. The reaction mixture was incubated in a DNA thermal cycler using the following incubating parameters (reaction time; 60 min at 4° C., enzyme inactivation; 10 min at 95° C., storage; 4° C.). The reaction mixtures were stored at −20° C. freezer until further use. The amount of glucose formed during the reaction was determined by following the protocol described in example 6. The maximum absorbance value for each lactase was used to determine μM of glucose formed per sec, described as 1 Unit of Activity with Lactose at pH 6.7 at 4° C. (UAL-2). The specific activity at pH 6.7 at 4° C. is defined as μM of glucose formed per second per μM of enzyme (μM of glucose/sec/μM of enzyme), and is determined by dividing UAL-2 by the protein concentration in μM, described as SUAL-2. The high specific activity at pH 6.7 at 4° C. is highly desired for the lactose hydrolysis for fresh/pasteurized milk applications. The detail results of the specific activity of enzymes at pH 6.7 at 4° C. are described in the FIG. 3.

Additionally the activity was described as µmole of glucose formed per minute per milligram of enzyme added. The results are shown in FIG. 28.

Example 9: Activity Determination Using Purified Enzymes on Lactose as Substrate at pH 6.7 at 43° C.

The purified lactases were diluted to 40× in buffer A (50 mM NaH$_2$PO$_4$ buffer pH 6.7 containing 100 µM of MgSO$_4$). In a separate reaction, the diluted enzyme was incubated with lactose solution prepared in buffer B (140 mM of lactose prepared in 100 mM sodium-citrate buffer of pH 6.7, containing 100 µM of MgSO$_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. freezer until further use. The amount of the glucose formed during the reaction was determined by following the protocol described in example 6. The maximum absorbance value for each lactase was used to determine µM of glucose formed per sec, described as 1 Unit of Activity with Lactose at pH 6.7 at 43° C. (UAL-3). The specific activity at pH 6.7 at 43° C. is defined as µM of glucose formed per second per µM of enzyme (µM of glucose/sec/µM of enzyme), and is determined by dividing UAL-3 by the protein concentration in µM, described as SUAL-3. The high specific activity at pH 6.7 at 43° C. is highly desired for the lactose hydrolysis for the fermented milk applications. The detail results of the specific activity of enzymes at pH 6.7 at 43° C. are described in FIG. 4.

Additionally the activity was described as µmole of glucose formed per minute per milligram of enzyme added. The results are shown in FIG. 28.

Example 10: Activity Determination Using Purified Enzymes on Lactose as Substrate at pH 5.5 at 4° C.

The purified lactases were diluted up to 40× in buffer A (50 mM NaH$_2$PO$_4$ buffer pH 6.7 containing 100 µM of MgSO$_4$). In a separate reaction, the diluted enzyme was incubated with lactose solution prepared in buffer E (140 mM of lactose prepared in 100 mM sodium-citrate buffer of pH 5.5, containing 100 µM of MgSO$_4$). The reaction mixture was prepared by mixing 13 µL of diluted purified enzyme and 37 µL of lactose solution in a PCR tube. The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7.

The reaction mixture was incubated in a DNA thermal cycler using the following incubating parameters (reaction time; 60 min at 4° C., enzyme inactivation; 10 min at 95° C., storage; 4° C.). The reaction mixtures were stored at −20° C. freezer until further use. To determine the amount of glucose formed during the reaction, 10 µL of the reaction mixture was transferred to one well of standard microtiter plate containing 80 µL of buffer C and incubated at 30° C. for 40 min. After 40 min, the absorbance was determined at 610 nm using FLUOStar Omega UV-plate reader (BMG Labtech, Germany). The absorbance value between 0.1 and 1.5 were used for calculations, if the A610 nm value >1.5, the reaction mixture was diluted up to 5× with buffer A. With each purified enzyme, the reactions were carried out in triplicate and the mean value of the triplicate measurement was used for calculations. The maximum absorbance value for each lactase was used to determine µM of glucose formed per sec, described as 1 Unit of Activity with Lactose at pH 5.5 at 4° C. (UAL-4). The specific activity at pH 5.5 at 4° C. is defined as µM of glucose formed per second per µM of enzyme (µM glucose/sec/µM of enzyme), and is determined by dividing UAL-4 by the protein concentration in µM, described as SUAL-4. The high specific activity at pH 5.5 at 4° C. is relevant for the lactose hydrolysis in the fermented milk applications. The detail results of the specific activity of enzymes at pH 5.5 at 4° C. are described in the FIG. 5.

Additionally the activity was described as µmole of glucose formed per minute per milligram of enzyme added. The results are shown in FIG. 29.

Example 11: Activity Determination Using Purified Enzymes on Lactose as Substrate at pH 5.5 at 37° C.

The purified lactases were diluted up to 40× in buffer A (50 mM NaH$_2$PO$_4$ buffer pH 6.7 containing 100 µM of MgSO$_4$). In a separate reaction, the diluted enzyme was incubated with lactose solution prepared in buffer E (140 mM of lactose prepared in 100 mM sodium-citrate buffer of pH 5.5, containing 100 µM of MgSO$_4$). The reaction mixture was prepared by mixing 13 µL of diluted purified enzyme and 37 µL of lactose solution in a PCR tube. The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7.

The reaction mixture was incubated in a DNA thermal cycler using the following incubating parameters (reaction time; 10 min at 37° C., enzyme inactivation; 10 min at 95° C., storage; 4° C.). The reaction mixtures were stored at −20° C. until further use. The amount of glucose formed during the reaction was determined by following the protocol as described in the example 10. The maximum absorbance value for each lactase was used to determine µM of glucose formed per sec, described as 1 Unit of Activity with Lactose at pH 5.5 at 37° C. (UAL-5). The specific activity at pH 5.5 at 37° C. is defined as µM of glucose formed per second per µM of enzyme (µM of glucose/sec/µM of enzyme), and is determined by dividing UAL-5 by the protein concentration in µM, described as SUAL-5. The high specific activity at pH 5.5 at 37° C. is relevant for the lactose hydrolysis in the fermented milk applications and sweet whey lactose hydrolysis. The detail results of the specific activity of enzymes at pH 5.5 at 37° C. are described in the FIG. 6.

Additionally the activity was described as µmole of glucose formed per minute per milligram of enzyme added. The results are shown in FIG. 29.

Example 12: Activity Determination Using Purified Enzymes on Lactose as Substrate at pH 5.5 at 43° C.

The purified lactases were diluted up to 40× in buffer A (50 mM NaH$_2$PO$_4$ buffer pH 6.7 containing 100 µM of MgSO$_4$). In a separate reaction, the diluted enzyme was incubated with lactose solution prepared in buffer E (140 mM of lactose prepared in 100 mM sodium-citrate buffer of pH 5.5, containing 100 μM of MgSO$_4$). The reaction mixture was prepared by mixing 13 μL of diluted purified enzyme and 37 μL of lactose solution in a PCR tube. The substrate solution was prepared in a buffer of pH 5.5 and enzyme solution had a pH of 6.7. To initiate the reaction, 13 μL of enzyme was added to 37 μL of substrate solution. This mixing of these two buffers eventually increases the reaction pH from 5.5 to 5.7.

The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. until further use. The amount of glucose formed during the reaction was determined by following the protocol described in the example 10. The maximum absorbance value for each lactase was used to determine μM of glucose formed per sec, described as 1 Unit of Activity with Lactose at pH 5.5 at 43° C. (UAL-6). The specific activity at pH 5.5 at 43° C. is defined as μM of glucose formed per second per μM of enzyme (μM of glucose/sec/μM of enzyme), and is determined by dividing UAL-6 by the protein concentration in μM, described as SUAL-6. The high specific activity at pH 5.5 at 43° C. is relevant for the lactose hydrolysis in the fermented milk applications and sweet whey lactose hydrolysis. The detail results of the specific activity of enzymes at pH 5.5 at 43° C. are described in the FIG. 7.

Additionally the activity was described as μmole of glucose formed per minute per milligram of enzyme added. The results are shown in FIG. 29.

Example 13: Activity Determination Using Purified Enzymes on Lactose as Substrate at pH 4.5 at 4° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer F (140 mM of lactose prepared in 100 mM sodium-citrate buffer of pH 4.5, containing 100 μM of MgSO$_4$). The reaction mixture was prepared by mixing 13 μL of diluted purified enzyme and 37 μL of lactose solution in a PCR tube. The substrate solution was prepared in a buffer of pH 4.5 and enzyme solution had a pH of 6.7. To initiate the reaction, 13 μL of enzyme was added to 37 μL of substrate solution. This mixing of these two buffers eventually increases the reaction pH from 4.5 to 4.7.

The reaction mixture was incubated in a DNA thermal cycler using the following incubating parameters (reaction time; 60 min at 4° C., enzyme inactivation; 10 min at 95° C., storage; 4° C.). To determine the amount of glucose formed during the reaction, 10 μL of the reaction mixture was transferred to one well of standard microtiter plate containing 80 μL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value >1.5, the reaction mixture was diluted up to 5× with buffer A. With each purified enzyme, the reactions were carried out in triplicate and the mean value of the triplicate measurement was used for calculation. The maximum absorbance value for each lactase was used to determine μM of glucose formed per sec, described as 1 Unit of Activity with Lactose at pH 4.5 at 4° C. (UAL-7). The specific activity at pH 4.5 at 4° C. is defined as μM of glucose formed per second per μM of enzyme (μM of glucose/sec/μM of enzyme), and is determined by dividing UAL-7 by the protein concentration in μM, described as SUAL-7. The high specific activity at pH 4.5 at 4° C. is relevant for the lactose hydrolysis in the fermented milk applications. The detail results of the specific activity of enzymes at pH 4.5 at 4° C. are described in the FIG. 8.

Additionally the activity was described as μmole of glucose formed per minute per milligram of enzyme added. The results are shown in FIG. 30.

Example 14: Activity Determination Using Purified Enzymes on Lactose as Substrate at pH 4.5 at 37° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer F (140 mM of lactose prepared in 100 mM sodium-citrate buffer of pH 4.5, containing 100 μM of MgSO$_4$). The reaction mixture was prepared by mixing 13 μL of diluted purified enzyme and 37 μL of lactose solution in a PCR tube. The substrate solution was prepared in a buffer of pH 4.5 and enzyme solution had a pH of 6.7. To initiate the reaction, 13 μL of enzyme was added to 37 μL of substrate solution. This mixing of these two buffers eventually increases the reaction pH from 4.5 to 4.7.

The reaction mixture was incubated in a DNA thermal cycler using the following incubating parameters (reaction time; 10 min at 37° C., enzyme inactivation; 10 min at 95° C., storage; 4° C.). The reaction mixtures were stored at −20° C. until further use. The amount of glucose formed during the reaction was determined by following the protocol described in the example 13. The maximum absorbance value for each lactase was used to determine μM of glucose formed per sec, described as 1 Unit of Activity with Lactose at pH 4.5 at 37° C. (UAL-8). The specific activity at pH 4.5 at 37° C. is defined as μM of glucose formed per second per μM of enzyme (μM of glucose/sec/μM of enzyme), and is determined by dividing UAL-8 by the protein concentration in μM, described as SUAL-8. The high specific activity at pH 4.5 at 37° C. is relevant for the lactose hydrolysis in the fermented milk applications and acidic whey lactose hydrolysis. The detail results of the specific activity of enzymes at pH 4.5 at 37° C. are described in the FIG. 9. Additionally the activity was described as μmole of glucose formed per minute per milligram of enzyme added. The results are shown in FIG. 30.

Example 15: Activity Determination Using Purified Enzymes on Lactose as Substrate at pH 4.5 at 43° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer F (140 mM of lactose prepared in 100 mM sodium-citrate buffer of pH 4.5, containing 100 μM of MgSO$_4$). The reaction mixture was prepared by mixing 13 μL of diluted purified enzyme and 37 μL of lactose solution in a PCR tube. The substrate solution was prepared in a buffer of pH 4.5 and enzyme solution had a pH of 6.7. To initiate the reaction, 13 μL of enzyme was added to 37 μL of substrate solution. This mixing of these two buffers eventually increases the reaction pH from 4.5 to 4.7. The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. until further use. The amount of glucose formed during the reaction was determined by following the protocol described in the example 13. The maximum absorbance value for each lactase was used to determine μM of glucose formed per sec, described as 1 Unit of Activity with Lactose at pH 4.5 at 43° C. (UAL-9). The specific activity at pH 4.5 at 43° C. is defined as μM of glucose formed per second per μM of enzyme (μM of glucose/sec/μM of enzyme), and is determined by dividing UAL-9 by the protein concentration in μM, described as SUAL-9. The high specific activity at pH 4.5 at 43° C. is relevant for the lactose hydrolysis in the fermented milk applications and acidic whey lactose hydrolysis. The detail results of the specific activity of enzymes at pH 4.5 at 43° C. are described in the FIG. 10.

Additionally the activity was described as μmole of glucose formed per minute per milligram of enzyme added. The results are shown in FIG. 30.

Example 16: Activity Determination in BLU Units

The commercially available NOLA® Fit enzyme (Chr-Hansen, Denmark) was diluted in a range from 0.5 BLU/mL to 2.5 BLU/mL in buffer G (50 mM NaH$_2$PO$_4$ buffer pH 7.0 containing 100 μM of MgSO$_4$, 0.045% Brij, Sigma Aldrich). The diluted enzyme was incubated with lactose solution prepared in buffer H (105 mM of lactose prepared in 100 mM sodium-citrate buffer of pH 6.7, containing 100 μM of MgSO$_4$). The reaction mixture was prepared by mixing 13 μL of diluted purified enzyme and 37 μL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). The amount of glucose conversion was determined by transferring 10 μL of the reaction mixture in a single well of standard microtiter plate containing 80 μL of buffer C and incubated at 30° C. for 40 min. After 40 min, the absorbance was determined at 610 nm using FLUOStar Omega UV-plate reader (BMG Labtech, Germany). The measured absorbance values were used to draw a standard curve against BLU/mL. The maximum slope of the curve was used to determine the activity of new enzymes in BLU/mL.

Example 17: Activity Determination of New Lactases in BLU/mL Using Lactose as Substrate The purified lactases were diluted up to 50× in buffer A (50 mM NaH$_2$PO$_4$ buffer pH 6.7 containing 100 μM of MgSO$_4$). In a separate reaction, the diluted enzyme was incubated with lactose solution prepared in buffer H (105 mM of lactose prepared in 100 mM sodium-citrate buffer of pH 6.7, containing 100 μM of MgSO$_4$). The reaction mixture was prepared by mixing 13 μL of diluted purified enzyme and 37 μL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). After the reaction, 10 μL of the reaction mixture was transferred to one well of standard microtiter plate containing 80 μL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value >1.5, the reaction mixture was diluted up to 5× with buffer A. The maximum absorbance values were used to calculate the enzyme activity in BLU/mL, using standard curve described in example 16.

Example 18: Percentage Residual Lactose Measurement in Fresh Milk at Cold Temperature 2 mL of commercial pasteurized milk (1.5% Fat pasteurized milk, Arla Food) was mixed with 10-125 μL of enzyme (equivalent to 10 BLU/mL) as determined in the example 17, in 10 mL glass tube. The samples were incubated under constant conditions for 24 hours at 4° C. After the incubation, the reaction was stopped by heat inactivation at 95° C. for 7 min, followed by storage at −20° C. until further use. The amount of remaining lactose in the milk was analyzed using an HPLC assay. Samples for analysis were treated with 1.8 mL protein precipitation solution (0.083 M PCA and 2 mM Na-EDTA) and 2 mL of MQW prior to centrifugation at 2800 rpm for 30 min at 4° C. An aliquot of the supernatant was diluted a total of 200-fold using a Janus dilution robot (PerkinElmer, Waltham, MA, USA). The diluted samples were analyzed on a Dionex ICS-5000 system (Thermo Fischer Scientific, Waltham (MA), USA) using 4×250 mm CarboPac SA20 analytical column (Thermo Fischer Scientific, Waltham, MA, USA) and a pulsed amperometric detector. The detector was set to a simple three-step potential waveform, selective for detection of carbohydrates. The eluent was set to 1 mM KOH and was continuously regenerated through a trap column (CR-TC, Thermo Fischer Scientific, Waltham (MA), USA). The flow rate of the eluent was 1.2 mL/min and the analysis time was 10 min per injection. The lactose in each sample was quantified using a three-point external calibration curve prepared by adding known amounts of lactose monohydrate (Sigma-Aldrich, St. Louis, MO, USA) to MQW. Concentrations were calculated based on the chromatographic peak heights. The measured percentage residual lactose in fresh milk is shown in FIG. 11.

Example 19: Activity Determination in UHT Milk at Room Temperature 2 mL of UHT milk (1.5% Fat UHT milk, Arla Food) was mixed with 2-25 μL of enzyme (equivalent to 2 BLU/mL) as determined in example 17, in 10 mL glass tube. The samples were incubated under constant conditions for 24 hours at 25° C. After the incubation, the reaction was stopped by heat inactivation at 95° C. for 7 min, followed by storage at −20° C. until further use. The amount of residual lactose in UHT milk was analyzed using HPLC by following the protocol as described in example 18. The percentage of residual lactose in fresh milk after hydrolysis is listed in the FIG. 12.

Example 20: Enzyme Performance at High Temperature in Buffer

The purified enzyme was diluted to 5 BLU/mL in buffer A (50 mM NaH$_2$PO$_4$ buffer pH 6.7 containing 100 μM of MgSO$_4$). In a separate reaction, 13 μL of the diluted enzyme was incubated in a DNA thermal cycler with lactose solution (105 mM lactose prepared in 100 mM sodium-citrate buffer of pH 6.7, containing 100 μM of MgSO$_4$). The reaction mixture was prepared by mixing 13 μL of enzyme and 37 μL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). After the reaction, 10 µL of the reaction mixture was transferred to one well of standard microtiter plate containing 80 µL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value >1.5, the reaction mixture was diluted up to 5× with buffer A. The measured absorbance was called Abs37° C., and considered as reference value for calculations.

To measure the impact of heat treatment on enzyme activity, in a separate reaction, 13 µL of the diluted enzyme (5 BLU/mL) was incubated in a DNA thermal cycler using the following incubating parameter (at 72° C. for 15 sec or 74° C. for 15 sec or 76° C. for 6 sec or 78° C. for 6 sec or 80° C. for 4 sec or 85° C. for 5 sec or 90° C. for 5 sec or 95° C. for 5 sec, followed by storage at 4°° C.). The activity of the heat treated enzyme was determined by incubation with the lactose solution (105 mM lactose prepared in 100 mM sodium-citrate buffer of pH 6.7, containing 100 µM of $MgSO_4$), as described above. The measured absorbance at different temperature (for example at 72° C., 74° C., 76° C., 78° C., 80° C., 85° C., 90° C. or 95° C.) was called as Abs72° C., Abs74° C., Abs76° C., Abs78° C., Abs80° C., Abs85° C., Abs90° C., Abs95° C.

The percentage residual activity at high temperature was determined using the formula, % residual activity=(Abs72° C./Abs37° C.)*100

The percentages residual activities of different enzymes at different temperature are described in FIG. 13.

Example 21: Percentage Residual Lactose after the High Heat Treatment

The effect of heat treatment on the enzyme performance in pasteurized milk was determined by incubating a fixed amount of enzyme in the milk followed by a heat treatment. In separate reactions, 50 µL of the pasteurized milk was mixed with 10 BLU/mL of purified enzyme (as determined in example 17), in a PCR tube. The milk sample was incubated at 72° C. for 15 or 76° C. for 10 sec or 85° C. for 5 sec and 90° C. for 5 sec, followed by incubation at 5° C. for 24 h. After 24 h at 5° C., the reaction was stopped by heating the reaction at 95° C. for 7 min, followed by storage at −20° C. The residual lactose was measured by using the LactoSens® assay kit (Chr. Hansen, Denmark), by following the supplied protocol. The measured residual lactose was determined in g/L was determined at different temperature. The detection limit of the LactoSens® kit is between 0.2 g/L to 10 g/L. The results are described in the table 3:

TABLE 3

The percentage residual lactose in the pasteurized milk treated with a fixed amount of the purified enzyme followed by incubation at different temperature (72° C. for 15 sec, 76° C. for 10 sec, 85° C. for 5 sec and 90° C. for 5 sec followed by incubation at 4C for 24 h), determined using LactoSens ® assay kit. The LactoSens ® kit detection limits are in range of 0.2 g/L to 10 g/L of lactose. Here ND; not determined.

| | Residual lactose at | | | | |
|---|---|---|---|---|---|
| G-No. | 4° C. (g/L) | 72° C. (g/L) | 76° C. (g/L) | 85° C. (g/L) | 90° C. (g/L) |
| G4 | <0.2 | >10.0 | ND | ND | ND |
| G11 | <0.2 | >10.0 | ND | ND | ND |
| G16 | <0.2 | >10.0 | ND | ND | ND |
| G33 | <0.2 | 4.7 | ND | ND | ND |
| G35 | <0.2 | >10.0 | >10.0 | ND | ND |
| G40 | <0.2 | <0.2 | <0.2 | >10.0 | ND |
| G44 | 0.9 | >10.0 | ND | ND | ND |
| G57 | <0.2 | >10.0 | ND | ND | ND |
| G62 | 8.4 | >10.0 | >10.0 | >10.0 | ND |
| G66 | 0.35 | >10.0 | ND | ND | ND |
| G83 | 0.3 | 2.1 | 6.0 | >10.0 | ND |
| G84 | 0.25 | 0.65 | 0.5 | 7.6 | >10 |
| G95 | 0.3 | 6.0 | 8.6 | >10 | ND |
| G100 | 0.4 | 2.4 | 2.6 | >10.0 | ND |
| G104 | 0.35 | 0.45 | 0.5 | 0.45 | >10 |
| G108 | 0.35 | 1.3 | 1.55 | ND | ND |
| G109 | 0.35 | 1.45 | 3.4 | >10.0 | ND |
| G118 | 0.45 | 0.95 | 0.8 | >10.0 | >10 |
| G158 | <0.2 | 3.9 | >10.0 | ND | ND |
| G256 | 0.3 | 1.0 | 0.75 | 3.4 | >10 |
| G282 | <0.2 | <0.2 | <0.2 | <0.2 | >10 |
| G335 | <0.2 | 0.35 | 8.0 | >10.0 | ND |
| G600 | <0.2 | >10.0 | >10.0 | >10.0 | ND |
| G500 | <0.2 | >10.0 | ND | ND | ND |

Example 22: Percentage Residual Lactose in Pasteurized Milk Incubated at Different Temperatures 1 mL of commercial pasteurized milk (1.5% fat milk containing 4.7% lactose, Arla Foods, Denmark) was mixed with 0.047 mg/mL of enzyme, in a 1.5 mL Eppendorf tube. The enzyme was mixed in the milk with gentle vortex or pipetting. 50 µL of the milk, containing the enzyme, was transferred to a PCR tube. For each enzyme the reaction was performed in 2×50 µL reaction volume. The reaction mixture was incubated in a DNA thermal cycler with the following incubation parameters (reaction temperatures and time; 37° C. for 30 min or 55° C. for 30 min or 60° C. for 30 min, enzyme inactivation temperature and time; 95° C. for 10 min, storage temperature: 4° C.). During the enzyme addition, pipetting and mixing the milk samples were kept on ice-water mixture to minimize the effect of temperature on enzyme performance. After the reaction, the milk samples were either used directly for the residual lactose measurement or stored at −20° C. until further use. The residual lactose in the milk was analyzed using LactoSens® assay kit (Chr. Hansen, Denmark) by following the protocol supplied with the kit. The measured percentage residual lactose in the pasteurized milk is shown in FIG. 14.

To test the lactose hydrolysis potential of these novel lactases, we incubated 0,047 mg enzyme per milliliter of the pasteurized milk and incubated at 37° C., 55° C. and 60° C. for 30 min. After 30 min incubation, the enzymes were inactivated by heating at 95° C. The residual lactose was determined using LactoSens® assay kit (Chr. Hansen, Denmark). At their optimal temperature (37° C.), both the Ha-Lactase and NOLA® fit showed a high residual lactose (>1% of residual lactose), suggesting that enzymes have lower activity and are not producing lactose free pasteurized milk in the given time frame. Moreover, a similar level of residual lactose was measured at 55° C. and 60° C. On the contrary, the G33, G44, G95 andG158 enzymes showed <0.1% residual lactose at 37° C., FIG. 15. Because of their high activity at elevated temperatures (55° C. or 60° C.), the novel enzymes showed <0.01% residual lactose after 30 min incubation. This shows that by using the current enzyme dose it is possible to produce essentially lactose free pasteurized and filtered milk in less than 30 min. Filtered milk is more like raw milk than like pasteurized milk. The lactose hydrolysis at elevated temperature (55° C.-60° C.) in short time reduces the chance of microbial growth without affecting the milk quality.

Example 23: Percentage Residual Lactose in Pasteurized Milk Incubated for Different Time Span 1 mL of commercial pasteurized milk (1.5% fat milk containing 4.7% lactose, Arla Foods, Denmark) was mixed with 0.047 mg/mL of enzyme, in a 1.5 mL Eppendorf tube. The enzyme was mixed in the milk with gentle vortex or pipetting. 50 µL of the milk, containing the enzyme, was transferred to a PCR tube. For each enzyme the reaction was performed in 2×50 µL reaction volume. The reaction mixture was incubated in a DNA thermal cycler with the following incubation parameters (reaction temperatures and time; 55° C. for 15 min or 55° C. for 30 min, enzyme inactivation temperature and time; 95° C. for 10 min, storage temperature: 4° C.). During the enzyme addition, pipetting and mixing the milk samples were kept on ice-water mixture to minimize the effect of temperature and time. After the reaction, the milk samples either used directly for the residual lactose measurement or stored at −20° C. until further use. The residual lactose in the milk was analyzed using LactoSens® assay kit (Chr. Hansen, Denmark), as described in the example 22. The measured percentage residual lactose in the pasteurized milk is shown in FIG. 16.

Example 24: Percentage Residual Lactose in Pasteurized Milk Incubated with Different Enzyme Doses 1 mL of commercial pasteurized milk (1.5% fat milk containing 4.7% lactose, Arla Foods, Denmark) was mixed with either different enzyme doses (0.024 mg/mL or 0.047 mg/mL), in 1.5 mL Eppendorf tube. The enzyme was mixed in the milk with gentle vortex or pipetting. 50 µL of the milk, containing the enzyme, was transferred to a PCR tube. For each enzyme the reaction was performed in 2×50 µL reaction volume. The reaction mixture was incubated in a DNA thermal cycler with the following incubation parameters (reaction temperatures and time; 55° C. for 30 min, enzyme inactivation temperature and time; 95° C. for 10 min, storage temperature: 4° C.). After the reaction, the samples either used directly for the residual lactose measurement or stored at −20° C. until further use. The residual lactose in the milk was analyzed by following the same protocol as described in example 22. The measured percentage residual lactose in the pasteurized milk is shown in FIG. 17.

Example 25: Percentage Residual Lactose in Pasteurized Milk Incubated with Different Enzyme Doses and for Different Reaction Time Span 1 mL of commercial pasteurized milk (1.5% fat milk containing 4.7% lactose, Arla Foods, Denmark) was mixed with different enzyme dose (0.024 or 0.047 mg/mL), in 1.5 mL Eppendorf tube. The enzyme was mixed in the milk with gentle vortex or pipetting. 50 µL of the milk, containing the enzyme, was transferred to a PCR tube. For each enzyme the reaction was performed in 2×50 µL reaction volume. The reaction mixture was incubated in a DNA thermal cycler with the following incubation parameters (reaction temperatures and time; 55° C. for 15 min or 55° C. for 30 min, enzyme inactivation temperature and time; 95° C. for 10 min, storage temperature: 4° C.). During the enzyme addition, pipetting and mixing the milk samples were kept on ice-water mixture to minimize the effect of temperature and time. After the reaction, the samples either used directly used the residual lactose measurement or stored at −20° C. until further use. The residual lactose was determined using the protocol described in example 22. The measured percentage residual lactose in the pasteurized milk is shown in FIG. 18.

Example 26: Percentage Residual Lactose in Filtered Milk 1 mL of commercial micro-filtered semi skimmed milk (1.5% fat milk containing 4.8% lactose, Marguerite, France) was mixed with 0.047 mg/mL of enzyme, in 1.5 mL Eppendorf tube. The enzyme was mixed in the milk with gentle vortex or pipetting. 50 µL of the milk, containing the enzyme, was transferred to a PCR tube. For each enzyme the reaction was performed in 2×50 µL reaction volume. The reaction mixture was incubated in a DNA thermal cycler with the following incubation parameters (reaction temperatures and time; 55° C. for 30 min, enzyme inactivation temperature and time; 95° C. for 10 min, storage temperature: 4° C.). During the enzyme addition, pipetting and mixing the milk samples were kept on ice-water mixture to minimize the effect of temperature and time. After the reaction, the samples either used directly for the residual lactose measurement or stored at −20° C. until further use. The amount of remaining lactose in the milk was analyzed using LactoSens® assay kit (Chr. Hansen, Denmark) by following the protocol supplied with the kit. The measured percentage residual lactose in the filtered milk is shown in FIG. 19.

This shows that by using the current enzyme dose it is possible to produce lactose free filtered milk (filtered milk is more like raw milk than pasteurized) in less than 30 min. The lactose hydrolysis at elevated temperature (55° C.-60° C.) in short time reduces the chance of microbial growth without affecting the milk quality.

Example 27: Percentage Residual Lactose in Filtered Milk Incubated with Different Enzyme Doses 1 mL of commercial micro-filtered semi skimmed milk (1.5% fat milk containing 4.8% lactose, Marguerite, France) was mixed with different enzyme doses (0.055 mg/mL, 0.55 µM or 0.11 mg/mL, 0.11 µM), in 1.5 mL Eppendorf tube. The enzyme was mixed in the milk with gentle vortex or pipetting. 50 µL of the milk, containing the enzyme, was transferred to a PCR tube. For each enzyme the reaction was performed in 2×50 µL reaction volume. The reaction mixture was incubated in a DNA thermal cycler with the following incubation parameters (reaction temperatures and time; 55° C. for 5 min, enzyme inactivation temperature and time; 95° C. for 10 min, storage temperature: 4° C.). During the enzyme addition, pipetting and mixing the milk samples were kept on ice-water mixture to minimize the effect of temperature and time. After the reaction, the samples were either used directly for the residual lactose measurement or stored at −20° C. until further use. The residual lactose in the milk was analyzed by following the protocol described in example 22. The measured percentage residual lactose in the filtered milk is shown in FIG. 20.

Example 28: Percentage Residual Lactose in Filtered Milk Incubated for Different Time Span 1 mL of commercial micro-filtered semi skimmed milk (1.5% fat milk containing 4.8% lactose, Marguerite, France) was mixed with 0.11 mg/mL (1 µM) of enzyme, in 1.5 mL Eppendorf tube. The enzyme was mixed in the milk with gentle vortex or pipetting. 50 µL of the milk, containing the enzyme, was transferred to a PCR tube. For each enzyme the reaction was performed in 2×50 µL reaction volume. The reaction mixture was incubated in a DNA thermal cycler with the following incubation parameters (reaction temperatures and time; 55° C. for 5 min or 55° C. for 6 min or 55° C. for 7 min, enzyme inactivation temperature and time; 95° C. for 10 min, storage temperature: 4° C.). During the enzyme addition, pipetting and mixing the milk samples were kept on ice-water mixture to minimize the effect of temperature and time. After the reaction, the samples either used directly for residual lactose measurement or stored at −20° C. until further use. The amount of remaining lactose in the milk was analyzed using LactoSens® assay kit (Chr. Hansen, Denmark) by following the protocol supplied with the kit. The measured percentage residual lactose in the filtered milk is shown in FIG. 21. This shows that by using the current enzyme dose it is possible to produce lactose free pasteurized and filtered milk (filtered milk is more like raw milk than pasteurized) in less than 5-30 min. The lactose hydrolysis at elevated temperature (55° C.-60° C.) in short time reduces the chance of microbial growth without affecting the milk quality.

Example 29: Enzyme Activity at 4-5° C.

To analyze the kinetics of lactose hydrolysis by the novel enzymes in pasteurized milk, 0.05 mg enzyme was added per milliliter of commercial pasteurized milk (1.5% fat milk containing 4.7% lactose, Arla Foods, Denmark). The enzyme was mixed well by gentle vortex and transferred into PCR tube, 10×100 µL of each. The reaction mixtures were incubated at 4° C., and after a fixed interval the samples was withdrawn. The reaction was stopped by heating at 95° C. for 10 min in PCR machine. The samples were cooled to room temperature and the residual lactose was measured using LactoSens® assay kit (Chr. Hansen, Denmark). The measured value of residual lactose was plotted against reaction time.

At 4-5° C. the known commercial products, NOLA® Fit (G600) and Ha-Lactase™ (G500) require between 8-12 hr and 18-24 hr to reduce the concentration of residual lactose in cow milk to less than <0.1% and <0.01%, respectively (as shown in FIGS. 22 and 23).

The lactases of the present invention are significantly more active under these conditions. For example, the G95 (the most active enzyme) reaches a residual concentration of lactose of <0.1% level (4 hr). The G158 and G33 are able to reduce the residual concentration of lactose to a level of <0.1% in between 5-6 hr and a level of <0.01% lactose in 8-12 hr. After 12 hr incubation, several of the lactases showed lower residual lactose than control enzymes (shown in FIGS. 24 and 25). These results show that the novel lactases are faster than Ha-Lactase™ and NOLA® Fit and result in lactose free pasteurized milk in significantly shorter time. These new enzymes can reduce the overall process time by 50%. Additionally, the novel enzymes provide the possibility to reduce the enzyme dose further between 25-50% to produce lactose free/reduced pasteurized milk (shown in FIG. 26).

These results thus show that the novel lactases can produce lactose free pasteurized milk in significantly shorter time (8-12 hr) with 50 mg/L enzyme dose. Moreover, it is possible to lower the enzyme dose by 25-50%, depending on the required lactose level.

Example 30: Enzyme Activity in Different Milk Types at 4-5° C.

To compare enzyme activity in different milk types, pasteurized and filtered milk was incubated using lactase enzyme in a concentration of 0.052 mg/L. The samples were mixed and stored at 4° C. for 24 hr.

The residual lactose content was determined using LactoSens® assay kit (Chr. Hansen, Denmark) and is shown in FIG. 27, which shows that many of the new lactase enzymes are highly active in digesting lactose in pasteurized and filtered milk at 4° C.

The invention claimed is:

1. A method for producing a dairy product, comprising:
   (a) mixing a milk-based substrate comprising lactose at a concentration of at least 10 g/L and a peptide or a dimeric peptide exhibiting beta-galactosidase activity at a concentration of 10 to 55 mg/L; and
   (b) incubating the mixture at a temperature from 1° C.-10° C. for a period of time sufficient to reduce the lactose concentration in the mixture to less than 0.2 g/L,
   wherein the peptide or the dimeric peptide exhibiting beta-galactosidase activity is selected from a peptide having the amino acid sequence of any one of SEQ ID NOs. 1-6 or 8-33, or a variant thereof having from 1 to 22 amino acid substitutions, additions, or deletions, and exhibits beta-galactosidase enzyme activity at a temperature from 1° C.-10° C.

2. A method for reducing the lactose content in a milk-based substrate, comprising:
   (a) mixing a milk-based substrate comprising lactose at a concentration of at least 10 g/L and a peptide or a dimeric peptide exhibiting beta-galactosidase activity at a concentration of 10 to 55 mg/L; and
   (b) incubating the mixture at a temperature from 1° C.-10° C. for a period of time sufficient to reduce the lactose concentration in the mixture to less than 0.2 g/L,
   wherein the peptide or the dimeric peptide exhibiting beta-galactosidase activity is selected from a peptide having the amino acid sequence of any one of SEQ ID NOs. 1-6 or 8-33, or a variant thereof having from 1 to 22 amino acid substitutions, additions, or deletions, and exhibits beta-galactosidase enzyme activity at a temperature from 1° C.-10° C.

3. The method according to claim 1, wherein the peptide or the dimeric peptide exhibiting beta-galactosidase activity is selected from a peptide having the amino acid sequence of any one of SEQ ID NOs. 22, 33, 14, 9, 11, 30 or 1, or a variant thereof having from 1 to 22 amino acid substitutions, additions, or deletions.

4. The method according to claim 1, wherein the peptide or the dimeric peptide exhibiting beta-galactosidase activity is added at a concentration of 35 to 52 mg/L.

5. The method according to claim 1, wherein the milk-based substrate comprising lactose is selected from:

(i) a pasteurized, raw, and/or filtered form of cow milk, sheep milk, goat milk, buffalo milk, or camel milk; or (ii) a fermented dairy product obtained from (i) by fermentation.

6. The method according to claim 5, wherein the milk-based substrate comprising lactose is cow milk comprising lactose at a concentration of about 37 to 50 g/L, or a heat treated, pasteurized, and/or filtered form thereof.

7. The method according to claim 1, wherein the lactose concentration of less than 0.2 g/l is reached after incubation for 4-24 hours.

8. The method according to claim 1, wherein the incubation temperature in step (b) is in the range of from 2° C.-7° C.

9. The method according to claim 1, wherein the incubation in step (b) reduces the lactose concentration in the mixture to less than 0.05 g/L.

10. The method according to claim 1, wherein the mixture comprising the milk-based substrate and the peptide or the dimeric peptide exhibiting beta-galactosidase activity is heated to a temperature of at least 60° C. for at least four seconds before or after incubating the mixture at a temperature from 1° C.-10° C.

11. The method according to claim 10, wherein the mixture comprising the milk-based substrate and the peptide or the dimeric peptide exhibiting beta-galactosidase activity is heated to a temperature of 72° C. for about 15 seconds before or after incubating the mixture at a temperature from 1° C.-10° C. in step (b).

12. The method according to claim 1, wherein the method comprises a step of fermenting the milk-based substrate with lactic acid bacteria.

13. The method according to claim 12, wherein the fermentation step is carried out before or after the incubation with the peptide or the dimeric peptide exhibiting beta-galactosidase activity.

14. The method according to claim 1, wherein the dairy product is selected from a fermented milk product, cheese, yoghurt, butter, dairy spread, butter milk, acidified milk drink, sour cream, whey based drink, ice cream, condensed milk, dulce de leche, and a flavored milk drink.

15. The method according to claim 1, wherein the peptide or the dimeric peptide exhibiting beta-galactosidase activity is selected from a peptide having the amino acid sequence of any one of SEQ ID NOs. 13, 19, 26, or 27, or a variant thereof having from 1 to 22 amino acid substitutions, additions, or deletions.

16. The method according to claim 1, wherein the peptide or the dimeric peptide exhibiting beta-galactosidase activity is added at a concentration of 45 to 52 mg/L.

17. The method according to claim 1, wherein the lactose concentration of less than 0.2 g/l lactose is reached after incubation for 24 hours.

18. The method according to claim 1, wherein the incubation in step (b) reduces the lactose concentration in the mixture to less than 0.01 g/L.

19. The method according to claim 10, wherein the mixture comprising the milk-based substrate and the peptide or the dimeric peptide exhibiting beta-galactosidase activity is heated to a temperature of 140° C. for about four seconds before or after incubating the mixture at a temperature from 1° C.-10° C.

20. The method according to claim 1, wherein the peptide or the dimeric peptide exhibiting beta-galactosidase activity is selected from a peptide having the amino acid sequence of any one of SEQ ID NOs. 1-6 or 8-33, or a variant thereof having from 1 to 5 amino acid substitutions, additions, or deletions.

21. The method according to claim 2, wherein the peptide or the dimeric peptide exhibiting beta-galactosidase activity is selected from a peptide having the amino acid sequence of any one of SEQ ID NOs. 1-6 or 8-33, or a variant thereof having from 1 to 5 amino acid substitutions, additions, or deletions.

\* \* \* \* \*